United States Patent
Temme et al.

(10) Patent No.: US 10,919,814 B2
(45) Date of Patent: *Feb. 16, 2021

(54) METHODS AND COMPOSITIONS FOR IMPROVING PLANT TRAITS

(71) Applicant: Pivot Bio, Inc., Berkeley, CA (US)

(72) Inventors: Karsten Temme, Oakland, CA (US);
Alvin Tamsir, San Francisco, CA (US);
Sarah Bloch, Oakland, CA (US);
Rosemary Clark, Emeryville, CA (US);
Emily Tung, Millbrae, CA (US)

(73) Assignee: Pivot Bio, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/685,997

(22) Filed: Nov. 15, 2019

(65) Prior Publication Data

US 2020/0087221 A1    Mar. 19, 2020

Related U.S. Application Data

(60) Division of application No. 15/954,557, filed on Apr. 16, 2018, which is a continuation of application No. 15/636,595, filed on Jun. 28, 2017, now Pat. No. 9,975,817, which is a continuation of application No. PCT/US2016/042170, filed on Jul. 13, 2016.

(60) Provisional application No. 62/213,567, filed on Sep. 2, 2015, provisional application No. 62/192,009, filed on Jul. 13, 2015.

(51) Int. Cl.

| | |
|---|---|
| *C05F 11/08* | (2006.01) |
| *C12N 9/02* | (2006.01) |
| *C12N 9/80* | (2006.01) |
| *C05C 1/00* | (2006.01) |
| *C05C 3/00* | (2006.01) |
| *C05C 5/00* | (2006.01) |
| *C05C 11/00* | (2006.01) |
| *C07K 14/195* | (2006.01) |
| *C12N 1/20* | (2006.01) |
| *C12N 9/22* | (2006.01) |
| *C12N 15/74* | (2006.01) |
| *C05G 3/90* | (2020.01) |
| *C12N 9/00* | (2006.01) |

(52) U.S. Cl.
CPC .............. *C05F 11/08* (2013.01); *C05C 1/00* (2013.01); *C05C 3/005* (2013.01); *C05C 5/005* (2013.01); *C05C 11/00* (2013.01); *C07K 14/195* (2013.01); *C12N 1/20* (2013.01); *C12N 9/0095* (2013.01); *C12N 9/80* (2013.01); *C12N 9/93* (2013.01); *C12Y 118/06001* (2013.01); *C12Y 305/01002* (2013.01); *C12Y 603/01002* (2013.01)

(58) Field of Classification Search
None
See application file for complete search history.

(56) References Cited

U.S. PATENT DOCUMENTS

| | | |
|---|---|---|
| 1,520,545 A | 12/1924 | Murphy |
| 4,782,022 A | 11/1988 | Puhler et al. |
| 4,832,728 A | 5/1989 | Allan et al. |
| 5,071,743 A | 12/1991 | Slilaty et al. |
| 5,229,291 A | 7/1993 | Nielsen et al. |
| 5,354,670 A | 10/1994 | Nickoloff et al. |
| 5,427,785 A | 6/1995 | Ronson et al. |
| 5,780,270 A | 7/1998 | Lesley |
| 5,789,166 A | 8/1998 | Bauer et al. |
| 5,916,029 A | 6/1999 | Smith et al. |
| 6,033,861 A | 3/2000 | Schafer et al. |
| 6,114,148 A | 9/2000 | Seed et al. |
| 6,391,548 B1 | 5/2002 | Bauer et al. |
| 6,548,289 B1 | 4/2003 | Beynon et al. |
| 6,596,509 B1 | 7/2003 | Bauer |
| 6,673,610 B2 | 1/2004 | Miyawaki et al. |
| 6,713,285 B2 | 3/2004 | Bauer et al. |
| 6,773,900 B2 | 8/2004 | Short et al. |
| 6,841,358 B1 | 1/2005 | Locht et al. |
| 7,084,331 B2 | 8/2006 | Isawa et al. |
| 7,132,265 B2 | 11/2006 | Bauer et al. |
| 7,470,427 B2 | 12/2008 | Cocking |
| 7,485,451 B2 | 2/2009 | Vandergheynst et al. |
| 8,076,142 B2 | 12/2011 | Huang et al. |

(Continued)

FOREIGN PATENT DOCUMENTS

| | | |
|---|---|---|
| CA | 2051071 A1 | 3/1993 |
| CN | 1552846 | 12/2004 |

(Continued)

OTHER PUBLICATIONS

Clancy et al., "The domains carrying the opposing activities in adenylyltransferase are separated by a central regulatory domain," FEBS Journal, 2007, 274:2865-2877.

(Continued)

*Primary Examiner* — Suzanne M Noakes
*Assistant Examiner* — Jae W Lee
(74) *Attorney, Agent, or Firm* — Fish & Richardson P.C.

(57) ABSTRACT

Disclosed herein are methods of increasing nitrogen fixation in a non-leguminous plant. The methods can comprise exposing the plant to a plurality of bacteria. Each member of the plurality comprises one or more genetic variations introduced into one or more genes or non-coding polynucleotides of the bacteria's nitrogen fixation or assimilation genetic regulatory network, such that the bacteria are capable of fixing atmospheric nitrogen in the presence of exogenous nitrogen. The bacteria are not intergeneric microorganisms. Additionally, the bacteria, in planta, produce 1% or more of the fixed nitrogen in the plant.

22 Claims, 17 Drawing Sheets

Specification includes a Sequence Listing.

(56) References Cited

U.S. PATENT DOCUMENTS

| | | |
|---|---|---|
| 8,137,665 B2 | 3/2012 | Cocking |
| 8,268,584 B1 | 9/2012 | Harwood et al. |
| 8,377,671 B2 | 2/2013 | Cournac et al. |
| 8,481,026 B1 | 7/2013 | Woodruff et al. |
| 8,795,965 B2 | 8/2014 | Zhang |
| 9,150,851 B2 | 10/2015 | Wigley et al. |
| 9,321,697 B2 | 4/2016 | Das et al. |
| 9,487,451 B2 | 11/2016 | Doty et al. |
| 9,512,431 B2 | 12/2016 | Mirsky et al. |
| 9,657,298 B2 | 5/2017 | Soto, Sr. et al. |
| 9,957,509 B2 | 5/2018 | Mirsky et al. |
| 9,975,817 B2 | 5/2018 | Temme et al. |
| 10,384,983 B2 | 8/2019 | Temme et al. |
| 10,556,839 B2 | 2/2020 | Temme et al. |
| 10,662,432 B2 | 5/2020 | Mirsky et al. |
| 2004/0235663 A1 | 11/2004 | Cocking |
| 2004/0241847 A1 | 12/2004 | Okuyama et al. |
| 2005/0081262 A1 | 4/2005 | Cook et al. |
| 2005/0266541 A1 | 12/2005 | Dillon |
| 2006/0127988 A1 | 6/2006 | Wood et al. |
| 2006/0243011 A1 | 11/2006 | Someus |
| 2008/0311632 A1 | 12/2008 | Figge et al. |
| 2009/0105076 A1 | 4/2009 | Stewart et al. |
| 2009/0137390 A1 | 5/2009 | Triplett |
| 2009/0162477 A1 | 6/2009 | Nadel |
| 2009/0258404 A1 | 10/2009 | Mikkelsen et al. |
| 2009/0308121 A1 | 12/2009 | Reddy et al. |
| 2010/0028870 A1 | 2/2010 | Welch et al. |
| 2010/0267147 A1 | 10/2010 | Qiao |
| 2011/0104690 A1 | 5/2011 | Yu et al. |
| 2012/0015806 A1 | 1/2012 | Paikray et al. |
| 2012/0107889 A1 | 5/2012 | Doty et al. |
| 2012/0192605 A1 | 8/2012 | McSpadden Gardener |
| 2012/0266332 A1 | 10/2012 | Kuykendall |
| 2012/0284813 A1 | 11/2012 | Olivier et al. |
| 2013/0126428 A1 | 5/2013 | Jones et al. |
| 2014/0011261 A1 | 1/2014 | Wang et al. |
| 2014/0155283 A1 | 6/2014 | Venkateswaran et al. |
| 2014/0230504 A1 | 8/2014 | Finlayson et al. |
| 2014/0273226 A1 | 9/2014 | Wu |
| 2014/0301990 A1 | 10/2014 | Gregory et al. |
| 2014/0329326 A1 | 11/2014 | Mirsky et al. |
| 2014/0336050 A1 | 11/2014 | Soto, Sr. et al. |
| 2015/0080261 A1 | 3/2015 | Wigley et al. |
| 2015/0101373 A1 | 4/2015 | Munusamy et al. |
| 2015/0128670 A1 | 5/2015 | Das |
| 2015/0237807 A1 | 8/2015 | Valiquette |
| 2015/0239789 A1 | 8/2015 | Kang et al. |
| 2015/0315570 A1 | 11/2015 | Zhao et al. |
| 2016/0174570 A1 | 6/2016 | Vujanovic et al. |
| 2016/0264929 A1 | 9/2016 | Barney et al. |
| 2016/0292355 A1 | 10/2016 | Lou et al. |
| 2016/0295868 A1 | 10/2016 | Jones et al. |
| 2017/0152519 A1 | 6/2017 | Mirsky et al. |
| 2017/0367349 A1 | 12/2017 | Gruver et al. |
| 2018/0002243 A1 | 1/2018 | Temme |
| 2018/0020671 A1 | 1/2018 | Bioconsortia |
| 2018/0065896 A1 | 3/2018 | Ibema et al. |
| 2018/0073028 A1 | 3/2018 | Mirsky et al. |
| 2018/0273437 A1 | 9/2018 | Temme |
| 2018/0290942 A1 | 10/2018 | Voigt et al. |
| 2018/0297905 A1 | 10/2018 | Temme |
| 2018/0297906 A1 | 10/2018 | Temme |
| 2019/0039964 A1 | 2/2019 | Temme et al. |
| 2019/0144352 A1 | 5/2019 | Temme et al. |
| 2020/0115715 A1 | 4/2020 | Mirsky et al. |

FOREIGN PATENT DOCUMENTS

| | | |
|---|---|---|
| CN | 103451130 | 12/2013 |
| EP | 0256889 | 2/1988 |
| EP | 3322679 | 5/2018 |
| FR | 2910230 | 6/2008 |
| JP | S63-501924 | 8/1988 |
| JP | H01225483 A | 9/1989 |
| JP | 02-131581 | 5/1990 |
| JP | 2014096996 | 5/2014 |
| JP | 2015037385 | 2/2015 |
| JP | 2015042633 | 3/2015 |
| JP | 2015113274 | 6/2015 |
| JP | 2015518023 | 6/2015 |
| JP | 2015519352 | 7/2015 |
| WO | WO 8704182 | 7/1987 |
| WO | WO-9305154 A1 | 3/1993 |
| WO | WO 1998/010088 | 3/1998 |
| WO | WO-9909834 A2 | 3/1999 |
| WO | WO 2000/057183 | 9/2000 |
| WO | WO-0107567 A1 | 2/2001 |
| WO | WO-2006005100 A1 | 1/2006 |
| WO | WO-2009060012 A2 | 5/2009 |
| WO | WO-2009091557 A1 | 7/2009 |
| WO | WO-2011099019 A1 | 8/2011 |
| WO | WO-2011099024 A1 | 8/2011 |
| WO | WO-2011154960 A1 | 12/2011 |
| WO | WO-2012174271 A2 | 12/2012 |
| WO | WO-2013076687 A2 | 5/2013 |
| WO | WO-2013132518 A1 | 9/2013 |
| WO | WO-2014042517 A2 | 3/2014 |
| WO | WO-2014071182 A1 | 5/2014 |
| WO | WO-2014201044 A2 | 12/2014 |
| WO | WO-2016016629 A1 | 2/2016 |
| WO | WO-2016016630 A1 | 2/2016 |
| WO | WO-2016100727 A1 | 6/2016 |
| WO | WO-2016146955 A1 | 9/2016 |
| WO | WO 2016/181228 | 11/2016 |
| WO | WO-2016178580 A2 | 11/2016 |
| WO | WO-2016179046 A1 | 11/2016 |
| WO | WO-2016191828 A1 | 12/2016 |
| WO | WO 2017/011602 | 1/2017 |
| WO | WO-2017042833 A1 | 3/2017 |
| WO | WO-2017062412 A1 | 4/2017 |
| WO | WO-2017069717 A1 | 4/2017 |
| WO | WO-2018132774 A1 | 7/2018 |
| WO | WO 2019/032926 | 2/2019 |
| WO | WO 2019/084342 | 5/2019 |
| WO | WO 2019/140125 | 7/2019 |

OTHER PUBLICATIONS

U.S. Appl. No. 15/954,557 Office Action dated Jun. 28, 2019.
U.S. Appl. No. 15/954,557 Office Action dated Mar. 4, 2019.
U.S. Appl. No. 16/159,542 Office Action dated Jul. 25, 2019.
Sanjuan and Olivares, "Multicopy plasmids carrying the Klebsiella pneumoniae nifA gene enhance Rhizobium meliloti nodulation competitiveness on alfalfa," Molecular Plant-Microbe Interactions, 1991, 4(4):365-369.
Idalia and Bernardo, "*Escherichia coli* as a model organism and its application in biotechnology," Recent Advances on Physiology, Pathogenesis, and Biotechnological Applications, Chapter 13, 2017, pp. 253-274.
"New Plant Breeding Techniques," Science Council of Japan, retrieved from URL <http://www.scj.go.jp/ja/info/kohyo/pdf/kohyo-22-h140826.pdf>, Aug. 26, 2014, 82 pages, (partial English translation).
International Preliminary Report on Patentability in PCT Appln. No. PCT/US2016/042170, dated Jan. 16, 2018, 19 pages.
International Search Report and Written Opinion in International Appln. No. PCT/US2016/042170, dated Dec. 2, 2016, 26 pages.
Partial European Search Report in EP Appln. No. 16825147.8, dated Mar. 4, 2019, 13 pages.
Supplementary European Search Report in EP Appln. No. 16825147.8, dated Jun. 6, 2019, 19 pages.
40 CFR 725.3 U.S. Government Publishing Office (Jul. 1, 2010) http://www.gpo.gov/fdsys/pkg/CFR-2010-title40-vol30/pdf/CFR-2010-title40-vol30-sec725-3.pdf.
An et al. Constitutive expression of the nifA gene activates associative nitrogen fixation of Enterobacter gergoviae 57-7, an opportunistic endophytic diazotroph. Journal of Applied Microbiology 103(3):613-620 (Sep. 1, 2007). First published Feb. 7, 2007.
Andersen, et al. Energetics of biological nitrogen fixation: determination of the ratio of formation of H2 to NH4+ catalysed by nitrogenase of Klebsiella pneumoniae in vivo. J Gen Microbiol. Nov. 1977;103(1):107-22.

(56) References Cited

OTHER PUBLICATIONS

Andrews et al. Use of Nitrogen Fixing Bacteria Inoculants as a Substitute for Nitrogen Fertiliser for Dryland Graminaceous Crops: Progress Made, Mechanisms of Action and Future Potential. Symbiosis 34 (2003). 21 pages.

Arsene, et al., Modulation of NifA activity by PII in Azospirillum brasilense: Evidence for a Regulatory role of the NifA N-Terminal Domain. Journal of Bacteriology, Aug. 1996, p. 4830-4838.

Austin, et al. Characterisation of the Klebsiella pneumoniae nitrogen-fixation regulatory proteins NIFA and NIFL in vitro. Eur J Biochem. Jan. 26, 1990;187(2):353-60.

Bali, et al., Excretion of Ammonium by a nifL Mutant of Azotobacter vinelandii fixing Nitrogen. Applied and Environmental Microbiology, May 1992, p. 1711-1718.

Barney, et al., Gene deletions resulting in increased nitrogen release by azotobacter vinelandii: application of a novel nitrogen biosensor. Appl. Environ. Microbiol. 2015; 81(13):4316-4328. Published online Apr. 17, 2015.

Barney, et al., Transcriptional analysis of an Ammonium-excreting stain of azotobacter vinelandii deregulated for nitrogen fixation. Appl. Environ. Microbiol. 2017; 83(20): 1-22.

Barrangou, R., Exploiting CRISPR-Cas immune systems for genome editing in bacteria. Curr. Opin. Biotechnol. 2016; 37:61-68.

Beringer, et al., Genetic engineering and nitrogen fixation. Biotech. Gen. Eng. Rev. 1984; 1(1):65-88.

Blanco, et al. Sequence and molecular analysis of the nifL gene of Azotobacter vinelandii. Mol Microbiol. Aug. 1993;9(4):869-79.

Blast. Basic local alignment search tool. Available at http://blast.ncbi.nlm.nih.gov/Blast.cgi. Accessed on Oct. 10, 2016.

Bosworth, et al. Alfalfa yield response to inoculation with recombinant strains of Rhizobium meliloti with an extra copy of dctABD and/or modified nifA expression. Appl Environ Microbiol. Oct. 1994;60(10):3815-32.

Brewin, et al., The Basis of Ammonium release in nifL Mutants of Azotobacter vinelandii. Journal of Bacteriology, Dec. 1999; 181(23): p. 7356-7362.

Buchanan-Wollaston, et al. Role of the nifA gene product in the regulation of nif expression in Klebsiella pneumoniae. Nature. Dec. 24, 1981;294(5843):776-8.

Buddrus-Schiemann, et al. Root colonization by *Pseudomonas* sp. DSMZ 13134 and impact on the indigenous rhizosphere bacterial community of barley. Microb Ecol. Aug. 2010;60(2):381-93. doi: 10.1007/s00248-010-9720-8. Epub Jul. 20, 2010.

Chen, et al., Complete genome sequence of Kosakonia sacchari type strain SP1T. Stand Genomic Sci. Jun. 15, 2014; 9(3): 1311-1318.

Chiang, et al., Mutagenic Oligonucleotide-directed PCR Amplification (Mod-PCR): An Efficient Method for Generating Random Base Substitution Mutations in a DNA sequence element. PCT methods and applications. 1993; 2:210-217.

Cohen, J.D., In vitro Tomato Fruit Cultures Demonstrate a Role for Indole-3-acetic Acid in Regulating Fruit Ripening. J. Amer. Soc. Hort. Sci. 121(3):520-524. 1996.

Colnaghi, R. et al., Strategies for increased ammonium production in free-living or plant associated nitrogen fixing bacteria. Plant and Soil, 1997; 194: 145-154.

Conniff, R., Microbes help grow better crops. Scientific american. http://www.scientificamerican.com/article/microbes-help-grow-better-crops/ Sep. 2013.

Contreras, et al. The product of the nitrogen fixation regulatory gene nfrX of Azotobacter vinelandii is functionally and structurally homologous to the uridylyltransferase encoded by glnD in enteric bacteria. J Bacteriol. Dec. 1991; 173(24): 7741-7749.

Curatti, et al., Genes required for rapid expression of nitrogenase activity in Azotobacter vinelandii. PNAS 2005; 102(18): 6291-6296.

Datsenko et al. One-step inactivation of chromosomal genes in *Escherichia coli* K-12 using PCR products. PNAS USA 97(12):6640-6645 (2000).

DeBruijn, F.J., et al., The Cloning and characterization of the glnF (ntrA) Gene of Klebsiella pneumoniae: Role of glnF (ntrA) in the Regulation of Nitrogen Fixation (nif) and other Nitrogen assimilation genes. Mol. Genet. 1983; 192:342-353.

Delaux, et al., Tracing the evolutionary path to nitrogen-fixing crops. Curr. Opin. Plant Biol. 2015; 26:95-99.

Dent, et al., Establishing symbiotic nitrogen fixation in cereals and other non-legume crops: The greener nitrogen revolution. Agric & Food Secur 2017; 6(7): 1-9.

Desnoues, N. et al., Nitrogen fixation genetics and regulation in a Pseudomonas stutzeri strain associated with rice. Microbiology, 2003; 149:2251-2262.

Dixon, R. and Kahn, D., Genetic regulation of biological nitrogen fixation. Nature Reviews 2004; 2: 621-631.

Dos; Santos., "Dos Santos, P.C. et al., Distribution of nitrogen fixation and nitrogenase-like sequences amongst microbial genomes. BMC Genomics, 2012; (13)162: 1-12".

Egener, et al., Identification of NifL-like protein in a diazotroph of the b-subgroup of the proteobacteria, *azoarcus* sp. strain BH72, Microbiology 2002; 148: 3203-3212.

Emboss. Emboss Needle: Pairwise Sequence Alignment (Nucleotide). Available at http://www.ebi.ac.uk/Tools/psa/emboss_needle/nucleotide.html. Accessed on Oct. 10, 2016.

Emboss. Emboss Water: Pairwise Sequence Alignment (Nucleotide). Available at http://www.ebi.ac.uk/Tools/psa/emboss_water/nucleotide.html. Accessed on Oct. 10, 2016.

EP16825147.8 Partial Supplementary European Search Report dated Mar. 4, 2019.

EP16825147.8 The Extended European Search Report dated Jun. 6, 2019.

Fox, et al., Major cereal crops benefit from biological nitrogen fixation when inoculated with the nitrogen-fixing bacterium Pseudomonas protegens Pf-5 X940. Environmental Microbiology 2016; 18(10):3522-3534.

Geddes, B.A., Use of plant colonizing bacteria as chassis for transfer of N2-fixation to cereals. Curr. Opin. Biotechnol. 2015; 32:216-222.

Gibson, A. H. Physical Environment and Symbiotic Nitrogen Fixation. Australian Journal of Biological Sciences. 1963; 16, 28-42.

Govantes, et al. Mechanism of coordinated synthesis of the antagonistic regulatory proteins NifL and NifA of Klebsiella pneumoniae. J Bacteriol. Dec. 1996; 178(23): 6817-6823.

Hale, et al., An efficient stress-free strategy to displace stable bacterial plasmids. BioTechniques 2010; 48:223-228.

Hidaka, et al. Promotion of the Growth of Rice by Inoculation of Nitrogen-Fixing-Activity-Enhanced Bacteria to the Rhizosphere. In Nitrogen Fixation: From Molecules to Crop Productivity (Part of the Current Plant Science and Biotechnology in Agriculture book series (PSBA, vol. 38)), pp. 445; 1999.

Hunter, P., "Genetically Modified Lite" placates public but not activists. EMBO Reports 2014; 15(2): 138-141.

Iniguez, et al., Nitrogen Fixation in Wheat Provided by Klebsiella pneumoniae 342. MPMI vol. 17, No. 10, 2004, pp. 1078-1085.

International Search report dated Dec. 2, 2016 for International Application No. PCT/US2016/042170.

Kant, et al., Understanding plant response to nitrogen limitation for the improvement of crop nitrogen use efficiency. Journal of Experimental Botany, 2011; vol. 62, No. 4, pp. 1499-1509.

Kerby, et al. Photoproduction of ammonium by immobilized mutant strains of Anabaena variabilis.Applied Microbiology and Biotechnology. Apr. 1986, vol. 24, Issue 1, pp. 42-46.

Kim, et al. Constitutive expression of nitrogenase system in Klebsiella oxytoca by gene targeting mutation to the chromosomal nifLA operon. Journal of Biotechnology. vol. 10, Issues 3-4, Jun. 1989, pp. 293-301.

Kurzweil, A. Plant Bacteria breakthrough enables crops worldwide to take nitrogen from the air. Aug. 1, 2013. http://www.kurzweilai.net/plant-bacteria-breakthrough-enables-crops-worldwide-to-take-nitrogen-from- the-air. 4 Pages.

Lauritsen, et al., A versatile one-step CRISPR-Cas9 based approach to plasmid-curing. Microb Cell Fact 2017; 16(135): 1-10.

Macneil, et al. Fine-structure mapping and complementation analysis of nif (nitrogen fixation) genes in Klebsiella pneumoniae. J Bacteriol. Oct. 1978; 136(1): 253-266.

(56) References Cited

OTHER PUBLICATIONS

Macneil, et al. Mutations in nif genes that cause Klebsiella pneumoniae to be derepressed for nitrogenase synthesis in the presence of ammonium. J Bacteriol. Nov. 1980; 144(2): 744-751.
Masepohl, et al., Organization and regulation of genes encoding the molybdenum nitrogenase and the alternative nitrogenase in Rhodobacter capsulatus. Arch. Microbiol. 1996;165:80-90.
Mengel, D., Roots, growth and nutrient uptake. Dept. of Agronomy publication #AGRY-95-08 (Rev. May 1995).
Mitra, Ranjana. Regulation of nifLA operon in Azotobacter vinelandii. Thesis submitted to the Jawaharlal Nehru University, New Delhi, for the degree of doctor of philosophy. 2000.
Mus, et al., Symbiotic nitrogen fixation and the challenges to its extension nonlegumes. Appl. Environ. Microbiol. 2016; 82(13): 3698-3710.
Nassar, et al. Promotion of plant growth by an auxin-producing isolate of the yeast *Williopsis saturnus* endophytic in maize (*Zea mays* L.) roots. Biology and Fertility of Soils; 2005; 42: 97-108.
Nelissen, et al., Translational research:from pot to plot. Plant Biotechnology Journal 2014; 12: 277-285.
Nestmann, E.R., Mutagenesis by nitrosoguanidine, ethyl methanesulfonate, and mutator gene mutH in continuous cultures of *Escherichia coli*. Science Direct. Jun. 1975; 28(3): 323-330.
Nichkawade, Anuradha. Studies on upstream regulatory sequence of the nifLA promoter of Klebsiella pnuemoniae. Thesis submitted to the Jawaharlal Nehru University, New Delhi, for the degree of doctor of philosophy. 1996.
Nielsen, K.M., Transgenic organisms—time for conceptual diversification? Nature Biotechnology 2003; 21: 227-228.
Okubo, et al. Effects of Elevated Carbon Dioxide, Elevated Temperature, and Rice Growth Stage on the Community Structure of Rice Root-Associated Bacteria. Microbes Environ. Jun. 2014; 29(2): 184-190.Published online May 31, 2014.doi: 10.1264/jsme2.ME14011.
Ortiz-Marquez, et al., Association with an Ammonium-excreting bacterium allows diazotrophic culture of oil-rich Eukaryotic microalagae. Appl. Microbiol. 2012; 78(7): 2345-2352.
PCT/US2018/013671 International Search Report and Written Opinion dated Mar. 22, 2018.
Qiu, et al. Construction of genetically engineered strains of Enterobacter cloacae (nifL~(-)A~(c)). Acta Phytophysiologica Sinica. [Jan. 1, 1999, 25(3):269-273].
Roberts, et al. Regulation and characterization of protein products coded by the nif (nitrogen fixation) genes of Klebsiella pneumoniae. J Bacteriol. Oct. 1978; 136(1): 267-279.
Rogers, et al., Synthetic biology approaches to engineering the nitrogen symbiosis in cereals. Journal of Experimental Botany, 2014; 65(8):1939-1946.
Roncato-Maccari, et al., Endophytic Herbaspirillum seropedicae expresses nif genes in gramineous plants. FEMS Microbiology Ecology. 2003; 45: 39-47.
Rosenblueth et al. Nitrogen Fixation in Cereals. Frontiers in Microbiology, vol. 9, Article 1794. (Aug. 9, 2018). 13 pages.
Saikia, et al., Biological nitrogen fixation with non-legumes: An achievable target or a dogma? Curr. Sci. 2007; 92(3): 317-322.
Santi, et al., Biological nitrogen fixation in non-legume plants. Annals of Botany 2013; 111: 743-767.
Schmitz, et al. Iron is required to relieve inhibitory effects on NifL on transcriptional activation by NifA in Klebsiella pneumoniae. J Bacteriol. Aug. 1996; 178(15): 4679-4687.
Schouten, et al. Do cisgenic plants warrant less stringent oversight? Nature Biotechnology 2006; 24: 753.
Service, R. Genetically engineered microbes make their own fertilizer, could feed the world's poorest. Science Apr. 2017: doi:I0.1126/science.aaII000.
Setten, et al., Engineering Pseudomonas protegens Pf-5 for Nitrogen Fixation and its application to improve plant growth under nitrogen-deficient conditions, PLOS One 2013; 8(5): 1-14.
Shamseldin, A. The rold of different genes involoved in symbiotic nitrogen fixation—review. Global Journal of Biotechnology & Biochemistry 8 (4): 84-94, 2013.
Sibold et al. A nif mutant of Klebsiella pneumoniae fixing nitrogen in the presence of ammonia. FEMS Microbiology Letters 10(1):37-41 (Jan. 1, 1981).
Sibold, et al. Constitutive expression of nitrogen fixation (nif) genes of Klebsiella pneumoniae due to a DNA duplication. EMBO J. 1982;1(12):1551-8.
Siddavattam, et al., Regulation of nif Gene expression in Enterobacter agglomerans: Nucleotide sequence of the nifLA operon and influence of temperature and ammonium on its transcription. Molecular and general genetics. Dec. 20, 1995; 249(6): 629-636.
Singh, et al. An L-methionine-D,L-sulfoximine-resistant mutant of the cyanobacterium Nostoc muscorum showing inhibitor-resistant γ-glutamyl-transferase, defective glutamine synthetase and producing extracellular ammonia during N2 fixation.FEBS Letters. vol. 154, Issue 1, Apr. 5, 1983, pp. 10-14.
Souza, et al., The N-Terminus of the NIFA protein of herbaspirillum seropedicae is probably involved in sensing of ammonia. In Tikhonovich et al. (Eds.) Proceedings of the 1Oth International Congress on Nitrogen Fixation, St. Petersburg, Russia, May 28-Jun. 3, 1995 (p. 260) Dordrecht: Kluwer.
Spiller, et al. Isolation and characterization of nitrogenase-derepressed mutant strains of cyanobacterium Anabaena variabilis. J Bacteriol. Feb. 1986; 165(2): 412-419.
Steenhoudt, et al., Azospirillum, a free-living nitrogen-fixing bacterium closely associated with grasses: genetic, biochemical and ecological aspects. FEMS Microbial. Rev. 2000; 24: 487-506.
Stemmer, W.P.C., DNA shuffling by random fragmentation and reassembly: In vitro recombination for molecular evolution. Oct. 1994. Proc. Natl. Acad. Sci. USA vol. 91, pp. 10747-10751.
Stemple, D.L., Tilling—a high-throughput harvest for functional genomics. Nature Reviews Genetics 5, 145-150 (Feb. 2004) | doi:10.1038/nrg1273.
Swain, et al., Nitrogen fixation and its improvement through genetic engineering. J. Global Biosciences 2013; 2(5): 98-112.
Temme, et al., Refactoring the nitrogen fixation gene cluster from Klebsiella oxytoca. PNAS, May 1, 2012; 109(18):7085-7090.
Thomas, et al. Ammonium Excretion by an I-Methionine-dl-Sulfoximine-Resistant Mutant of the Rice Field Cyanobacterium Anabaena siamensis.Appl Environ Microbiol. Nov. 1990; 56(11): 3499-3504.
Triplett, E.W. Diazotrophic endophytes: progress and prospects for nitrogen fixation in monocots. Plant and Soil 1996; 186: 29-38.
Tritt, et al., An Integrated Pipeline for de Novo Assembly of Microbial Genomes. Sep. 13, 2012. PLOS one. https://doi.org/10.1371/journal.pone.0042304.
U.S. Appl. No. 15/636,595 Notice of Allowance dated Mar. 30, 2018.
U.S. Appl. No. 15/636,595 Office Action dated Dec. 18, 2017.
U.S. Appl. No. 15/950,534 Notice of Allowance dated May 2, 2019.
U.S. Appl. No. 15/950,534 Office Action dated Aug. 10, 2018.
U.S. Appl. No. 15/954,558 Office Action dated May 2, 2019.
U.S. Appl. No. 16/159,542 Office Action dated Mar. 8, 2019.
Ueda, et al., Remarkable N2-Fixing Bacterial Diversity Detected in Rice Roots by Molecular Evolutionary Analysis of nifH Gene Sequences. Journal of Bacteriology, Mar. 1995, p. 1414-1417.
Vernon, et al., Analysis of 16S rRNA gene sequences and circulating cell-free DNA from plasma of chronic fatigue syndrome and non-fatigued subjects. BMC Microbiology 2002; 2:39.
Villa, et al., Azotobacter vinelandii siderophore can provide nitrogen to support the culture of the green algae *Neochloris oleoabundans* and *scenedesmus*. FEMS Microbial. Lett. 2014; 351(1): 70-77.
Wang, et al., A minimal nitrogen fixation gene cluster from *paenibacillus* sp. WLY78 enables expression of active nitrogenase in *Escheichia coli*. Plos Genetics. Oct. 17, 2013; 9(10): 1-11; DOI:10.1371/journal.pgen.1003865.
Wang, et al., Using Synthetic biology to distinguish and overcome regulatory and functional barriers related to nitrogen fixation. PLOS One 2013; 8(7): 1-11.
Yoshida, T. and Yoneyama, T., Atmospheric dinitrogen fixation in the flooded rice rhizosphere as determined by the N-15 isotope

(56) References Cited

OTHER PUBLICATIONS technique. Soil Science and Plant Nutrition, 26:4, 551-559, DOI: 10.1080/00380768.1980.10431242.
Young, C. and Pratt-Szeliga, A., Ceres Trust. 2012. https://cerestrust.org/wp-content/uploads/NitrogenFixingBacteriaCorn.pdf. 9 Pages.
Zehr, et al. New Nitrogen-Fixing Microorganisms Detected in Oligotrophic Oceans by Amplification of Nitrogenase (nifH) Genes. Appl Environ Microbiol. Sep. 1998; 64(9): 3444-3450.
Zhang, et al., Involvement of the ammonium transporter AmtB in nitrogenase regulation and ammonium excretion in Pseudomonas stutzeri A1501. Res. Microbial. 2012; 163: 332-339.
Aita, T., Husimi, Y. Adaptive walks by the fittest among finite random mutants on a Mt. Fugi-type fitness landscape. J. Theor. Biol. 193:383-405 (1998).
Alper et al., "Tuning genetic control through promoter engineering," Proc Natl Acad Sci U SA, 2005, 102(36):12678-12683.
Altschul et al. "Basic local alignment search tool," J Mol Biol., 1990, 215(3):403-441.
Altschul et al., "Gapped BLAST and PSI-BLAST: a new generation of protein database search programs," Nucleic Acids Res., 1977, 25:3389-3402.
Andersen et al. "Herpesvirus-mediated gene delivery into the rat brain: specificity and efficiency of the neuron-specific enolase promoter," Cell. Mol. Neurobiol., 1993, 13:503-515.
Anderson, J.C., et al. "BglBricks: A flexible standard for biological part assembly," Journal of Biological Engineering, 2010, 4:1, 12 pages.
Andrianantoandro E, et al., "Synthetic biology: new engineering rules for an emerging discipline," Mol Syst Biol 2:2006.0028 (2006).
Arbuthnot et al. "In vitro and in vivo hepatoma cell-specific expression of a gene transferred with an adenoviral vector," Hum Gene Ther., 1996, 7(13):1503-1514.
Arnold et al., (1988) Nucleotide sequence of a 24,206-base-pair DNA fragment carrying the entire nitrogen fixation gene cluster of Klebsiella pneumoniae. J Mol Biol 203(3):715-738.
Bageshwar, et al. An Environmentally Friendly Engineered Azotobacter Strain That Replaces a Substantial Amount of Urea Fertilizer while Sustaining the Same Wheat Yield. Appl Environ Microbial. Aug. 1, 2017; 83(15): e00590-17.
Batista et al. "Manipulating nitrogen regulation in diazotrophic bacteria for agronomic benefit," Biochem Soc Trans., 2019, 47(2):603-614.
Batzer et al., "Enhanced evolutionary PCR using oligonucleotides with inosine at the 3'-termins," Nucleic Acid Res. 19: 5081 (1991).
Bayer TS, et al. (2009) Synthesis of Methyl Halides from Biomass Using Engineered Microbes. J Am Chem Soc 131 (18):6508-6515.
Beynon J, Cannon M, Buchanan-Wollaston V, & Cannon F (1983) The nifpromoters of Klebsiella pneumoniae have a characteristic primary structure. Cell 34(2):665-671.
Biggins JB, Liu, X., Feng, Z., Brady, S.F. (2011) Metabolites from the induced expression of crypic single operons found in the genome of Burkolderia pseudomallei. JACS 133:1638-1641.
Bikard et al., "The synthetic integron: an in vivo genetic shuffling device," Nucleic Acids Res., 2010, 38(15):e153.
Bilitchenko et al., Eugene—a domain specific language for specifying and constraining synthetic biological parts, devices, and systems. PLoS One. Apr. 29, 2011;6(4):e18882.
Bonde et al., "MODEST: a web-based design tool for oligonucleotide-mediated genome engineering and recombineering," Nucleic Acids Res., 2014, 42(W1):W408-W415.
Boshart et al. "A very strong enhancer is located upstream of an immediate early gene of human cytomegalovirus," Cell, 1985, 41(2):521-30.
Boyle et al. "Tools for genome-wide strain design and construction," Curr Opin Biotechnol., 2012, 23(5):666-671. doi: 10.1016/j.copbio.2012.01.012.
Brandl et al., "*Salmonella* interactions with plants and their associated microhiota," Phytopathology, 2013, 103:316-325.
Buck M & Cannon W (1987) Frameshifts close to the Klebsiella pneumoniae nifH promoter prevent multicopy inhibition by hybrid nifH plasmids. Mal Gen Genet 207(2-3):492-498.
Buckley Lab NifH database, retrieved via WayBack Machine from URL <http://www.css.cornell.edu/faculty/buckley/nifh.htm>, available on or before Jan. 10, 2018, 2 pages.
Burris et al., "Nitrogenases," J Biol Chem., 266(15):9339-9342.
Cardinale, S., & Arkin, A.P. Contextualizing context for synthetic biology identifying causes of failure of synthetic biological systems. Biotechnol. J. 7:856-866 (2012).
Carr et al., "Enhanced multiplex genome engineering through co-operative oligonucleotide coselection," Nucleic Acids Res., 2012, 40(17):e132.
Chan et al., "Refactoring bacteriophage T7," Molecular Systems Biology, 2005, 1(1):E1-E10.
Chen, et al. "Expression of rat bone sialoprotein promoter in transgenic mice." J Bone Miner Res., May 1996, 11(5):654-64.
Chen, Y.J., et al. Characterization of 582 natural and synthetic terminators and quantification of their design constraints. Nat. Methods, 2013, 10:659-664.
Chin JW "Programming and engineering biological networks," Curr Opin Struct Biol 16: 551-556 (2006).
Choi, et al. A Tn7-based broad-range bacterial cloning and expression system. Nat Methods. Jun. 2005;2(6):443-8.
Choudhary, et al. Interactions of *Bacillus* spp. and Plants—With Special Reference to Induced Systemic Resistance (ISR). Microbiological Research. 2009, vol. 164, No. 5; pp. 493-513.
Cobb et al., Directed evolution: an evolving and enabling synthetic biology tool. Curr Opin Chem Biol. Aug. 2012;16(3-4):285-91.
Colebatch et al. "Symbiotic nitrogen fixation research in the postgenomics era," New Phytologist., 2002, 153(1):37-42 doi:10.1046/j.0028-646X.2001.00304.x.
Colnaghi, et al. Lethality of glnD null mutations in Azotobacter vinelandii is suppressible by prevention of glutamine synthetase adenylylation Microbiology. May 2001;147(Pt 5):1267-76.
Cornelis et al., "The type III secretion injectisome," Nature Reviews Mocrobilogy, 2006, 4(11):811-825.
Crameri, A., Dawes, G., Rodriguez Jr., E., Silver, S., & Stemmer, W.P.C. Molecular evolution of an arsenate detoxification pathway by DNA shuffling. Nat. Biotechnol. 15:436-438 (1997).
Crook, N.C., Freeman, E.S., & Alper, H.S. Re-engineering multicloning sites for function and convenience. Nucl. Acids Res. 39:e92, 2011.
Czar MJ, Anderson JC, Bader JS, & Peccoud J (2009) Gene synthesis demystified. Trends Biotechnol 27(2):63-72.
Dandekar, T., Snel, B., Huynen, M., & Bork, P. Conservation of gene order: a fingerprint of proteins that physically interact. Trends Biochem. Sci. 23:324-328 (1998).
De Raad, M., Kooijmans, S.A.A., Teunissen, E.A., & Mastrobattista, E. A solid-phase platform for combinatorial and scarless multipart gene assembly. ACS Synth. Biol. 2:316-326 (2013).
Dixon RA & Postgate JR (1972) Genetic transfer of nitrogen fixation from Klebsiella pneumoniae to *Escherichia coli*. Nature 237(5350):102-103.
Dong, et al. Kinetics and Strain Specificity of Rhizosphere and Endophytic Colonization by Enteric Bacteria on Seedlings of *Medicago sativa* and *Medicago truncatula*. Appl Environ Microbial. Mar. 2003; 69(3): 1783-1790.
Du et al., Customized optimization of metabolic pathways by combinatorial transcriptional engineering. Nucleic Acids Res. Oct. 2012;40(18):e142.
Dykxhoorn et al., (1996) A set of compatible tac promoter expression vectors. Gene 177(1-2):133-136.
Easter, et al., "Role of the parCBA Operon of the Broad-Host-Range Plasmid RK2 in Stable Plasmid Maintenance," Journal Of Bacteriology, 1998, 180(22):6023-6030.
Endy et al., "Foundations for engineering biology," Nature, 2005, 438:449-453.
Engler, et al. "A one pot, one step, precision cloning method with high throughput capability," PLoS One, 2008;3(11):e3647.
Engler, et al. "Golden gate shuffling: a one-pot DNA shuffling method based on type IIs restriction enzymes," PLoS One. 2009;4(5):e5553.

(56) References Cited

OTHER PUBLICATIONS

Enkh-Amgalan, et al., "Molecular evolution of the nif gene cluster carrying nifl1 and nifl2 genes in the Gram-positive phototrophic bacterium *Heliobacterium chlorum*," International Journal of Systematic and Evolutionary Microbiology, 2006, 56:65-74.
EP Extended European Search Report in European Appln. No. 12800054.4, dated Dec. 19, 2014, 8 pages.
EP Extended European Search Report in European Appln. No. 16854192.8, dated Feb. 20, 2019, 11 pages.
EP Extended European Search Report in European Appln. No. 19186353.9, dated Nov. 13, 2019, 9 pages.
Estrem, et al., "Identification of an UP element consensus sequence for bacterial promoters," PNAS, 95 (11): 9761-9766 (1998).
Fani et al., "Molecular evolution of nitrogen fixation: the evolutionary history of the niID, nifK, nifE, and nifN gene," J Mo/ Evol., 2000, 51 ( 1 ): 1-11.
Feher, et al. In the fast lane: large-scale bacterial genome engineering. J Biotechnol. Jul. 31, 2012;160(1-2):72-9.
Ferrieres, et al. The yjbEFGH locus in *Escherichia coli* K-12 is an operon encoding proteins involved in exopolysaccharide production. Microbiology. Apr. 2007;153(Pt 4):1070-80.
Fischbach et al., "Prokaryotic gene clusters: A rich toolbox for synthetic biology," Biotechnology Journal, 2010, 15(12): 1277-1296.
Fischbach, et al., The evolution of gene collectives: how natural selection drives chemical innovation. Proc. Natl. Acad. Sci. USA 105:4601-4608 (2008).
Fontana, et al., RNA folding and combinatory landscapes. Phys. Rev. E. 47:2083-2099 (1993).
Frasch et al., Design-based re-engineering of biosynthetic gene clusters: plug-and-play in practice. Curr Opin Biotechnol. Dec. 2013;24(6):1144-50.
Gaby and Buckley, "A comprehensive aligned nifH gene database: a multipurpose tool for studies of nitrogen-fixing bacteria." Database 2014 (2014): bau001.
Gamer, et al. A T7 RNA polymerase-dependent gene expression system for Bacillus megaterium. Appl Micro biol Biotechnol. Apr. 2009;82(6) :1195-203.
Gebeyehu, G., et al., "Novel biotinylated nucleotide-analogs for labeling and colorimetric detection of DNA," Nucl. Acids Res. 15:4513 (1987).
Georg J & Hess WR (2011) cis-antisense RNA, another level of gene regulation in bacteria. Microbiol Mol Biol Rev 75(2):286-300.
Gibson DG, et al. (2009) Enzymatic assembly of DNA molecules up to several hundred kilobases. Nat Methods 6(5):343-345.
Gibson, et al., Chemical synthesis of the mouse mitochondrial genome. Nat. Methods 7, 901-903 (2010).
Gosink, Franklin and Roberts, The product of the Klebsiella pneumoniae nifX gene is a negative regulator of the nitrogen fixation (nit) regulon, J Bacteriology, 1990, 172(3):1441-1447.
Gossen et al. Tight control of gene expression in mammalian cells by tetracycline-responsive promoters. PNAS USA89.12 (1992): 5547-5551.
Gossen et al. Transcriptional activation by tetracyclines in mammalian cells. Science 268(5218):1766-1769 (1995).
Gottelt et al., (2010) Deletion of a regulatory gene within the cpk gene cluster reveals novel antibacterial activity in Streptomyces coelicolor A3(2). Microbiology 156:2343-2353.
Guell et al., (2011) Bacterial transcriptomics: what is beyond the RNA horiz-ome? Nature reviews. Microbiology 9(9):658-669.
Guell, M., et al. Transcriptome complexity in a genome-reduced bacterium. Science 326: 1268-1271 (2009).
Guo et al., Discovery of Reactive Microbiota-Derived Metabolites that Inhibit Host Proteases. Cell. Jan. 26, 2017;168(3):517-526.e18.
Haapalainen, et al., Soluble plant cell signals induce the expression of the type Ill secretion system of Pseudomonas syringae and upregulate the production of pilus protein HrpA. Mol. Plant Microbe Interact. 22, 282-290 (2009).
Hansal, et al. Cutting Edge: Induction of antigen-specific hyporesponsiveness by transplantation of hemopoietic cells containing an MHC class I transgene regulated by a lymphocyte-specific promoter. J Immunol. Aug. 1, 1998;161(3):1063-8.
Harvey, et al. Inducible control of gene expression: prospects for gene therapy. Curr Opin Chem Biol. Aug. 1998;2(4):512-8.
Herlache, et al. Characterization of the Agrobacterium vitis pehA gene and comparison of the encoded polygalacturonase with the homologous enzymes from Erwinia carotovora and Ralstonia solanacearum. Appl Environ Microbial. Jan. 1997; 63(1): 338-346.
Hernandez, J.A., et al. "Biochemical analysis of the recombinant Fur (ferric uptake regulator) protein from Anabaena PCC 7119: factors affecting its oligomerization state," Biochem J., 2002, 366:315-322.
Holden, et al. Colonization outwith the colon: plants as an alternative environmental reservoir for human pathogenic enterobacteria. FEMS Microbiol. Rev. 33, 689-703 (2009).
Hu et al., (2008) Assembly of nitrogenase MoFe protein. Biochemistry 47(13):3973-3981.
Huynen,et al., Smoothness within ruggedness: the role of neutrality in adaptation. Proc. Natl. Acad. Sci. USA 93:397-401 (1996).
Iber, D. A quantitative study of the benefits of co-regulation using the spoIIA operon as an example. Mol. Sys. Biol. 2, 1-6 (2006).
International Preliminary Report on Patentability dated Jul. 16, 2019 in connection with Application No. PCT/US2018/013671, 6 pages.
International Preliminary Report on Patentability dated May 14, 2015 in connection with Application No. PCT/US2013/068055.
International Preliminary Report on Patentability in International Appln. No. PCT/US2018/046148, dated Feb. 11, 2020, 12 pages.
International Preliminary Report on Patentability in International Appln. No. PCT/US2018/057174, dated Apr. 28, 2020, 5 pages.
International Preliminary Report on Patentability in International Appln. No. PCT/US2018/057613, dated Apr. 28, 2020, 8 pages.
International Preliminary Report on Patentability in PCT Appln. No. PCT/US2012/042502, dated Dec. 17, 2013, 8 pages.
International Preliminary Report on Patentability dated Apr. 19, 2018 for Application No. PCT/US2016/055429.
International Search Report and Written Opinion in International Appln. No. PCT/US2012/042502, dated Jan. 31, 2013, 11 pages.
International Search Report and Written Opinion in International Appln. No. PCT/US2013/068055, dated Feb. 18, 2014, 15 pages.
International Search Report and Written Opinion in International Appln. No. PCT/US2016/055429, dated Dec. 30, 2016, 16 pages.
International Search Report and Written Opinion in International Appln. No. PCT/US2018/046148, dated Dec. 3, 2018, 6 pages.
International Search Report and Written Opinion in International Appln. No. PCT/US2018/057613, dated Mar. 5, 2019.
International Search Report and Written Opinion in International Appln. No. PCT/US2019/068152, dated Jun. 25, 2020.
Ishihama A (2010) Prokaryotic genome regulation: multifactor promoters, multitarget regulators and hierarchic networks. FEMS Microbial Rev 34(5):628-645.
Ivanova et al. "Artificial Regulation of Genes, Of the coding proteins of the nitrogenase complex Rhizobial bacteria," Natural Sciences, 2014, 13(174):36-39 (Machine Translation).
Izquierdo et al., "Distribution of Extensive nifH Gene Diversity Across Physical Soil Microenvironments," Microbial Ecology, 2006, 51(4):441-452.
Jacob et al., (1987) Solid-state NMR studies of Klebsiella pneumoniae grown under nitrogen-fixing conditions. J Biol Chem 262(1):254-259.
Jacoby et al., "The Role of Soil Microorganisms in Plant Mineral Nutrition—Current Knowledge and Future Directions," Frontiers in Plant Scients, 2017, 8(19):1-19.
Jaschke, et al. A fully decompressed synthetic bacteriophage 0X174 genome assembled and archived in yeast. Virology 434, 278-284 (2012).
Jensen, K.F. The *Escherichia coli* K-12 "wild types" W3110 and MG1655 have an rph frameshift mutation that leads to pyrimidine starvation due to low pyre expression levels. J. Bacteriol. 175:3401-3407 (1993).
Johnson ZI & Chisholm SW (2004) Properties of overlapping genes are conserved across microbial genomes. Genome Res 14(11):2268-2272.

(56) References Cited

OTHER PUBLICATIONS

Kalir S, et al. (2001) Ordering genes in a flagella pathway by analysis of expression kinetics from living bacteria. Science 292(5524):2080-2083.
Kaneko, T., et al. Complete genomic structure of the cultivated rice endophyte *Azospirillum* sp. B510. DNA Res. 17:37-50 (2010).
Karlin, et al. Applications and statistics for multiple high-scoring segments in molecular sequences. Proc Natl Acad Sci USA. Jun. 15, 1993;90(12):5873-7.
Karlin, et al. Methods for assessing the statistical significance of molecular sequence features by using general scoring schemes. Proc Natl Acad Sci USA. Mar. 1990;87(6):2264-8.
Kececiglu, J., et al. "Of mice and men: Algorithms for evolutionary distances between genomes with translocation," SODA: Proceedings of the sixth annual ACM-SIA< symposium on Discrete algorithms, 1995, 10 pages.
Kelly JR, et al. (2009) Measuring the activity of BioBrick promoters using an in vivo reference standard. J Biol Eng 3 :4.
Kent et al., "A Transposable Partitioning Locus Used To Stabilize Plasmid-Borne Hydrogen Oxidation and Trifolitoxin Production Genes in a Sinorhizobium Strain," Appl. Environ. Microbiol., 1998, 64(5):1657-1662.
Kingsford et al., " Rapid, accurate, computational discovery of Rho-independent transcription terminators illuminates their relationship to DNA uptake," Genome Bio. 2007, 8(2):R22.
Kitano H (2002) Systems biology: a brief overview. Science 295(5560): 1662-1664.
Knight, T., "Idempotent Vector Design for Standard Assembly of Biobricks," MIT Artificial Intelligence Laboratory, The TTL Data Book for Design Engineers, 2003, 11 pages.
Kovacs et al., (2009) Stochasticity in protein levels drives colinearity of gene order in metabolic operons of *Escherichia coli*. PLoS Biol 7(5):e1000115.
Kutter, et al. Colonization of barley (*Hordeum vulgare*) with *Salmonella enterica* and *Listeria* spp. FEMS Microbial. Ecol. 56, 262-271 (2006).
Leang, et al. Genome-wide analysis of the RpoN regulon in Geobacter sulfurreducens. BMC Genomics. Jul. 22, 2009;10:331.
Lee et al., "The class IId bacteriocin thuricin-17 increases plant growth," Planta, 2009, 229:747-755.
Levin-Karp, A., et al. Quantifying translational coupling in *E. coli* synthetic operons using RBS modulation and fluorescent reporters. ACS Synth. Biol. 2:327-336 (2013).
Liang et al., Minimal effect of gene clustering on expression in *Escherichia coli*. Genetics. Feb. 2013;193(2):453-65.
Lim, et al. Fundamental relationship between operon organization and gene expression. Proc Natl. Acad Sci US =A. Jun. 28, 2011;108(26):10626-31.
Liu, et al. Whole genome analysis of halotolerant and alkalotolerant plant growth-promoting *Rhizobacterium klebsiella* sp. D5A. Sci Rep. May 24, 2016; 6: 1-10.
Lombo et al., (1999) The mithramycin gene cluster of Streptomyces argillaceus contains a positive regulatory gene and two repeated DNA sequences that are located at both ends of the cluster. J. Bacterial. 181:642-647.
Lucks et al., Toward scalable parts families for predictable design of biological circuits. Curr. Opin. Microbiol. 11, 567-573 (2008).
Ma et al., "Effect of nicotine from tobacco root exudates on chemotaxis, growth, biocontrol efficiency, and colonization byPseudomonas aeruginosaNXHG29," Antonie van Leeuwenhoek, 2018, 111(7):1237-1257.
Maduro M (2011) Random DNA Generator, retrieved from URL <http://www.faculty.ucr.edu/~mmaduro/random.htm>, 1 page.
Magari, et al. Pharmacologic control of a humanized gene therapy system implanted into nude mice. J Clin Invest. Dec. 1, 1997; 100(11):2865-2872.
Mandal M & Breaker RR (2004) Gene regulation by riboswitches. Nat Rev Mol Cell Biol 5(6):451-463.

Marroqui et al. "Enhanced Symbiotic Performance by Rhizobium tropici Glycogen Synthase 17, 18 Mutants," Journal of Bacteriology, Feb. 1, 2001, vol. 183, No. 3, pp. 854-864.
Martinez-Noel et al., NifB and NifEN protein levels are regulated by ClpX2 under nitrogen fixation conditions in Azotobacter vinelandii. Mol Microbiol. Mar. 2011;79(5):1182-93.
Marx, et al. Broad-host-range ere-lox system for antibiotic marker recycling in gram-negative bacteria. Biotechniques. Nov. 2002;33(5):1062-7.
Mason CA & Hamer G (1987) Cryptic Growth in Klebsiella-Pneumoniae. Appl Microbiol Biot 25(6):577-584.
Matsubayashi, et al. Peptide hormones in plants. Annu Rev Plant Biol. 2006;57:649-74.
Medema et al., (2011) Synthetic biology in Streptomyces bacteria. Methods Enzymol 497:485-502.
Medema et al., Computational tools for the synthetic design of biochemical pathways. Nat Rev Microbiol. Jan. 23, 2012;10(3):191-202.
Medema, et al., Exploiting plug-and-play synthetic biology for drug discovery and production in microorganisms. Nat. Rev. Microbiol. 9:131-137 (2011).
Merriam-Webster "originate" accessed Jul. 7, 2020 (Year: 2020).
Mirsky, Ethan M., Refactoring the *Salmonella* Type Ill Secretion System. (Doctoral Dissertation) Apr. 12, 2012, 60 pages.
Mirzahoseini, et al., "Heterologous Proteins Production in *Escherichia coli*: An Investigation on the Effect of Codon Usage and Expression Host Optimization," Cell Journal (Yakhteh) 12(4):453 Winter 2011.
Miyazaki K (2003) Creating random mutagenesis libraries by megaprimer PCR of whole plasmid (MEGAWHOP). Methods Mol Biol 231 :23-28.
Moon et al., Genetic programs constructedfrom layered logic gates in single cells. Nature. Nov. 8, 2012;491(7423):249-53.
Mueller, et al. Closing yield gaps through nutrient and water management. Nature 490, 254-257 (2012).
Mutalik, V.K., et al. Quantitative estimation of activity and quality for collections of functional genetic elements. Nat. Methods 10:347-353 (2013).
No, et al., "Ecdysone-inducible gene expression in mammalian cells and transgenic mice" Proc. Natl. Acad. Sci. USA vol. 93, Issue 8, pp. 3346-3351, Apr. 1996.
Noskov, V.N., et al. Assembly of large, high G+C bacterial DNA fragments in yeast. ACS Synth. Biol. 1:267-273 (2012).
Oh, et al., "Organization of nif gene cluster in *Frankia* sp. EuIK1 strain, a symbiont of Elaeagnus umbellata," Arch Microbiol., 2012, 194:29-34.
Ohtsuka et al., "An alternative approach to deoxyoligonucleotides as hybridization probes by insertion of deoxyinosine at ambiguous codon positions," J. Biol. Chem. 260:2605-2608 (1985).
Orme-Johnson WH (1985) Molecular basis of biological nitrogen fixation. Annu Rev Biophys Biophys Chem 14:419-459.
Pfleger et al., "Combinatorial engineering of intergenic regions in operons tunes expression of multiple genes"; Nature Biotechnology; 24(8):1027-1031 (2006).
Philippe et al., (2004) Improvement of pCVD442, a suicide plasmid for gene allele exchange in bacteria. Plasmid 51(3):246-255.
Piccioli, et al. Neuroantibodies: ectopic expression of a recombinant anti-substance P antibody in the central nervous system of transgenic mice. Neuron. Aug. 1995;15(2):373-84.
Piccioli, et al. Neuroantibodies: molecular cloning of a monoclonal antibody against substance P for expression in the central nervous system. Proc Natl Acad Sci U SA. Jul. 1, 1991; 88(13): 5611-5615.
Pickens LB, Tang, Y., Chooi, Y-H. (2011) Metabolic engineering for the production of natural products. Annu. Rev. Chem. Biomol. Eng. 2:211-236.
Plotnikova, et a. Pathogenesis of the human opportunistic pathogen Pseudomonas aeruginosa PA14 in *Arabidopsis*. Plant Physiol. 124, 1766-1774 (2000).
Price, M.N., Arkin, A.P., & Alm, E.J. The life-cycle of operons. PLoS Genet. 2, e96. (2006).
Price, M.N., Huang, K.H., Arkin, A.P. & Alm, E.J. Operon formation is driven by coregulation and not by horizontal gene transfer. Genome Res. 15, 809-819 (2005).

(56) References Cited

OTHER PUBLICATIONS

Purnick PE & Weiss R (2009) The second wave of synthetic biology: from modules to systems. Nat Rev Mol Cell Biol 10(6):410-422.
Ramon, A., & Smith, H.O. Single-step linker-based combinatorial assembly of promoter and gene cassettes for pathway engineering. Biotechnol. Lett. 33:549-555 (2011).
Ran et al., Genome erosion in a nitrogen-fixing vertically transmitted endosymbiotic multicellular cyanobacterium. PLoS One. Jul. 8, 2010;5(7):e11486.
Resendis-Antonio, et al. Systems biology of bacterial nitrogen fixation: High-throughput technology and its integrative description with constraint-based modeling. BMC Syst Biol. 2011; 5: 120.
Riedel et al., (1983) Nitrogen fixation by Klebsiella pneumoniae is inhibited by certain multicopy hybrid nif plasmids. J Bacterial 153(1):45-56.
Rommens, et al. Intergeneric transfer and functional expression of the tomato disease resistance gene Pto. Plant Cell. Oct. 1995; 7(10): 1537-1544.
Rong et al., "Promoter specificity determinants of T7 RNA polymerase," Proc. Natl. Acad. Sci. USA, 95(2):515-519 (1998).
Rosenblueth, et al. Bacterial endophytes and their interactions with hosts. Mol Plant Microbe Interact. Aug. 2006 ;19(8):827-37.
Rossolini et al., "Use of Deoxyinosine-Containing Primers vs Degenerate Primers for Polymerase Chain Reaction Based on Ambiguous Sequence Information" Mol. Cell. Probes 8:91-98 (1994).
Rubio and Ludden, Maturation of Nitrogenase: a Biochemical Puzzle, J. Bacteriology, 2005, 187(2):405-414.
Salis et al., (2009) Automated design of synthetic ribosome binding sites to control protein expression. Nat Biotechnol 27(10):946-950.
Sandoval, et al. Strategy for directing combinatorial genome engineering in *Escherichia coli*. Proc Natl Acad Sci USA. Jun. 26, 2012;109(26):10540-5.
Schmidt-Dannert, et al., Molecular breeding of carotenoid biosynthetic pathways. Nat. Biotechnol. 18:750-753 (2000).
Shetty et al., (2008) Engineering BioBrick vectors from BioBrick parts. J Biol Eng 2:5.
Simon et al., (1996) Perturbation of niff expression in Klebsiella pneumoniae has limited effect on nitrogen fixation. J Bacteriol 178(10):2975-2977.
Sivaraman et al., "Codon choice in genes depends on flanking sequence information—implications for theoretical reverse translation," Nucleic Acids Res. 36:e16 (2008).
Sleight et al., Designing and engineering evolutionary robust genetic circuits. J Biol Engin. 2010;4(12):1-20.
Sleight, S.C., & Sauro, H.M. Randomized BioBrick assembly: a novel DNA assembly method for randomizing and optimizing genetic circuits and metabolic pathways. ACS Synth. Biol., 2013, 2(9):506-518.
Smanski et al., "Engineered Streptomyces platensis strains that overproduce antibiotics platensimycin and platencin," Antimicrob. Agents Chemother., 2009, 53:1299-12304.
Smanski et al., Synthetic biology to access and expand nature's chemical diversity. Nat Rev Microbial. Mar. 2016;14(3):135-49.
Smanski, et al. "Functional optimization of gene clusters by combinatorial design and assembly," Nat Biotechnol., 2014, 32(12):1241-1249.
Sorek and Cossart, Prokaryotic transcriptomics: a new view on regulation, physiology, and pathogenicity. Nat. Rev. Genet. 11:9-16 (2010).
Staron et al., "The Third Pillar of Bacterial Signal Transduction: Classification of the Extracytoplasmic Function (ECF) Sigma Factor Protein Family," Mol Microbiol 14(3): 557-81 (2009).
Stein, et al. The osteocalcin gene: a model for multiple parameters of skeletal-specific transcriptional control. Mol Biol Rep. Aug. 1997;24(3):185-96.
Stephanopoulos. Challenges in engineering microbes for biofuels production. Science. Feb. 9, 2007;315(5813):801-4.
Stewart et al., (1967) In situ studies on nitrogen fixation with the acetylene reduction technique. Science 158(3800):536.
Stucken, K., et al. The smallest known genomes of multicellular and toxic cyanobacteria: comparison, minimal gene sets for linked traits and the evolutionary implications. PLoS ONE 5:e9235 (2010).
Subtil, et al. Secretion of Predicted Inc Proteins of Chlamydia pneumoniae by a Heterologous Type III Machinery. Molecular Microbiology. Feb. 2001, vol. 39, No. 3; pp. 792-800.
Suh,et al., Functional expression of the FeMo-cofactor-specific biosynthetic genes nifEN as a NifE-N fusion protein synthesizing unit in Azotobacter vinelandii. Biochem. Biophys. Res. Comm. 299:233-240 (2002).
"T7 RNA Polymerase Expression System for Bacillus megaterium"; T7 RNAP Expression System Handbook, Jan. 2010, © MoBiTec GmbH, 18 pages.
Tamsir et al., (2011) Robust multicellular computing using genetically encoded NOR gates and chemical 'wires'. Nature 469(7329):212-215.
Tan C, "A synthetic biology challenge: making cells compute," Mol Biosyst 3: 343-353 (2007).
Temme et al., "Designing and Engineering Complex Behavior in Living Machines." (Doctoral Dissertation) Oct. 1, 2011. Retrieved from URL <escholarship.org/uc/item/lr41x99s>, 75 pages.
Temme et al., Modular control of multiple pathways using engineered orthogonal T7 polymerases. Nucleic Acids Res. Sep. 1, 2012;40(17):8773-81.
Temme K, et al. (2008) Induction and relaxation dynamics of the regulatory network controlling the type III secretion system encoded within *Salmonella* pathogenicity island 1. J Mol Biol 377(1):47-61.
Thiel, T., Lyons, E.M. & Erker, J.C., Characterization of genes for a second Modependent nitrogenase in the cyanobacterium Anabaena variabilis. J. Bact. 179:5222-5225 (1997).
Tilman et al. "Global food demand and the sustainable intensification of agriculture." PNAS 108:20260-20264 (2011).
Van Dongen, S.A., "Performance criteria for graph clustering and Markov cluster experiments," CWI, 2000, 36 pages.
Villalobos et al., (2006) Gene Designer: a synthetic biology tool for constructing artificial ONA segments. BMC Bioinformatics 7:285.
Voigt, "Genetic parts to program bacteria, "Current Opinion in Biotechnology, 2006, 17(5):548-557.
Voigt, C., "Gaining Access: Rebuilding Genetics from the Ground Up". Institute of Medicine Board on Global Health Forum on Microbial Threats. Mar. 14, 2011. Retrieved from the web at iom.edu/-/media/Files/ActivityFiles/PublicHealth/MicrobialThreats/2011-MAR- 14Noigt.pdf.
Wang et al., Positive and negative regulation of gene expression in eukaryotic cells with an inducible transcriptional regulator. Gene Ther., 4.5 (May 1997): 432-441.
Wang, et al. Ligand-inducible and liver-specific target gene expression in transgenic mice. Nat Biotechnol. Mar. 1997;15(3):239-43.
Wang, et al. Programming cells by multiplex genome engineering and accelerated evolution. Nature. Aug. 13, 2009;460(7257):894-8.
Watanabe et al., (2006) Total biosynthesis of antitumor nonribosomal peptides in *Escherichia coli*. Nature Chemical Biology, 2:423-428.
Watanabe et al., Chapter 15. Plasmid-borne gene cluster assemblage and heterologous biosynthesis of nonribosomal peptides in *Escherichia coli*. Methods Enzymol. 2009; 458:379-99.
Weber, et al. A modular cloning system for standardized assembly of multigene constructs. PLoS One. Feb. 18, 2011;6(2):e16765.
Wei et al. (Biology and fertility of soils 50.4 (2014): 657-666). (Year: 2014).
Welch et al. (2009) "Design Parameters to Control Synthetic Gene Expression in *Escherichia coli*" PLoS One 4(9):e7002.
Wells, J.A. Additivity of mutational effects in proteins. Biochemistry 29:8509-8517 (1990).
Wenzel SC & Muller R (2005) Recent developments towards the heterologous expression of complex bacterial natural product biosynthetic pathways. Curr Opin Biotechnol 16(6):594-606.
Werner et al., Fast track assembly of multigene constructs using Golden Gate cloning and the MoClo system. Bioeng Bugs. Jan. 1, 2012 ;3(1):38-43.
Widmaier, et al. Engineering the *Salmonella* type III secretion system to export spider silk monomers. Mol. Syst. Biol. 5, 309 (2009).

(56) References Cited

OTHER PUBLICATIONS

Wootton, et al. Statistics of local complexity in amino acid sequences and sequence databases. Computers & Chemistry. vol. 17, Issue 2, Jun. 1993, pp. 149-163.

Wu et al., "Root exudates from two tobacco cultivars affect colonization of Ralstonia solanacearum and the disease index," European Journal of Plant Pathology, 2014, 141(4):667-677.

Wu, J., et al. Multivariate modular metabolic engineering of *Escherichia coli* to produce resveratrol from L-tyrosine. J. Biotechnol. (2013), 167:404-411.

Xu, et al., ePathBrick: a synthetic biology platform for engineering metabolic pathways in *E. coli*. ACS Synth. Biol., 1:256-266 (2012).

Yarza, et al., "Uniting the classification of cultured and uncultured bacteria and archaea using 16S rRNA gene sequences," Nature Rev. Micro., 2014 12:635-345.

Ye et al., "Primer-BLAST: a tool to design target-specific primers for polymerase chain reaction," BMC Bioinformatics., Jun. 2012, 13(134), 1-11.

Yokobayashi et al, (2002) Directed evolution of a genetic circuit. Proc Natl Acad Sci USA 99(26):16587-16591.

Zaslaver et al., (2006) Optimal gene partition into operons correlates with gene functional order. Phys Biol 3(3): 183-189.

Zazopoulos E, et al. (2003) A genomics-guided approach for discovering and expressing cryptic metabolic pathways. Nat Biotechnol 21 (2): 187-190.

Zehr lab NifH database, retrieved from URL <https://wwwzehr.pmc.ucsc.edu/nifH_Database_Public/>, Apr. 4, 2014, 1 page.

Zhang et al., "Influence of different factors on the nitrogenase activity of the engineered *Escherichia coli* 78-7," World J Microbiol Biotechnol. Jun. 2015, 31(6):921-7.

Zhang, et al. "GlnD Is Essential for NifA Activation, NtrB/NtrC-Regulated Gene Expression, and Posttranslational Regulation of Nitrogenase Activity in the Photosynthetic, Nitrogen-Fixing Bacterium *Rhodospirillum rubrum*," J. Bacteriol., Feb. 2005, 187(4): 1254-1265.

Zhao et al., "Evidence for nifU and nifS participation in the biosynthesis of the iron-molybdenum cofactor of nitrogenase," J. Biol. Chem., 2007, 282(51):37016-37025.

Zomer AL (2011) PPP: Perform Promoter Prediction, retireved from URL <http://bioinformatics.biol.rug.nl/websoftware/ppp/ppp_start.php>, 2 pages.

Magasanik "Genetic Control of Nitrogen Assimilation In Bacteria" Ann. Rev. Genet 1982. 16:135-68 (Year: 1982).

Davin-Regli et al. "Enterobacter aerogenes and Enterobacter cloacae; versatile bacterial 1-3, 7, 12, 17-24, 26-32, pathogens confronting antibiotic treatment," Front Microbiol, 2015, 6, 35, 41-45, 49, 54, 56-66, 392:1-10.

De Freitas J R Ed—Eisenhalter Nico et al: "Yield and N assimilation of winter wheat (Triticum aestivum L., var. Norstar) inoculated with rhizobacteria"Pedobiologia, Elsevier, Amsterdam. NL, vol. 44, No. 2, Jan. 1, 2000 (Jan. 1, 2000), pp. 97-104.

"Levican et al, "Comparative genomic analysis of carbon and nitrogen assimilation mechanisms in three indigenous bioleaching bacteria: predictions and validations" BMC Genomics 2008, 9:581, 19 pages (Year: 2008)".

Ohta et al., "Associative N2-fixation of Rice with Soil and Microorganisms", 1985, 27:17-27.

Takeshi Uozumi et al: "Cloning and Expression of the nit A Gene of Klebsiella oxytoca in K. pneumoniae and Azospirillum lipoferum", Agricultural and Biological Chemistry 1986, 50(6):1539-1544.

van Heeswijk et al. "Nitrogen Assimilation in *Escherichia coli*: Putting Molecular Data into a Systems Perspective" Microbiology and Molecular Biology Reviews p. 628-695 Dec. 2013 vol. 77 No. 4 (Year: 2013).

Pellicle of enriched nitrogen fixing bacteria

|  | no glutamine | 1 mM glutamine | 10 mM glutamine | |
|---|---|---|---|---|
| amtB | 716462 | 175150 | 1045 | |
| galK | 15 | 405 | 814 | |
| glnB | 8025 | 10275 | 7493 | |
| glnK | 752360 | 183994 | 320 | |
| nifA | 306663 | 92963 | 194 | 0% air |
| nifH | 12387186 | 3599183 | 161 | |
| nifL | 226368 | 42825 | 123 | |
| ntrB | 50439 | 25236 | 1081 | |
| ntrC | 78056 | 35760 | 1216 | |
| amtB | 241247 | 139599 | 1207 | |
| galK | 404 | 770 | 1012 | |
| glnB | 8296 | 6899 | 9376 | |
| glnK | 241645 | 158973 | 288 | |
| nifA | 237483 | 115545 | 197 | 10% air |
| nifH | 4702957 | 2448758 | 108 | |
| nifL | 173765 | 66818 | 75 | |
| ntrB | 25676 | 19630 | 1118 | |
| ntrC | 40312 | 30703 | 1295 | |
| amtB | 160293 | 167736 | 1353 | |
| galK | 1311 | 976 | 1200 | |
| glnB | 8522 | 8185 | 9445 | |
| glnK | 166653 | 191992 | 366 | |
| nifA | 200774 | 164973 | 198 | 20% air |
| nifH | 862984 | 2337297 | 80 | |
| nifL | 129054 | 99096 | 80 | |
| ntrB | 17326 | 21370 | 1146 | |
| ntrC | 24115 | 31446 | 1370 | |

FIG. 5

METHODS AND COMPOSITIONS FOR IMPROVING PLANT TRAITS

CROSS-REFERENCE

This application is a divisional application of U.S. patent application Ser. No. 15/954,557, filed on Apr. 16, 2018, which application is a continuation application of U.S. patent application Ser. No. 15/636,595, filed on Jun. 28, 2017, which application is a continuation of International Patent Application No. PCT/US2016/042170, filed Jul. 13, 2016, which application claims priority to U.S. Provisional Patent Application No. 62/192,009, filed Jul. 13, 2015, and U.S. Provisional Patent Application No. 62/213,567, filed Sep. 2, 2015, each of which is entirely incorporated herein by reference.

STATEMENT AS TO FEDERALLY SPONSORED RESEARCH

This invention was made with the support of the United States government under SBIR grant 1520545 awarded by the National Science Foundation. The government has certain rights in the disclosed subject matter.

SEQUENCE LISTING

The instant application contains a Sequence Listing which has been submitted electronically in ASCII format and is hereby incorporated by reference in its entirety. Said ASCII copy, created on Aug. 11, 2017, is named 47736-701_301_SL.txt and is 66,798 bytes in size.

BACKGROUND OF THE INVENTION

Plants are linked to the microbiome via a shared metabolome. A multidimensional relationship between a particular crop trait and the underlying metabolome is characterized by a landscape with numerous local maxima. Optimizing from an inferior local maximum to another representing a better trait by altering the influence of the microbiome on the metabolome may be desirable for a variety of reasons, such as for crop optimization. Economically-, environmentally-, and socially-sustainable approaches to agriculture and food production are required to meet the needs of a growing global population. By 2050 the United Nations' Food and Agriculture Organization projects that total food production must increase by 70% to meet the needs of the growing population, a challenge that is exacerbated by numerous factors, including diminishing freshwater resources, increasing competition for arable land, rising energy prices, increasing input costs, and the likely need for crops to adapt to the pressures of a drier, hotter, and more extreme global climate.

One area of interest is in the improvement of nitrogen fixation. Nitrogen gas ($N_2$) is a major component of the atmosphere of Earth. In addition, elemental nitrogen (N) is an important component of many chemical compounds which make up living organisms. However, many organisms cannot use $N_2$ directly to synthesize the chemicals used in physiological processes, such as growth and reproduction. In order to utilize the $N_2$, the $N_2$ must be combined with hydrogen. The combining of hydrogen with $N_2$ is referred to as nitrogen fixation. Nitrogen fixation, whether accomplished chemically or biologically, requires an investment of large amounts of energy. In biological systems, an enzyme known as nitrogenase catalyzes the reaction which results in nitrogen fixation. An important goal of nitrogen fixation research is the extension of this phenotype to non-leguminous plants, particularly to important agronomic grasses such as wheat, rice, and maize. Despite enormous progress in understanding the development of the nitrogen-fixing symbiosis between rhizobia and legumes, the path to use that knowledge to induce nitrogen-fixing nodules on non-leguminous crops is still not clear. Meanwhile, the challenge of providing sufficient supplemental sources of nitrogen, such as in fertilizer, will continue to increase with the growing need for increased food production.

SUMMARY OF THE INVENTION

In view of the foregoing, there is a need to improve the traits of plants imparted by an associated microbiome. The present disclosure addresses this need, and provides additional advantages as well. In some cases, both the species composing the microbiome and their underlying genetics are targets for modulating microbial influence on the metabolome.

In one aspect, the present disclosure provides a method of increasing nitrogen fixation in a non-leguminous plant, the method comprising exposing the plant to a plurality of bacteria, each member of the plurality comprising one or more genetic variations introduced into one or more genes or non-coding polynucleotides of the bacteria's nitrogen fixation or assimilation genetic regulatory network, such that the bacteria are capable of fixing atmospheric nitrogen in the presence of exogenous nitrogen; wherein the bacteria are not intergeneric microorganisms; and wherein the bacteria, in planta, produce 1% or more of the fixed nitrogen in the plant.

In some embodiments, the bacteria, in planta, produce 5% or more of the fixed nitrogen in the plant. In some embodiments, the bacteria, in planta, produce 10% or more of the fixed nitrogen in the plant.

In some embodiments, the one or more genetic variations comprise an introduced control sequence operably linked to said one or more genes of the nitrogen fixation or assimilation genetic regulatory network. In further embodiments, the control sequence is a promoter. In further embodiments, the promoter is an inducible promoter. In some embodiments, the bacteria do not comprise a constitutive promoter operably linked to a gene of the nitrogen fixation or assimilation genetic regulatory network. In some embodiments, the bacteria do not comprise a constitutive promoter operably linked to a gene in the nif gene cluster.

In some embodiments, the bacteria, in planta, excrete the nitrogen-containing products of nitrogen fixation. In some embodiments, the plurality of bacteria exposed to the plant do not stimulate an increase in the uptake of exogenous non-atmospheric nitrogen.

In some embodiments, the plant is grown in soil from a field which has been administered about 50 lbs of nitrogen-containing fertilizer per acre, and wherein the nitrogen-containing fertilizer comprises at least 5% nitrogen by weight. In further embodiments, the nitrogen-containing fertilizer comprises ammonium or an ammonium containing molecule. In some embodiments, the exogenous nitrogen is selected from fertilizer comprising one or more of glutamine, ammonia, ammonium, urea, nitrate, nitrite, ammonium-containing molecules, nitrate-containing molecules, and nitrite-containing molecules.

In some embodiments, the plurality of bacteria comprise at least two different species of bacteria. In some embodiments, the plurality of bacteria comprise at least two different strains of the same species of bacteria. In some embodiments, the plurality of bacteria are of the genus *Enterobacter*. In some embodiments, the plurality of bacteria are endophytic, epiphytic, or rhizospheric. In some embodiments, the plurality of bacteria colonize the plant such that the bacteria are present in the plant at least $10^5$ cfu per gram of fresh weight of the plant.

In some embodiments, the one or more genes or non-coding polynucleotides of the bacteria's nitrogen fixation or assimilation genetic regulatory network are selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifK, nifY, nifE, nifN, nifU, nifS, nifV, nifW, nifZ, nifM, nifF, nifB, and nifQ. In some embodiments, the one or more genetic variations is a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD. In some embodiments, the one or more genetic variations is (A) a knock-out mutation; (B) alters or abolishes a regulatory sequence of a target gene; or (C) comprises the insertion of a heterologous regulatory sequence.

In some embodiments, the plant is an agricultural crop plant. In further embodiments, the agricultural crop plant is selected from sorghum, canola, tomato, strawberry, barley, rice, maize, and wheat. In further embodiments, the plant is a genetically modified organism. In further embodiments, the plant is not a genetically modified organism. In some embodiments, the plant has been genetically engineered or bred for efficient nitrogen use.

In one aspect, the present disclosure provides a bacterial population comprising bacteria comprising one or more genetic variations introduced into one or more genes or non-coding polynucleotides of the bacteria's nitrogen fixation or assimilation genetic regulatory network, such that the bacteria are capable of fixing atmospheric nitrogen in the presence of exogenous nitrogen; wherein the bacteria are not intergeneric microorganisms; and wherein the bacteria, in planta, produce 1% or more of the fixed nitrogen in a plant grown in the presence of the population of bacteria.

In some embodiments, the bacteria, in planta, produce 5% or more of the fixed nitrogen in the plant. In some embodiments, the bacteria, in planta, produce 10% or more of the fixed nitrogen in the plant.

In some embodiments, the one or more genetic variations comprise an introduced control sequence operably linked to said one or more genes of the nitrogen fixation or assimilation genetic regulatory network. In further embodiments, the control sequence is a promoter. In further embodiments, the promoter is an inducible promoter. In some embodiments, the bacteria do not comprise a constitutive promoter operably linked to a gene of the nitrogen fixation or assimilation genetic regulatory network. In some embodiments, the bacteria do not comprise a constitutive promoter operably linked to a gene in the nif gene cluster.

In some embodiments, the bacteria, in planta, excrete the nitrogen-containing products of nitrogen fixation. In some embodiments, the plurality of bacteria exposed to the plant do not stimulate an increase in the uptake of exogenous non-atmospheric nitrogen. In some embodiments, the exogenous nitrogen is selected from fertilizer comprising one or more of glutamine, ammonia, ammonium, urea, nitrate, nitrite, ammonium-containing molecules, nitrate-containing molecules, and nitrite-containing molecules.

In some embodiments, the bacterial population comprises at least two different species of bacteria. In some embodiments, the bacterial population comprises at least two different strains of the same species of bacteria. In some embodiments, the plurality of bacteria are of the genus *Enterobacter*. In some embodiments, the plurality of bacteria are endophytic, epiphytic, or rhizospheric. In some embodiments, the plurality of bacteria colonize the plant such that the bacteria are present in the plant at least $10^5$ cfu per gram of fresh weight of the plant.

In some embodiments, the one or more genes or non-coding polynucleotides of the bacteria's nitrogen fixation or assimilation genetic regulatory network are selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, and nifQ. In some embodiments, the one or more genetic variations is a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD. In some embodiments, the one or more genetic variations is (A) a knock-out mutation; (B) alters or abolishes a regulatory sequence of a target gene; or (C) comprises the insertion of a heterologous regulatory sequence.

In some embodiments, the plant is an agricultural crop plant. In further embodiments, the agricultural crop plant is selected from sorghum, canola, tomato, strawberry, barley, rice, maize, and wheat. In further embodiments, the plant is a genetically modified organism. In further embodiments, the plant is not a genetically modified organism. In some embodiments, the plant has been genetically engineered or bred for efficient nitrogen use.

In one aspect, the present disclosure provides a composition comprising a bacterial population of the present disclosure. In some embodiments, the composition comprises the bacterial population coated on a surface of a seed. In some embodiments, the composition is formulated as a liquid or powder.

In one aspect, the present disclosure provides an isolated bacterium deposited as ATCC Accession Deposit No. PTA-122293 or PTA-122294.

In one aspect, the present disclosure provides a non-intergenic bacterium comprising one or more genetic variations introduced into one or more genes or non-coding polynucleotides of the bacteria's nitrogen fixation or assimilation genetic regulatory network, such that the bacterium is capable of fixing atmospheric nitrogen in the presence of exogenous nitrogen.

In some embodiments, the one or more genetic variations comprise an introduced control sequence operably linked to said one or more genes of the nitrogen fixation or assimilation genetic regulatory network. In further embodiments, the control sequence is a promoter. In further embodiments, the promoter is an inducible promoter. In some embodiments, the bacteria do not comprise a constitutive promoter operably linked to a gene of the nitrogen fixation or assimilation genetic regulatory network. In some embodiments, the bacteria do not comprise a constitutive promoter operably linked to a gene in the nif gene cluster.

In some embodiments, the one or more genes or non-coding polynucleotides of the bacteria's nitrogen fixation or assimilation genetic regulatory network are selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, and nifQ. In some embodiments, the one or more genetic variations is a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD. In some embodiments, the one or more genetic variations is (A) a knock-out mutation; (B) alters or abolishes a regulatory sequence of a target gene; or (C) comprises the insertion of a heterologous regulatory sequence.

In some embodiments, the bacterium is from the genus *Enterobacter*. In some embodiments, the bacterium is endophytic, epiphytic, or rhizospheric.

In one aspect, the present disclosure provides a method of producing one or more bacteria. In one embodiment, the method comprises (a) isolating bacteria from tissue or soil of a first plant; (b) introducing a genetic variation (e.g. one or more genetic variations) into one or more of the bacteria to produce one or more variant bacteria; (c) exposing a plurality of plants to the variant bacteria; (d) isolating bacteria from tissue or soil of one of the plurality of plants, wherein the plant from which the bacteria is isolated has an improved trait relative to other plants in the plurality of plants; and (e) repeating steps (b) to (d) with bacteria isolated in step (d). The improved trait may be enhanced nitrogen fixation in the plant from which bacteria are isolated, and/or in plants exposed to the bacteria. The genetic variation can be variation in a gene selected from the group consisting of: nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ. The genetic variation can be a variation in a gene encoding a protein with functionality selected from the group consisting of: glutamine synthetase, glutaminase, glutamine synthetase adenylyltransferase, transcriptional activator, anti-transcriptional activator, pyruvate flavodoxin oxidoreductase, flavodoxin, or NAD+-dinitrogen-reductase ADP-D-ribosyltransferase. In some embodiments, the genetic variation is a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD. The genetic variation can be a knock-out mutation, result in elimination or abolishment of activity of a protein domain, alter or abolish a regulatory sequence of a target gene, and/or comprise insertion of a heterologous regulatory sequence. In some embodiments, the genetic variation comprises insertion of a regulatory sequence found within a genome of a bacterial species or genus corresponding to the bacteria into which the genetic variation is introduced. The regulatory sequence may optionally be selected based on expression level of a gene in a bacterial culture or within plant tissue. Genetic variation can be a random mutation at a random location, a random mutation at a target site, or a predetermined genetic variation specifically introduced to a target site. The genetic variation can comprise insertion, deletion, or replacement of one or more nucleotides, or any combination of these. The genetic variation can be produced by chemical mutagenesis. In some embodiments, the method further comprises exposing the plants to biotic or abiotic stressors. In some embodiments, bacteria isolated after repeating steps (b) to (d) one or more times produce 1% or more (e.g. at least 2%, 5%) 10%, or more) of nitrogen in a second plant of the same type as the first plant, or in a plant exposed to the bacteria. Such production may still be achieved when the second plant is grown in the presence of fertilizer supplemented with glutamine, ammonia, or other chemical source of nitrogen. In some embodiments, bacteria isolated after repeating steps (b) to (d) one or more times exhibit at least a 2-fold increase (e.g. at least 5-fold increase) in nitrogen fixation as compared to bacteria isolated form the first plant. The first plant, or plants in the plurality of plants, can be an agricultural crop plant, such as a plant selected from barley, rice, maize, wheat, sorghum, sweet corn, sugar cane, onions, tomatoes, strawberries, or asparagus. The first plant, or plants in the plurality of plants, can be a model plant, such as a plant selected from *Setaria, Brachypodium*, or *Arabidopsis*. In some embodiments, step (a) further comprises performing genetic analysis of isolated bacteria. In some embodiments, step (b) further comprises applying a selection pressure to enrich for bacteria comprising the genetic variation, and optionally isolating bacteria that survive the selection pressure. The selection pressure can comprise cleaving genomes lacking the genetic variation introduced to a target site, wherein cleavage occurs within 100 nucleotides of the target site. The cleavage can be directed by a site-specific nuclease, such as a nuclease selected from the group consisting of a Zinc Finger nuclease, a CRISPR nuclease, a TALE nuclease, or a meganuclease. In some cases, a CRISPR nuclease may be preferred. Bacteria isolated after repeating steps (b) to (d) one or more times are endophytic, epiphytic, or rhizospheric. The bacteria may be isolated from plant tissue (e.g. seeds). The bacteria may comprise a plurality of different bacterial taxa. In some embodiments, isolating bacteria in step (a) comprises isolating bacteria from a seed of the first plant.

In one aspect, the present disclosure provides a method of increasing nitrogen fixation in a plant. In one embodiment, the method comprises exposing the plant to bacteria comprising one or more genetic variations introduced into one or more genes regulating nitrogen fixation, wherein the bacteria produce 1% or more (e.g. at least 2%, 5%, 10%, or more) of nitrogen in the plant. The bacteria may produce the nitrogen in the presence of fertilizer supplemented with glutamine, ammonia, or other chemical source of supplemental nitrogen. In some embodiments, genetic variation is a variation in a gene selected from the group consisting of: nifA, nifL, ntrB, ntrC, glutamine synthetase, glnA, glnB, glnK, draT, amtB, glutaminase, glnD, glnE, nifJ, nifH, nifD, nifK, nifY, nifE, nifN, nifU, nifS, nifV, nifW, nifZ, nifM, nifF, nifB, and nifQ. The genetic variation can be a mutation that results in one or more of: increased expression or activity of nifA or glutaminase; decreased expression or activity of nifL, ntrB, glutamine synthetase, glnB, glnK, draT, amtB; decreased adenylyl-removing activity of GlnE; or decreased uridylyl-removing activity of GlnD. In some embodiments, the genetic variation (a) is a knock-out mutation; (b) alters or abolishes a regulatory sequence of a target gene; or (c) comprises insertion of a heterologous regulatory sequence. The bacteria can be endophytic, epiphytic, or rhizospheric. In some cases, the bacteria are of the genus *Enterobacter* or *Rahnella*. The bacteria can comprise a plurality of different bacterial taxa. In some embodiments, the plant is an agricultural crop plant, such as a plant selected from sorghum, canola, tomato, strawberry, barley, rice, maize, and wheat. The plant can be a non-leguminous plant. The plant can be a genetically modified organism (a GMO; e.g. a plant having a genome altered to carry a heterologous gene), a non-genetically modified organism (non-GMO), or have been genetically engineered or bred for efficient nitrogen use.

In one aspect, the present disclosure provides a bacterial population. In one embodiment, the bacterial population comprises bacteria comprising one or more genetic variations introduced into one or more genes regulating nitrogen fixation, wherein the bacteria produce 1% or more (e.g. at least 2%, 5%, 10%, or more) of nitrogen in a plant grown in the presence of the population of bacteria. The bacteria may produce the nitrogen in the presence of fertilizer supplemented with glutamine, ammonia, or other chemical source of supplemental nitrogen. In some embodiments, the genetic variation is a variation in a gene selected from the group consisting of: nifA, nifL, ntrB, ntrC, glutamine synthetase, glnA, glnB, glnK, draT, amtB, glutaminase, glnD, glnE, nifJ, nifH, nifD, nifK, nifY, nifE, nifN, nifU, nifS, nifV, nifW, nifZ, nifM, nifF, nifB, and nifQ. The genetic variation can be a mutation that results in one or more of: increased expression of nifA or glutaminase; decreased expression of nifL, ntrB, glutamine synthetase, glnB, glnK, draT, amtB; decreased adenylyl-removing activity of GlnE; or decreased uridylyl-removing activity of GlnD. In some embodiments, the genetic variation (a) is a knock-out mutation; (b) alters or abolishes a regulatory sequence of a target gene; or (c) comprises insertion of a heterologous regulatory sequence. The bacteria can be endophytic, epiphytic, or rhizospheric. In some cases, the bacteria are of the genus *Enterobacter* or *Rahnella*. The bacteria can comprise a plurality of different bacterial taxa.

In one aspect, the present disclosure provides a composition comprising a bacterial population, such as a bacterial population as described herein. The composition can comprise the bacterial population coated on a surface of a seed. In some embodiments, the composition is formulated as a liquid or a powder.

In one aspect, the present disclosure provides a bacterium having ATCC deposit number PTA-122293. In one aspect, the present disclosure provides a bacterium having ATCC deposit number PTA-122294.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

(FIG. 1A) Nfb agar plate was used to isolate single colonies of nitrogen fixing bacteria. (FIG. 1B) Semi-solid Nfb agar casted in Balch tube. The arrow points to pellicle of enriched nitrogen fixing bacteria.

FIG. 5 depicts in culture expression profile of 9 different genes in strains CI006 involved in diazaotrophic nitrogen fixation. Numbers represent counts of each transcript. Various conditions (0, 1, 10 mM Glutamine and 0%, 10%, 20% atmospheric air in N2) are indicated.

DETAILED DESCRIPTION OF THE INVENTION

Figure 1A:
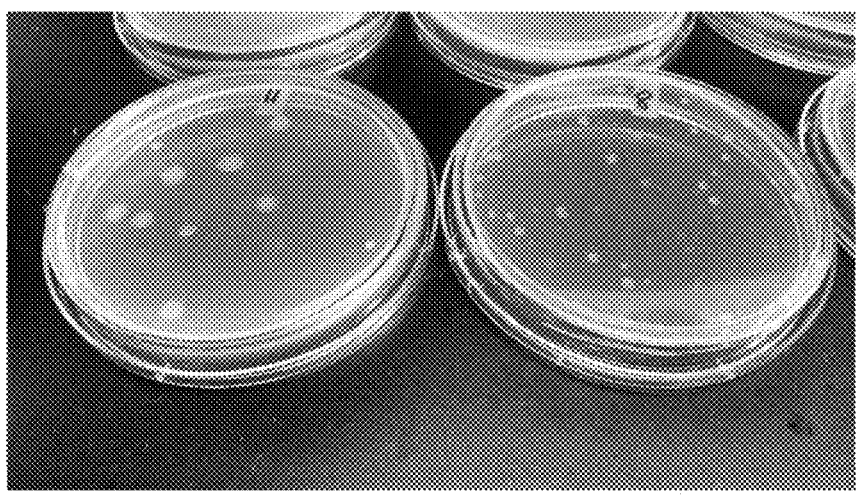
FIG. 1A-B depicts enrichment and isolation of nitrogen fixing bacteria.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner according to base complementarity. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the enzymatic cleavage of a polynucleotide by an endonuclease. A second sequence that is complementary to a first sequence is referred to as the "complement" of the first sequence. The term "hybridizable" as applied to a polynucleotide refers to the ability of the polynucleotide to form a complex that is stabilized via hydrogen bonding between the bases of the nucleotide residues in a hybridization reaction.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

In general, "stringent conditions" for hybridization refer to conditions under which a nucleic acid having complementarity to a target sequence predominantly hybridizes with a target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Technniques In Biochemistry And Molecular Biology-Hybridization With Nucleic Acid Probes Part I, Second Chapter "Overview of principles of hybridization and the strategy of nucleic acid probe assay", Elsevier, N.Y.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "about" is used synonymously with the term "approximately." Illustratively, the use of the term "about" with regard to an amount indicates that values slightly outside the cited values, e.g., plus or minus 0.1% to 10%.

The term "biologically pure culture" or "substantially pure culture" refers to a culture of a bacterial species described herein containing no other bacterial species in quantities sufficient to interfere with the replication of the culture or be detected by normal bacteriological techniques.

"Plant productivity" refers generally to any aspect of growth or development of a plant that is a reason for which the plant is grown. For food crops, such as grains or vegetables, "plant productivity" can refer to the yield of grain or fruit harvested from a particular crop. As used herein, improved plant productivity refers broadly to improvements in yield of grain, fruit, flowers, or other plant parts harvested for various purposes, improvements in growth of plant parts, including stems, leaves and roots, promotion of plant growth, maintenance of high chlorophyll content in leaves, increasing fruit or seed numbers, increasing fruit or seed unit weight, reducing $NO_2$ emission due to reduced nitrogen fertilizer usage and similar improvements of the growth and development of plants.

Microbes in and around food crops can influence the traits of those crops. Plant traits that may be influenced by microbes include: yield (e.g., grain production, biomass generation, fruit development, flower set); nutrition (e.g., nitrogen, phosphorus, potassium, iron, micronutrient acquisition); abiotic stress management (e.g., drought tolerance, salt tolerance, heat tolerance); and biotic stress management (e.g., pest, weeds, insects, fungi, and bacteria). Strategies for altering crop traits include: increasing key metabolite concentrations; changing temporal dynamics of microbe influence on key metabolites; linking microbial metabolite production/degradation to new environmental cues; reducing negative metabolites; and improving the balance of metabolites or underlying proteins.

As used herein, a "control sequence" refers to an operator, promoter, silencer, or terminator.

As used herein, "in planta" refers to in the plant, and wherein the plant further comprises leaves, roots, stems, seed, ovules, pollen, flowers, fruit, etc.

In some embodiments, native or endogenous control sequences of genes of the present disclosure are replaced with one or more intrageneric control sequences.

As used herein, "introduced" refers to the introduction by means of modern biotechnology, and not a naturally occurring introduction.

In some embodiments, the bacteria of the present disclosure have been modified such that they are not naturally occurring bacteria.

In some embodiments, the bacteria of the present disclosure are present in the plant in an amount of at least $10^3$ cfu, $10^4$ cfu, $10^5$ cfu, $10^6$ cfu, $10^7$ cfu, $10^8$ cfu, $10^9$ cfu, $10^{10}$ cfu, $10^{11}$ cfu, or $10^{12}$ cfu per gram of fresh or dry weight of the plant. In some embodiments, the bacteria of the present disclosure are present in the plant in an amount of at least about $10^3$ cfu, about $10^4$ cfu, about $10^5$ cfu, about $10^6$ cfu, about $10^7$ cfu, about $10^8$ cfu, about $10^9$ cfu, about $10^{10}$ cfu, about $10^{11}$ cfu, or about $10^{12}$ cfu per gram of fresh or dry weight of the plant. In some embodiments, the bacteria of the present disclosure are present in the plant in an amount of at least $10^3$ to $10^9$, $10^3$ to $10^7$, $10^3$ to $10^5$, $10^5$ to $10^9$, $10^5$ to $10^7$, $10^6$ to $10^{10}$, $10^6$ to $10^7$ cfu per gram of fresh or dry weight of the plant.

Fertilizers and exogenous nitrogen of the present disclosure may comprise the following nitrogen-containing molecules: ammonium, nitrate, nitrite, ammonia, glutamine, etc. Nitrogen sources of the present disclosure may include anhydrous ammonia, ammonia sulfate, urea, diammonium phosphate, urea-form, monoammonium phosphate, ammonium nitrate, nitrogen solutions, calcium nitrate, potassium nitrate, sodium nitrate, etc.

As used herein, "exogenous nitrogen" refers to non-atmospheric nitrogen readily available in the soil, field, or growth medium that is present under non-nitrogen limiting conditions, including ammonia, ammonium, nitrate, nitrite, urea, uric acid, ammonium acids, etc.

As used herein, "non-nitrogen limiting conditions" refers to non-atmospheric nitrogen available in the soil, field, media at concentrations greater than about 4 mM nitrogen, as disclosed by Kant et al. (2010. J. Exp. Biol. 62(4):1499-1509), which is incorporated herein by reference.

As used herein, an "intergeneric microorganism" is a microorganism that is formed by the deliberate combination of genetic material originally isolated from organisms of different taxonomic genera. An "intergeneric mutant" can be used interchangeably with "intergeneric microorganism". An exemplary "intergeneric microorganism" includes a microorganism containing a mobile genetic element which was first identified in a microorganism in a genus different from the recipient microorganism. Further explanation can be found, inter alia, in 40 C.F.R. § 725.3.

As used herein, an "intrageneric microorganism" is a microorganism that is formed by the deliberate combination of genetic material originally isolated from organisms of the same taxonomic genera. An "intrageneric mutant" can be used interchangeably with "intrageneric microorganism".

As used herein, "introduced genetic material" means genetic material that is added to, and remains as a component of, the genome of the recipient.

In some embodiments, the nitrogen fixation and assimilation genetic regulatory network comprises polynucleotides encoding genes and non-coding sequences that direct, modulate, and/or regulate microbial nitrogen fixation and/or assimilation and can comprise polynucleotide sequences of the nif cluster (e.g., nifA, nifB, nifC, . . . nifZ), polynucleotides encoding nitrogen regulatory protein C, polynucleotides encoding nitrogen regulatory protein B, polynucleotide sequences of the gln cluster (e.g. glnA and glnD), draT, and ammonia transporters/permeases.

In some embodiments, fertilizer of the present disclosure comprises at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% nitrogen by weight.

In some embodiments, fertilizer of the present disclosure comprises at least about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% nitrogen by weight.

In some embodiments, fertilizer of the present disclosure comprises about 5% to 50%, about 5% to 75%, about 10% to 50%, about 10% to 75%, about 15% to 50%, about 15% to 75%, about 20% to 50%, about 20% to 75%, about 25% to 50%, about 25% to 75%, about 30% to 50%, about 30% to 75%, about 35% to 50%, about 35% to 75%, about 40% to 50%, about 40% to 75%, about 45% to 50%, about 45% to 75%, or about 50% to 75% nitrogen by weight.

In some embodiments, the increase of nitrogen fixation and/or the production of 1% or more of the nitrogen in the plant are measured relative to control plants which have not been exposed to the bacteria of the present disclosure. All increases or decreases in bacteria are measured relative to control bacteria. All increases or decreases in plants are measured relative to control plants.

As used herein, a "constitutive promoter" is a promoter which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development. Non-limiting exemplary constitutive promoters include, CaMV 35S promoter, opine promoters, ubiquitin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, a "tissue specific" promoter is a promoter that initiates transcription only in certain tissues. Unlike constitutive expression of genes, tissue-specific expression is the result of several interacting levels of gene regulation. As such, in the art sometimes it is preferable to use promoters from homologous or closely related species to achieve efficient and reliable expression of transgenes in particular tissues. This is one of the main reasons for the large amount of tissue-specific promoters isolated from particular tissues found in both scientific and patent literature.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA One trait that may be targeted for regulation by the methods described herein is nitrogen fixation. Nitrogen fertilizer is the largest operational expense on a farm and the biggest driver of higher yields in row crops like corn and wheat. Described herein are microbial products that can deliver renewable forms of nitrogen in non-leguminous crops. While some endophytes have the genetics necessary for fixing nitrogen in pure culture, the fundamental technical challenge is that wild-type endophytes of cereals and grasses stop fixing nitrogen in fertilized fields. The application of chemical fertilizers and residual nitrogen levels in field soils signal the microbe to shut down the biochemical pathway for nitrogen fixation.

Changes to the transcriptional and post-translational levels of nitrogen fixation regulatory network are required to develop a microbe capable of fixing and transferring nitrogen to corn in the presence of fertilizer. To that end, described herein is Host-Microbe Evolution (HoME) technology to precisely evolve regulatory networks and elicit novel phenotypes. Also described herein are unique, proprietary libraries of nitrogen-fixing endophytes isolated from corn, paired with extensive omics data surrounding the interaction of microbes and host plant under different environmental conditions like nitrogen stress and excess. This enables precision evolution of the genetic regulatory network of endophytes to produce microbes that actively fix nitrogen even in the presence of fertilizer in the field. Also described herein are evaluations of the technical potential of evolving microbes that colonize corn root tissues and produce nitrogen for fertilized plants and evaluations of the compatibility of endophytes with standard formulation practices and diverse soils to determine feasibility of integrating the microbes into modern nitrogen management strategies.

In order to utilize elemental nitrogen (N) for chemical synthesis, life forms combine nitrogen gas ($N_2$) available in the atmosphere with hydrogen in a process known as nitrogen fixation. Because of the energy-intensive nature of biological nitrogen fixation, diazotrophs (bacteria and archaea that fix atmospheric nitrogen gas) have evolved sophisticated and tight regulation of the nif gene cluster in response to environmental oxygen and available nitrogen. Nif genes encode enzymes involved in nitrogen fixation (such as the nitrogenase complex) and proteins that regulate nitrogen fixation. Shamseldin (2013. Global J. Biotechnol. Biochem. 8(4):84-94) discloses detailed descriptions of nif genes and their products, and is incorporated herein by reference. Described herein are methods of producing a plant with an improved trait comprising isolating bacteria from a first plant, introducing a genetic variation into a nif gene of the isolated bacteria, exposing a second plant to the variant bacteria, isolating bacteria from the second plant having an improved trait relative to the first plant, and repeating the steps with bacteria isolated from the second plant.

In Proteobacteria, regulation of nitrogen fixation centers around the σm-dependent enhancer-binding protein NifA, the positive transcriptional regulator of the nif cluster. Intracellular levels of active NifA are controlled by two key factors: transcription of the nifLA operon, and inhibition of NifA activity by protein-protein interaction with NifL. Both of these processes are responsive to intraceullar glutamine levels via the PII protein signaling cascade. This cascade is mediated by GlnD, which directly senses glutamine and catalyzes the uridylylation or deuridylylation of two PII regulatory proteins—GlnB and GlnK—in response the absence or presence, respectively, of bound glutamine. Under conditions of nitrogen excess, unmodified GlnB signals the deactivation of the nifLA promoter. However, under conditions of nitrogen limitation, GlnB is post-translationally modified, which inhibits its activity and leads to transcription of the nifLA operon. In this way, nifLA transcription is tightly controlled in response to environmental nitrogen via the PII protein signaling cascade. On the post-translational level of NifA regulation, GlnK inhibits the NifL/NifA interaction in a matter dependent on the overall level of free GlnK within the cell.

NifA is transcribed from the nifLA operon, whose promoter is activated by phosphorylated NtrC, another $\sigma_{54}$-dependent regulator. The phosphorylation state of NtrC is mediated by the histidine kinase NtrB, which interacts with deuridylylated GlnB, but not uridylylated GlnB. Under conditions of nitrogen excess, a high intraceullular level of glutamine leads to deuridylylation of GlnB, which then interacts with NtrB to deactivate its phosphorylation activity and activate its phosphatase activity, resulting in dephosphorylation of NtrC and the deactivation of the nifLA promoter. However, under conditions of nitrogen limitation, a low level of intracellular glutamine results in uridylylation of GlnB, which inhibits its interaction with NtrB and allows the phosphorylation of NtrC and transcription of the nifLA operon. In this way, nifLA expression is tightly controlled in response to environmental nitrogen via the PII protein signaling cascade. nifA, ntrB, ntrC, and glnB, are all genes that can be mutated in the methods described herein.

The activity of NifA is also regulated post-translationally in response to environmental nitrogen, most typically through NifL-mediated inhibition of NifA activity. In general, the interaction of NifL and NifA is influenced by the PII protein signaling cascade via GlnK, although the nature of the interactions between GlnK and NifL/NifA varies significantly between diazotrophs. In *Klebsiella pneumoniae*, both forms of GlnK inhibit the NifL/NifA interaction, and the interaction between GlnK and NifL/NifA is determined by the overall level of free GlnK within the cell. Under nitrogen-excess conditions, deuridylylated GlnK interacts with the ammonium transporter AmtB, which serves to both block ammonium uptake by AmtB and sequester GlnK to the membrane, allowing inhibition of NifA by NifL. On the other hand, in *Azotobacter vinelandii*, interaction with deuridylylated GlnK is required for the NifL/NifA interaction and NifA inhibition, while uridylylation of GlnK inhibits its interaction with NifL. In diazotrophs lacking the nifL gene, there is evidence that NifA activity is inhibited directly by interaction with the deuridylylated forms of both GlnK and GlnB under nitrogen-excess conditions. Regardless of the mechanism, post-translational inhibition of NifA is an important regulator of the nif cluster in most known diazotrophs. Additionally, nifL, amtB, and glnK, are genes that can be mutated in the methods described herein.

In addition to regulating the transcription of the nif gene cluster, many diazotrophs have evolved a mechanism for the direct post-translational modification and inhibition of the nitrogenase enzyme itself, known as nitrogenase shutoff. This is mediated by ADP-ribosylation of the Fe protein (NifH) under nitrogen-excess conditions, which disrupts its interaction with the MoFe protein complex (NifDK) and abolishes nitrogenase activity. DraT catalyzes the ADP-ribosylation of the Fe protein and shutoff of nitrogenase, while DraG catalyzes the removal of ADP-ribose and reactivation of nitrogenase. As with nifLA transcription and NifA inhibition, nitrogenase shutoff is also regulated via the PII protein signaling cascade. Under nitrogen-excess conditions, deuridylylated GlnB interacts with and activates DraT, while deuridylylated GlnK interacts with both DraG and AmtB to form a complex, sequestering DraG to the membrane. Under nitrogen-limiting conditions, the uridylylated forms of GlnB and GlnK do not interact with DraT and DraG, respectively, leading to the inactivation of DraT and the diffusion of DraG to the Fe protein, where it removes the ADP-ribose and activates nitrogenase. The methods described herein also contemplate introducing genetic variation into the nifH, nifD, nifK, and draT genes.

Although some endophytes have the ability to fix nitrogen in vitro, often the genetics are silenced in the field by high levels of exogenous chemical fertilizers. One can decouple the sensing of exogenous nitrogen from expression of the nitrogenase enzyme to facilitate field-based nitrogen fixation. Improving the integral of nitrogenase activity across time further serves to augment the production of nitrogen for utilization by the crop. Specific targets for genetic variation to facilitate field-based nitrogen fixation using the methods described herein include one or more genes selected from the group consisting of nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ.

An additional target for genetic variation to facilitate field-based nitrogen fixation using the methods described herein is the NifA protein. The NifA protein is typically the activator for expression of nitrogen fixation genes. Increasing the production of NifA (either constitutively or during high ammonia condition) circumvents the native ammonia-sensing pathway. In addition, reducing the production of NifL proteins, a known inhibitor of NifA, also leads to an increased level of freely active NifA. In addition, increasing the transcription level of the nifAL operon (either constitutively or during high ammonia condition) also leads to an overall higher level of NifA proteins. Elevated level of nifAL expression is achieved by altering the promoter itself or by reducing the expression of NtrB (part of ntrB and ntrC signaling cascade that originally would result in the shutoff of nifAL operon during high nitrogen condition). High level of NifA achieved by these or any other methods described herein increases the nitrogen fixation activity of the endophytes.

Another target for genetic variation to facilitate field-based nitrogen fixation using the methods described herein is the GlnD/GlnB/GlnK PII signaling cascade. The intracellular glutamine level is sensed through the GlnD/GlnB/GlnK PII signaling cascade. Active site mutations in GlnD that abolish the uridylyl-removing activity of GlnD disrupt the nitrogen-sensing cascade. In addition, reduction of the GlnB concentration short circuits the glutamine-sensing cascade. These mutations "trick" the cells into perceiving a nitrogen-limited state, thereby increasing the nitrogen fixation level activity.

The amtB protein is also a target for genetic variation to facilitate field-based nitrogen fixation using the methods described herein. Ammonia uptake from the environment can be reduced by decreasing the expression level of amtB protein. Without intracellular ammonia, the endophyte is not able to sense the high level of ammonia, preventing the down-regulation of nitrogen fixation genes. Any ammonia that manages to get into the intracellular compartment is converted into glutamine. Intracellular glutamine level is the major currency of nitrogen sensing. Decreasing the intracellular glutamine level prevents the cells from sensing high ammonium levels in the environment. This can be done by increasing the expression level of glutaminase, an enzyme that converts glutamine into glutamate. In addition, intracellular glutamine can also be reduced by decreasing glutamine synthase (an enzyme that converts ammonia into glutamine). In diazotrophs, fixed ammonia is quickly assimilated into glutamine and glutamate to be used for cellular processes. Disruptions to ammonia assimilation may enable diversion of fixed nitrogen to be exported from the cell as ammonia. The fixed ammonia is predominantly assimilated into glutamine by glutamine synthetase (GS), encoded by glnA, and subsequently into glutamine by glutamine oxoglutarate aminotransferase (GOGAT). In some examples, glnS encodes a glutamine synthetase. GS is regulated post-translationally by GS adenylyl transferase (GlnE), a bi-functional enzyme encoded by glnE that catalyzes both the adenylylation and de-adenylylation of GS through activity of its adenylyl-transferase (AT) and adenylyl-removing (AR) domains, respectively. Under nitrogen limiting conditions, glnA is expressed, and GlnE's AR domain de-adynylylates GS, allowing it to be active. Under conditions of nitrogen excess, glnA expression is turned off, and GlnE's AT domain is activated allosterically by glutamine, causing the adenylylation and deactivation of GS.

Furthermore, the draT gene may also be a target for genetic variation to facilitate field-based nitrogen fixation using the methods described herein. Once nitrogen fixing enzymes are produced by the cell, nitrogenase shut-off represents another level in which cell downregulates fixation activity in high nitrogen condition. This shut-off could be removed by decreasing the expression level of DraT.

Methods for imparting new microbial phenotypes can be performed at the transcriptional, translational, and post-translational levels. The transcriptional level includes changes at the promoter (such as changing sigma factor affinity or binding sites for transcription factors, including deletion of all or a portion of the promoter) or changing transcription terminators and attenuators. The translational level includes changes at the ribosome binding sites and changing mRNA degradation signals. The post-translational level includes mutating an enzyme's active site and changing protein-protein interactions. These changes can be achieved in a multitude of ways. Reduction of expression level (or complete abolishment) can be achieved by swapping the native ribosome binding site (RBS) or promoter with another with lower strength/efficiency. ATG start sites can be swapped to a GTG, TTG, or CTG start codon, which results in reduction in translational activity of the coding region. Complete abolishment of expression can be done by knocking out (deleting) the coding region of a gene. Frameshifting the open reading frame (ORF) likely will result in a premature stop codon along the ORF, thereby creating a non-functional truncated product. Insertion of in-frame stop codons will also similarly create a non-functional truncated product. Addition of a degradation tag at the N or C terminal can also be done to reduce the effective concentration of a particular gene.

Conversely, expression level of the genes described herein can be achieved by using a stronger promoter. To ensure high promoter activity during high nitrogen level condition (or any other condition), a transcription profile of the whole genome in a high nitrogen level condition could be obtained, and active promoters with a desired transcription level can be chosen from that dataset to replace the weak promoter. Weak start codons can be swapped out with an ATG start codon for better translation initiation efficiency. Weak ribosomal binding sites (RBS) can also be swapped out with a different RBS with higher translation initiation efficiency. In addition, site specific mutagenesis can also be performed to alter the activity of an enzyme.

Increasing the level of nitrogen fixation that occurs in a plant can lead to a reduction in the amount of chemical fertilizer needed for crop production and reduce greenhouse gas emissions (e.g., nitrous oxide).

Serial Passage

Production of bacteria to improve plant traits (e.g., nitrogen fixation) can be achieved through serial passage. This can be done by selecting plants which have a particular improved trait which is influenced by the microbial flora, in addition to identifying bacteria and/or compositions that are capable of imparting one or more improved traits to one or more plants. One method of producing a bacteria to improve a plant trait includes the steps of: (a) isolating bacteria from tissue or soil of a first plant; (b) introducing a genetic variation into one or more of the bacteria to produce one or more variant bacteria; (c) exposing a plurality of plants to the variant bacteria; (d) isolating bacteria from tissue or soil of one of the plurality of plants, wherein the plant from which the bacteria is isolated has an improved trait relative to other plants in the plurality of plants; and (e) repeating steps (b) to (d) with bacteria isolated from the plant with an improved trait (step (d)). Steps (b) to (d) can be repeated any number of times (e.g., once, twice, three times, four times, five times, ten times, or more) until the improved trait in a plant reaches a desired level. Further, the plurality of plants can be more than two plants, such as 10 to 20 plants, or 20 or more, 50 or more, 100 or more, 300 or more, 500 or more, or 1000 or more plants.

In addition to obtaining a plant with an improved trait, a bacterial population comprising bacteria comprising one or more genetic variations introduced into one or more genes (e.g., genes regulating nitrogen fixation) is obtained. By repeating the steps described above, a population of bacteria can be obtained that include the most appropriate members of the population that correlate with a plant trait of interest. The bacteria in this population can be identified and their beneficial properties determined, such as by genetic and/or phenotypic analysis. Genetic analysis may occur of isolated bacteria in step (a). Phenotypic and/or genotypic information may be obtained using techniques including: high through-put screening of chemical components of plant origin, sequencing techniques including high throughput sequencing of genetic material, differential display techniques (including DDRT-PCR, and DD-PCR), nucleic acid microarray techniques, RNA-seq (Whole Transcriptome Shotgun Sequencing), and qRT-PCR (quantitative real time PCR). Information gained can be used to obtain community profiling information on the identity and activity of bacteria present, such as phylogenetic analysis or microarray-based screening of nucleic acids coding for components of rRNA operons or other taxonomically informative loci. Examples of taxonomically informative loci include 16S rRNA gene, 23S rRNA gene, 5S rRNA gene, 5.8S rRNA gene, 12S rRNA gene, 18S rRNA gene, 28S rRNA gene, gyrB gene, rpoB gene, fusA gene, recA gene, coxl gene, nifD gene. Example processes of taxonomic profiling to determine taxa present in a population are described in US20140155283. Bacterial identification may comprise characterizing activity of one or more genes or one or more signaling pathways, such as genes associated with the nitrogen fixation pathway. Synergistic interactions (where two components, by virtue of their combination, increase a desired effect by more than an additive amount) between different bacterial species may also be present in the bacterial populations.

The genetic variation may be a gene selected from the group consisting of: nifA, nifL, ntrB, ntrC, glnA, glnB, glnK, draT, amtB, glnD, glnE, nifJ, nifH, nifD, nifK, nifY, nifE, nifty, nifU, nifS, nifV, nifW, nifZ, nifM, nifF, nifB, and nifQ. The genetic variation may be a variation in a gene encoding a protein with functionality selected from the group consisting of: glutamine synthetase, glutaminase, glutamine synthetase adenylyltransferase, transcriptional activator, anti-transcriptional activator, pyruvate flavodoxin oxidoreductase, flavodoxin, or NAD+-dinitrogen-reductase aDP-D-ribosyltransferase. The genetic variation may be a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD. Introducing a genetic variation may comprise insertion and/or deletion of one or more nucleotides at a target site, such as 1, 2, 3, 4, 5, 10, 25, 50, 100, 250, 500, or more nucleotides. The genetic variation introduced into one or more bacteria of the methods disclosed herein may be a knock-out mutation (e.g. deletion of a promoter, insertion or deletion to produce a premature stop codon, deletion of an entire gene), or it may be elimination or abolishment of activity of a protein domain (e.g. point mutation affecting an active site, or deletion of a portion of a gene encoding the relevant portion of the protein product), or it may alter or abolish a regulatory sequence of a target gene. One or more regulatory sequences may also be inserted, including heterologous regulatory sequences and regulatory sequences found within a genome of a bacterial species or genus corresponding to the bacteria into which the genetic variation is introduced. Moreover, regulatory sequences may be selected based on the expression level of a gene in a bacterial culture or within a plant tissue. The genetic variation may be a pre-determined genetic variation that is specifically introduced to a target site. The genetic variation may be a random mutation within the target site. The genetic variation may be an insertion or deletion of one or more nucleotides. In some cases, a plurality of different genetic variations (e.g. 2, 3, 4, 5, 10, or more) are introduced into one or more of the isolated bacteria before exposing the bacteria to plants for assessing trait improvement. The plurality of genetic variations can be any of the above types, the same or different types, and in any combination. In some cases, a plurality of different genetic variations are introduced serially, introducing a first genetic variation after a first isolation step, a second genetic variation after a second isolation step, and so forth so as to accumulate a plurality of genetic variations in bacteria imparting progressively improved traits on the associated plants.

In general, the term "genetic variation" refers to any change introduced into a polynucleotide sequence relative to a reference polynucleotide, such as a reference genome or portion thereof, or reference gene or portion thereof. A genetic variation may be referred to as a "mutation," and a sequence or organism comprising a genetic variation may be referred to as a "genetic variant" or "mutant". Genetic variations can have any number of effects, such as the increase or decrease of some biological activity, including gene expression, metabolism, and cell signaling. Genetic variations can be specifically introduced to a target site, or introduced randomly. A variety of molecular tools and methods are available for introducing genetic variation. For example, genetic variation can be introduced via polymerase chain reaction mutagenesis, oligonucleotide-directed mutagenesis, saturation mutagenesis, fragment shuffling mutagenesis, homologous recombination, CRISPR/Cas9 systems, chemical mutagenesis, and combinations thereof. Chemical methods of introducing genetic variation include exposure of DNA to a chemical mutagen, e.g., ethyl methanesulfonate (EMS), methyl methanesulfonate (MMS), N-nitrosourea (EN U), N-methyl-N-nitro-N'-nitrosoguanidine, 4-nitroquinoline N-oxide, diethyl sulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Genetic variation can also be introduced into a nucleic acid using, e.g., trimethylpsoralen with ultraviolet light. Random or targeted insertion of a mobile DNA element, e.g., a transposable element, is another suitable method for generating genetic variation. Genetic variations can be introduced into a nucleic acid during amplification in a cell-free in vitro system, e.g., using a polymerase chain reaction (PCR) technique such as error-prone PCR. Genetic variations can be introduced into a nucleic acid in vitro using DNA shuffling techniques (e.g., exon shuffling, domain swapping, and the like). Genetic variations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Example descriptions of various methods for introducing genetic variations are provided in e.g., Stemple (2004) Nature 5:1-7; Chiang et al. (1993) PCR Methods Appl 2(3): 210-217; Stemmer (1994) Proc. Natl. Acad. Sci. USA 91:10747-10751; and U.S. Pat. Nos. 6,033,861, and 6,773,900.

As a cyclic amplification technique, polymerase chain reaction (PCR) mutagenesis uses mutagenic primers to introduce desired mutations. PCR is performed by cycles of denaturation, annealing, and extension. After amplification by PCR, selection of mutated DNA and removal of parental plasmid DNA can be accomplished by: 1) replacement of dCTP by hydroxymethylated-dCTP during PCR, followed by digestion with restriction enzymes to remove non-hydroxymethylated parent DNA only; 2) simultaneous mutagenesis of both an antibiotic resistance gene and the studied gene changing the plasmid to a different antibiotic resistance, the new antibiotic resistance facilitating the selection of the desired mutation thereafter; 3) after introducing a desired mutation, digestion of the parent methylated template DNA by restriction enzyme Dpn1 which cleaves only methylated DNA, by which the mutagenized unmethylated chains are recovered; or 4) circularization of the mutated PCR products in an additional ligation reaction to increase the transformation efficiency of mutated DNA. Further description of exemplary methods can be found in e.g. U.S. Pat. Nos. 7,132,265, 6,713,285, 6,673,610, 6,391,548, 5,789,166, 5,780,270, 5,354,670, 5,071,743, and US20100267147.

Oligonucleotide-directed mutagenesis, also called site-directed mutagenesis, typically utilizes a synthetic DNA primer. This synthetic primer contains the desired mutation and is complementary to the template DNA around the mutation site so that it can hybridize with the DNA in the gene of interest. The mutation may be a single base change (a point mutation), multiple base changes, deletion, or insertion, or a combination of these. The single-strand primer is then extended using a DNA polymerase, which copies the rest of the gene. The gene thus copied contains the mutated site, and may then be introduced into a host cell as a vector and cloned. Finally, mutants can be selected by DNA sequencing to check that they contain the desired mutation.

Genetic variations can be introduced using error-prone PCR. In this technique the gene of interest is amplified using a DNA polymerase under conditions that are deficient in the fidelity of replication of sequence. The result is that the amplification products contain at least one error in the sequence. When a gene is amplified and the resulting product(s) of the reaction contain one or more alterations in sequence when compared to the template molecule, the resulting products are mutagenized as compared to the template. Another means of introducing random mutations is exposing cells to a chemical mutagen, such as nitrosoguanidine or ethyl methanesulfonate (Nestmann, Mutat Res 1975 June; 28(3):323-30), and the vector containing the gene is then isolated from the host.

Saturation mutagenesis is another form of random mutagenesis, in which one tries to generate all or nearly all possible mutations at a specific site, or narrow region of a gene. In a general sense, saturation mutagenesis is comprised of mutagenizing a complete set of mutagenic cassettes (wherein each cassette is, for example, 1-500 bases in length) in defined polynucleotide sequence to be mutagenized (wherein the sequence to be mutagenized is, for example, from 15 to 100,000 bases in length). Thusly, a group of mutations (e.g. ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Fragment shuffling mutagenesis, also called DNA shuffling, is a way to rapidly propagate beneficial mutations. In an example of a shuffling process, DNAse is used to fragment a set of parent genes into pieces of e.g. about 50-100 bp in length. This is then followed by a polymerase chain reaction (PCR) without primers—DNA fragments with sufficient overlapping homologous sequence will anneal to each other and are then be extended by DNA polymerase. Several rounds of this PCR extension are allowed to occur, after some of the DNA molecules reach the size of the parental genes. These genes can then be amplified with another PCR, this time with the addition of primers that are designed to complement the ends of the strands. The primers may have additional sequences added to their 5' ends, such as sequences for restriction enzyme recognition sites needed for ligation into a cloning vector. Further examples of shuffling techniques are provided in US20050266541.

Homologous recombination mutagenesis involves recombination between an exogenous DNA fragment and the targeted polynucleotide sequence. After a double-strand break occurs, sections of DNA around the 5' ends of the break are cut away in a process called resection. In the strand invasion step that follows, an overhanging 3' end of the broken DNA molecule then "invades" a similar or identical DNA molecule that is not broken. The method can be used to delete a gene, remove exons, add a gene, and introduce point mutations. Homologous recombination mutagenesis can be permanent or conditional. Typically, a recombination template is also provided. A recombination template may be a component of another vector, contained in a separate vector, or provided as a separate polynucleotide. In some embodiments, a recombination template is designed to serve as a template in homologous recombination, such as within or near a target sequence nicked or cleaved by a site-specific nuclease. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. Non-limiting examples of site-directed nucleases useful in methods of homologous recombination include zinc finger nucleases, CRISPR nucleases, TALE nucleases, and meganuclease. For a further description of the use of such nucleases, see e.g. U.S. Pat. No. 8,795,965 and US20140301990.

CRISPR/Cas9 (Clustered regularly interspaced short palindromic repeats)/CRISPR-associated (Cas) systems provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on association of the protein with two naturally occurring or synthetic RNA molecules called crRNA and tracrRNA (also called guide RNAs). In some cases, the two molecules are covalently linked to form a single molecule (also called a single guide RNA ("sgRNA"). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-strand break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Further exemplary descriptions of CRISPR systems for introducing genetic variation can be found in, e.g. U.S. Pat. No. 8,795, 965.

Mutagens that create primarily point mutations and short deletions, insertions, transversions, and/or transitions, including chemical mutagens or radiation, may be used to create genetic variations. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)amino-propylamino]acridine dihydrochloride and formaldehyde.

Introducing genetic variation may be an incomplete process, such that some bacteria in a treated population of bacteria carry a desired mutation while others do not. In some cases, it is desirable to apply a selection pressure so as to enrich for bacteria carrying a desired genetic variation. Traditionally, selection for successful genetic variants involved selection for or against some functionality imparted or abolished by the genetic variation, such as in the case of inserting antibiotic resistance gene or abolishing a metabolic activity capable of converting a non-lethal compound into a lethal metabolite. It is also possible to apply a selection pressure based on a polynucleotide sequence itself, such that only a desired genetic variation need be introduced (e.g. without also requiring a selectable marker). In this case, the selection pressure can comprise cleaving genomes lacking the genetic variation introduced to a target site, such that selection is effectively directed against the reference sequence into which the genetic variation is sought to be introduced. Typically, cleavage occurs within 100 nucleotides of the target site (e.g. within 75, 50, 25, 10, or fewer nucleotides from the target site, including cleavage at or within the target site). Cleaving may be directed by a site-specific nuclease selected from the group consisting of a Zinc Finger nuclease, a CRISPR nuclease, a TALE nuclease (TALEN), or a meganuclease. Such a process is similar to processes for enhancing homologous recombination at a target site, except that no template for homologous recombination is provided. As a result, bacteria lacking the desired genetic variation are more likely to undergo cleavage that, left unrepaired, results in cell death. Bacteria surviving selection may then be isolated for use in exposing to plants for assessing conferral of an improved trait.

A CRISPR nuclease may be used as the site-specific nuclease to direct cleavage to a target site. An improved selection of mutated microbes can be obtained by using Cas9 to kill non-mutated cells. Plants are then inoculated with the mutated microbes to re-confirm symbiosis and create evolutionary pressure to select for efficient symbionts. Microbes can then be re-isolated from plant tissues. CRISPR nuclease systems employed for selection against non-variants can employ similar elements to those described above with respect to introducing genetic variation, except that no template for homologous recombination is provided. Cleavage directed to the target site thus enhances death of affected cells.

Other options for specifically inducing cleavage at a target site are available, such as zinc finger nucleases, TALE nuclease (TALEN) systems, and meganuclease. Zinc-finger nucleases (ZFNs) are artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double strand breaks. Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. Meganucleases (homing endonuclease) are endodeoxyribonucleases characterized by a large recognition site (double-stranded DNA sequences of 12 to 40 base pairs. Meganucleases can be used to replace, eliminate or modify sequences in a highly targeted way. By modifying their recognition sequence through protein engineering, the targeted sequence can be changed. Meganucleases can be used to modify all genome types, whether bacterial, plant or animal and are commonly grouped into four families: the LAGLIDADG family (SEQ ID NO: 1), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

Methods of the present disclosure may be employed to introduce or improve one or more of a variety of desirable traits. Examples of traits that may introduced or improved include: root biomass, root length, height, shoot length, leaf number, water use efficiency, overall biomass, yield, fruit size, grain size, photosynthesis rate, tolerance to drought, heat tolerance, salt tolerance, resistance to nematode stress, resistance to a fungal pathogen, resistance to a bacterial pathogen, resistance to a viral pathogen, level of a metabolite, and proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the improved traits) grown under identical conditions. A preferred trait to be introduced or improved is nitrogen fixation, as described herein. In some cases, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under the same conditions in the soil.

The trait to be improved may be assessed under conditions including the application of one or more biotic or abiotic stressors. Examples of stressors include abiotic stresses (such as heat stress, salt stress, drought stress, cold stress, and low nutrient stress) and biotic stresses (such as nematode stress, insect herbivory stress, fungal pathogen stress, bacterial pathogen stress, and viral pathogen stress).

The trait improved by methods and compositions of the present disclosure may be nitrogen fixation, including in a plant not previously capable of nitrogen fixation. In some cases, bacteria isolated according to a method described herein produce 1% or more (e.g. 2%, 3%, 4%, 5%, 6%, 7%, 8%, 9%, 10%, 15%, 20%, or more) of a plant's nitrogen, which may represent an increase in nitrogen fixation capability of at least 2-fold (e.g. 3-fold, 4-fold, 5-fold, 6-fold, 7-fold, 8-fold, 9-fold, 10-fold, 20-fold, 50-fold, 100-fold, 1000-fold, or more) as compared to bacteria isolated from the first plant before introducing any genetic variation. In some cases, the bacteria produce 5% or more of a plant's nitrogen. The desired level of nitrogen fixation may be achieved after repeating the steps of introducing genetic variation, exposure to a plurality of plants, and isolating bacteria from plants with an improved trait one or more times (e.g. 1, 2, 3, 4, 5, 10, 15, 25, or more times). In some cases, enhanced levels of nitrogen fixation are achieved in the presence of fertilizer supplemented with gluamine, ammonia, or other chemical source of nitrogen. Methods for assessing degree of nitrogen fixation are known, examples of which are described herein.

Nitrogen Fixation

Described herein are methods of increasing nitrogen fixation in a plant, comprising exposing the plant to bacteria comprising one or more genetic variations introduced into one or more genes regulating nitrogen fixation, wherein the bacteria produce 1% or more of nitrogen in the plant (e.g. 2%, 5%, 10%, or more), which may represent a nitrogen-fixation capability of at least 2-fold as compared to the plant in the absence of the bacteria. The bacteria may produce the nitrogen in the presence of fertilizer supplemented with glutamine or ammonia. Genetic variations can be any genetic variation described herein, including examples provided above, in any number and any combination. The genetic variation may be introduced into a gene selected from the group consisting of nifA, nifL, ntrB, ntrC, glutamine synthetase, glnA, glnB, glnK, draT, amtB, glutaminase, glnD, glnE, nifJ, nifH, nifD, nifK, nifY, nifE, nifN, nifU, nifS, nifV, nifW, nifZ, nifM, nifF, nifB, and nifQ. The genetic variation may be a mutation that results in one or more of: increased expression or activity of nifA or glutaminase; decreased expression or activity of nifL, ntrB, glutamine synthetase, glnB, glnK, draT, amtB; decreased adenylyl-removing activity of GlnE; or decreased uridylyl-removing activity of GlnD. The genetic variation introduced into one or more bacteria of the methods disclosed herein may be a knock-out mutation or it may abolish a regulatory sequence of a target gene, or it may comprise insertion of a heterologous regulatory sequence, for example, insertion of a regulatory sequence found within the genome of the same bacterial species or genus. The regulatory sequence can be chosen based on the expression level of a gene in a bacterial culture or within plant tissue. The genetic variation may be produced by chemical mutagenesis. The plants grown in step (c) may be exposed to biotic or abiotic stressors.

The amount of nitrogen fixation that occurs in the plants described herein may be measured in several ways, for example by an acetylene-reduction (AR) assay. An acetylene-reduction assay can be performed in vitro or in vivo. Evidence that a particular bacterium is providing fixed nitrogen to a plant can include: 1) total plant N significantly increases upon inoculation, preferably with a concomitant increase in N concentration in the plant; 2) nitrogen deficiency symptoms are relieved under N-limiting conditions upon inoculation (which should include an increase in dry matter); 3) $N_2$ fixation is documented through the use of an $^{15}N$ approach (which can be isotope dilution experiments, $^{15}N_2$ reduction assays, or $^{15}N$ natural abundance assays); 4) fixed N is incorporated into a plant protein or metabolite; and 5) all of these effects are not be seen in uninoculated plants or in plants inoculated with a mutant of the inoculum strain.

The wild-type nitrogen fixation regulatory cascade can be represented as a digital logic circuit where the inputs $O_2$ and $NH_4^+$ pass through a NOR gate, the output of which enters an AND gate in addition to ATP. In some embodiments, the methods disclosed herein disrupt the influence of $NH_4^+$ on this circuit, at multiple points in the regulatory cascade, so that microbes can produce nitrogen even in fertilized fields. However, the methods disclosed herein also envision altering the impact of ATP or $O_2$ on the circuitry, or replacing the circuitry with other regulatory cascades in the cell, or altering genetic circuits other than nitrogen fixation. Gene clusters can be re-engineered to generate functional products under the control of a heterologous regulatory system. By eliminating native regulatory elements outside of, and within, coding sequences of gene clusters, and replacing them with alternative regulatory systems, the functional products of complex genetic operons and other gene clusters can be controlled and/or moved to heterologous cells, including cells of different species other than the species from which the native genes were derived. Once re-engineered, the synthetic gene clusters can be controlled by genetic circuits or other inducible regulatory systems, thereby controlling the products' expression as desired. The expression cassettes can be designed to act as logic gates, pulse generators, oscillators, switches, or memory devices. The controlling expression cassette can be linked to a promoter such that the expression cassette functions as an environmental sensor, such as an oxygen, temperature, touch, osmotic stress, membrane stress, or redox sensor.

As an example, the nifL, nifA, nifT, and nifX genes can be eliminated from the nif gene cluster. Synthetic genes can be designed by codon randomizing the DNA encoding each amino acid sequence. Codon selection is performed, specifying that codon usage be as divergent as possible from the codon usage in the native gene. Proposed sequences are scanned for any undesired features, such as restriction enzyme recognition sites, transposon recognition sites, repetitive sequences, sigma 54 and sigma 70 promoters, cryptic ribosome binding sites, and rho independent terminators. Synthetic ribosome binding sites are chosen to match the strength of each corresponding native ribosome binding site, such as by constructing a fluorescent reporter plasmid in which the 150 bp surrounding a gene's start codon (from −60 to +90) is fused to a fluorescent gene. This chimera can be expressed under control of the Ptac promoter, and fluorescence measured via flow cytometry. To generate synthetic ribosome binding sites, a library of reporter plasmids using 150 bp (−60 to +90) of a synthetic expression cassette is generated. Briefly, a synthetic expression cassette can consist of a random DNA spacer, a degenerate sequence encoding an RBS library, and the coding sequence for each synthetic gene. Multiple clones are screened to identify the synthetic ribosome binding site that best matched the native ribosome binding site. Synthetic operons that consist of the same genes as the native operons are thus constructed and tested for functional complementation. A further exemplary description of synthetic operons is provided in US20140329326.

Bacterial Species

Microbes useful in the methods and compositions disclosed herein can be obtained by extracting microbes from surfaces or tissues of native plants; grinding seeds to isolate microbes; planting seeds in diverse soil samples and recovering microbes from tissues; or inoculating plants with exogenous microbes and determining which microbes appear in plant tissues. Non-limiting examples of plant tissues include a seed, seedling, leaf, cutting, plant, bulb or tuber. In some cases, bacteria are isolated from a seed. The parameters for processing samples may be varied to isolate different types of associative microbes, such as rhizospheric, epiphytes, or endophytes. Bacteria may also be sourced from a repository, such as environmental strain collections, instead of initially isolating from a first plant. The microbes can be genotyped and phenotyped, via sequencing the genomes of isolated microbes; profiling the composition of communities in planta; characterizing the transcriptomic functionality of communities or isolated microbes; or screening microbial features using selective or phenotypic media (e.g., nitrogen fixation or phosphate solubilization phenotypes). Selected candidate strains or populations can be obtained via sequence data; phenotype data; plant data (e.g., genome, phenotype, and/or yield data); soil data (e.g., pH, N/P/K content, and/or bulk soil biotic communities); or any combination of these.

The bacteria and methods of producing bacteria described herein may apply to bacteria able to self-propagate efficiently on the leaf surface, root surface, or inside plant tissues without inducing a damaging plant defense reaction, or bacteria that are resistant to plant defense responses. The bacteria described herein may be isolated by culturing a plant tissue extract or leaf surface wash in a medium with no added nitrogen. However, the bacteria may be unculturable, that is, not known to be culturable or difficult to culture using standard methods known in the art. The bacteria described herein may be an endophyte or an epiphyte or a bacterium inhabiting the plant rhizosphere (rhizospheric bacteria). The bacteria obtained after repeating the steps of introducing genetic variation, exposure to a plurality of plants, and isolating bacteria from plants with an improved trait one or more times (e.g. 1, 2, 3, 4, 5, 10, 15, 25, or more times) may be endophytic, epiphytic, or rhizospheric. Endophytes are organisms that enter the interior of plants without causing disease symptoms or eliciting the formation of symbiotic structures, and are of agronomic interest because they can enhance plant growth and improve the nutrition of plants (e.g., through nitrogen fixation). The bacteria can be a seed-borne endophyte. Seed-borne endophytes include bacteria associated with or derived from the seed of a grass or plant, such as a seed-borne bacterial endophyte found in mature, dry, undamaged (e.g., no cracks, visible fungal infection, or prematurely germinated) seeds. The seed-borne bacterial endophyte can be associated with or derived from the surface of the seed; alternatively, or in addition, it can be associated with or derived from the interior seed compartment (e.g., of a surface-sterilized seed). In some cases, a seed-borne bacterial endophyte is capable of replicating within the plant tissue, for example, the interior of the seed. Also, in some cases, the seed-borne bacterial endophyte is capable of surviving desiccation.

The bacterial isolated according to methods of the disclosure can comprise a plurality of different bacterial taxa in combination. By way of example, the bacteria may include Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobiun, Sinorhizobium* and *Halomonas*), Firmicutes (such as *Bacillus, Paenibacillus, Lactobacillus, Mycoplasma*, and *Acetabacterium*), and Actinobacteria (such as *Streptomyces, Rhodacoccus, Microbacterium*, and *Curtobacterium*). Bacteria that can be produced by the methods disclosed herein include *Azotobacter* sp., *Bradyrhizobium* sp., *Klebsiella* sp., and *Sinorhizobium* sp. The bacteria may be selected from the group consisting of: *Azotobacter vinelandii, Bradyrhizobium japonicum, Klebsiella pneumoniae*, and *Sinorhizobium meliloti*. The bacteria may be of the genus *Enterobacter* and *Rahnella*.

The bacteria may be obtained from any general terrestrial environment, including its soils, plants, fungi, animals (including invertebrates) and other biota, including the sediments, water and biota of lakes and rivers; from the marine environment, its biota and sediments (for example, sea water, marine muds, marine plants, marine invertebrates (for example, sponges), marine vertebrates (for example, fish)); the terrestrial and marine geosphere (regolith and rock, for example, crushed subterranean rocks, sand and clays); the cryosphere and its meltwater; the atmosphere (for example, filtered aerial dusts, cloud and rain droplets); urban, industrial and other man-made environments (for example, accumulated organic and mineral matter on concrete, roadside gutters, roof surfaces, and road surfaces).

The plants from which the bacteria are obtained may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the bacteria may be collected from commercial crops grown in such environments, or more specifically from individual crop plants best displaying a trait of interest amongst a crop grown in any specific environment: for example the fastest-growing plants amongst a crop grown in saline-limiting soils, or the least damaged plants in crops exposed to severe insect damage or disease epidemic, or plants having desired quantities of certain metabolites and other compounds, including fibre content, oil content, and the like, or plants displaying desirable colors, taste or smell. The bacteria may be collected from a plant of interest or any material occurring in the environment of interest, including fungi and other animal and plant biota, soil, water, sediments, and other elements of the environment as referred to previously.

The bacteria may be isolated from plant tissue. This isolation can occur from any appropriate tissue in the plant, including for example root, stem and leaves, and plant reproductive tissues. By way of example, conventional methods for isolation from plants typically include the sterile excision of the plant material of interest (e.g. root or stem lengths, leaves), surface sterilization with an appropriate solution (e.g. 2% sodium hypochlorite), after which the plant material is placed on nutrient medium for microbial growth. Alternatively, the surface-sterilized plant material can be crushed in a sterile liquid (usually water) and the liquid suspension, including small pieces of the crushed plant material spread over the surface of a suitable solid agar medium, or media, which may or may not be selective (e.g. contain only phytic acid as a source of phosphorus). This approach is especially useful for bacteria which form isolated colonies and can be picked off individually to separate plates of nutrient medium, and further purified to a single species by well-known methods. Alternatively, the plant root or foliage samples may not be surface sterilized but only washed gently thus including surface-dwelling epiphytic microorganisms in the isolation process, or the epiphytic microbes can be isolated separately, by imprinting and lifting off pieces of plant roots, stem or leaves onto the surface of an agar medium and then isolating individual colonies as above. This approach is especially useful for bacteria, for example. Alternatively, the roots may be processed without washing off small quantities of soil attached to the roots, thus including microbes that colonize the plant rhizosphere. Otherwise, soil adhering to the roots can be removed, diluted and spread out onto agar of suitable selective and non-selective media to isolate individual colonies of rhizospheric bacteria.

Biologically pure cultures of *Rahnella aquatilis* and *Enterobacter sacchari* were deposited on Jul. 14, 2015 with the American Type Culture Collection (ATCC; an International Depositary Authority), Manassas, Va., USA, and assigned ATTC Patent Deposit Designation numbers PTA-122293 and PTA-122294, respectively. These deposits were made under the provisions of the Budapest Treaty on the International Recognition of the Deposit of Microorganisms for the Purpose of Patent Procedure and the Regulations (Budapest Treaty).

Compositions

Compositions comprising bacteria or bacterial populations produced according to methods described herein and/or having characteristics as described herein may also be used to improve plant traits. The compositions comprising bacterial populations may be coated on a surface of a seed, and may be in liquid form. The compositions include seed coatings for commercially important agricultural crops, for example, sorghum, canola, tomato, strawberry, barley, rice, maize, and wheat. The compositions may also be sprayed on the plant aerial parts, or applied to the roots by inserting into furrows in which the plant seeds are planted, watering to the soil, or dipping the roots in a suspension of the composition. The compositions may be dehydrated in a suitable manner that maintains cell viability and the ability to artificially inoculate and colonize host plants. The bacterial species may be present in the compositions at a concentration of between $10^8$ to $10^{10}$ CFU/ml. The compositions may be supplemented with trace metal ions, such as molybdenum ions, iron ions, manganese ions, or combinations of these ions. The concentration of ions in the compositions described herein may between about 0.1 mM and about 50 mM. The compositions may also be formulated with a carrier, such as beta-glucan, carboxylmethyl cellulose (CMC), bacterial extracellular polymeric substance (EPS), sugar, animal milk, or other suitable carriers. Alternatively, peat or planting materials can be used as a carrier, or biopolymers in which the composition is entrapped in the biopolymer can be used as a carrier. The compositions comprising the bacterial populations described herein can improve plant traits, such as promoting plant growth, maintaining high chlorophyll content in leaves, increasing fruit or seed numbers, and increasing fruit or seed unit weight.

The compositions comprising the bacterial populations described herein may be coated onto the surface of a seed. As such, compositions comprising a seed coated with one or more bacteria described herein are also contemplated. The seed coating can be formed by mixing the bacterial population with a porous, chemically inert granular carrier. Alternatively, the compositions may be inserted directly into the furrows into which the seed is planted or sprayed onto the plant leaves or applied by dipping the roots into a suspension of the composition. An effective amount of the composition can be used to populate the sub-soil region adjacent to the roots of the plant with viable bacterial growth, or populate the leaves of the plant with viable bacterial growth. In general, an effective amount is an amount sufficient to result in plants with improved traits (e.g. a desired level of nitrogen fixation).

Bacterial compositions described herein can be formulated using an agriculturally acceptable carrier. The formulation useful for these embodiments may include at least one member selected from the group consisting of a tackifier, a microbial stabilizer, a fungicide, an antibacterial agent, an herbicide, a nematicide, an insecticide, a plant growth regulator, a fertilizer, a rodenticide, a dessicant, and a nutrient. For example, any of the compositions described herein can include an agriculturally acceptable carrier (e.g., one or more of a fertilizer such as a non-naturally occurring fertilizer, an adhesion agent such as a non-naturally occurring adhesion agent, and a pesticide such as a non-naturally occurring pesticide). A non-naturally occurring adhesion agent can be, for example, a polymer, copolymer, or synthetic wax. For example, any of the coated seeds, seedlings, or plants described herein can contain such an agriculturally acceptable carrier in the seed coating. In any of the compositions or methods described herein, an agriculturally acceptable carrier can be or can include a non-naturally occurring compound (e.g., a non-naturally occurring fertilizer, a non-naturally occurring adhesion agent such as a polymer, copolymer, or synthetic wax, or a non-naturally occurring pesticide). Non-limiting examples of agriculturally acceptable carriers are described below. Additional examples of agriculturally acceptable carriers are known in the art.

In some cases, bacteria are mixed with an agriculturally acceptable carrier. The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in the composition. Water-in-oil emulsions can also be used to formulate a composition that includes the isolated bacteria (see, for example, U.S. Pat. No. 7,485,451). Suitable formulations that may be prepared include wettable powders, granules, gels, agar strips or pellets, thickeners, and the like, micro-encapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the bacteria, such as barley, rice, or other biological materials such as seed, plant parts, sugar cane bagasse, hulls or stalks from grain processing, ground plant material or wood from building site refuse, sawdust or small fibers from recycling of paper, fabric, or wood.

For example, a fertilizer can be used to help promote the growth or provide nutrients to a seed, seedling, or plant. Non-limiting examples of fertilizers include nitrogen, phosphorous, potassium, calcium, sulfur, magnesium, boron, chloride, manganese, iron, zinc, copper, molybdenum, and selenium (or a salt thereof). Additional examples of fertilizers include one or more amino acids, salts, carbohydrates, vitamins, glucose, NaCl, yeast extract, $NH_4H_2PO_4$, $(NH_4)_2SO_4$, glycerol, valine, L-leucine, lactic acid, propionic acid, succinic acid, malic acid, citric acid, KH tartrate, xylose, lyxose, and lecithin. In one embodiment, the formulation can include a tackifier or adherent (referred to as an adhesive agent) to help bind other active agents to a substance (e.g., a surface of a seed). Such agents are useful for combining bacteria with carriers that can contain other compounds (e.g., control agents that are not biologic), to yield a coating composition. Such compositions help create coatings around the plant or seed to maintain contact between the microbe and other agents with the plant or plant part. In one embodiment, adhesives are selected from the group consisting of: alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers.

In some embodiments, the adhesives can be, e.g. a wax such as carnauba wax, beeswax, Chinese wax, shellac wax, spermaceti wax, candelilla wax, castor wax, ouricury wax, and rice bran wax, a polysaccharide (e.g., starch, dextrins, maltodextrins, alginate, and chitosans), a fat, oil, a protein (e.g., gelatin and zeins), gum arables, and shellacs. Adhesive agents can be non-naturally occurring compounds, e.g., polymers, copolymers, and waxes. For example, non-limiting examples of polymers that can be used as an adhesive agent include: polyvinyl acetates, polyvinyl acetate copolymers, ethylene vinyl acetate (EVA) copolymers, polyvinyl alcohols, polyvinyl alcohol copolymers, celluloses (e.g., ethylcelluloses, methylcelluloses, hydroxymethylcelluloses, hydroxypropylcelluloses, and carboxymethylcelluloses), polyvinylpyrolidones, vinyl chloride, vinylidene chloride copolymers, calcium lignosulfonates, acrylic copolymers, polyvinylacrylates, polyethylene oxide, acylamide polymers and copolymers, polyhydroxyethyl acrylate, methylacrylamide monomers, and polychloroprene.

In some examples, one or more of the adhesion agents, anti-fungal agents, growth regulation agents, and pesticides (e.g., insecticide) are non-naturally occurring compounds (e.g., in any combination). Additional examples of agriculturally acceptable carriers include dispersants (e.g., polyvinylpyrrolidone/vinyl acetate PVPIVA S-630), surfactants, binders, and filler agents.

The formulation can also contain a surfactant. Non-limiting examples of surfactants include nitrogen-surfactant blends such as Prefer 28 (Cenex), Surf-N(US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision). In one embodiment, the surfactant is present at a concentration of between 0.01% v/v to 10% v/v. In another embodiment, the surfactant is present at a concentration of between 0.1% v/v to 1% v/v.

In certain cases, the formulation includes a microbial stabilizer. Such an agent can include a desiccant, which can include any compound or mixture of compounds that can be classified as a desiccant regardless of whether the compound or compounds are used in such concentrations that they in fact have a desiccating effect on a liquid inoculant. Such desiccants are ideally compatible with the bacterial population used, and should promote the ability of the microbial population to survive application on the seeds and to survive desiccation. Examples of suitable desiccants include one or more of trehalose, sucrose, glycerol, and Methylene glycol. Other suitable desiccants include, but are not limited to, non reducing sugars and sugar alcohols (e.g., mannitol or sorbitol). The amount of desiccant introduced into the formulation can range from about 5% to about 50% by weight/volume, for example, between about 10% to about 40%, between about 15% to about 35%, or between about 20% to about 30%. In some cases, it is advantageous for the formulation to contain agents such as a fungicide, an antibacterial agent, an herbicide, a nematicide, an insecticide, a plant growth regulator, a rodenticide, or a nutrient. Non-limiting examples of growth regulators include brassinosteroids, cytokinines (e.g., kinetin and zeatin), auxins (e.g., indolylacetic acid and indolylacetyl aspartate), flavonoids and isoflavanoids (e.g., formononetin and diosmetin), phytoaixins (e.g., glyceollin), and phytoalexin-inducing oligosaccharides (e.g., pectin, chitin, chitosan, polygalacuronic acid, and oligogalacturonic acid), and gibellerins. Such agents are ideally compatible with the agricultural seed or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

In the liquid form, for example, solutions or suspensions, bacterial populations can be mixed or suspended in water or in aqueous solutions. Suitable liquid diluents or carriers include water, aqueous solutions, petroleum distillates, or other liquid carriers.

Solid compositions can be prepared by dispersing the bacterial populations in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

Plant Species

The methods and bacteria described herein are suitable for any of a variety of plants, such as plants in the genera *Hordeum, Oryza, Zea*, and *Triticeae*. Other non-limiting examples of suitable plants include mosses, lichens, and algae. In some cases, the plants have economic, social and/or environmental value, such as food crops, fiber crops, oil crops, plants in the forestry or pulp and paper industries, feedstock for biofuel production and/or ornamental plants. Non-limiting examples of crop plants include maize, rice, wheat, barley, sorghum, millet, oats, rye triticale, buckwheat, sweet corn, sugar cane, onions, tomatoes, strawberries, and asparagus.

Plants that may be obtained or improved using the methods and composition disclosed herein also include pineapple, banana, coconut, lily, and grass; and dicotyledonous plants, such as, for example, peas, alfalfa, tomatillo, melon, chickpea, chicory, clover, kale, lentil, soybean, tobacco, potato, sweet potato, radish, cabbage, rape, apple trees, grape, cotton, sunflower, thale cress, canola, citrus (including orange, mandarin, kumquat, lemon, lime, grapefruit, tangerine, tangelo, citron, and pomelo), pepper, bean, and lettuce.

In some cases, the plant to be improved is not readily amenable to experimental conditions. For example, a crop plant may take too long to grow enough to practically assess an improved trait serially over multiple iterations. Accordingly, a first plant from which bacteria are initially isolated, and/or the plurality of plants to which genetically manipulated bacteria are applied may be a model plant, such as a plant more amenable to evaluation under desired conditions. Non-limiting examples of model plants include *Setaria, Brachypodium*, and *Arabidopsis*. Ability of bacteria isolated according to a method of the disclosure using a model plant may then be applied to a plant of another type (e.g. a crop plant) to confirm conferral of the improved trait.

Traits that may be improved by the methods disclosed herein include any observable characteristic of the plant, including, for example, growth rate, height, weight, color, taste, smell, changes in the production of one or more compounds by the plant (including for example, metabolites, proteins, drugs, carbohydrates, oils, and any other compounds). Selecting plants based on genotypic information is also envisaged (for example, including the pattern of plant gene expression in response to the bacteria, or identifying the presence of genetic markers, such as those associated with increased nitrogen fixation). Plants may also be selected based on the absence, suppression or inhibition of a certain feature or trait (such as an undesirable feature or trait) as opposed to the presence of a certain feature or trait (such as a desirable feature or trait).

EXAMPLES

The examples provided herein describe methods of bacterial isolation, bacterial and plant analysis, and plant trait improvement. The examples are for illustrative purposes only and are not to be construed as limiting in any way.

Example 1: Isolation of Microbes from Plant Tissue

Topsoil was obtained from various agricultural areas in central California. Twenty soils with diverse texture characteristics were collected, including heavy clay, peaty clay loam, silty clay, and sandy loam. Seeds of various field corn, sweet corn, heritage corn and tomato were planted into each soil, as shown in Table 1.

Plants were uprooted after 2-4 weeks of growth and excess soil on root surfaces was removed with deionized water. Following soil removal, plants were surface sterilized with bleach and rinsed vigorously in sterile water. A cleaned, 1 cm section of root was excised from the plant and placed in a phosphate buffered saline solution containing 3 mm steel beads. A slurry was generated by vigorous shaking of the solution with a Qiagen TissueLyser II.

Figure 1B:
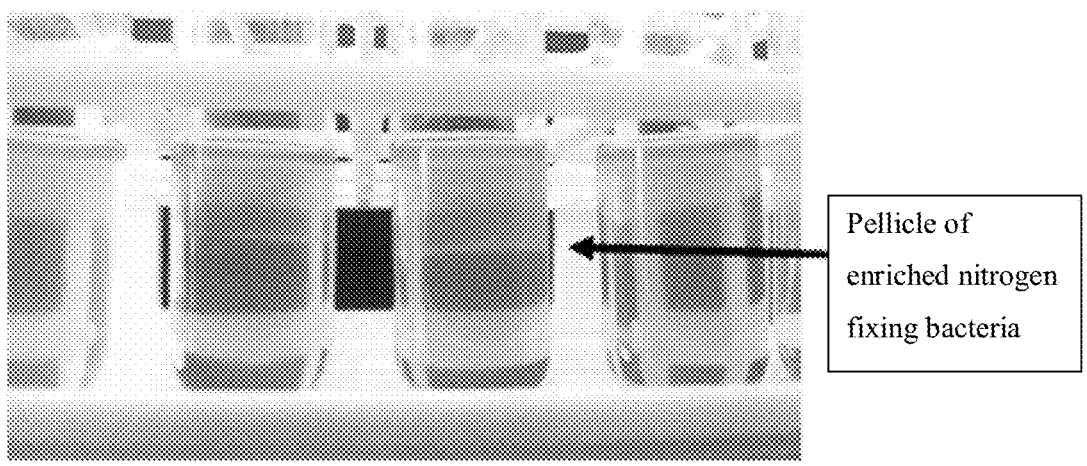

The root and saline slurry was diluted and inoculated onto various types of growth media to isolate rhizospheric, endophytic, epiphytic, and other plant-associated microbes. R2A and Nfb agar media were used to obtain single colonies, and semisolid Nfb media slants were used to obtain populations of nitrogen fixing bacteria. After 2-4 weeks incubation in semi-solid Nfb media slants, microbial populations were collected and streaked to obtain single colonies on R2A agar, as shown in FIG. 1A-B. Single colonies were resuspended in a mixture of R2A and glycerol, subjected to PCR analysis, and frozen at −80° C. for later analysis. Approximately 1,000 single colonies were obtained and designated "isolated microbes."

Figure 2:
FIG. 2 depicts a representative nifH PCR screen. Positive bands were observed at ~350 bp for two colonies in this screen. Lower bands represent primer-dimers.

Isolates were then subjected to a colony PCR screen to detect the presence of the nifH gene in order to identify diazotrophs. The previously-described primer set Ueda 19F/388R, which has been shown to detect over 90% of diazotrophs in screens, was used to probe the presence of the nif cluster in each isolate (Ueda et al. 1995; J. Bacteriol. 177: 1414-1417). Single colonies of purified isolates were picked, resuspended in PBS, and used as a template for colony PCR, as shown in FIG. 2. Colonies of isolates that gave positive PCR bands were re-streaked, and the colony PCR and re-streaking process was repeated twice to prevent false positive identification of diazotrophs. Purified isolates were then designated "candidate microbes."

Example 2: Characterization of Isolated Microbes

Sequencing, Analysis and Phylogenetic Characterization

Sequencing of 16S rDNA with the 515f-806r primer set was used to generate preliminary phylogenetic identities for isolated and candidate microbes (see e.g. Vernon et al.; BMC Microbiol. 2002 Dec. 23; 2:39.). The microbes comprise diverse genera including: *Enterobacter, Burkholderia, Klebsiella, Bradyrhizobium, Rahnella, Xanthomonas, Raoultella, Pantoea, Pseudomonas, Brevundimonas, Agrobacterium*, and *Paenibacillus*, as shown in Table 2.

TABLE 1

Crop Type and Varieties planted into soil with diverse characteristics

| Crop Type | Field Corn | Sweet Corn | Heritage Corn | Tomato |
|---|---|---|---|---|
| Varieties | Mo17 | Ferry-Morse 'Golden Cross Bantam T-51' | Victory Seeds 'Moseby Prolific' | Ferry-Morse Roma VF |
| | B73 | Ferry-Morse 'Silver Queen Hybrid' | Victory Seeds 'Reid's Yellow Dent' | Stover Roma |
| | DKC 66-40 | Ferry-Morse 'Sugar Dots' | Victory Seeds 'Hickory King' | Totally Tomatoes 'Micro Tom Hybrid' |
| | DKC 67-07 | | | Heinz 1015 |
| | DKC 70-01 | | | Heinz 2401 |
| | | | | Heinz 3402 |
| | | | | Heinz 5508 |
| | | | | Heinz 5608 |
| | | | | Heinz 8504 |

TABLE 2

Diversity of microbes isolated from tomato plants as determined by deep 16S rDNA sequencing.

| Genus | Isolates |
|---|---|
| Achromobacter | 7 |
| Agrobacterium | 117 |
| Agromyces | 1 |
| Alicyclobacillus | 1 |
| Asticcacaulis | 6 |
| Bacillus | 131 |
| Bradyrhizobium | 2 |
| Brevibacillus | 2 |
| Burkholderia | 2 |
| Caulobacter | 17 |
| Chryseobacterium | 42 |
| Comamonas | 1 |
| Dyadobacter | 2 |
| Flavobacterium | 46 |
| Halomonas | 3 |
| Leptothrix | 3 |
| Lysobacter | 2 |
| Neisseria | 13 |
| Paenibacilius | 1 |
| Paenisporosarcina | 3 |
| Pantoea | 14 |
| Pedobacter | 16 |
| Pimelobacter | 2 |
| Pseudomonas | 212 |
| Rhizobium | 4 |
| Rhodoferax | 1 |
| Sphingobacterium | 13 |
| Sphingobium | 23 |
| Sphingomonas | 3 |
| Sphingopyxis | 1 |
| Stenotrophomanas | 59 |
| Streptococcus | 3 |
| Variovorax | 37 |
| Xylanimicrobium | 1 |
| unidentified | 75 |

Subsequently, the genomes of 39 candidate microbes were sequenced using Illumina Miseq platform. Genomic DNA from pure cultures was extracted using the QIAmp DNA mini kit (QIAGEN), and total DNA libraries for sequencing were prepared through a third party vendor (SeqMatic, Hayward). Genome assembly was then carried out via the A5 pipeline (Tritt et al. 2012; PLoS One 7(9):e42304). Genes were identified and annotated, and those related to regulation and expression of nitrogen fixation were noted as targets for mutagenesis.

Transcriptomic Profiling of Candidate Microbes

Transcriptomic profiling of strain CI010 was performed to identify promoters that are active in the presence of environmental nitrogen. Strain CI010 was cultured in a defined, nitrogen-free media supplemented with 10 mM glutamine. Total RNA was extracted from these cultures (QIAGEN RNeasy kit) and subjected to RNAseq sequencing via Illumina HiSeq (SeqMatic, Fremont Calif.). Sequencing reads were mapped to CI010 genome data using Geneious, and highly expressed genes under control of proximal transcriptional promoters were identified. Tables 3A-C lists genes and their relative expression level as measured through RNASeq sequencing of total RNA. Sequences of the proximal promoters were recorded for use in mutagenesis of nif pathways, nitrogen utilization related pathways, or other genes with a desired expression level.

Assessment of Genetic Tractability

Candidate microbes were characterized based on transformability and genetic tractability. First, optimal carbon source utilization was determined by growth on a small panel of relevant media as well as a growth curve in both nitrogen-free and rich media. Second, the natural antibiotic resistance of each strain was determined through spot-plating and growth in liquid culture containing a panel of antibiotics used as selective markers for mutagenesis. Third, each strain was tested for its transformability through electroporation of a collection of plasmids. The plasmid collection comprises the combinatorial expansion of seven origins of replication, i.e., p15a, pSC101, CloDF, colA, RK2, pBBR1, and pRO1600 and four antibiotic resistance markers, i.e CmR, KmR, SpecR, and TetR. This systematic evaluation of origin and resistance marker compatibility was used to identify vectors for plasmid-based mutagenesis in candidate microbes.

Example 3: Mutagenesis of Candidate Microbes

Lambda-Red Mediated Knockouts

Several mutants of candidate microbes were generated using the plasmid pKD46 or a derivative containing a kanamycin resistance marker (Datsenko et al. 2000; PNAS 97(12): 6640-6645). Knockout cassettes were designed with 250 bp homology flanking the target gene and generated via overlap extension PCR. Candidate microbes were transformed with pKD46, cultured in the presence of arabinose to induce Lambda-Red machinery expression, prepped for electroporation, and transformed with the knockout cassettes to produce candidate mutant strains. Four candidate microbes and one laboratory strain, *Klebsiella oxytoca* M5A1, were used to generate thirteen candidate mutants of the nitrogen fixation regulatory genes nifL, glnB, and amtB, as shown in Table 4.

TABLE 4

List of single knockout mutants created through Lambda-red mutagenesis

| Strain | nifL | glnB | amtB |
|---|---|---|---|
| M5A1 | X | X | X |
| CI006 | X | X | X |
| CI010 | X | X | X |
| CI019 | X | X | |
| CI028 | X | X | |

Oligo-Directed Mutagenesis with Cas9 Selection

Oligo-directed mutagenesis was used to target genomic changes to the rpoB gene in *E. coli* DH10B, and mutants were selected with a CRISPR-Cas system. A mutagenic oligo (ss1283: "G\*T\*T\*G\*ATCAGACCGATG-TTCGGACCTTCcaagGTTTCGATCGGACAT-ACGCGACCGTA GTGGGTCGGGTGTACGTCTCGAACTTCAAAGCC" (SEQ ID NO: 2), where * denotes phosphorothioate bond) was designed to confer rifampicin resistance through a 4-bp mutation to the rpoB gene. Cells containing a plasmid encoding Cas9 were induced for Cas9 expression, prepped for electroporation, and then electroporated with both the mutagenic oligo and a plasmid encoding constitutive expression of a guide RNA (gRNA) that targets Cas9 cleavage of the WT rpoB sequence. Electroporated cells were recovered in nonselective media overnight to allow sufficient segregation of the resulting mutant chromosomes. After plating on selection for the gRNA-encoding plasmid, two out of ten colonies screened were shown to contain the desired mutation, while the rest were shown to be escape mutants generated through protospacer mutation in the gRNA plasmid or Cas9 plasmid loss.

Lambda-Red Mutagenesis with Cas9 Selection

Figure 3:
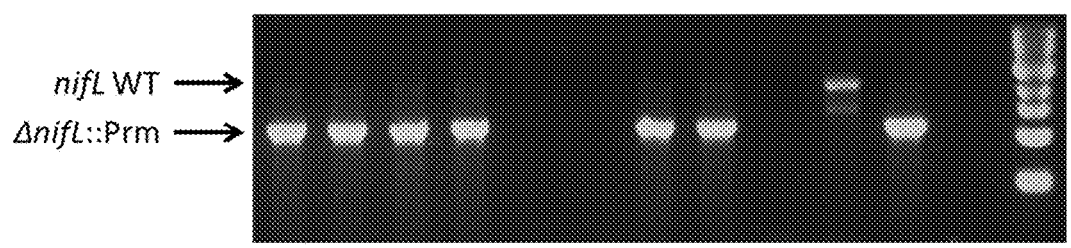
FIG. 3 depicts an example of a PCR screen of colonies from CRISPR-Cas-selected mutagenesis. CI006 colonies were screened with primers specific for the nifL locus. The wild type PCR product is expected at ~2.2 kb, whereas the mutant is expected at ~1.1 kb. Seven of ten colonies screened unambiguously show the desired deletion.

Mutants of candidate microbes CI006 and CI010 were generated via lambda-red mutagenesis with selection by CRISPR-Cas. Knockout cassettes contained an endogenous promoter identified through transcriptional profiling (as described in Example 2 and depicted in Table 3) and ~250 bp homology regions flanking the deletion target. CI006 and CI010 were transformed with plasmids encoding the Lambda-red recombination system (exo, beta, gam genes) under control of an arabinose inducible promoter and Cas9 under control of an IPTG inducible promoter. The Red recombination and Cas9 systems were induced in resulting transformants, and strains were prepared for electroporation. Knockout cassettes and a plasmid-encoded selection gRNA were subsequently transformed into the competent cells. After plating on antibiotics selective for both the Cas9 plasmid and the gRNA plasmid, 7 of the 10 colonies screened showed the intended knockout mutation, as shown in FIG. 3.

Example 4: In Vitro Phenotyping of Candidate Molecules

The impact of exogenous nitrogen on nitrogenase biosynthesis and activity in various mutants was assessed. The Acetylene Reduction Assay (ARA) (Temme et. al. 2012; 109(18): 7085-7090) was used to measure nitrogenase activity in pure culture conditions. Strains were grown in air-tight test tubes, and reduction of acetylene to ethylene was quantified with an Agilent 6890 gas chromatograph. ARA activities of candidate microbes and counterpart candidate mutants grown in nitrogen fixation media supplemented with 0 to 10 mM glutamine are shown in FIGS. 4A-B and FIGS. 10A-C.

Figure 11:
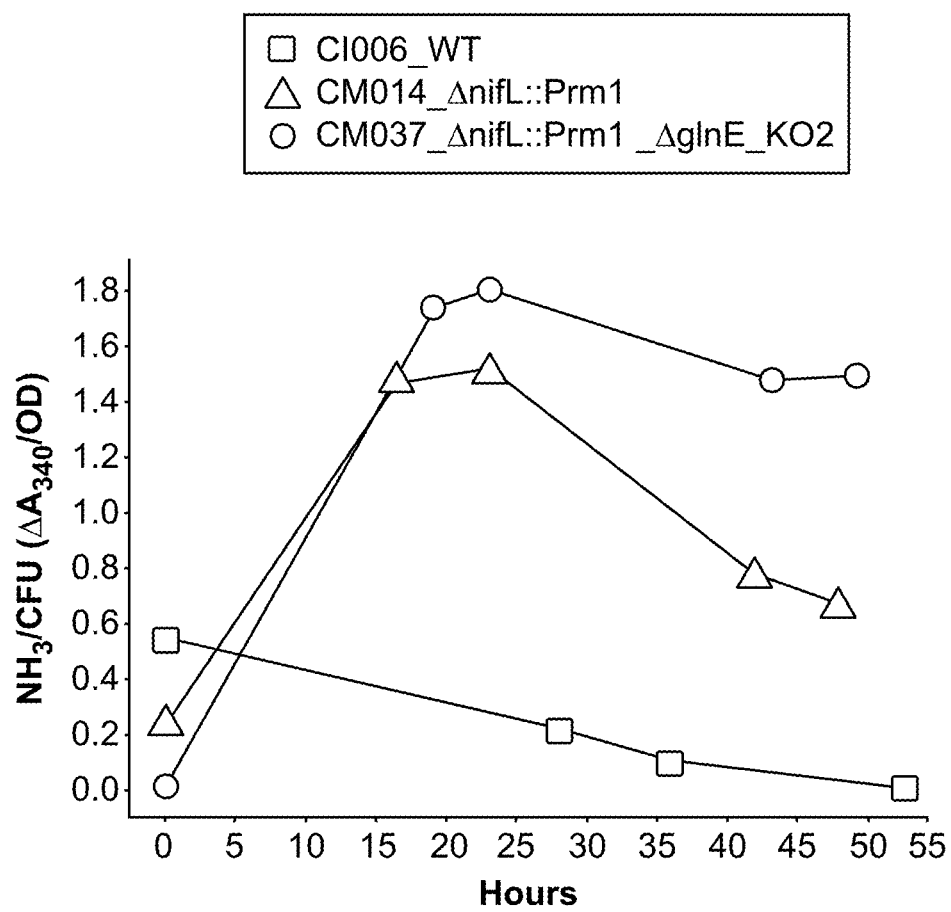
FIG. 11 depicts a double mutant that exhibits higher ammonia excretion than the single mutant from which it was derived.

Under anaerobic culture conditions, a range of glutamine and ammonia concentrations was tested to quantify impact on nitrogen fixation activity. In wild-type cells, activity quickly diminished as glutamine concentrations increased. However, in a series of initial knock-out mutations, a class of mutation was validated enabling expression of nitrogen fixation genes under concentrations of glutamine that would otherwise shut off activity in wild type. This profile was generated in four different species of diazotrophs, as seen in FIG. 4C. In addition, by rewiring the regulatory network using genetic parts that have been identified, the nitrogen fixation activity level was tuned predictably. This is seen in FIG. 4B, which illustrates strains CM023, CM021, CM015, and CI006. Strain CM023 is an evolved strain low; strain CM021 is an evolved strain high; strain CM015 is an evolved strain mid; strain CI006 is a wild-type (strain 2). Ammonia excreted into culture supernatants was tested using a enzymatic-based assay (MEGAZYME). The assay measures the amount of NADPH consumed in the absorbance of 340 nm. The assay was conducted on bacterial cultures grown in nitrogen-free, anaerobic environment with a starting density of 1E9 CFU/ml. Across a panel of six evolved strains, one strain excreted up to 100 µM of ammonia over a course of a 48 hour period, as seen in FIG. 4D. Further, a double mutant exhibited higher ammonia excretion than the single mutant from which it was derived, as seen in FIG. 11. This demonstrates a microbial capacity to produce ammonia in excess of its physiological needs.

Transcription Profiling of Pure Cultures

Transcriptional activity of CI006 was measured using the Nanostring Elements platform. Cells were grown in nitrogen-free media and 10E8 cells were collected after 4 hours incubation. Total RNA was extracted using the Qiagen RNeasy kit. Purified RNA was submitted to Core Diagnostics in Palo Alto, Calif., for probe hybridization and Digital Analyzer analysis, as shown in FIG. 5.

Example 5: In Planta Phenotyping of Candidate Microbes

Colonization of Plants by Candidate Microbes

Figure 6:
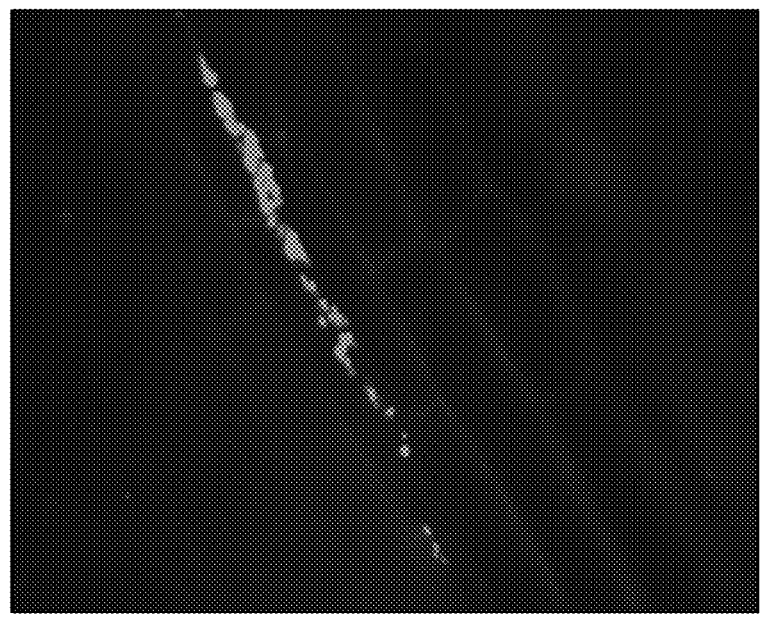
FIG. 6 depicts CI006 colonization of corn roots. Corn seedlings were inoculated with CI006 harboring an RFP expression plasmid. After two weeks of growth and plasmid maintenance through watering with the appropriate antibiotic, roots were harvested and imaged through fluorescence microscopy. Colonization of the root intercellular space is observed.

Colonization of desired host plants by a candidate microbe was quantified through short-term plant growth experiments. Corn plants were inoculated with strains expressing RFP either from a plasmid or from a Tn5-integrated RFP expression cassette. Plants were grown in both sterilized sand and nonsterile peat medium, and inoculation was performed by pipetting 1 mL of cell culture directly over the emerging plant coleoptile three days post-germination. Plasmids were maintained by watering plants with a solution containing the appropriate antibiotic. After three weeks, plant roots were collected, rinsed three times in sterile water to remove visible soil, and split into two samples. One root sample was analyzed via fluorescence microscopy to identify localization patterns of candidate microbes. Microscopy was performed on 10 mm lengths of the finest intact plant roots, as shown in FIG. 6.

A second quantitative method for assessing colonization was developed. A quantitative PCR assay was performed on whole DNA preparations from the roots of plants inoculated with the endophytes. Seeds of corn (Dekalb DKC-66-40) were germinated in previously autoclaved sand in a 2.5 inch by 2.5 inch by 10 inch pot. One day after planting, 1 ml of endophyte overnight culture (SOB media) was drenched right at the spot of where the seed was located. 1 mL of this overnight culture is roughly equivalent to about $10^9$ cfu, varying within 3-fold of each other, depending on which strain is being used. Each seedling was fertilized 3× weekly with 50 mL modified Hoagland's solution supplemented with either 2.5 mM or 0.25 mM ammonium nitrate. At four weeks after planting, root samples were collected for DNA extraction. Soil debris were washed away using pressurized water spray. These tissue samples were then homogenized using QIAGEN Tissuelyzer and the DNA was then extracted using QIAmp DNA Mini Kit (QIAGEN) according to the recommended protocol. qPCR assay was performed using Stratagene Mx3005P RT-PCR on these DNA extracts using primers that were designed (using NCBI's Primer BLAST) to be specific to a loci in each of the endophyte's genome. The presence of the genome copies of the endophytes was quantified. To further confirm the identity of the endophytes, the PCR amplification products were sequenced and are confirmed to have the correct sequence. The summary of the colonization profile of strain CI006 and CI008 from candidate microbes are presented in Table 5. Colonization rate as high as $10^7$× cfu/g fw of root was demonstrated in strain CI008.

TABLE 5

Colonization of corn as measured by qPCR

| Strain | Colonization Rate (CFU/g fw) |
| --- | --- |
| CI006 | $1.45 \times 10^5$ |
| CI008 | $1.24 \times 10^7$ |

In Planta RNA Profiling

Biosynthesis of nif pathway components in planta was estimated by measuring the transcription of nif genes. Total RNA was obtained from root plant tissue of CI006 inoculated plants (planting methods as described previously). RNA extraction was performed using RNEasy Mini Kit according to the recommended protocol (QIAGEN). Total RNA from these plant tissues was then assayed using Nanostring Elements kits (NanoString Technologies, Inc.) using probes that were specific to the nif genes in the genome of strain CI006. The data of nif gene expression in planta is summarized in Table 6. Expression of nifH genes was detected in plants inoculated by CM013 strains whereas nifH expression was not detectable in CI006 inoculated plants. Strain CM013 is a derivative of strain CI006 in which the nifL gene has been knocked out.

Highly expressed genes of CM011, ranked by transcripts per kilobase million (TPM), were measured in planta under fertilized condition. The promoters controlling expression of some of these highly expressed genes were used as templates for homologous recombination into targeted nitrogen fixation and assimilation loci. RNA samples from greenhouse grown CM011 inoculated plant were extracted, rRNA removed using Ribo-Zero kit, sequenced using Illumina's Truseq platform and mapped back to the genome of CM011. Highly expressed genes from CM011 are listed in Table 7.

TABLE 6

Expression of nifH in planta

| Strains | Relative Transcript Expression |
| --- | --- |
| CI006 | 9.4 |
| CM013 | 103.25 |

TABLE 7

| Gene Name | Gene Location | Direction | Raw Read Count | TPM (Transcripts Per Kilobase Million) |
| --- | --- | --- | --- | --- |
| rpsH CDS | 18196-18588 | reverse | 4841.5 | 27206.4 |
| rplQ CDS | 11650-12039 | reverse | 4333 | 24536.2 |
| rpsJ CDS | 25013-25324 | reverse | 3423 | 24229 |
| rplV CDS | 21946-22278 | reverse | 3367.5 | 22333 |
| rpsN CDS | 18622-18927 | reverse | 2792 | 20150.1 |
| rplN CDS | 19820-20191 | reverse | 3317 | 19691.8 |
| rplF CDS | 17649-18182 | reverse | 4504.5 | 18628.9 |
| rpsD CDS | 13095-13715 | reverse | 5091.5 | 18106.6 |
| rpmF CDS | 8326-8493 | forward | 1363.5 | 17923.8 |
| rplW CDS | 23429-23731 | reverse | 2252 | 16413.8 |
| rpsM CDS | 14153-14509 | reverse | 2269 | 14036.2 |
| rplR CDS | 17286-17639 | reverse | 2243.5 | 13996.1 |
| rplC CDS | 24350-24979 | reverse | 3985 | 13969.2 |
| rplK CDS | 25526-25954 | reverse | 2648.5 | 13634.1 |
| rplP CDS | 20807-21217 | reverse | 2423 | 13019.5 |
| rplX CDS | 19495-19809 | reverse | 1824 | 12787.8 |
| rpsQ CDS | 20362-20616 | reverse | 1460.5 | 12648.7 |
| bhsA 3 CDS | 79720-79977 | reverse | 1464 | 12531.5 |
| rpmC CDS | 20616-20807 | reverse | 998.5 | 11485 |
| rpoA CDS | 12080-13069 | reverse | 4855 | 10830.2 |
| rplD CDS | 23728-24333 | reverse | 2916.5 | 10628.5 |
| bhsA 1 CDS | 78883-79140 | reverse | 1068 | 9141.9 |
| rpsS CDS | 22293-22571 | reverse | 1138.5 | 9011.8 |
| rpmA CDS | 2210-2467 | forward | 1028.5 | 8803.7 |
| rpmD CDS | 16585-16764 | reverse | 694.5 | 8520.8 |
| rplB CDS | 22586-23410 | reverse | 3132 | 8384 |
| rpsC CDS | 21230-21928 | reverse | 2574.5 | 8133.9 |
| rplE CDS | 18941-19480 | reverse | 1972.5 | 8066.9 |
| rplO CDS | 16147-16581 | reverse | 1551 | 7874.2 |
| preprotein translocase subunit SecY CDS | 14808-16139 | reverse | 4657 | 7721.2 |
| rpsE CDS | 16771-17271 | reverse | 1671.5 | 7368 |
| rpsK CDS | 13746-14135 | reverse | 1223.5 | 6928.2 |
| tufA CDS | 27318-28229 | reverse | 2850 | 6901.3 |

TABLE 7-continued

| Gene Name | Gene Location | Direction | Raw Read Count | TPM (Transcripts Per Kilobase Million) |
| --- | --- | --- | --- | --- |
| rpmI CDS | 38574-38771 | forward | 615 | 6859.5 |
| rplU CDS | 1880-2191 | forward | 935.5 | 6621.7 |
| rplT CDS | 38814-39170 | forward | 1045 | 6464.4 |
| bhsA 2 CDS | 79293-79550 | reverse | 754 | 6454.1 |
| rpmB CDS | 8391-8627 | reverse | 682 | 6355.1 |
| rplJ CDS | 23983-24480 | reverse | 1408 | 6243.9 |
| fusA 2 CDS | 481-2595 | reverse | 5832 | 6089.6 |
| rpsA CDS | 25062-26771 | reverse | 4613 | 5957.6 |
| rpmJ CDS | 14658-14774 | reverse | 314 | 5926.9 |
| rpsR CDS | 52990-53217 | forward | 603 | 5840.7 |
| rpsG CDS | 2692-3162 | reverse | 1243 | 5828.2 |
| rpsI CDS | 11354-11746 | reverse | 980.5 | 5509.8 |
| cspC 1 CDS | 8091-8300 | reverse | 509 | 5352.8 |
| rpsF CDS | 52270-52662 | forward | 916 | 5147.4 |
| rpsT CDS | 55208-55471 | reverse | 602 | 5035.9 |
| infC CDS | 38128-38478 | forward | 755 | 4750.3 |
| cspG CDS | 30148-30360 | forward | 446 | 4624.2 |

$^{15}$N Assay

The primary method for demonstrating fixation uses the nitrogen isotope 15N, which is found in the atmosphere at a set rate relative to 14N. By supplementing either fertilizer or atmosphere with enriched levels of 15N, one can observe fixation either directly, in heightened amounts of 15N fixed from an atmosphere supplemented with 15N2 gas (Yoshida 1980), or inversely, through dilution of enriched fertilizer by atmospheric N2 gas in plant tissues (Iniguez 2004). The dilution method allows for the observation of cumulative fixed nitrogen over the course of plant growth, while the $15N_2$ gas method is restricted to measuring the fixation that occurs over the short interval that a plant can be grown in a contained atmosphere (rate measurement). Therefore, the gas method is superior in specificity (as any elevated $15N_2$ levels in the plant above the atmospheric rate can be attributed unambiguously to fixation) but cannot show cumulative activity.

Figure 7:
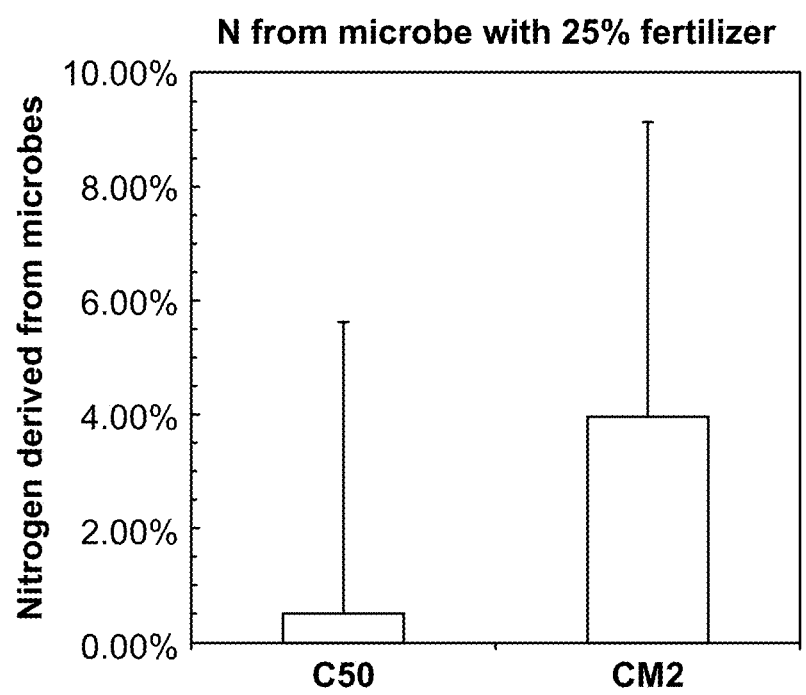
FIG. 7 depicts nitrogen derived from microbe level in WT (CI050) and optimized (CM002) strain.
Figure 12:
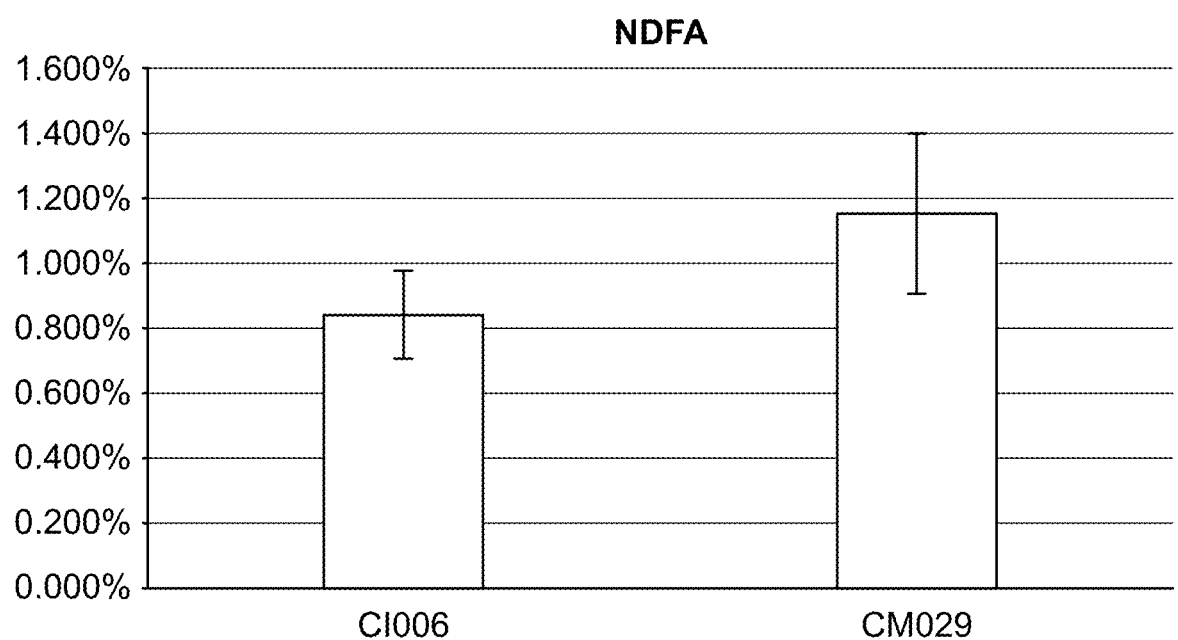
FIG. 12 depicts NDFA obtained from 15N Gas Uptake experiment (extrapolated back using days exposed) to measure NDFA in Corn plants in fertilized condition.
Figure 13:
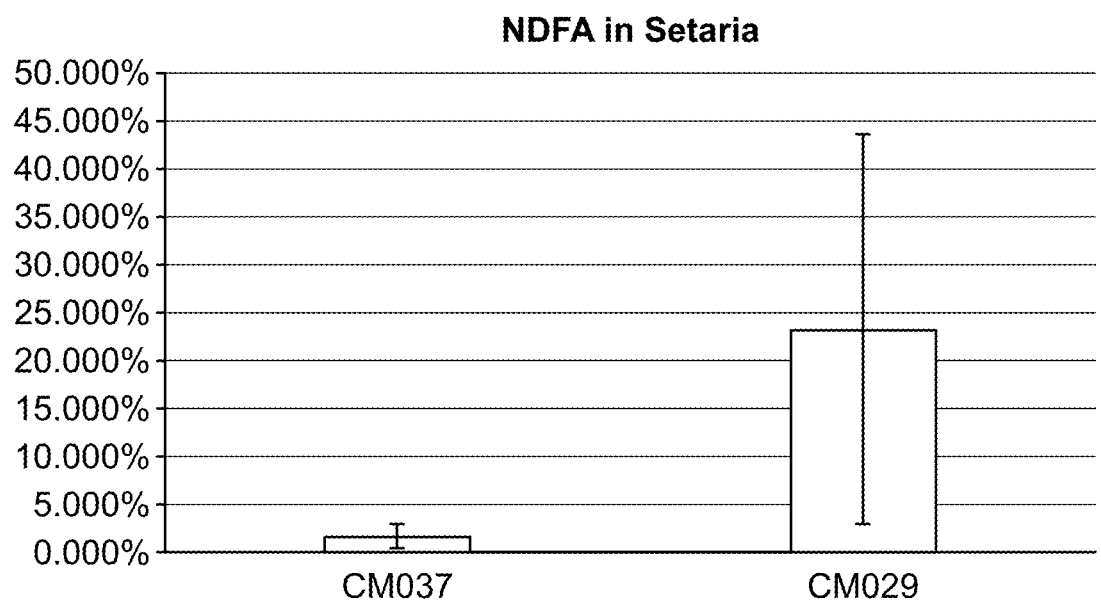
FIG. 13 depicts NDFA value obtained from 15N Gas Uptake experiment (extrapolated back using days exposed) to measure NDFA in *Setaria* plants in fertilized condition.
Figure 14A:
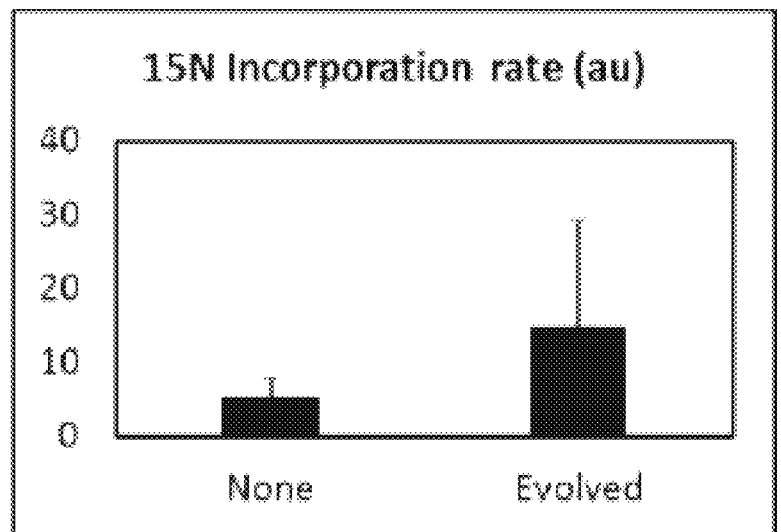
FIG. 14A depicts rate of incorporation of 15N gas. Plants inoculated with evolved strain showed increase in 15N gas incorporation compared to uninoculated plants.
Figure 14B:
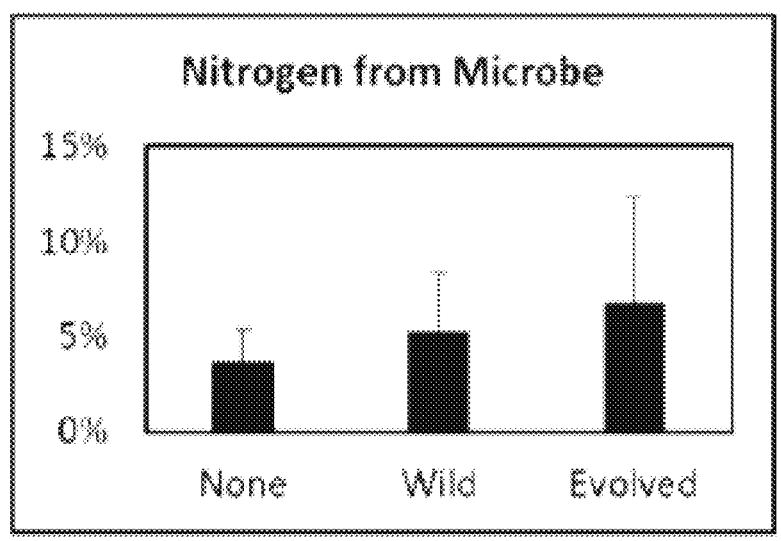
FIG. 14B depicts 4 weeks after planting, up to 7% of the nitrogen in plants inoculated with an evolved strain is derived from microbially fixed nitrogen.
Figure 14C:
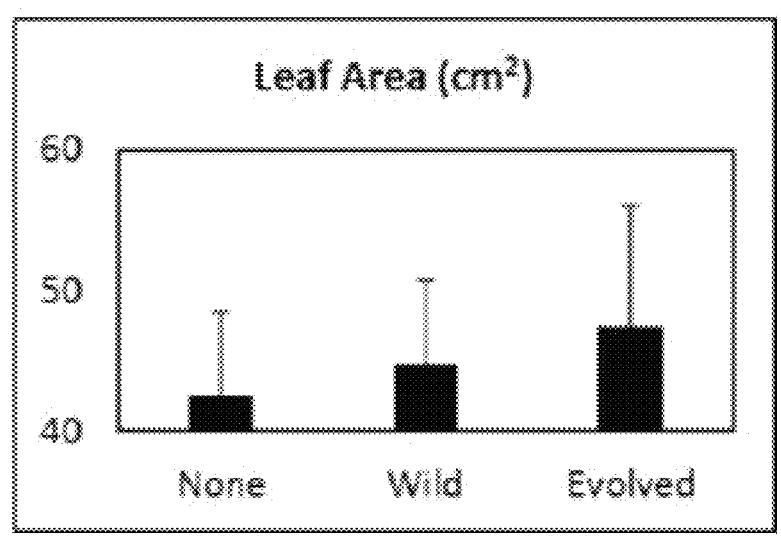
FIG. 14C depicts leaf area (and other biomass measurement, data not shown) is increased in plants inoculated with an evolved strain when compared to uninoculated or wild type inoculated plants.

Both types of assay has been performed to measure fixation activity of improved strains relative to wild-type and uninoculated corn plants, and elevated fixation rates were observed in planta for several of the improved strains (FIG. 12, FIG. 14A, and FIG. 14B). These assays are instrumental in demonstrating that the activity of the strains observed in vitro translates to in vivo results. Furthermore, these assays allow measurement of the impact of fertilizer on strain activity, suggesting suitable functionality in an agricultural setting. Similar results were observed when setaria plants were inoculated with wild-type and improved strains (FIG. 13). In planta fixation activity shown in FIGS. 14A-14C is further backed up by transcriptomic data. Evolved strains exhibit increased nifH transcript level relative to wild-type counterparts. Furthermore, the microbe derived nitrogen level in planta is also correlated with the colonization level on a plant by plant basis. These results (FIG. 12, FIG. 13, FIGS. 14A-14C, FIG. 15A, and FIG. 15B) support the hypothesis that the microbe, through the improved regulation of the nif gene cluster, is the likely reason for the increase in atmospheric derived nitrogen seen in the plant tissue. In addition to measuring fixation directly, the impact of inoculating plants with the improved strains in a nitrogen-stressed plant biomass assay was measured. While plant biomass may be related to many possible microbe interactions with the plant, one would expect that the addition of fixed nitrogen would impact the plant phenotype when nitrogen is limited. Inoculated plants were grown in the complete absence of nitrogen, and significant increases in leaf area, shoot fresh and dry weight, and root fresh and dry weight in inoculated plants relative to untreated controls was observed (FIG. 14C). Although these differences cannot be attributed to nitrogen fixation exclusively, they support the conclusion that the improved strains are actively providing nitrogen to the plant. Corn and *setaria* plants were grown and inoculated as described above. Fertilizer comprising 1.2% $^{15}$N was regularly supplied to plants via watering. Nitrogen fixation by microbes was quantified by measuring the $^{15}$N level in the plant tissue. Fourth leaf tissue was collected and dried at 4 weeks after planting. Dried leaf samples were homogenized using beads (QIAGEN Tissuelyzer) and aliquoted out into tin capsules for IRMS (MBL Stable Isotope Laboratory at The Ecosystems Center, Woods Hole, Mass.). Nitrogen derived from the atmosphere (NDFA) was calculated, and nitrogen production by CI050 and CM002 are shown in FIG. 7.

Phytohormone Production Assay

Figure 8:
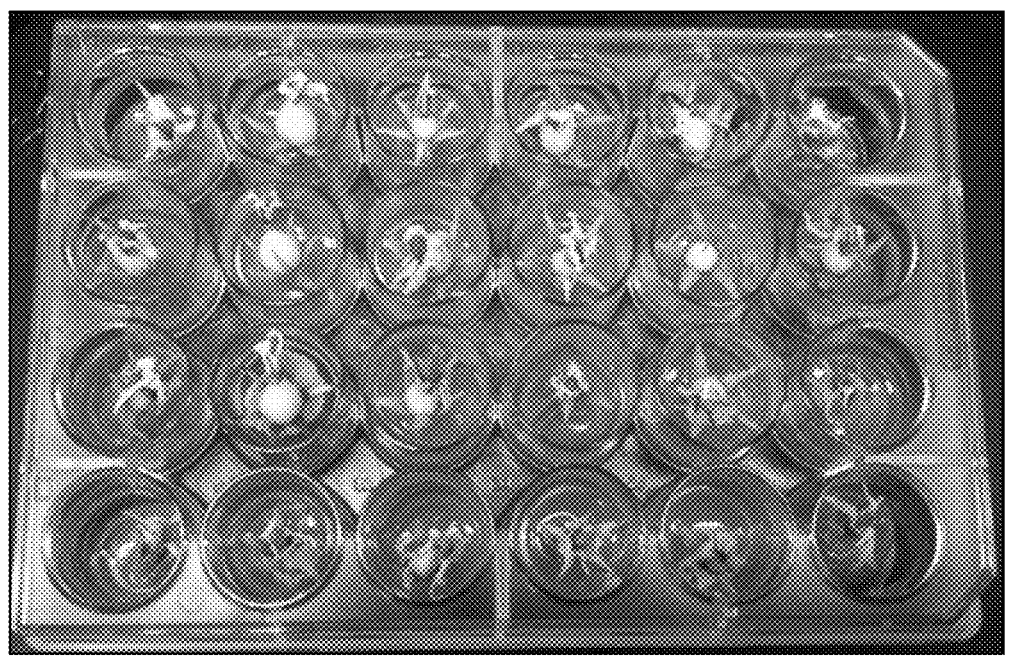
FIG. 8 shows an experimental setup for a Micro-Tom fruiting mass assay.
Figure 9:
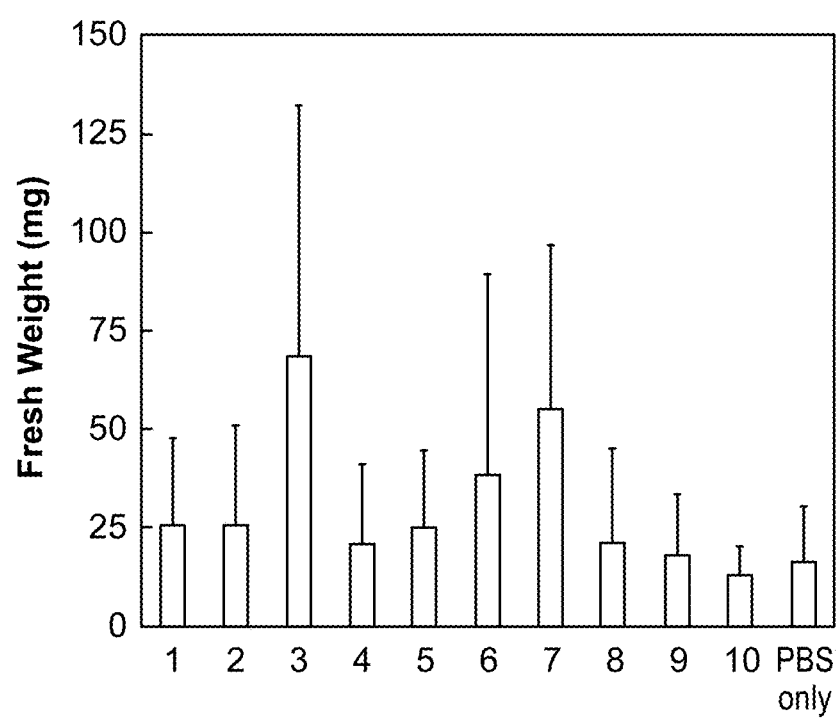
FIG. 9 shows a screen of 10 strains for increase in Micro-Tom plant fruit mass. Results for six replicates are presented. For column 3, p=0.07. For column 7, p=0.05.

The dwarf tomato (*Solanum lycopersicum*) cultivar 'Micro-Tom' has previously been used to study the influence of indole-3-acetic acid on fruit ripening through an in vitro assay (Cohen 1996; J Am Soc Hortic Sci 121: 520-524). To evaluate phytohormone production and secretion by candidate microbes, a plate-based screening assay using immature Micro-Tom fruit was developed. Twelve-well tissue culture test plates were prepared by filling wells with agar medium, allowing it to solidify, and spotting 10 uL of overnight microbial cultures onto the agar surface, as shown in FIG. 8. Wells with agar containing increasing amounts of gibberellic acid (GA) but no bacterial culture were used as a positive control and standards. Flowers one day post-anthesis abscised from growing Micro-Tom plants were inserted, stem-first, into the agar at the point of the bacterial spot culture. These flowers were monitored for 2-3 weeks, after which the fruits were harvested and weighed. An increase in plant fruit mass across several replicates indicates production of plant hormone by the inoculant microbe, as shown in FIG. 9.

Example 6: Cyclical Host-Microbe Evolution

Corn plants were inoculated with CM013 and grown 4 weeks to approximately the V5 growth stage. Those demonstrating improved nitrogen accumulation from microbial sources via $^{15}$N analysis were uprooted, and roots were washed using pressurized water to remove bulk soil. A 0.25 g section of root was cut and rinsed in PBS solution to remove fine soil particles and non-adherent microbes. Tissue samples were homogenized using 3 mm steel beads in QIAGEN TissueLyser II. The homogenate was diluted and plated on SOB agar media. Single colonies were resuspended in liquid media and subjected to PCR analysis of 16s rDNA and mutations unique to the inoculating strain. The process of microbe isolation, mutagenesis, inoculation, and re-isolation can be repeated iteratively to improve microbial traits, plant traits, and the colonization capability of the microbe.

Example 7: Compatibility Across Geography

The ability of the improved microbes to colonize an inoculated plant is critical to the success of the plant under field conditions. While the described isolation methods are designed to select from soil microbes that may have a close relationship with crop plants such as corn, many strains may not colonize effectively across a range of plant genotypes, environments, soil types, or inoculation conditions. Since colonization is a complex process requiring a range of interactions between a microbial strain and host plant, screening for colonization competence has become a central method for selecting priority strains for further development. Early efforts to assess colonization used fluorescent tagging of strains, which was effective but time-consuming and not scalable on a per-strain basis. As colonization activity is not amenable to straightforward improvement, it is imperative that potential product candidates are selected from strains that are natural colonizers.

An assay was designed to test for robust colonization of the wild-type strains in any given host plant using qPCR and primers designed to be strain-specific in a community sample. This assay is intended to rapidly measure the colonization rate of the microbes from corn tissue samples. Initial tests using strains assessed as probable colonizers using fluorescence microscopy and plate-based techniques indicated that a qPCR approach would be both quantitative and scalable.

A typical assay is performed as follows: Plants, mostly varieties of maize and wheat, are grown in a peat potting mix in the greenhouse in replicates of six per strain. At four or five days after planting, a 1 mL drench of early stationary phase cultures of bacteria diluted to an OD590 of 0.6-1.0 (approximately 5E+08 CFU/mL) is pipetted over the emerging coleoptile. The plants are watered with tap water only and allowed to grow for four weeks before sampling, at which time, the plants are uprooted and the roots washed thoroughly to remove most peat residues. Samples of clean root are excised and homogenized to create a slurry of plant cell debris and associated bacterial cells. We developed a high-throughput DNA extraction protocol that effectively produced a mixture of plant and bacterial DNA to use as template for qPCR. Based on bacterial cell spike-in experiments, this DNA extraction process provides a quantitative bacterial DNA sample relative to the fresh weight of the roots. Each strain is assessed using strain-specific primers designed using Primer BLAST (Ye 2012) and compared to background amplification from uninoculated plants. Since some primers exhibit off-target amplification in uninoculated plants, colonization is determined either by presence of amplification or elevated amplification of the correct product compared to the background level.

Figure 16A:
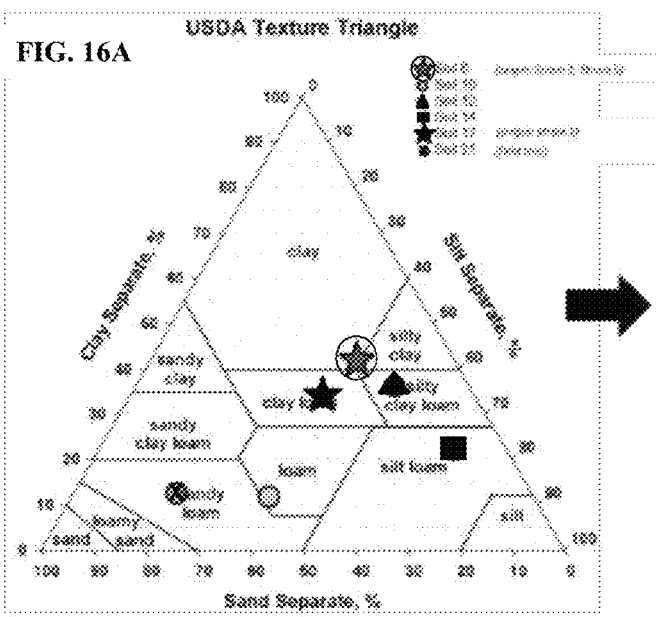
FIG. 16A depicts a soil texture map of various field soils tested for colonization. Soils in which a few microbes were originally source from are indicated as stars.
Figure 16B:
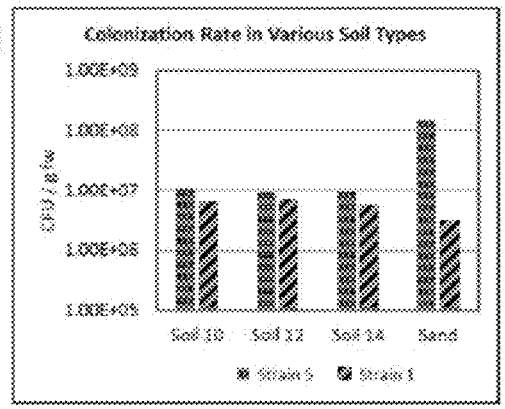
FIG. 16B depicts the colonization rate of Strain 1 and Strain 5 that are tested across four different soil types (circles). Both strains showed relatively robust colonization profile across diverse soil types.

This assay was used to measure the compatibility of the microbial product across different soil geography. Field soil qualities and field conditions can have a huge influence on the effect of a microbial product. Soil pH, water retention capacity, and competitive microbes are only a few examples of factors in soil that can affect inoculum survival and colonization ability. A colonization assay was performed using three diverse soil types sampled from agricultural fields in California as the plant growth medium (FIG. 16A). An intermediate inoculation density was used to approximate realistic agricultural conditions. Within 3 weeks, Strain 5 colonized all plants at 1E+06 to 1E+07 CFU/g FW. After 7 weeks of plant growth, an evolved version of Strain 1 exhibited high colonization rates (1E+06 CFU/g FW) in all soil types. (FIG. 16B).

Figure 16C:
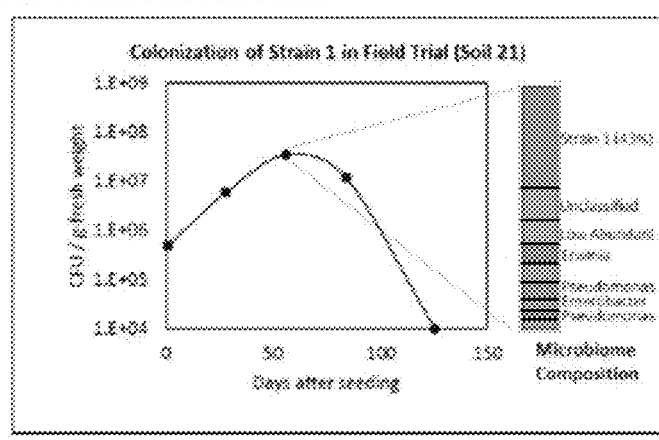
FIG. 16C depicts colonization of Strain 1 as tested in a field trial over the span of a growing season. Strain 1 persists in the corn tissue up to week 12 after planting and starts to show decline in colonization after that time.

Additionally, to assessment colonization in the complexity of field conditions, a 1-acre field trial in San Luis Obispo in June of 2015 was initiated to assess the impacts and colonization of seven of the wild-type strains in two varieties of field corn. Agronomic design and execution of the trial was performed by a contract field research organization, Pacific Ag Research. For inoculation, the same peat culture seed coating technique tested in the inoculation methods experiment was employed. During the course of the growing season, plant samples were collected to assess for colonization in the root and stem interior. Samples were collected from three replicate plots of each treatment at four and eight weeks after planting, and from all six reps of each treatment shortly before harvest at 16 weeks. Additional samples were collected from all six replicate plots of treatments inoculated with Strain 1 and Strain 2, as well as untreated controls, at 12 weeks. Numbers of cells per gram fresh weight of washed roots were assessed as with other colonization assays with qPCR and strain-specific primers. Two strains, Strain 1 and Strain 2, showed consistent and widespread root colonization that peaked at 12 weeks and then declined precipitously (FIG. 16C). While Strain 2 appeared to be present in numbers an order of magnitude lower than Strain 1, it was found in more consistent numbers from plant to plant. No strains appeared to effectively colonize the stem interior. In support of the qPCR colonization data, both strains were successfully re-isolated from the root samples using plating and 16S sequencing to identify isolates of matching sequence The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 3A

| Name | Minimum | Maximum | Length | Direction |
|---|---|---|---|---|
| murein lipoprotein CDS | 2,929,898 | 2,930,134 | 237 | forward |
| membrane protein CDS | 5,217,517 | 5,217,843 | 327 | forward |
| zinc/cadmium-binding protein CDS | 3,479,979 | 3,480,626 | 648 | forward |
| acyl carrier protein CDS | 4,563,344 | 4,563,580 | 237 | reverse |
| ompX CDS | 4,251,002 | 4,251,514 | 513 | forward |
| DNA-binding protein HU-beta CDS | 375,156 | 375,428 | 273 | forward |
| sspA CDS | 629,998 | 630,636 | 639 | reverse |
| tatE CDS | 3,199,435 | 3,199,638 | 204 | reverse |
| LexA repressor CDS | 1,850,457 | 1,851,065 | 609 | forward |
| hisS CDS | <3999979 | 4,001,223 | >1245 | forward |

TABLE 3B

| Name | Differential Expression Absolute Confidence | Differential Expression Ratio | RNASeq_nifL - Raw Read Count | RNASeq_nifL - Raw Transcript Count | RNASeq_WT - Raw Read Count | RNASeq_WT - Raw Transcript Count |
|---|---|---|---|---|---|---|
| murein lipoprotein CDS | 1000 | −1.8 | 12950.5 | 10078.9 | 5151.5 | 4106.8 |
| membrane protein CDS | 1000 | −1.3 | 9522.5 | 5371.3 | 5400 | 3120 |
| zinc/cadmium-binding protein CDS | 3.3 | 1.1 | 6461 | 1839.1 | 5318 | 1550.6 |
| acyl carrier protein CDS | 25.6 | 1.6 | 1230.5 | 957.6 | 1473.5 | 1174.7 |
| ompX CDS | 1.7 | 1.1 | 2042 | 734.2 | 1687.5 | 621.5 |
| DNA-binding protein HU-beta CDS | 6.9 | −1.3 | 1305 | 881.7 | 725 | 501.8 |
| sspA CDS | 0.2 | 1 | 654 | 188.8 | 504.5 | 149.2 |
| tatE CDS | 1.4 | 1.3 | 131 | 118.4 | 125 | 115.8 |
| LexA repressor CDS | 0.1 | −1.1 | 248 | 75.1 | 164 | 50.9 |
| hisS CDS | 0 | −1.1 | 467 | 69.2 | 325 | 49.3 |

TABLE 3C

| Name | Prm (In Forward direction, -250 to +10 region) | SEQ ID NO: | Expressed Seequence | SEQ ID NO: | Neighbor Sequence | SEQ ID NO: |
|---|---|---|---|---|---|---|
| murein lipoprotein CDS | GCCTCTCGGGGCG CTTTTTTTTATTCC GGCACTAGCCGCT ATTAATAAAAATG CAAATCGGAATTT ACTATTTAACGCG AGATTATCTAAGA TGAATCCGATGGA AGCGCGCTGTTTTC ACTCGCCTTTTTAA AGTTACGTGATGA TTTCGATGCTTCTT TGAGCGAACGATC AAAAATAAGCGTA TTCAGGTAAAAAA ATATTCTCATCACA AAAAAGTTTGTGT AATACTTGTAACG CT--- ACATGGAGATTAA CTC | 3 | ATGAATCGTACTA AACTGGTACTGGG CGCGGTAATCCTG GGTTCTACTCTGCT GGCTGGTTGCTCCA GCAATGCTAAAAT CGATCAGCTGTCTT CTGACGTTCAGACT CTGAACGCTAAAG TTGACCAGCTGAG CAACGACGTGAAC GCAATGCGTTCCG ACGTTCAGGCTGCT AAAGATGACGCAG CTCGCGCTAACCA GCGTCTGGACAAC GCAGCTACTAAAT ACCGTAAGTAA | 13 | ATGAAAAAGACCA AAATTGTTTGCACC ATCGGTCCGAAAA CCGAATCCGAAGA GATGTTGACCAAA ATGCTGGACGCGG GCATGAACGTTAT GCGTCTGAACTTCT CTCACGGTGACTAT GCGGAACACGGTC AGCGCATCCAGAA TCTGCGCAATGTG ATGAGTAAAACCG GTAAGAAAGCGGC AATCCTGCTGGAC ACCAAAGGTCCGG AAATCCGTACCATT AAGCTGGAAGGCG GCAACGACGTCTC CCTGAAAGCGGGC CAGACCTTCACCTT CACCACCGATAAA TCCGTTGTCGGTAA TAACGAAATCGTT GCGGTGACCTATG AAGGCTTCACCAG CGACCTGAGCGTT GGCAACACGGTAC TGGTTGACGATGG TCTGATCGGTATGG AAGTGACCGCTAT CGAAGGCAACAAA GTTGTTTGTAAAGT GCTGAACAACGGC GACCTCGGCGAGA ACAAAGGCGTTAA CCTGCCGGGCGTA TCTATCGCGCTGCC GGCGCTGGCTGAA AAAGACAAACAGG ATCTGATCTTCGGT TGCGAACAGGGCG TTGACTTTGTTGCG GCATCCTTTATCCG TAAGCGTTCTGAC GTTGTTGAAATCCG TGAGCACCTGAAA GCCCACGGCGGCG AGAAGATCCAGAT CATCTCCAAAATC GAAAACCAGGAAG GCCTGAACAACTT CGACGAAATCCTC GAAGCCTCTGACG GCATCATGGTAGC CCGTGGCGACCTG GGCGTTGAAATCC CGGTTGAAGAAGT TATCTTCGCGCAGA AGATGATGATCGA GAAATGTATCCGC GCGCGTAAAGTCG TTATCACCGCGACC CAGATGCTGGATT CCATGATCAAAAA CCCGCGTCCGACC CGTGCGGAAGCAG GCGACGTGGCCAA CGCCATCCTCGAC GGCACCGACGCAG TTATGCTGTCCGGC GAATCCGCGAAAG GTAAATACCCGCT GGAAGCGGTCACC ATCATGGCGACCA TCTGCGAACGTAC | 23 |

TABLE 3C-continued

| Name | Prm (In Forward direction, −250 to +10 region) | SEQ ID NO: | Expressed Seequence | SEQ ID NO: | Neighbor Sequence | SEQ ID NO: |
|---|---|---|---|---|---|---|
| | | | | | CGACCGCGTCATG ACCAGCCGTCTTG AGTACAACAACGA CAACCGTAAGCTG CGCATCACCGAAG CGGTGTGCCGCGG TGCGGTAGAAACG GCTGAAAAACTGG AAGCGCCGCTGAT CGTTGTGGCAACC CAGGGCGGTAAAT CCGCGCGCGCCGT ACGTAAATACTTCC CGGATGCCACTAT CCTGGCGCTGACC ACCAACGAAACCA CCGCGCGTCAGCT GGTGCTGAGCAAA GGCGTTGTGGCAC AGCTGGTTGAAGA TATCTCCTCTACCG ATGCGTTCTACATC CAGGGTAAAGAAC TGGCGCTGCAGAG CGGTCTGGCGCGT AAAGGCGACGTGG TTGTTATGGTTTCC GGCGCGTTAGTCC CGAGCGGAACCAC CAATACCGCTTCCG TGCACGTGCTGTA A | |
| membrane protein CDS | GGTTCACATAAAC ATAATTATCGCCAC GGCGATAGCCGTA CGCTTTTTGCGTCA CAACATCCATGGT GAAGCCGGCTTTTT CAAGAACACGCGC CACCTCATCGGGTC TTAAATACATACTC ATTCCTCATTATCT TTTTACCGCACGTTA ACCTTACCTTATTC ATTAAAGGCAACG CTTTCGGAATATTC CATAAAGGGCTAT TTACAGCATAATTC AAAATCTTGTCCTA CACTTATAGACTCA ATGGAATTAAGGG A | 4 | ATGGCCAACCGAG CAAACCGCAACAA CGTAGAAGAGAGC GCTGAAGATATCC ATAACGATGTCAG CCAATTAGCGGAT ACGCTGGAAGAGG TGCTGAAATCGTG GGGCAGCGACGCC AAAGACGAAGCGG AGGCCGCGCGCAA AAAAGCGCAGGCG CTGCTGAAAGAGA CCCGCGCCCGGCTT AACGGCAACAACC GCGTCCAGCAGGC GGCGTGCGACGCC ATGGGCTGCGCTG ACAGCTACGTGCG CGACAAACCGTGG CAAAGCGTCGGCG CCGCAGCAGCCGT TGGGGTATTTATTG GCGTATTACTGAAT TTACGTCGATAA | 14 | ATGTATTTAAGACC CGATGAGGTGGCG CGTGTTCTTGAAAA AGCCGGCTTCACC ATGGATGTTGTGA CGCAAAAAGCGTA CGGCTATCGCCGT GGCGATAATTATG TTTATGTGAACCGT GAAGCTCGTATGG GGCGTACCGCGTT AATTATTCATCCGG CTTTAAAAGAGCG CAGCACAACGCTT GCGGAGCCCGCGT CGGATATCAAAAC CTGCGATCATTATG AGCAGTTCCCGCTC TATTTAGCGGGGG ATGCTCAACAGCA TTATGGTATTCCAC ACGGGTTCAGTTC GCGAATGGCGCTT GAGCGTTTTCTGAG TGGCCTGTTTGGCG AAACGCAGTATAG CTGA | 24 |
| zinc/ cadmium- binding protein CDS | GCGCGGAAAATCG ACGCATAGCGCAT TCTCAGAAGCCGG CCTGGTCTCGGTGG AAAAGCGAATCTT TCCCACGACCGCC GGGCCTTTAACAA AGAATCAATGAC CTGATTAATGTCGC TATCCATTCTCTCT CCGCGTAATGCGA TCTTTTTTTCATCAT ACCTAACAAACTG GCAGAGGGAAAAG CCGCGCGGTTTTTC | 5 | ATGACCAAAAGA TTTCCGCCCTAGCG TTTGGCATTGGCAT GGTAATGGCGAGC AGCCAGGCTTTTGC CCACGGTCACCAT AGTCATGGCCCGG CGCTGACCGAAGC GGAACAAAAGGCG AGTGAAGGCATTT TTGCTGACCAGGA CGTAAAGGACAGG GCGCTGAGCGACT GGGAGGGGATCTG GCAGTCGGTTAAC | 15 | ATGGATAGCGACA TTAATCAGGTCATT GATTCTTTTGTTAA AGGCCCGGCGGTC GTGGGAAAGATTC GCTTTTCCACCGAG ACCAGGCCGGCTT CTGAGAATGCGCT ATGCGTCGATTTTC CGCGCCTCGAAAT CATGCTTGCGGGTC AGCTTCACGATCC GGCGATTAAAGCC GATCGCGCCCAGC TCATGCCGCACGA | 25 |

TABLE 3C-continued

| Name | Prm (In Forward direction, -250 to +10 region) | SEQ ID NO: | Expressed Seequence | SEQ ID NO: | Neighbor Sequence | SEQ ID NO: |
|---|---|---|---|---|---|---|
| | TGCGAAGTGTATT GTAAGATTTGTTTG ATATGTTATATCGT AACATATTATTGCA AACAT | | CCCTATCTGCTGAA CGGGGATTTAGAT CCGGTTCTGGAGC AGAAGGCCAAAAA GGCCGGTAAAAGC GTGGCGGAATATC GGGAATATTATAA GAAGGGCTACGCT ACCGATGTCGACC AGATTGGTATCGA GGATAACGTCATG GAGTTTCACGTCG GGAAAACCGTCAA CGCCTGTAAGTAC AGCTATTCCGGTTA CAAAATTCTGACCT ACGCATCCGGTAA AAAAGGCGTGCGC TACCTGTTCGAATG CCAGCAGGCGGAT TCAAAAGCGCCGA AGTTTGTTCAGTTT AGCGATCACACCA TCGCGCCACGCAA GTCCCAGCATTTCC ACATCTTTATGGGC AATGAGTCCCAGG AAGCGCTGCTGAA AGAGATGGATAAC TGGCCAACCTACT ATCCTTATGCGCTG CATAAAGAGCAGA TTGTCGACGAAAT GCTGCACCACTAA | | TGTGCTGTATATTC CCGCTGGCGGATG GAATGACCCGCAA TGGCTGGCGCCCTC CACTCTGCTCACTA TCTTATTTGGTAAA CAGCAGCTGGAAT TCGTCCTGCGCCAC TGGGACGGCAGCG CGCTTAACGTGCTG GATAAACAGCAGG TTCCGCGCCGCGGT CCCCGGGTCGGCT CTTTTCTGCTGCAG GCGCTGAATGAAA TGCAGATGCAGCC GCGGGAGCAGCAC ACGGCCCGCTTTAT TGTCACCAGCCTGC TCAGCCACTGTGCC GATCTGCTGGGCA GCCAGGTACAAAC CTCATCGCGCAGC CAGGCGCTTTTTGA AGCGATTCGTAAG CATATTGACGCCC ACTTTGCCGACCCG TTAACCCGGGAGT CGGTGGCGCAGGC GTTTTACCTCTCGC CAAACTATCTATCC CACCTGTTCCAGA AATGCGGGCCAAT GGGCTTTAACGAG TATCTGAATCACAT CCGCCTGGAGCAG GCCAGAATGCTGT TAAAAGGCCACGA TATGAAAGTGAAA GATATCGCCCACG CCTGCGGTTTCGCC GACAGCAACTACT TCTGCCGCCTGTTT CGCAAAAACACCG AACGCTCGCCGTC GGAGTATCGCCGT CAATATCACAGCC AGCTGACGGAAAA AACAGCCCCGGCA AAAAACTAG | |
| acyl carrier protein CDS | CTGACGAAGCGAG TTACATCACCGGTG AAACTCTGCACGT CAACGGCGGAATG TATATGGTCTGACC GAGATTTGCGCAA AACGCTCAGGAAC CGCGCAGTCTGTG CGGTTCACTGTAAT GTTTTGTACAAAAT GATTTGCGTTATGA GGGCAAACAGCCG CAAAATAGCGTAA AATCGTGGTAAGA CCTGCCGGATTTA GTTGCAAATTTTC AACATTTTATACAC TACGAAAACCATC GCGAAAGCGAGTT TTGA | 6 | ATGAGCACTATCG AAGAACGCGTTAA GAAAATTATCGGC GAACAGCTGGGCG TTAAGCAGGAAGA AGTTACCAACAAT GCTTCCTTCGTTGA AGACCTGGGCGCT GATTCTCTTGACAC CGTTGAGCTGGTA ATGGCTCTGGAAG AAGAGTTTGATAC TGAGATTCCGGAC GAAGAAGCTGAGA AAATCACTACTGTT CAGGCTGCCATTG ATTACATCAACGG CCACCAGGCGTAA | 16 | ATGAGTTTTGAAG GAAAAATCGCGCT GGTTACCGGTGCA AGTCGCGGGATTG GCCGCGCAATCGC TGAAACGCTCGTT GCCCGTGGCGCGA AAGTTATCGGGAC TGCGACCAGCGAA AGCGGCGCGCAGG CGATCAGCGATTA TTTAGGTGCTAACG GTAAAGGTCTGCT GCTGAATGTGACC GATCCTGCATCTAT TGAATCTGTTCTGG GAAATATTCGCGC AGAATTTGGTGAA GTTGATATCCTGGT GAACAATGCCGGG ATCACTCGTGATA ACCTGTTAATGCGC ATGAAAGATGATG AGTGGAACGATAT TATCGAAACCAAC | 26 |

TABLE 3C-continued

| Name | Prm (In Forward direction, -250 to +10 region) | SEQ ID NO: | Expressed Seequence | SEQ ID NO: | Neighbor Sequence | SEQ ID NO: |
|---|---|---|---|---|---|---|
| | | | CTGTCATCTGTTTT CCGTCTGTCAAAA GCGGTAATGCGCG CTATGATGAAAAA GCGTCATGGACGT ATTATCACTATCGG TTCTGTGGTTGGTA CCATGGGAAATGC GGGTCAGGCCAAC TACGCTGCGGCGA AAGCGGGTCTGAT TGGCTTCAGTAAAT CACTGGCTCGCGA AGTTGCGTCCCGC GGTATTACTGTAA ACGTTGTTGCTCCG GGCTTTATTGAAAC GGACATGACGCGT GCGCTGACCGATG AGCAGCGTGCGGG TACGCTGGCGGCA GTTCCTGCGGGGC GCCTCGGCTCTCCA AATGAAATCGCCA GTGCGGTGGCATTT TTAGCCTCTGACGA AGCGAGTTACATC ACCGGTGAAACTC TGCACGTCAACGG CGGAATGTATATG GTCTGA | | | |
| ompX CDS | ACGCCTGGGGCGC CGACCAGCGGGAA GAGTGATTTGGCC AACGAGGCGCCGC TCTGAATGGAAAT CATGGCGATTAAA ATAACCAGTATCG GCAACCATGCCGG TACCTTACGAGAC GAGCCGGGCATCC TTTCTCCTGTCAAT TTTGTCAAATGCGG TAAAGGTTCCAGT GTAATTGAATTACC CCGCGCCGGTTGA GCTAATGTTGAAA AAAAGGGTCTTAA AAGCAGTACAATA GGGCGGGTCTGAA GATAATTTCA | 7 | ATGAATAAAATTG CACGTTTTTCAGCA CTGGCCGTTGTTCT GGCTGCATCCGTA GGTACCACTGCTTT CGCTGCGACTTCTA CCGTTACCGGTGG CTACGCGCAGAGC GACATGCAGGGTG AAGCGAACAAAGC TGGCGGTTTCAACC TGAAGTACCGCTA CGAGCAAGACAAC AACCCGCTGGGTG TTATCGGTTCTTTC ACCTACACCGAAA AAGATCGTTCTGA ATCTGGCGTTTACA AAAAAGGCCAGTA CTACGGCATCACC GCAGGTCCGGCTT ACCGTCTGAACGA CTGGGCTAGCATCT ACGGCGTAGTGGG TGTTGGTTACGGTA AATTCCAGGACAA CAGCTACCCGAAC AAATCTGATATGA GCGACTACGGTTTC TCTTACGGCGCTGG TCTGCAGTTCAACC CGATCGAAAACGT TGCCCTGGACTTCT CCTACGAGCAGTC TCGCATTCGTAACG TTGACGTTGGCACC TGGATTGCTGGCGT AGGTTACCGCTTCT AA | 17 | ATGCCCGGCTCGTC TCGTAAGGTACCG GCATGGTTGCCGA TACTGGTTATTTTA ATCGCCATGATTTC CAT | 27 |
| DNA-binding protein HU-beta CDS | TCTGATTCCTGATG AAAATAAACGCGA CCTTGAAGAAATT CCGGATAACGTTA | 8 | GTGAATAAATCTC AACTGATTGACAA AATTGCTGCCGGT GCGGACATTTCTA | 18 | ATGAATCCTGAGC GTTCTGAACGCATT GAAATCCCCGTATT GCCGTTGCGCGAT | 28 |

TABLE 3C-continued

| Name | Prm (In Forward direction, -250 to +10 region) | SEQ ID NO: | Expressed Seequence | SEQ ID NO: | Neighbor Sequence | SEQ ID NO: |
|---|---|---|---|---|---|---|
| | TCGCCGATTTAGAT ATCCATCCGGTGA AACGAATCGAGGA AGTTCTGGCACTTG CGCTACAGAACGA ACCGTTTGGAATG GAAGTCGTCACGG CAAAATAGTGATT TCGCGCAAATAGC GCTAAGAAAAATA GGGCTGGTAAGTA AATTCGTACTTGCC AGCCTTTTTTTGTG TAGCTAACTTAGAT CGCTGGCAGGGGG GTCAATT | | AAGCCGCAGCTGG ACGTGCGTTAGAT GCTTTAATCGCTTC TGTTACTGAATCTC TGCAGGCTGGAGA TGACGTTGCGCTG GTAGGGTTTGGTA CTTTTGCTGTTAAA GAGCGCGCTGCCC GTACTGGTCGCAA TCCGCAAACAGGC AAAGAAATCACCA TTGCTGCTGCTAAA GTTCCGGGTTTCCG CGCAGGTAAAGCG CTGAAAGACGCGG TAAACTGA | | GTGGTGGTTTATCC GCACATGGTCATA CCCCTGTTTGTAGG GCGGGAAAAATCT ATCCGTTGTCTCGA AGCAGCCATGGAC CATGATAAAAAAA TCATGCTGGTTGCG CAGAAAGAAGCCT CGACGGATGAGCC GGGTGTAAACGAT CTTTTCACCGTCGG GACCGTGGCGTCT ATTTTGCAAATGCT GAAGCTACCGGAC GGTACTGTTAAAG TGCTGGTCGAAGG TTTGCAGCGCGCG CGCATCTCTGCGCT GTCTGATAATGGC GAACATTTTTCGGC GAAGGCGGAATAC CTTGAATCGCCGG CGATTGACGAACG CGAGCAGGAAGTG CTGGTTCGTACCGC TATCAGCCAGTTTG AAGGCTACATCAA GCTGAACAAAAAA ATCCCTCCGGAAG TGCTGACGTCGCTG AATAGCATCGACG ATCCGGCGCGTCT GGCGGATACCATC GCTGCGCATATGC CGCTGAAGCTGGC GGACAAACAGTCC GTGCTGGAGATGT CCGACGTTAACGA GCGTCTGGAATAT CTGATGGCGATGA TGGAGTCGGAAAT CGATCTGCTGCAG GTGGAGAAGCGTA TTCGCAACCGCGT GAAAAAGCAGATG GAGAAATCTCAGC GCGAGTACTATCT GAATGAGCAAATG AAAGCCATTCAAA AAGAGCTCGGCGA GATGGACGACGCC CCGGACGAGAACG AAGCGCTGAAGCG TAAGATCGACGCG GCGAAAATGCCGA AAGAGGCAAAAGA GAAAACCGAAGCG GAACTGCAAAAAC TGAAAATGATGTC CCCGATGTCGGCG GAAGCGACCGTCG TTCGCGGCTACATC GACTGGATGGTGC AGGTACCGTGGAA CGCTCGCAGCAAG GTTAAAAAGACC TGCGTCAGGCTCA GGAGATCCTCGAT ACCGATCACTACG GCCTTGAGCGCGT GAAGGATCGCATT CTTGAGTACCTCGC GGTGCAGAGCCGT GTTAACAAGCTCA AAGGGCCGATCCT | |

TABLE 3C-continued

| Name | Prm (In Forward direction, -250 to +10 region) | SEQ ID NO: | Expressed Seequence | SEQ ID NO: | Neighbor Sequence | SEQ ID NO: |
|---|---|---|---|---|---|---|
| | | | | | GTGCCTGGTTGGG | |
| | | | | | CCTCCGGGGGTAG | |
| | | | | | GTAAAACCTCTCTC | |
| | | | | | GGCCAATCCATCG | |
| | | | | | CCAAAGCAACTGG | |
| | | | | | ACGCAAATATGTG | |
| | | | | | CGTATGGCGCTGG | |
| | | | | | GCGGCGTGCGTGA | |
| | | | | | TGAAGCGGAAATC | |
| | | | | | CGCGGTCACCGCC | |
| | | | | | GTACCTATATTGGC | |
| | | | | | TCAATGCCGGGCA | |
| | | | | | AACTGATCCAGAA | |
| | | | | | AATGGCTAAAGTG | |
| | | | | | GGCGTTAAAAACC | |
| | | | | | CGCTGTTCTTGCTG | |
| | | | | | GATGAGATCGACA | |
| | | | | | AGATGTCTTCTGAC | |
| | | | | | ATGCGCGGCGATC | |
| | | | | | CGGCCTCGGCGCT | |
| | | | | | GCTGGAGGTGTTG | |
| | | | | | GATCCGGAACAGA | |
| | | | | | ACGTGGCCTTTAAC | |
| | | | | | GACCACTATCTGG | |
| | | | | | AAGTGGATTACGA | |
| | | | | | TCTCAGCGACGTG | |
| | | | | | ATGTTCGTTGCGAC | |
| | | | | | CTCTAACTCCATGA | |
| | | | | | ACATCCCGGCGCC | |
| | | | | | GCTGCTGGATCGT | |
| | | | | | ATGGAAGTGATCC | |
| | | | | | GCCTCTCCGGCTAT | |
| | | | | | ACCGAAGATGAGA | |
| | | | | | AGCTAAACATCGC | |
| | | | | | CAAACGCCATCTG | |
| | | | | | CTGTCAAAACAGA | |
| | | | | | TTGAGCGTAACGC | |
| | | | | | GCTCAAGAAAGGC | |
| | | | | | GAGCTGACGGTGG | |
| | | | | | ATGACAGCGCGAT | |
| | | | | | TATCGGCATCATTC | |
| | | | | | GCTACTACACCCGT | |
| | | | | | GAAGCAGGCGTGC | |
| | | | | | GTGGTCTGGAGCG | |
| | | | | | TGAAATCTCGAAA | |
| | | | | | CTGTGCCGCAAAG | |
| | | | | | CGGTGAAACAGCT | |
| | | | | | GCTGCTGGATAAG | |
| | | | | | TCGCTGAAACACA | |
| | | | | | TCGAGATTAACGG | |
| | | | | | CGACAACCTGCAC | |
| | | | | | GATTTCCTTGGCGT | |
| | | | | | GCAGCGCTACGAC | |
| | | | | | TATGGTCGTGCGG | |
| | | | | | ATAGCGAAAACCG | |
| | | | | | CGTAGGTCAGGTG | |
| | | | | | ACCGGACTGGCGT | |
| | | | | | GGACGGAAGTGGG | |
| | | | | | CGGCGATCTGCTG | |
| | | | | | ACCATTGAAACCG | |
| | | | | | CCTGCGTTCCGGGT | |
| | | | | | AAAGGCAAACTGA | |
| | | | | | CCTACACCGGTTCA | |
| | | | | | CTGGGTGAAGTCA | |
| | | | | | TGCAGGAATCCAT | |
| | | | | | CCAGGCGGCGCTG | |
| | | | | | ACGGTGGTTCGTTC | |
| | | | | | ACGTGCGGATAAG | |
| | | | | | CTGGGTATTAACTC | |
| | | | | | AGACTTTTACGAA | |
| | | | | | AAACGTGATATTC | |
| | | | | | ACGTTCACGTGCC | |
| | | | | | GGAAGGCGCGACG | |
| | | | | | CCGAAGGATGGTC | |
| | | | | | CAAGCGCCGGTAT | |
| | | | | | CGCGATGTGCACC | |

TABLE 3C-continued

| Name | Prm (In Forward direction, -250 to +10 region) | SEQ ID NO: | Expressed Seequence | SEQ ID NO: | Neighbor Sequence | SEQ ID NO: |
|---|---|---|---|---|---|---|
| | | | | | GCGCTGGTTTCCTG TCTGACGGGTAAT CCGGTACGCGCCG ACGTGGCGATGAC CGGTGAGATTACC CTCCGTGGCCAGG TATTGCCGATTGGT GGTCTGAAGGAAA AACTGTTGGCCGC GCATCGCGGCGGC ATTAAGACTGTTCT GATTCCTGATGAA AATAAACGCGACC TTGAAGAAATTCC GGATAACGTTATC GCCGATTTAGATAT CCATCCGGTGAAA CGAATCGAGGAAG TTCTGGCACTTGCG CTACAGAACGAAC CGTTTGGAATGGA AGTCGTCACGGCA AAATAG | |
| sspA CDS | GTAAGAAAGTCGG CCTGCGTAAAGCA CGTCGTCGTCCTCA GTTCTCCAAACGTT AATTGTTTTCTGCT CACGCAGAACAAT TTGCGAAAAAACC CGCTTCGGCGGGTT TTTTTATGGATAAA TTTGCCATTTTCCC TCTACAAACGCCC CATTGTTACCACTT TTTCAGCATTTCCA GAATCCCCTCACC ACAACGTCTTCAA AATCTGGTAAACT ATCATCCAATTTTC TGCCCAAATGCAG GTGATTGTTCATTT TT | 9 | ATGGCTGTCGCTGC CAACAAACGTTCG GTAATGACGCTGTT TTCTGGTCCTACTG ACATCTATAGCCAT CAGGTCCGCATCG TGCTGGCCGAAAA AGGTGTTAGTTTTG AGATAGAGCACGT GGAGAAGGACAAC CCGCCTCAGGATCT GATTGACCTCAAC CCGAATCAAAGCG TACCGACGCTTGTG GATCGTGAGCTCA CTCTGTGGGAATCT CGCATCATTATGG AATATCTGGATGA GCGTTTCCCGCATC CGCCGCTCATGCC GGTTTACCCGGTG GCGCGTGGGGAAA GCCGTCTGTATATG CAGCGTATCGAAA AGGACTGGTATTC GTTGATGAATACC ATTCAGACCGGTA CCGCTGCGCAGGC TGATACTGCGCGT AAGCAGCTGCGTG AAGAACTACAGGC GATTGCGCCAGTTT TCACCCAGAAGCC CTACTTCCTGAGCG ATGAGTTCAGCCT GGTGGACTGCTAC CTGGCACCACTGCT GTGGCGTCTGCCG GTTCTCGGCGTAG AGCTGGTCGGCGC TGGCGCGAAAGAG CTTAAAGGCTATAT GACTCGCGTATTTG AGCGCGACTCTTTC CTCGCTTCTTTAAC TGAAGCCGAACGT GAAATGCGTCTCG GTCGGGGCTAA | 19 | ATGGCTGAAAATC AATACTACGGCAC CGGTCGCCGCAAA AGTTCCGCAGCTC GCGTTTTCATCAAA CCGGGCAACGGTA AAATCGTTATCAA CCAGCGTTCTCTGG AACAGTACTTCGG TCGTGAAACTGCC CGCATGGTAGTTC GTCAGCCGCTGGA ACTGGTCGACATG GTTGAGAAATTAG ATCTGTACATCACC GTTAAAGGTGGTG GTATCTCTGGTCAG GCTGGTGCGATCC GTCACGGTATCAC CCGCGCTCTGATG GAGTACGACGAGT CCCTGCGTGGCGA ACTGCGTAAAGCT GGTTTCGTTACTCG TGATGCTCGTCAG GTTGAACGTAAGA AAGTCGGCCTGCG TAAAGCACGTCGT CGTCCTCAGTTCTC CAAACGTTAA | 29 |
| tatE CDS | GTCAAAGCCGTAT TATCGACCCCTTAG GGACAACGCTTGC | 10 | ATGGGTGAGATTA GTATTACCAAACT GCTGGTAGTCGCA | 20 | ATGTTTGTTGCTGC CGGACAATTTGCC GTAACGCCGGACT | 30 |

TABLE 3C-continued

| Name | Prm (In Forward direction, -250 to +10 region) | SEQ ID NO: | Expressed Seequence | SEQ ID NO: | Neighbor Sequence | SEQ ID NO: |
|---|---|---|---|---|---|---|
| | CGGGGCGGGAGAG CGGCCGCAGTTGA TTTTTGCCGAACTT TCAGCTGATTATAT TCAGCAGGTACGC GAGCGCCTGCCGG TGTTGCGCAATCGC CGCTTTGCGCCACC GCAATTATTATGAC GTTTTTTTAAACAA GGCTTGATTCACCT TGTTACAGATTGCT ATTGTGTCCGCGCG TCAAATAGCCGTT AATTGTATGCGTGT ATGATGGCGTATTC G | | GCGCTGATTATCCT GGTGTTTGGTACCA AAAAGTTACGCAC GCTGGGTGGAGAC CTGGGCTCGGCTAT CAAAGGCTTTAAA AAAGCCATGAGCG ATGACGATGACAG TGCGAAGAAGACC AGTGCTGAAGAAG CGCCGGCACAGAA GCTCTCTCATAAAG AGTAA | | GGACGGGAAACGC GCAGACCTGCGTC AGCATGATGCGCC AGGCCGCGGAGCG GGGGGCGTCGCTT CTGGTTCTGCCTGA GGCGTTGCTGGCG CGAGACGATAACG ATGCGGATTTATCG GTTAAATCCGCCC AGCAGCTGGATGG CGGCTTCTTACAGC TCTTGCTGGCGGA GAGCGAAAACAGC GCTTTGACGACGG TGCTGACCCTGCAT ATCCCTTCCGGCGA AGGTCGAGCGACG AATACGCTGGTGG CCCTGCGTCAGGG GAAGATTGTGGCG CAATATCAGAAAC TGCATCTCTATGAT GCGTTCAATATCCA GGAATCCAGGCTG GTCGATGCCGGGC GGCAAATTCCGCC GCTGATCGAAGTC GACGGGATGCGCG TCGGGCTGATGAC CTGCTACGATTTAC GTTTCCCTGAGCTG GCGCTGTCGTTAGC GCTCAGCGGCGCG CAGCTCATAGTGTT GCCTGCCGCGTGG GTAAAAGGGCCGC TGAAGGAACATCA CTGGGCGACGCTG CTGGCGGCGCGGG CGCTGGATACAAC CTGCTATATTGTCG CCGCAGGAGAGTG CGGGACGCGTAAT ATCGGTCAAAGCC GTATTATCGACCCC TTAGGGACAACGC TTGCCGGGGCGGG AGAGCGGCCGCAG TTGATTTTTGCCGA ACTTTCAGCTGATT ATATTCAGCAGGT ACGCGAGCGCCTG CCGGTGTTGCGCA ATCGCCGCTTTGCG CCACCGCAATTATT ATGA | |
| LexA repressor CDS | GAGGCGGTGGTTG ACCGTATCGGTCCC GAGCATCATGAGC TTTCGGGGCGAGC GAAAGATATGGGA TCGGCGGCGGTAC TGCTGGCGATTATC ATCGCGCTGATCG CGTGGGGAACGCT GCTGTGGGCGAAC TACCGCTAAGTCTT GTCGTAGCTGCTCG CAAAACGGAAAGA AACTCCTGATTTTT GTGTGAAATGTGG TTCCAAAATCACC GTTAGCTGTATATA CTCACAGCATAAC | 11 | ATGAAAGCGTTAA CGACCAGGCAGCA AGAGGTGTTTGAT CTCATTCGGGATCA TATCAGCCAGACG GGCATGCCGCCGA CGCGTGCGAGAT TGCTCAGCGCTTGG GGTTTCGCTCCCCA AACGCGGCGGAAG AGCATCTGAAAGC GCTGGCGCGTAAA GGCGCAATCGAGA TCGTTTCCGGCGCC TCCCGCGGTATTCG TCTGCTGACGAAG GAGAAACCGGTC TGCCGCTTATTGGC | 21 | ATGGCCAATAATA CCACTGGGTTAAC CCGAATTATTAAA GCGGCCGGGTATT CCTGGAAAGGATT CCGTGCGGCGTGG GTCAATGAGGCCG CATTTCGTCAGGA AGGCATCGCGGCC GTTATTGCCGTGGC GATCGCCTGCTGGT TGGACGTCGATGC CATCACGCGGGTG CTGCTCATTAGCTC GGTCCTGTTAGTGA TGATAGTTGAAATT ATCAATAGCGCGA TTGAGGCGGTGGT | 31 |

TABLE 3C-continued

| Name | Prm (In Forward direction, -250 to +10 region) | SEQ ID NO: | Expressed Seequence | SEQ ID NO: | Neighbor Sequence | SEQ ID NO: |
|---|---|---|---|---|---|---|
| | TGTATATACACCCAGGGGGC | | CGCGTCGCGGCAGGTGAGCCGCTGCTAGCGCAGCAGCACATTGAAGGCCACTACCAGGTGGACCCGGCCATGTTTAAGCCGAACGCCGATTTTCTGCTGCGTGTTAGCGGTATGTCGATGAAGGATATCGGTATTCTCGATGGCGACCTGCTGGCTGTCCATAAAACGCAGGATGTGCGCAATGGTCAGGTGGTTGTGGCGCGTATCGACGAAGAAGTGACCGTGAAGCGTCTGAAAAAACAGGGTAACGTCGTGGAATTGCTGCCGGAAAACAGCGAATTCTCGCCGATCGTGGTCGACCTTCGCGAACAAAGCTTTACTATTGAAGGCCTGGCCGTCGGCGTTATCCGCAACGGCAACTGGCAATAA | | TGACCGTATCGGTCCCGAGCATCATGAGCTTTCGGGGCGAGCGAAAGATATGGGATCGGCGGCGGTACTGCTGGCGATTATCATCGCGCTGATCGCGTGGGGAACGCTGCTGTGGGCGAACTACCGCTAA | |
| hisS CDS | TAAGAAAAGCGGCCTGTACGAAGACGGCGTACGTAAAGACAGGCTGGATAACGACGATATGATCGATCAGCTGGAAGCGCGTATTCGCGCTAAAGCATCGATGCTGGATGAGGCGCGTCGTATCGATATCCAGCAGGTTGAAGCGAAATAACGTGTTGGGAAGCGATACGCTTCCCGTGTATGATTGAACCTGCGGGCGCGAGGCGCCGGGGTTCATTTTTGTATATATAAAGAGAATAAACGTGGCAAAGAACATTCAA | 12 | ...ATGAACGATTATCTGCCGGGCGAAACCGCTCTCTGGCAGCGCATTGAAGGCTCACTGAAGCAGGTGCTTGGTAGCTACGGTTACAGCGAAATCCGTTTGCCGATTGTAGAGCAGACCCCGTTATTCAAACGCGCTATCGGCGAAGTGACCGACGTGGTTGAAAAAGAGATGTACACCTTTGAGGACCGTAACGGCGATAGCCTGACTCTACGTCCGGAAGGCACGGCTGGCTGCGTACGCGCCGGTATCGAACATGGTCTCCTGTACAATCAAGAACAGCGCCTGTGGTACATTGGGCCGATGTTCCGCCACGAACGTCCGCAAAAAGGCCGCTACCGTCAGTTCCACCAGATTGGCGCCGAAGCGTTTGGCCTGCAGGGGCCGGATATCGATGCCGAGCTGATTATGCTGACCGCCCGCTGGTGGCGCGAGCTGGGCATCTCCGGCCACGTTGCGCTGGAGCTGAACTCTATCGGTTCGCTGGAGGCTCGCGCTAACTATCGCGACGCGCTGGTGGCCTATCTTGAGCAGTTTAAAGATAAGCTGGACGAAGACTGCAAACGCCGCATGTACACCAACCCGCTGCGCGTGCTGGATTCTAAAAACCCGGACGTCCAGG | 22 | ATGCATAACCAGGCTCCGATTCAACGTAGAAAATCAAAACGAATTTACGTTGGGAATGTGCCGATTGGCGATGGCGCCCCCATCGCCGTACAGTCGATGACAAACACGCGCACCACCGATGTGGCGGCGACGGTAAATCAAATTAAAGCCCTCGAGCGCGTTGGCGCGGATATCGTGCGCGTTTCGGTGCCGACGATGGATGCGGCGGAAGCGTTCAAACTTATCAAACAGCAGGTTAACGTCCGCTGGTTGCCGATATCCACTTCGATTACCGCATTGCGCTGAAGGTAGCGGAATACGGCGTTGATTGCCTGCGTATTAACCCGGGCAATATCGGCAACGAAGAGCGTATCCGCATGGTGGTGGACTGCGCTCGCGATAAAAATATTCCTATCCGTATCGGGGTAAACGCCGGTTCTCTGGAAAAAGATCTCCAGGAAAAATACGGCGAACCGACTCCGCAGGCGCTGCTGGAATCGGCAATGCGCCATGTTGATCATCTCGATCGTCTCAACTTCGATCAGTTTAAAGTCAGCGTAAAAGCCTCCGATGTGTTCCTCGCGGTTGAATCCTATCGCCTGTTGGCGAAACAGATCGATCAGCCTCTGCACCTCGGGATCACCGA | 32 |

TABLE 3C-continued

| Name | Prm (In Forward direction, -250 to +10 region) | SEQ ID NO: | Expressed Seequence | SEQ ID NO: | Neighbor Sequence | SEQ ID NO: |
|---|---|---|---|---|---|---|
| | | | CGCTGCTGAACGA | | AGCGGGCGGCGCG | |
| | | | CGCCCCGACGCTG | | CGCAGCGGCGCGG | |
| | | | GGCGACTATCTTG | | TGAAGTCCGCGAT | |
| | | | ATGAAGAGTCCAA | | CGGCCTCGGCCTG | |
| | | | AACGCATTTTGCCG | | CTGCTGTCTGAAG | |
| | | | GGCTGTGCGCGCT | | GGATTGGCGATAC | |
| | | | GCTGGATGATGCC | | GCTGCGCGTCTCTC | |
| | | | GGTATTCGCTATAC | | TGGCGGCGGATCC | |
| | | | CGTGAATCAGCGT | | CGTTGAAGAGATC | |
| | | | CTGGTACGCGGTCT | | AAAGTGGGCTTCG | |
| | | | CGACTACTACAAC | | ATATTCTCAAGTCG | |
| | | | CGCACCGTGTTTGA | | CTGCGTATTCGCTC | |
| | | | GTGGGTCACCACC | | TCGCGGGATCAAC | |
| | | | AGCCTCGGTTCCCA | | TTTATTGCCTGCCC | |
| | | | GGGCACCGTCTGC | | GACCTGTTCACGTC | |
| | | | GCCGGAGGCCGTT | | AGGAGTTTGACGT | |
| | | | ACGATGGTCTGGTT | | TATCGGTACCGTTA | |
| | | | GAGCAGCTTGGCG | | ACGCGCTGGAGCA | |
| | | | GTCGCGCTACCCCT | | GCGCCTGGAAGAT | |
| | | | GGCGTCGGCTTTGC | | ATCATTACGCCGAT | |
| | | | GATGGGGCTGGAA | | GGATATTTCGATCA | |
| | | | CGTCTTGTTTTACT | | TTGGCTGCGTGGTA | |
| | | | GGTTCAGGCAGTG | | AACGGTCCCGGCG | |
| | | | AATCCGGAATTTA | | AGGCGCTGGTTTCC | |
| | | | AAGCCGATCCTGTT | | ACCCTCGGCGTAA | |
| | | | GTCGATATATACCT | | CCGGCGGCAATAA | |
| | | | GGTAGCCTCCGGA | | GAAAAGCGGCCTG | |
| | | | ACTGACACCCAGT | | TACGAAGACGGCG | |
| | | | CCGCAGCAATGCG | | TACGTAAAGACAG | |
| | | | TCTGGCTGAACAG | | GCTGGATAACGAC | |
| | | | GTACGCGATGCGT | | GATATGATCGATC | |
| | | | TACCCGGCGTTAA | | AGCTGGAAGCGCG | |
| | | | GCTGATGACCAAC | | TATTCGCGCTAAA | |
| | | | CATGGCGGCGGCA | | GCATCGATGCTGG | |
| | | | ACTTTAAGAAGCA | | ATGAGGCGCGTCG | |
| | | | GTTTGCGCGCGCTG | | TATCGATATCCAGC | |
| | | | ATAAATGGGCGC | | AGGTTGAAGCGAA | |
| | | | TCGCGTTGCGCTGG | | ATAA | |
| | | | TGCTGGGCGAATC | | | |
| | | | AGAAATCGCCGAC | | | |
| | | | GGAAACGTGGTAG | | | |
| | | | TGAAAGATTTACG | | | |
| | | | CTCAGGTGAGCAA | | | |
| | | | ACTACCGTAACGC | | | |
| | | | AGGATAGCGTTGC | | | |
| | | | TGCGCATTTGCGCA | | | |
| | | | CACTTCTGGGTTAA | | | |

Table of Strains

| Sort | First Reference | Current Name | Universal Name | Lineage | Mutagenic DNA Description | Genotype | Gene 1 mutation | SEQ ID NO: |
|---|---|---|---|---|---|---|---|---|
| 1 | Application text | CI006 | CI006 | Isolated strain from *Enterobacter genera* | None | WT | | |
| 2 | Application text | CI008 | CI008 | Isolated strain from *Burkholderia genera* | None | WT | | |

| | | | | | | | | |
|---|---|---|---|---|---|---|---|---|
| 3 | Application text | CI010 | CI010 | Isolated strain from *Klebsiella genera* | None | | WT | |
| 4 | Application text | CI019 | CI019 | Isolated strain from *Rahnella genera* | None | | WT | |
| 5 | Application text | CI028 | CI028 | Isolated strain from *Enterobacter genera* | None | | WT | |
| 6 | Application text | CI050 | CI050 | Isolated strain from *Klebsiella genera* | None | | WT | |
| 7 | Application text | CM002 | CM002 | Mutant of CI050 | Disruption of nifL gene with a kanamycin resistance expression cassette (KanR) encoding the aminoglycoside O-phosphotransferase gene aph1 inserted. | ΔnifL::KanR | ATGAGCCATATT CAACGGGAAACG TCTTGCTCCAGG CCGCGATTAAAT TCCAACATGGAT GCTGATTTATAT GGGTATAAATGG GCTCGCGATAAT GTCGGGCAATCA GGTGCGACAATC TATCGATTGTAT GGGAAGCCCGAT GCGCCAGAGTTG TTTCTGAAACAT GGCAAAGGTAGC GTTGCCAATGAT GTTACAGATGAG ATGGTCAGACTA AACTGGCTGACG GAATTTATGCCT CTTCCGACCATC AAGCATTTTATC CGTACTCCTGAT GATGCATGGTTA CTCACCACTGCG ATCCCCGGGAAA ACAGCATTCCAG GTATTAGAAGAA TATCCTGATTCA GGTGAAAATATT GTTGATGCGCTG GCAGTGTTCCTG CGCCGGTTGCAT TCGATTCCTGTTT GTAATTGTCCTTT TAACAGCGATCG CGTATTTCGTCTC GCTCAGGCGCAA TCACGAATGAAT AACGGTTTGGTT GATGCGAGTGAT TTTGATGACGAG CGTAATGGCTGG CCTGTTGAACAA GTCTGGAAAGAA ATGCATAAGCTT TTGCCATTCTCA CCGGATTCAGTC GTCACTCATGGT GATTTCTCACTT GATAACCTTATT TTTGACGAGGGG AAATTAATAGGT TGTATTGATGTT | 33 |

-continued

| | | | | | | | GGACGAGTCGGA ATCGCAGACCGA TACCAGGATCTT GCCATCCTATGG AACTGCCTCGGT GAGTTTTCTCCTT CATTACAGAAAC GGCTTTTTCAAA AATATGGTATTG ATAATCCTGATA TGAATAAATTGC AGTTTCATTTGA TGCTCGATGAGT TTTTCTAATAAG CCTGCCTGGTTC TGCGTTTCCCGC TCTTTAATACCCT GACCGGAGGTGA GCAATGA | |
|---|---|---|---|---|---|---|---|---|
| 8 | Application text | CM011 | CM011 | Mutant of CI019 | Disruption of nifL gene with a spectinomycin resistance expression cassette (SpecR) encoding the streptomycin 3"-O-adenylyl-transferase gene aadA inserted. | ΔnifL::SpecR | ATGAGCATCACG GCGTTATCAGCA TCATTTCCTGAG GGGAATATCGCC AGCCGCTTGTCG CTGCAACATCCT TCACTGTTTTATA CCGTGGTTGAAC AATCTTCGGTGG CGAGCGTGTTGA GTCATCCTGACT AGCTGAGATGAG GGCTCGCCCCCT CGTCCCGACACT TCCAGATCGCCA TAGCGCACAGCG CCTCGAGCGGTG GTAACGGCGCAG TGGCGGTTTTCA TGGCTTGTTATG ACTGTTTTTTGG GGTACAGTCTAT GCCTCGGGCATC CAAGCAGCAAGC GCGTTACGCCGT GGGTCGATGTTT GATGTTATGGAG CAGCAACGATGT TACGCAGCAGGG CAGTCGCCCTAA AACAAAGTTAAA CATCATGAGGGA AGCGGTGATCGC CGAAGTATCGAC TCAACTATCAGA GGTAGTTGGCGT CATCGAGCGCCA TCTCGAACCGAC GTTGCTGGCCGT ACATTTGTACGG CTCCGCAGTGGA TGGCGGCCTGAA GCCACACAGTGA TATTGATTTGCT GGTTACGGTGAC CGTAAGGCTTGA TGAAACAACGCG GCGAGCTTTGAT CAACGACCTTTT GGAAACTTCGGC TTCCCCTGGAGA GAGCGAGATTCT CCGCGCTGTAGA AGTCACCATTGT TGTGCACGACGA CATCATTCCGTG GCGTTATCCAGC TAAGCGCGAACT GCAATTTGGAGA | 34 |

| | | | | | | | |
|---|---|---|---|---|---|---|---|
| | | | | | | | ATGGCAGCGCAATGACATTCTTGCAGGTATCTTCGAGCCAGCCACGATCGACATTGATCTGGCTATCTTGCTGACAAAGCAAGAGAACATAGCGTTGCCTTGGTAGGTCCAGCGGCGGAGGAACTCTTTGATCCGGTTCCTGAACAGGATCTATTTGAGGCGCTAAATGAAACCTTAACGCTATGGAACTCGCCGCCCGACTGGGCTGGCGATGAGCGAAATGTAGTGCTTACGTTGTCCCGCATTTGGTACAGCGCAGTAACCGGCAAAATCGCGCCGAAGGATGTCGCTGCCGACTGGGCAATGGAGCGCCTGCCGGCCCAGTATCAGCCCGTCATACTTGAAGCTAGACAGGCTTATCTTGGACAAGAAGAAGATCGCTTGGCCTCGCGCGCAGATCAGTTGGAAGAATTTGTCCACTACGTGAAAGGCGAGATCACCAAGGTAGTCGGCAAATAATGTCTAACAATTCGTTCAAGCCGACGCCGCTTCGCGGCGCGGCTTAACTCAAGCGTTAGATGCACTAAGCACATAATTGCTCACAGCCAAACTATCAGGTCAAGTCTGCTTTTATTATTTTTAAGCGTGCATAATAAGCCCTACACAAATGGTACCCGACCGGTGGTGAATTTAATCTCGCTGACGTGTAGACATTCCCTTATCCAGACGCTGATCGCCCATCATCGCGGTTCTTTAGATCTCTCGGTCCGCCCTGATGGCGGCACCTTGCTGACGTTACGCCTGCCGGTACAGCAGGTTATCACCGGAGGCTTAAAATGA | |
| 9 | Application text | CM013 | CM013 | Mutant of C1006 | Disruption of nifL gene with a kanamycin resistance expression cassette (KanR) encoding the amino-glycoside O-phospho-transferase | ΔnifL::KanR | CTGATCCTTCAACTCAGCAAAAGTTCGATTTATTCAACAAAGCCACGTTGTGTCTCAAAATCTCTGATGTTACATTGCACAAGATAAAAATATATCATCATGAACAATAAAACTGTCTGCTTACATAAACAGTAATACAAGGGG | 35 |

Figure 4A:
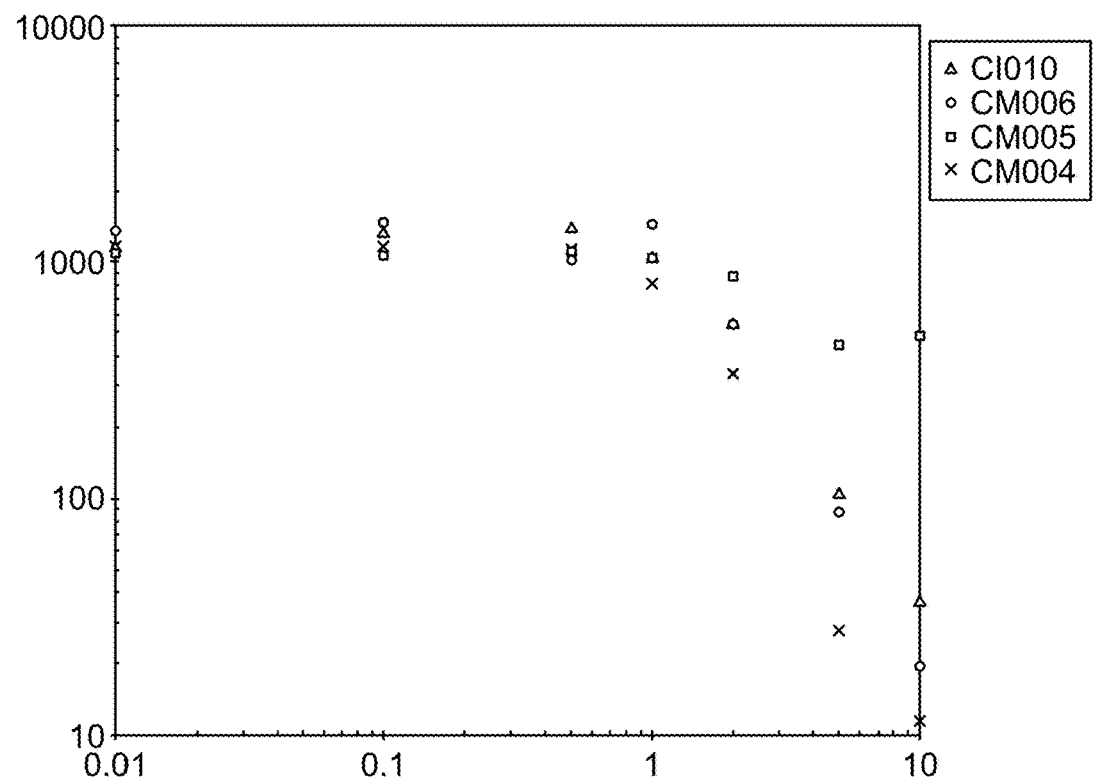
FIGS. 4A-D depict in vitro phenotypes of various strains. The Acetylene Reduction Assay (ARA) activities of mutants of strain CI010 (FIG. 4A) and mutants of strain CI006 (FIG. 4B) grown in nitrogen fixation media supplemented with 0 to 10 mM glutamine. ARA activities of additional strains are shown in FIG. 4C, and the ammonium excretion profile across time of two strains is shown in FIG. 4D.
Figure 4B:
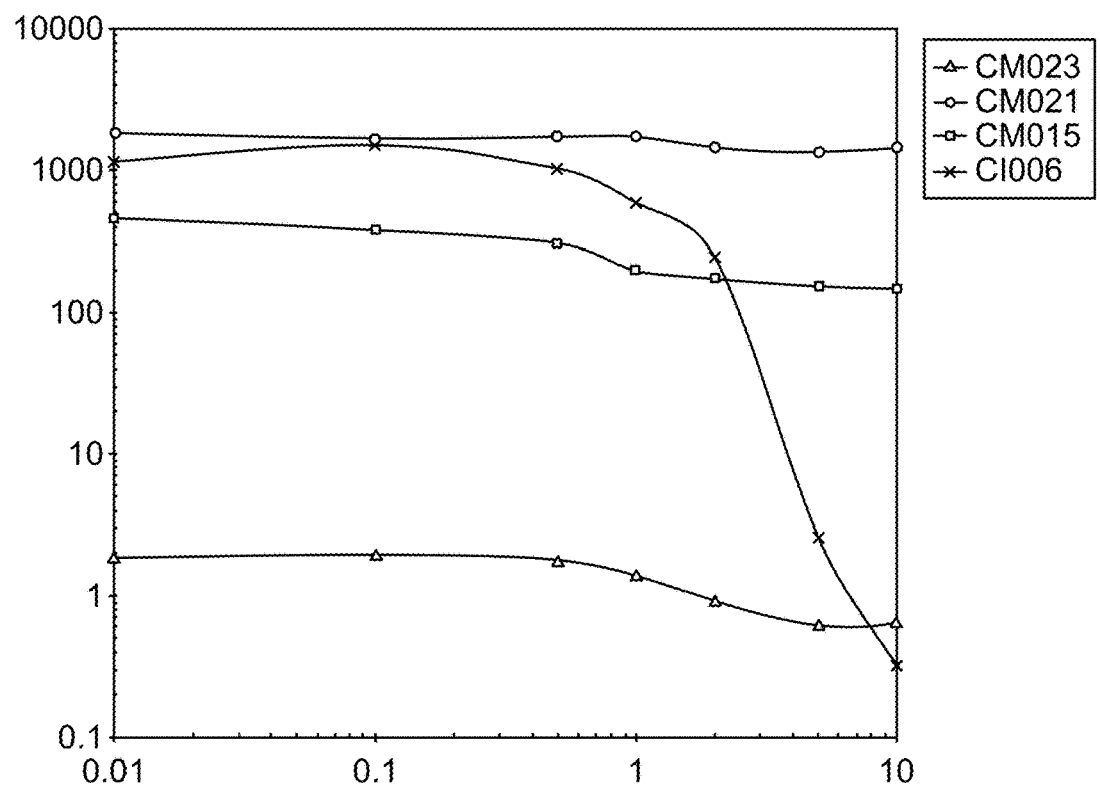
Figure 4C:
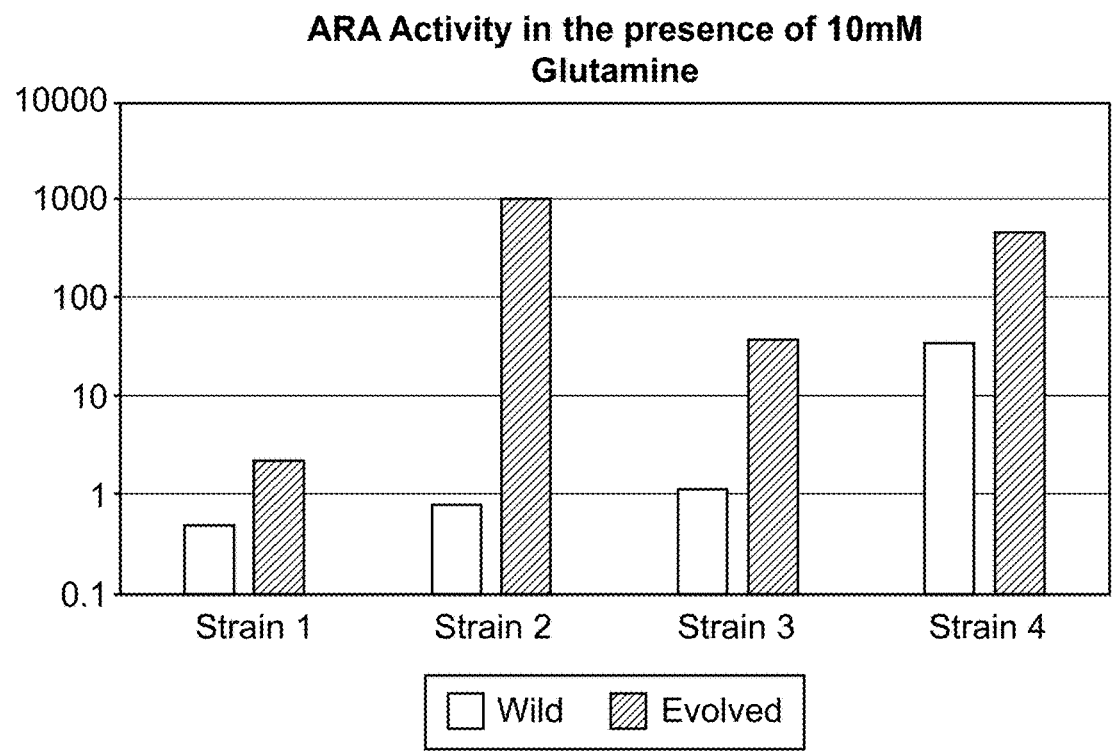
Figure 4D:
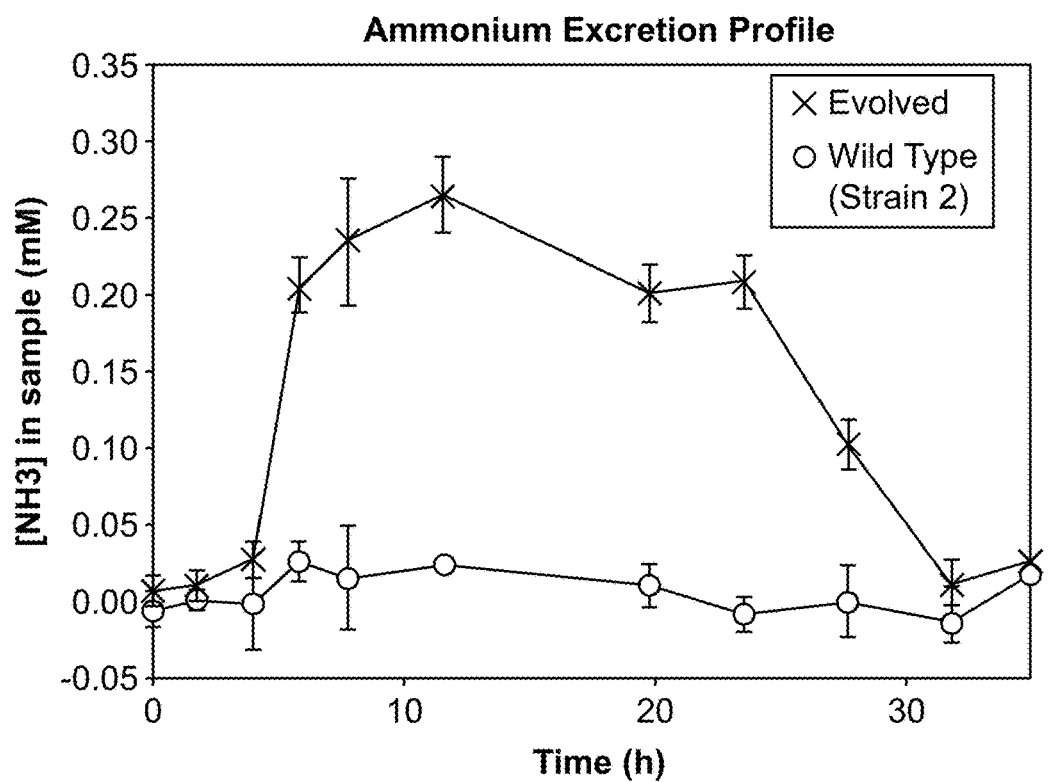

| | | | | | | | | |
|---|---|---|---|---|---|---|---|---|
| | | | | | gene aph1 inserted. | | TGTTATGAGCCA TATTCAACGGGA AACGTCTTGCTC CAGGCCGCGATT AAATTCCAACAT GGATGCTGATTT ATATGGGTATAA ATGGGCTCGCGA TAATGTCGGGCA ATCAGGTGCGAC AATCTATCGATT GTATGGGAAGCC CGATGCGCCAGA GTTGTTTCTGAA ACATGGCAAAGG TAGCGTTGCCAA TGATGTTACAGA TGAGATGGTCAG ACTAAACTGGCT GACGGAATTTAT GCCTCTTCCGAC CATCAAGCATTT TATCCGTACTCC TGATGATGCATG GTTACTCACCAC TGCGATCCCCGG GAAAACAGCATT CCAGGTATTAGA AGAATATCCTGA TTCAGGTGAAAA TATTGTTGATGC GCTGGCAGTGTT CCTGCGCCGGTT GCATTCGATTCC TGTTTGTAATTGT CCTTTTAACAGC GATCGCGTATTT CGTCTCGCTCAG GCGCAATCACGA ATGAATAACGGT TTGGTTGATGCG AGTGATTTTGAT GACGAGCGTAAT GGCTGGCCTGTT GAACAAGTCTGG AAAGAAATGCAT AAGCTTTTGCCA TTCTCACCGGAT TCAGTCGTCACT CATGGTGATTTC TCACTTGATAAC CTTATTTTTGACG AGGGGAAATTAA TAGGTTGTATTG ATGTTGGACGAG TCGGAATCGCAG ACCGATACCAGG ATCTTGCCATCC TATGGAACTGCC TCGGTGAGTTTT CTCCTTCATTAC AGAAACGGCTTT TTCAAAAATATG GTATTGATAATC CTGATATGAATA AATTGCAGTTTC ATTTGATGCTCG ATGAGTTTTTCT AATAAGCCTTGA CCCTACGATTCC CGCTATTTCATTC ACTGACCGGAGG TTCAAAATGA | |
| 10 | FIG. 4A | CM004 | CM004 | Mutant of CI010 | Disruption of amtB gene with a kanamycin resistance | ΔamtB::KanR | ATGAAGATAGCA ACAATGAAAACA GGTCTGGGAGCG TTGGCTCTTCTTC CCTGATCCTTCA | 36 |

| | |
|---|---|
| expression cassette (KanR) encoding the aminoglycoside O-phosphotransferase gene aph1 inserted. | ACTCAGCAAAAG TTCGATTTATTCA ACAAAGCCACGT TGTGTCTCAAAA TCTCTGATGTTA CATTGCACAAGA TAAAAATATATC ATCATGAACAAT AAAACTGTCTGC TTACATAAACAG TAATACAAGGGG TGTTATGAGCCA TATTCAACGGGA AACGTCTTGCTC CCGTCCGCGCTT AAACTCCAACAT GGACGCTGATTT ATATGGGTATAA ATGGGCTCGCGA TAATGTCGGGCA ATCAGGTGCGAC AATCTATCGCTT GTATGGGAAGCC CGATGCGCCAGA GTTGTTTCTGAA ACATGGCAAAGG TAGCGTTGCCAA TGATGTTACAGA TGAGATGGTCCG TCTCAACTGGCT GACGGAGTTTAT GCCTCTCCCGAC CATCAAGCATTT TATCCGTACTCC TGATGATGCGTG GTTACTCACCAC CGCGATTCCTGG GAAAACAGCCTT CCAGGTATTAGA AGAATATCCTGA TTCAGGTGAAAA TATTGTTGATGC GCTGGCCGTGTT CCTGCGCCGGTT ACATTCGATTCC TGTTTGTAATTGT CCTTTTAACAGC GATCGTGTATTT CGTCTTGCTCAG GCGCAATCACGC ATGAATAACGGT TTGGTTGATGCG AGTGATTTTGAT GACGAGCGTAAT GGCTGGCCTGTT GAACAAGTCTGG AAAGAAATGCAC AAGCTCTTGCCA TTCTCACCGGAT TCAGTCGTCACT CATGGTGATTTC TCACTTGATAAC CTTATTTTTGACG AGGGGAAATTAA TAGGTTGTATTG ATGTTGGACGGG TCGGAATCGCAG ACCGTTACCAGG ACCTTGCCATTC TTTGGAACTGCC TCGGTGAGTTTT CTCCTTCATTAC AGAAACGGCTTT TTCAAAAATATG GTATTGATAATC CTGATATGAATA AATTGCAGTTTC ATTTGATGCTCG ATGAGTTTTTCT |

| | | | | | | | | |
|---|---|---|---|---|---|---|---|---|
| | | | | | | | AATAAGCCTGTG AAGGGCTGGACG TAAACAGCCACG GCGAAAACGCCT ACAACGCCTGA | |
| 11 | FIG. 4A | CM005 | CM005 | Mutant of CI010 | Disruption of nifL gene with a kanamycin resistance expression cassette (KanR) encoding the amino- eglycosid O- phospho- transferase gene aph1 inserted. | ΔnifL::KanR | ATGACCCTGAAT ATGATGCTCGAT AACGCCGTACCC GAGGCGATTGCC GGCTGATCCTTC AACTCAGCAAAA GTTCGATTTATTC AACAAAGCCACG TTGTGTCTCAAA ATCTCTGATGTT ACATTGCACAAG ATAAAAATATAT CATCATGAACAA TAAAACTGTCTG CTTACATAAACA GTAATACAAGGG GTGTTATGAGCC ATATTCAACGGG AAACGTCTTGCT CCCGTCCGCGCT TAAACTCCAACA TGGACGCTGATT TATATGGGTATA AATGGGCTCGCG ATAATGTCGGGC AATCAGGTGCGA CAATCTATCGCT TGTATGGGAAGC CCGATGCGCCAG AGTTGTTTCTGA AACATGGCAAAG GTAGCGTTGCCA ATGATGTTACAG ATGAGATGGTCC GTCTCAACTGGC TGACGGAGTTTA TGCCTCTCCCGA CCATCAAGCATT TTATCCGTACTC CTGATGATGCGT GGTTACTCACCA CCGCGATTCCTG GGAAAACAGCCT TCCAGGTATTAG AAGAATATCCTG ATTCAGGTGAAA ATATTGTTGATG CGCTGGCCGTGT TCCTGCGCCGGT TACATTCGATTC CTGTTTGTAATT GTCCTTTTAACA GCGATCGTGTAT TTCGTCTTGCTCA GGCGCAATCACG CATGAATAACGG TTTGGTTGATGC GAGTGATTTTGA TGACGAGCGTAA TGGCTGGCCTGT TGAACAAGTCTG GAAAGAAATGCA CAAGCTCTTGCC ATTCTCACCGGA TTCAGTCGTCAC TCATGGTGATTT CTCACTTGATAA CCTTATTTTTGAC GAGGGGAAATTA ATAGGTTGTATT GATGTTGGACGG GTCGGAATCGCA GACCGTTACCAG | 37 |

-continued

| | | | | | | | | GACCTTGCCATT CTTTGGAACTGC CTCGGTGAGTTT TCTCCTTCATTAC AGAAACGGCTTT TTCAAAAATATG GTATTGATAATC CTGATATGAATA AATTGCAGTTTC ATTTGATGCTCG ATGAGTTTTTCT AATAAGCCTTGG TTCTGCGTTTCCC GCTCTTTAATAC CCTGACCGGAGG TGAGCAATGA | |
|---|---|---|---|---|---|---|---|---|---|
| 12 | FIG. 4B | CM015 | CM015 | Mutant of CI006 | Disruption of nifL gene with a fragment of the region upstream of the ompX gene inserted (Prm5). | ΔnifL::Prm5 | ATGACCCTGAAT ATGATGATGGAT GCCGGCGGACAT CATCGCGACAAA CAATATTAATAC CGGCAACCACAC CGGCAATTTACG AGACTGCGCAGG CATCCTTTCTCCC GTCAATTTCTGT CAAATAAAGTAA AAGAGGCAGTCT ACTTGAATTACC CCCGGCTGGTTG AGCGTTTGTTGA AAAAAAGTAACT GAAAAATCCGTA GAATAGCGCCAC TCTGATGGTTAA TTAACCTATTCA ATTAAGAATTAT CTGGATGAATGT GCCATTAAATGC GCAGCATAATGG TGCGTTGTGCGG GAAAACTGCTTT TTTTTGAAAGGG TTGGTCAGTAGC GGAAACAACTCA CTTCACACCCCG AAGGGGGAAGTT GCCTGACCCTAC GATTCCCGCTAT TTCATTCACTGA CCGGAGGTTCAA AATGA | 38 |
| 13 | FIG. 4B | CM021 | CM021 | Mutant of CI006 | Disruption of nifL gene with a fragment of the region upstream of an unanotated gene and the first 73 bp of that gene inserted (Prm2). | ΔnifL::Prm2 | ATGACCCTGAAT ATGATGATGGAT GCCGGCTCACCA CGGCGATAACCA TAGGTTTTCGGC GTGGCCACATCC ATGGTGAATCCC ACTTTTTCCAGC ACGCGCGCCACT TCATCGGGTCTT AAATACATAGAT TTTCCTCGTCATC TTTCCAAAGCCT CGCCACCTTACA TGACTGAGCATG GACCGTGACTCA GAAAATTCCACA AACGAACCTGAA AGGCGTGATTGC CGTCTGGCCTTA AAAATTATGGTC TAAACTAAAATT TACATCGAAAAC GAGGGAGGATCC TATGTTTAACAA | 39 |

Figure 10A:
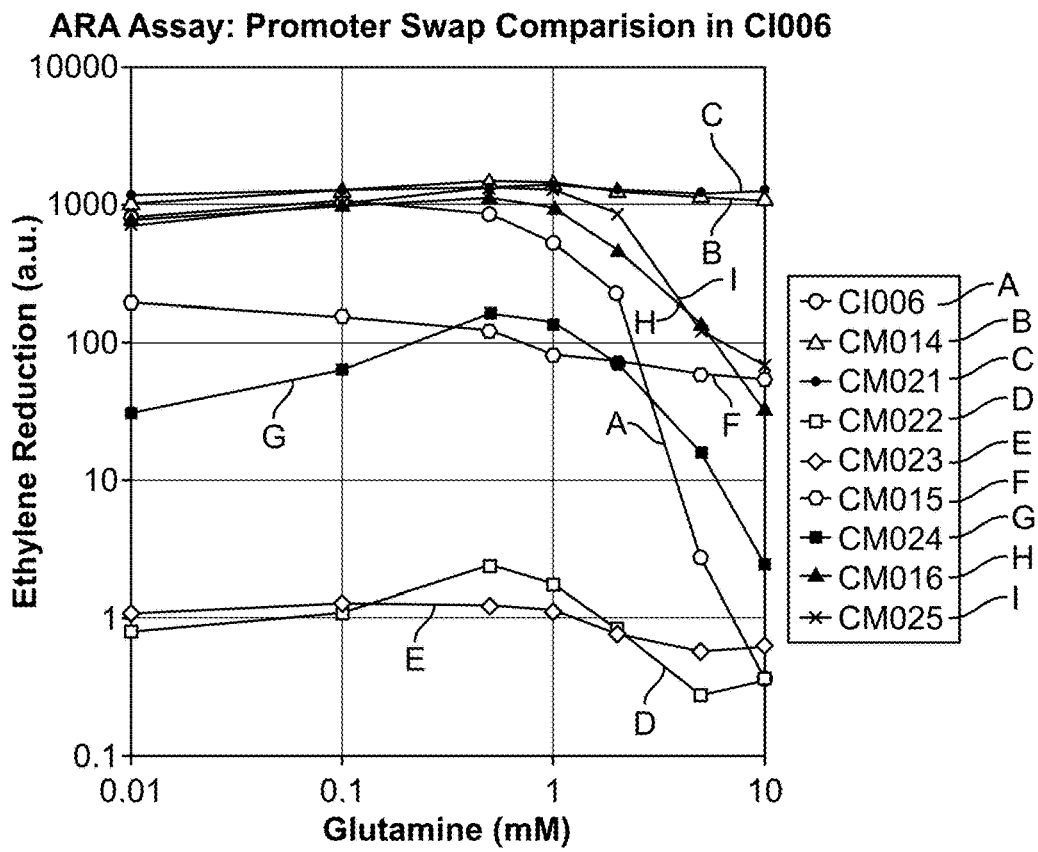
FIGS. 10A-C depicts additional results for ARA activities of candidate microbes and counterpart candidate mutants grown in nitrogen fixation media supplemented with 0 to 10 mM glutamine.

| | | | | | | | | |
|---|---|---|---|---|---|---|---|---|
| | | | | | | | ACCGAATCGCCG TGACGTAGATGA AGGTGTTGAGGA TATTAACCACGA TGTTAACCAGCT CGAACTCACTTC ACACCCCGAAGG GGGAAGTTGCCT GACCCTACGATT CCCGCTATTTCA TTCACTGACCGG AGGTTCAAAATG A | |
| 14 | FIG. 4B | CM023 | CM023 | Mutant of CI006 | Disruption of nifL gene with a fragment of the region upstream of the acpP gene and the first 121 bp of the acpP gene inserted (Prm4). | ΔnifL::Prm4 | ATGACCCTGAAT ATGATGATGGAT GCCGGCTGACGA GGCAGGTTACAT CACTGGTGAAAC CCTGCACGTCAA TGGCGGAATGTA TATGGTTTAACC ACGATGAAAATT ATTTGCGTTATT AGGGCGAAAGG CCTCAAAATAGC GTAAAATCGTGG TAAGAACTGCCG GGATTTAGTTGC AAATTTTTCAAC ATTTTATACACT ACGAAAACCATC GCGAAAGCGAGT TTTGATAGGAAA TTTAAGAGTATG AGCACTATCGAA GAACGCGTTAAG AAAATTATCGGC GAACAGCTGGGC GTTAAGCAGGAA GAAGTTACCAAC AATGCTTCCTTC GTTGAAGACCTG GGCGCTGATTCT CTTGACACCGAA CTCACTTCACAC CCCGAAGGGGA AGTTGCCTGACC CTACGATTCCCG CTATTTCATTCAC TGACCGGAGGTT CAAAATGA | 40 |
| 15 | FIG. 10A | CM014 | CM014 | Mutant of CI006 | Disruption of nifL gene with a fragment of the region upstream of the lpp gene and the first 29 bp of the lpp gene inserted (Prm1). | ΔnifL::Prm1 | ATGACCCTGAAT ATGATGATGGAT GCCGGCCGTCCT GTAATAATAACC GGACAATTCGGA CTGATTAAAAAA GCGCCCTTGTGG CGCTTTTTTTATA TTCCCGCCTCCA TTTAAAATAAAA AATCCAATCGGA TTTCACTATTTAA ACTGGCCATTAT CTAAGATGAATC CGATGGAAGCTC GCTGTTTTAACA CGCGTTTTTTAA CCTTTTATTGAA AGTCGGTGCTTC TTTGAGCGAACG ATCAAATTTAAG TGGATTCCCATC AAAAAAATATTC TCAACCTAAAAA AGTTTGTGTAAT ACTTGTAACGCT | 41 |

-continued

| | | | | | | | | ACATGGAGATTA ACTCAATCTAGA GGGTATTAATAA TGAATCGTACTA AACTGGTACTGG GCGCAACTCACT TCACACCCCGAA GGGGGAAGTTGC CTGACCCTACGA TTCCCGCTATTTC ATTCACTGACCG GAGGTTCAAAAT GA | |
|---|---|---|---|---|---|---|---|---|---|
| 16 | FIG. 10A | CM016 | CM016 | Mutant of CI006 | Disruption of nifL gene with a fragment of the region upstream of the lexA 3 gene and the first 21 bp of the lexA 3 gene inserted (Prm9). | ΔnifL::Prm9 | ATGACCCTGAAT ATGATGATGGAT GCCGGCATATTG ACACCATGACGC GCGTAATGCTGA TTGGTTCTGTGA CGCTGGTAATGA TTGTCGAAATTC TGAACAGTGCCA TCGAAGCCGTAG TAGACCGTATTG GTGCAGAATTCC ATGAACTTTCCG GGCGGGCGAAG GATATGGGGTCG GCGGCGGTGCTG ATGTCCATCCTG CTGGCGATGTTT ACCTGGATCGCA TTACTCTGGTCA CATTTTCGATAA CGCTTCCAGAAT TCGATAACGCCC TGGTTTTTTGCTT AAATTTGGTTCC AAAAATCGCCTTT AGCTGTATATAC TCACAGCATAAC TGTATATACACC CAGGGGGCGGG ATGAAAGCATTA ACGGCCAGGAAC TCACTTCACACC CCGAAGGGGGA AGTTGCCTGACC CTACGATTCCCG CTATTTCATTCAC TGACCGGAGGTT CAAAATGA | 42 |
| 17 | FIG. 10A | CM022 | CM022 | Mutant of CI006 | Disruption of nifL gene with a fragment of the region upstream of the mntP 1 gene and the first 53 bp of the mntP 1 gene inserted (Prm3). | ΔnifL::Prm3 | ATGACCCTGAAT ATGATGATGGAT GCCGGCATCATA TTGCGCTCCCTG GTTATCATTTGTT ACTAAATGAAAT GTTATAATATAA CAATTATAAATA CCACATCGCTTT CAATTCACCAGC CAAATGAGAGGA GCGCCGTCTGAC ATAGCCAGCGCT ATAAAACATAGC ATTATCTATATG TTTATGATTAAT AACTGATTTTG CGTTTTGGATTT GGCTGTGGCATC CTTGCCGCTCTTT TCGCAGCGTCTG CGTTTTTGCCCTC CGGTCAGGGCAT TTAAGGGTCAGC AATGAGTTTTTA | 43 |

-continued

| | | | | | | | | CGCAATTACGAT TCTTGCCTTCGG CATGTCGATGGA TGCTTTAACTCA CTTCACACCCCG AAGGGGGAAGTT GCCTGACCCTAC GATTCCCGCTAT TTCATTCACTGA CCGGAGGTTCAA AATGA | |
|---|---|---|---|---|---|---|---|---|---|
| 18 | FIG. 10A | CM024 | CM024 | Mutant of CI006 | Disruption of nifL gene with a fragment of the region upstream of the sspA gene inserted (Prm7). | ΔnifL::Prm7 | ATGACCCTGAAT ATGATGATGGAT GCCGGCCGCGTC AGGTTGAACGTA AAAAAGTCGGTC TGCGCAAAGCAC GTCGTCGTCCGC AGTTCTCCAAAC GTTAATTGGTTT CTGCTTCGGCAG AACGATTGGCGA AAAAACCCGGTG CGAACCGGGTTT TTTTATGGATAA AGATCGTGTTAT CCACAGCAATCC ATTGATTATCTCT TCTTTTTCAGCAT TTCCAGAATCCC CTCACCACAAAG CCCGCAAAATCT GGTAAACTATCA TCCAATTTTCTGC CCAAATGGCTGG GATTGTTCATTTT TTGTTTGCCTTAC AACGAGAGTGAC AGTACGCGCGGG TAGTTAACTCAA CATCTGACCGGT CGATAACTCACT TCACACCCCGAA GGGGGAAGTTGC CTGACCCTACGA TTCCCGCTATTTC ATTCACTGACCG GAGGTTCAAAAT GA | 44 |
| 19 | FIG. 10A | CM025 | CM025 | Mutant of CI006 | Disruption of nifL gene with a fragment of the region upstream of the hisS gene and the first 52 bp of the hisS gene inserted (Prm10). | ΔnifL::Prm10 | ATGACCCTGAAT ATGATGATGGAT GCCGGCCCTGTA TGAAGATGGCGT GCGCAAAGATCG CCTGGATAACAG CGATATGATTAG CCAGCTTGAAGC CCGCATTCGCGC GAAAGCGTCAAT GCTGGACGAAGC GCGTCGTATCGA TGTGCAACAGGT AGAAAAATAAG GTTGCTGGGAAG CGGCAGGCTTCC CGTGTATGATGA ACCCGCCCGGCG CGACCCGTTGTT CGTCGCGGCCCC GAGGGTTCATTT TTTGTATTAATA AAGAGAATAAAC GTGGCAAAAAT ATTCAAGCCATT CGCGGCATGAAC GATTATCTGCCT GGCGAACTCACT | 45 |

Figure 10B:
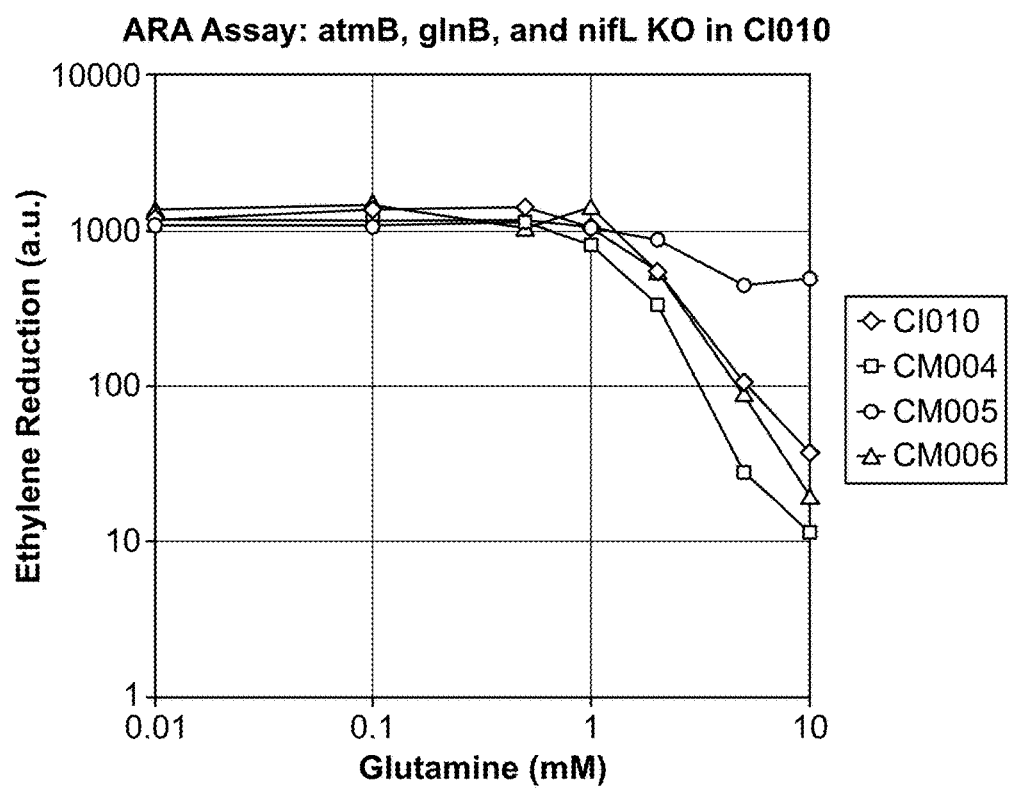

| | | | | | | | | |
|---|---|---|---|---|---|---|---|---|
| 20 | FIG. 10B | CM006 | CM006 | Mutant of CI010 | Disruption of glnB gene with a kanamycin resistance expression cassette (KanR) encoding the aminoglycoside O-phosphotransferase gene aph1 inserted. | ΔglnB::KanR | ATGAAAAAGATT GATGCGATTATT AAACCTTTCAAA CTGGATGACGTG CGCTGATCCTTC AACTCAGCAAAA GTTCGATTTATTC AACAAAGCCACG TTGTGTCTCAAA ATCTCTGATGTT ACATTGCACAAG ATAAAAATATAT CATCATGAACAA TAAAACTGTCTG CTTACATAAACA GTAATACAAGGG GTGTTATGAGCC ATATTCAACGGG AAACGTCTTGCT CCCGTCCGCGCT TAAACTCCAACA TGGACGCTGATT TATATGGGTATA AATGGGCTCGCG ATAATGTCGGGC AATCAGGTGCGA CAATCTATCGCT TGTATGGGAAGC CCGATGCGCCAG AGTTGTTTCTGA AACATGGCAAAG GTAGCGTTGCCA ATGATGTTACAG ATGAGATGGTCC GTCTCAACTGGC TGACGGAGTTTA TGCCTCTCCCGA CCATCAAGCATT TTATCCGTACTC CTGATGATGCGT GGTTACTCACCA CCGCGATTCCTG GGAAAACAGCCT TCCAGGTATTAG AAGAATATCCTG ATTCAGGTGAAA ATATTGTTGATG CGCTGGCCGTGT TCCTGCGCCGGT TACATTCGATTC CTGTTTGTAATT GTCCTTTTAACA GCGATCGTGTAT TTCGTCTTGCTCA GGCGCAATCACG CATGAATAACGG TTTGGTTGATGC GAGTGATTTTGA TGACGAGCGTAA TGGCTGGCCTGT TGAACAAGTCTG GAAAGAAATGCA CAAGCTCTTGCC ATTCTCACCGGA TTCAGTCGTCAC TCATGGTGATTT CTCACTTGATAA CCTTATTTTTGAC GAGGGGAAATTA ATAGGTTGTATT GATGTTGGACGG | 46 |

-continued

TCACACCCCGAA GGGGGAAGTTGC CTGACCCTACGA TTCCCGCTATTTC ATTCACTGACCG GAGGTTCAAAAT GA

-continued

Figure 10C:
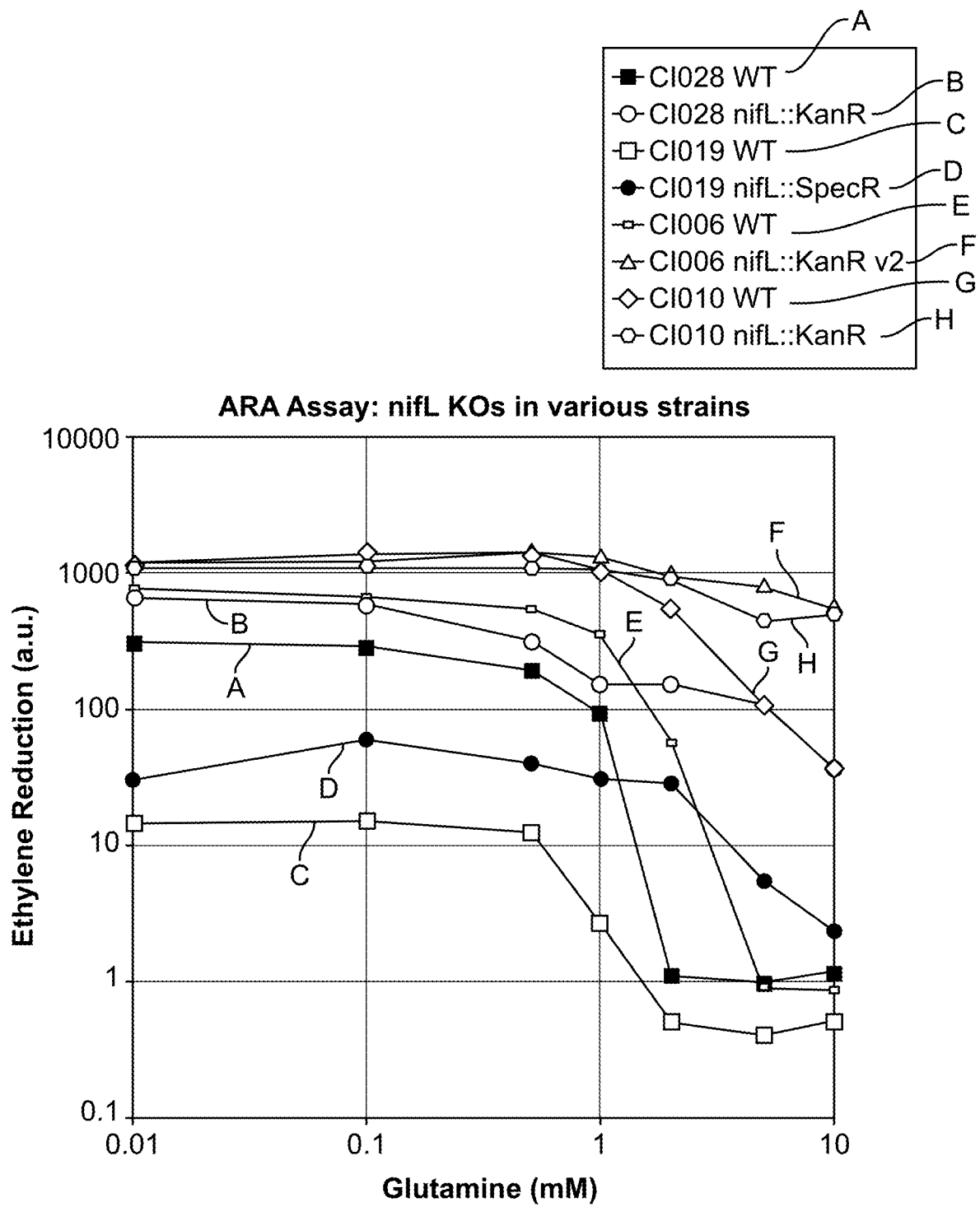

| | | | | | | | GTCGGAATCGCA
GACCGTTACCAG
GACCTTGCCATT
CTTTGGAACTGC
CTCGGTGAGTTT
TCTCCTTCATTAC
AGAAACGGCTTT
TTCAAAAATATG
GTATTGATAATC
CTGATATGAATA
AATTGCAGTTTC
ATTTGATGCTCG
ATGAGTTTTTCT
AATAAGCCTCGC
GCGTGATTCGTA
TCCGCACCGGCG
AAGAAGACGAC
GCGGCGATTTAA | |
|---|---|---|---|---|---|---|---|---|
| 21 | FIG. 10C | CI028 nifL: KanR | CM017 | Mutant of CI028 | Disruption of nifL gene with a kanamycin resistance expression cassette (KanR) encoding the amino-glycoside O-phospho-transferase gene aph1 inserted. | ΔnifL::KanR | ATGACCATGAAC
CTGATGACGGAT
GTCGTCTCAGCC
ACCGGGATCGCC
GGGTTGCTTTCA
CGACAACACCCG
ACGCTGTTTTTA
CACTAATTGAAC
AGGCCCCCGTGG
CGATCACGCTGA
CGGATACCGCTG
CCCGCATTGTCT
ATGCCAACCCGG
GCGTGTTGAGTC
ATCCTGACTAGC
TGAGATGAGGGC
TCGCCTGATCCT
TCAACTCAGCAA
AAGTTCGATTTA
TTCAACAAAGCC
ACGTTGTGTCTC
AAAATCTCTGAT
GTTACATTGCAC
AAGATAAAAATA
TATCATCATGAA
CAATAAAACTGT
CTGCTTACATAA
ACAGTAATACAA
GGGGTGTTATGA
GCCATATTCAAC
GGGAAACGTCTT
GCTCCAGGCCGC
GATTAAATTCCA
ACATGGATGCTG
ATTTATATGGGT
ATAAATGGGCTC
GCGATAATGTCG
GGCAATCAGGTG
CGACAATCTATC
GATTGTATGGGA
AGCCCGATGCGC
CAGAGTTGTTTC
TGAAACATGGCA
AAGGTAGCGTTG
CCAATGATGTTA
CAGATGAGATGG
TCAGACTAAACT
GGCTGACGGAAT
TTATGCCTCTTCC
GACCATCAAGCA
TTTTATCCGTACT
CCTGATGATGCA
TGGTTACTCACC
ACTGCGATCCCC
GGGAAAACAGC
ATTCCAGGTATT
AGAAGAATATCC
TGATTCAGGTGA
AAATATTGTTGA
TGCGCTGGCAGT | 47 |

| | | | | | | | | |
|---|---|---|---|---|---|---|---|---|
| | | | | | | | GTTCCTGCGCCG GTTGCATTCGAT TCCTGTTTGTAAT TGTCCTTTTAAC AGCGATCGCGTA TTTCGTCTCGCTC AGGCGCAATCAC GAATGAATAACG GTTTGGTTGATG CGAGTGATTTTG ATGACGAGCGTA ATGGCTGGCCTG TTGAACAAGTCT GGAAAGAAATGC ATAAGCTTTTGC CATTCTCACCGG ATTCAGTCGTCA CTCATGGTGATT TCTCACTTGATA ACCTTATTTTGA CGAGGGGAAATT AATAGGTTGTAT TGATGTTGGACG AGTCGGAATCGC AGACCGATACCA GGATCTTGCCAT CCTATGGAACTG CCTCGGTGAGTT TTCTCCTTCATTA CAGAAACGGCTT TTTCAAAAATAT GGTATTGATAAT CCTGATATGAAT AAATTGCAGTTT CATTTGATGCTC GATGAGTTTTC TAATAAGCCTGA CCGGTGGTGAAT TTAATCTCGCTG ACGTGTAGACAT TCATCGATCTGC ATCCACGGTCCG GCGGCGGTACCT GCCTGACGCTAC GTTTACCGCTCTT TTATGAACTGAC CGGAGGCCCAAG ATGA | |
| 22 | FIG. 10C | CI019 nifL: SpecR | CM011 | Mutant of CI019 | Disruption of nifL gene with a spectinomycin resistance expression cassette (SpecR) encoding the streptomycin 3"-O-adenylyl-transferase gene aadA inserted. | ΔnifL::SpecR | ATGAGCATCACG GCGTTATCAGCA TCATTTCCTGAG GGGAATATCGCC AGCCGCTTGTCG CTGCAACATCCT TCACTGTTTTATA CCGTGGTTGAAC AATCTTCGGTGG CGAGCGTGTTGA GTCATCCTGACT AGCTGAGATGAG GGCTCGCCCCCT CGTCCCGACACT TCCAGATCGCCA TAGCGCACAGCG CCTCGAGCGGTG GTAACGGCGCAG TGGCGGTTTTCA TGGCTTGTTATG ACTGTTTTTTGG GGTACAGTCTAT GCCTCGGGCATC CAAGCAGCAAGC GCGTTACGCCGT GGGTCGATGTTT GATGTTATGGAG CAGCAACGATGT TACGCAGCAGGG CAGTCGCCCTAA | 48 |

```
AACAAAGTTAAA
CATCATGAGGGA
AGCGGTGATCGC
CGAAGTATCGAC
TCAACTATCAGA
GGTAGTTGGCGT
CATCGAGCGCCA
TCTCGAACCGAC
GTTGCTGGCCGT
ACATTTGTACGG
CTCCGCAGTGGA
TGGCGGCCTGAA
GCCACACAGTGA
TATTGATTTGCT
GGTTACGGTGAC
CGTAAGGCTTGA
TGAAACAACGCG
GCGAGCTTTGAT
CAACGACCTTTT
GGAAACTTCGGC
TTCCCCTGGAGA
GAGCGAGATTCT
CCGCGCTGTAGA
AGTCACCATTGT
TGTGCACGACGA
CATCATTCCGTG
GCGTTATCCAGC
TAAGCGCGAACT
GCAATTTGGAGA
ATGGCAGCGCAA
TGACATTCTTGC
AGGTATCTTCGA
GCCAGCCACGAT
CGACATTGATCT
GGCTATCTTGCT
GACAAAAGCAA
GAGAACATAGCG
TTGCCTTGGTAG
GTCCAGCGGCGG
AGGAACTCTTTG
ATCCGGTTCCTG
AACAGGATCTAT
TTGAGGCGCTAA
ATGAAACCTTAA
CGCTATGGAACT
CGCCGCCCGACT
GGGCTGGCGATG
AGCGAAATGTAG
TGCTTACGTTGT
CCCGCATTTGGT
ACAGCGCAGTAA
CCGGCAAAATCG
CGCCGAAGGATG
TCGCTGCCGACT
GGGCAATGGAGC
GCCTGCCGGCCC
AGTATCAGCCCG
TCATACTTGAAG
CTAGACAGGCTT
ATCTTGGACAAG
AAGAAGATCGCT
TGGCCTCGCGCG
CAGATCAGTTGG
AAGAATTTGTCC
ACTACGTGAAAG
GCGAGATCACCA
AGGTAGTCGGCA
AATAATGTCTAA
CAATTCGTTCAA
GCCGACGCCGCT
TCGCGGCGCGGC
TTAACTCAAGCG
TTAGATGCACTA
AGCACATAATTG
CTCACAGCCAAA
CTATCAGGTCAA
GTCTGCTTTTATT
ATTTTTAAGCGT
GCATAATAAGCC
```

| | | | | | | | | |
|---|---|---|---|---|---|---|---|---|
| | | | | | | | CTACACAAATGG TACCCGACCGGT GGTGAATTTAAT CTCGCTGACGTG TAGACATTCCCT TATCCAGACGCT GATCGCCCATCA TCGCGGTTCTTT AGATCTCTCGGT CCGCCCTGATGG CGGCACCTTGCT GACGTTACGCCT GCCGGTACAGCA GGTTATCACCGG AGGCTTAAAATG A | |
| 23 | FIG. 10C | CI006 nifL: KanR | CM013 | Mutant of CI006 | Disruption of nifL gene with a kanamycin resistance expression cassette (KanR) encoding the amino- glycoside O- phospho- transferase gene aph1 inserted. | ΔnifL::KanR | CTGATCCTTCAA CTCAGCAAAAGT TCGATTTATTCA ACAAAGCCACGT TGTGTCTCAAAA TCTCTGATGTTA CATTGCACAAGA TAAAAATATATC ATCATGAACAAT AAAACTGTCTGC TTACATAAACAG TAATACAAGGGG TGTTATGAGCCA TATTCAACGGGA AACGTCTTGCTC CAGGCCGCGATT AAATTCCAACAT GGATGCTGATTT ATATGGGTATAA ATGGGCTCGCGA TAATGTCGGGCA ATCAGGTGCGAC AATCTATCGATT GTATGGGAAGCC CGATGCGCCAGA GTTGTTTCTGAA ACATGGCAAAGG TAGCGTTGCCAA TGATGTTACAGA TGAGATGGTCAG ACTAAACTGGCT GACGGAATTTAT GCCTCTTCCGAC CATCAAGCATTT TATCCGTACTCC TGATGATGCATG GTTACTCACCAC TGCGATCCCCGG GAAAACAGCATT CCAGGTATTAGA AGAATATCCTGA TTCAGGTGAAAA TATTGTTGATGC GCTGGCAGTGTT CCTGCGCCGGTT GCATTCGATTCC TGTTTGTAATTGT CCTTTTAACAGC GATCGCGTATTT CGTCTCGCTCAG GCGCAATCACGA ATGAATAACGGT TTGGTTGATGCG AGTGATTTTGAT GACGAGCGTAAT GGCTGGCCTGTT GAACAAGTCTGG AAAGAAATGCAT AAGCTTTTGCCA TTCTCACCGGAT TCAGTCGTCACT CATGGTGATTTC | 49 |

| | | | | | | | | |
|---|---|---|---|---|---|---|---|---|
| | | | | | | | TCACTTGATAAC CTTATTTTTGACG AGGGGAAATTAA TAGGTTGTATTG ATGTTGGACGAG TCGGAATCGCAG ACCGATACCAGG ATCTTGCCATCC TATGGAACTGCC TCGGTGAGTTTT CTCCTTCATTAC AGAAACGGCTTT TTCAAAAATATG GTATTGATAATC CTGATATGAATA AATTGCAGTTTC ATTTGATGCTCG ATGAGTTTTCT AATAAGCCTTGA CCCTACGATTCC CGCTATTTCATTC ACTGACCGGAGG TTCAAAATGA | |
| 24 | FIG. 10C | CI010 nifL: KanR | CM005 | Mutant of CI010 | Disruption of nifL gene with a kanamycin resistance expression cassette (KanR) encoding the amino-glycoside O-phospho-transferase gene aph1 inserted. | ΔnifL::KanR | ATGACCCTGAAT ATGATGCTCGAT AACGCCGTACCC GAGGCGATTGCC GGCTGATCCTTC AACTCAGCAAAA GTTCGATTTATTC AACAAAGCCACG TTGTGTCTCAAA ATCTCTGATGTT ACATTGCACAAG ATAAAAATATAT CATCATGAACAA TAAAACTGTCTG CTTACATAAACA GTAATACAAGGG GTGTTATGAGCC ATATTCAACGGG AAACGTCTTGCT CCCGTCCGCGCT TAAACTCCAACA TGGACGCTGATT TATATGGGTATA AATGGGCTCGCG ATAATGTCGGGC AATCAGGTGCGA CAATCTATCGCT TGTATGGGAAGC CCGATGCGCCAG AGTTGTTTCTGA AACATGGCAAAG GTAGCGTTGCCA ATGATGTTACAG ATGAGATGGTCC GTCTCAACTGGC TGACGGAGTTTA TGCCTCTCCCGA CCATCAAGCATT TTATCCGTACTC CTGATGATGCGT GGTTACTCACCA CCGCGATTCCTG GGAAAACAGCCT TCCAGGTATTAG AAGAATATCCTG ATTCAGGTGAAA ATATTGTTGATG CGCTGGCCGTGT TCCTGCGCCGGT TACATTCGATTC CTGTTTGTAATT GTCCTTTTAACA GCGATCGTGTAT TTCGTCTTGCTCA GGCGCAATCACG | 50 |

-continued

|  |  |  |  |  |  |  |  |
|---|---|---|---|---|---|---|---|
|  |  |  |  |  |  |  | CATGAATAACGG |
|  |  |  |  |  |  |  | TTTGGTTGATGC |
|  |  |  |  |  |  |  | GAGTGATTTTGA |
|  |  |  |  |  |  |  | TGACGAGCGTAA |
|  |  |  |  |  |  |  | TGGCTGGCCTGT |
|  |  |  |  |  |  |  | TGAACAAGTCTG |
|  |  |  |  |  |  |  | GAAAGAAATGCA |
|  |  |  |  |  |  |  | CAAGCTCTTGCC |
|  |  |  |  |  |  |  | ATTCTCACCGGA |
|  |  |  |  |  |  |  | TTCAGTCGTCAC |
|  |  |  |  |  |  |  | TCATGGTGATTT |
|  |  |  |  |  |  |  | CTCACTTGATAA |
|  |  |  |  |  |  |  | CCTTATTTTTGAC |
|  |  |  |  |  |  |  | GAGGGGAAATTA |
|  |  |  |  |  |  |  | ATAGGTTGTATT |
|  |  |  |  |  |  |  | GATGTTGGACGG |
|  |  |  |  |  |  |  | GTCGGAATCGCA |
|  |  |  |  |  |  |  | GACCGTTACCAG |
|  |  |  |  |  |  |  | GACCTTGCCATT |
|  |  |  |  |  |  |  | CTTTGGAACTGC |
|  |  |  |  |  |  |  | CTCGGTGAGTTT |
|  |  |  |  |  |  |  | TCTCCTTCATTAC |
|  |  |  |  |  |  |  | AGAAACGGCTTT |
|  |  |  |  |  |  |  | TTCAAAATATG |
|  |  |  |  |  |  |  | GTATTGATAATC |
|  |  |  |  |  |  |  | CTGATATGAATA |
|  |  |  |  |  |  |  | AATTGCAGTTTC |
|  |  |  |  |  |  |  | ATTTGATGCTCG |
|  |  |  |  |  |  |  | ATGAGTTTTTCT |
|  |  |  |  |  |  |  | AATAAGCCTTGG |
|  |  |  |  |  |  |  | TTCTGCGTTTCCC |
|  |  |  |  |  |  |  | GCTCTTTAATAC |
|  |  |  |  |  |  |  | CCTGACCGGAGG |
|  |  |  |  |  |  |  | TGAGCAATGA |
| 25 | FIG. 4C | Strain 2 | CI006 | Isolated strain from *Enterobacter genera* | None | WT |  |
| 26 | FIG. 4C | Strain 4 | CI010 | Isolated strain from *Klebsiella genera* | None | WT |  |
| 27 | FIG. 4C | Strain 1 | CI019 | Isolated strain from *Rahnella genera* | None | WT |  |
| 28 | FIG. 4C | Strain 3 | CI028 | Isolated strain from *Enterobacter genera* | None | WT |  |
| 29 | FIG. 4B | Strain 2 | CI006 | Isolated strain from *Enterobacter genera* | None | WT |  |
| 30 | FIG. 4B | High | CM014 | Mutant of CI006 | Disruption of nifL gene with a fragment of the region upstream of the lpp gene and the first 29 bp of the lpp gene inserted (Prm1). | ΔAnifL:Prm1 | ATGACCCTGAAT ATGATGATGGAT GCCGGCCGTCCT GTAATAATAACC GGACAATTCGGA CTGATTAAAAAA GCGCCCTTGTGG CGCTTTTTTTATA TTCCCGCCTCCA TTTAAAATAAAA AATCCAATCGGA | 51 |

| | | | | | | | |
|---|---|---|---|---|---|---|---|
| | | | | | | | TTTCACTATTTAA ACTGGCCATTAT CTAAGATGAATC CGATGGAAGCTC GCTGTTTTAACA CGCGTTTTTTAA CCTTTTATTGAA AGTCGGTGCTTC TTTGAGCGAACG ATCAAATTTAAG TGGATTCCCATC AAAAAAATATTC TCAACCTAAAAA AGTTTGTGTAAT ACTTGTAACGCT ACATGGAGATTA ACTCAATCTAGA GGGTATTAATAA TGAATCGTACTA AACTGGTACTGG GCGCAACTCACT TCACACCCCGAA GGGGGAAGTTGC CTGACCCTACGA TTCCCGCTATTC ATTCACTGACCG GAGGTTCAAAAT GA | |
| 31 | FIG. 4B | Med | CM015 | Mutant of CI006 | Disruption of nifL gene with a fragment of the region upstream of the ompX gene inserted (Prm5). | ΔnifL:Prm5 | ATGACCCTGAAT ATGATGATGGAT GCCGGCGGACAT CATCGCGACAAA CAATATTAATAC CGGCAACCACAC CGGCAATTTACG AGACTGCGCAGG CATCCTTTCTCCC GTCAATTTCTGT CAAATAAAGTAA AAGAGGCAGTCT ACTTGAATTACC CCCGGCTGGTTG AGCGTTTGTTGA AAAAAAGTAACT GAAAAATCCGTA GAATAGCGCCAC TCTGATGGTTAA TTAACCTATTCA ATTAAGAATTAT CTGGATGAATGT GCCATTAAATGC GCAGCATAATGG TGCGTTGTGCGG GAAAACTGCTTT TTTTTGAAAGGG TTGGTCAGTAGC GGAAACAACTCA CTTCACACCCCG AAGGGGGAAGTT GCCTGACCCTAC GATTCCCGCTAT TTCATTCACTGA CCGGAGGTTCAA AATGA | 52 |
| 32 | FIG. 4B | Low | CM023 | Mutant of CI006 | Disruption of nifL gene with a fragment of the region upstream of the acpP gene and the first 121 bp of the acpP gene inserted (Prm4). | ΔnifL::Prm4 | ATGACCCTGAAT ATGATGATGGAT GCCGGCTGACGA GGCAGGTTACAT CACTGGTGAAAC CCTGCACGTCAA TGGCGGAATGTA TATGGTTTAACC ACGATGAAAATT ATTTGCGTTATT AGGGCGAAAGG CCTCAAAATAGC GTAAAATCGTGG | 53 |

-continued

| | | | | | | | |
|---|---|---|---|---|---|---|---|
| | | | | | | | TAAGAACTGCCG GGATTTAGTTGC AAATTTTTCAAC ATTTTATACACT ACGAAAACCATC GCGAAAGCGAGT TTTGATAGGAAA TTTAAGAGTATG AGCACTATCGAA GAACGCGTTAAG AAAATTATCGGC GAACAGCTGGGC GTTAAGCAGGAA GAAGTTACCAAC AATGCTTCCTTC GTTGAAGACCTG GGCGCTGATTCT CTTGACACCGAA CTCACTTCACAC CCCGAAGGGGGA AGTTGCCTGACC CTACGATTCCCG CTATTTCATTCAC TGACCGGAGGTT CAAAATGA | |
| 33 | FIG. 4D | Strain 2 | CI006 | Isolated strain from *Enterobacter genera* | None | WT | |
| 34 | FIG. 4D | Evolved | CM029 | Mutant of CI006 | Disruption of nifL gene with a fragment of the region upstream of the ompX gene inserted (Prm5) and deletion of the 1287 bp after the start codon of the glnE gene containing the adenylyl-removing domain of glutamate-ammonia-ligase adenylyl-transferase (ΔglnE-AR_KO1). | ΔnifL::Prm5 ΔglnE-AR_KO1 | ATGACCCTGAAT ATGATGATGGAT GCCGGCGGACAT CATCGCGACAAA CAATATTAATAC CGGCAACCACAC CGGCAATTTACG AGACTGCGCAGG CATCCTTTCTCCC GTCAATTTCTGT CAAATAAAGTAA AAGAGGCAGTCT ACTTGAATTACC CCCGGCTGGTTG AGCGTTTGTTGA AAAAAAGTAACT GAAAAATCCGTA GAATAGCGCCAC TCTGATGGTTAA TTAACCTATTCA ATTAAGAATTAT CTGGATGAATGT GCCATTAAATGC GCAGCATAATGG TGCGTTGTGCGG GAAAACTGCTTT TTTTTGAAAGGG TTGGTCAGTAGC GGAAACAACTCA CTTCACACCCCG AAGGGGGAAGTT GCCTGACCCTAC GATTCCCGCTAT TCATTCACTGA CCGGAGGTTCAA AATGA | 54 |
| 35 | FIG. 14C | Wild | CI006 | Isolated strain from *Enterobacter genera* | None | WT | |

-continued

| 36 | FIG. 14C | Evolved | CM014 | Mutant of CI006 | Disruption of nifL gene with a fragment of the region upstream of the lpp gene and the first 29 bp of the lpp gene inserted (Prm1). | ΔnifL::Prm1 | ATGACCCTGAAT ATGATGATGGAT GCCGGCCGTCCT GTAATAATAACC GGACAATTCGGA CTGATTAAAAAA GCGCCCTTGTGG CGCTTTTTTTATA TTCCCGCCTCCA TTTAAAATAAAA AATCCAATCGGA TTTCACTATTTAA ACTGGCCATTAT CTAAGATGAATC CGATGGAAGCTC GCTGTTTTAACA CGCGTTTTTTAA CCTTTTATTGAA AGTCGGTGCTTC TTTGAGCGAACG ATCAAATTTAAG TGGATTCCCATC AAAAAAATATTC TCAACCTAAAAA AGTTTGTGTAAT ACTTGTAACGCT ACATGGAGATTA ACTCAATCTAGA GGGTATTAATAA TGAATCGTACTA AACTGGTACTGG GCGCAACTCACT TCACACCCCGAA GGGGGAAGTTGC CTGACCCTACGA TTCCCGCTATTTC ATTCACTGACCG GAGGTTCAAAAT GA | 55 |
| 37 | FIG. 14B | Wild | CI019 | Isolated strain from Rahnella genera | None | WT | | |
| 38 | FIG. 14B | Evolved | CM011 | Mutant of CI019 | Disruption of nifL gene with a spectinomycin resistance expression cassette (SpecR) encoding the streptomycin 3"-O-adenylyl-transferase gene aadA inserted. | ΔnifL::SpecR | ATGAGCATCACG GCGTTATCAGCA TCATTTCCTGAG GGGAATATCGCC AGCCGCTTGTCG CTGCAACATCCT TCACTGTTTTATA CCGTGGTTGAAC AATCTTCGGTGG CGAGCGTGTTGA GTCATCCTGACT AGCTGAGATGAG GGCTCGCCCCCT CGTCCCGACACT TCCAGATCGCCA TAGCGCACAGCG CCTCGAGCGGTG GTAACGGCGCAG TGGCGGTTTTCA TGGCTTGTTATG ACTGTTTTTTGG GGTACAGTCTAT GCCTCGGGCATC CAAGCAGCAAGC GCGTTACGCCGT GGGTCGATGTTT GATGTTATGGAG CAGCAACGATGT TACGCAGCAGGG CAGTCGCCCTAA AACAAAGTTAAA CATCATGAGGGA AGCGGTGATCGC | 56 |

```
CGAAGTATCGAC
TCAACTATCAGA
GGTAGTTGGCGT
CATCGAGCGCCA
TCTCGAACCGAC
GTTGCTGGCCGT
ACATTTGTACGG
CTCCGCAGTGGA
TGGCGGCCTGAA
GCCACACAGTGA
TATTGATTTGCT
GGTTACGGTGAC
CGTAAGGCTTGA
TGAAACAACGCG
GCGAGCTTTGAT
CAACGACCTTTT
GGAAACTTCGGC
TTCCCCTGGAGA
GAGCGAGATTCT
CCGCGCTGTAGA
AGTCACCATTGT
TGTGCACGACGA
CATCATTCCGTG
GCGTTATCCAGC
TAAGCGCGAACT
GCAATTTGGAGA
ATGGCAGCGCAA
TGACATTCTTGC
AGGTATCTTCGA
GCCAGCCACGAT
CGACATTGATCT
GGCTATCTTGCT
GACAAAAGCAA
GAGAACATAGCG
TTGCCTTGGTAG
GTCCAGCGGCGG
AGGAACTCTTTG
ATCCGGTTCCTG
AACAGGATCTAT
TTGAGGCGCTAA
ATGAAACCTTAA
CGCTATGGAACT
CGCCGCCCGACT
GGGCTGGCGATG
AGCGAAATGTAG
TGCTTACGTTGT
CCCGCATTTGGT
ACAGCGCAGTAA
CCGGCAAAATCG
CGCCGAAGGATG
TCGCTGCCGACT
GGGCAATGGAGC
GCCTGCCGGCCC
AGTATCAGCCCG
TCATACTTGAAG
CTAGACAGGCTT
ATCTTGGACAAG
AAGAAGATCGCT
TGGCCTCGCGCG
CAGATCAGTTGG
AAGAATTTGTCC
ACTACGTGAAAG
GCGAGATCACCA
AGGTAGTCGGCA
AATAATGTCTAA
CAATTCGTTCAA
GCCGACGCCGCT
TCGCGGCGCGGC
TTAACTCAAGCG
TTAGATGCACTA
AGCACATAATTG
CTCACAGCCAAA
CTATCAGGTCAA
GTCTGCTTTTATT
ATTTTTAAGCGT
GCATAATAAGCC
CTACACAAATGG
TACCCGACCGGT
GGTGAATTTAAT
```

| | | | | | | CTCGCTGACGTG TAGACATTCCCT TATCCAGACGCT GATCGCCCATCA TCGCGGTTCTTT AGATCTCTCGGT CCGCCCTGATGG CGGCACCTTGCT GACGTTACGCCT GCCGGTACAGCA GGTTATCACCGG AGGCTTAAAATG A | |
|---|---|---|---|---|---|---|---|
| 39 | FIG. 14A | Evolved CM011 | Mutant of CI019 | Disruption of nifL gene with a spectinomycin resistance expression cassette (SpecR) encoding the streptomycin 3"-O-adenylyl-transferase gene aadA inserted. | ΔnifL::SpecR | ATGAGCATCACG GCGTTATCAGCA TCATTTCCTGAG GGGAATATCGCC AGCCGCTTGTCG CTGCAACATCCT TCACTGTTTTATA CCGTGGTTGAAC AATCTTCGGTGG CGAGCGTGTTGA GTCATCCTGACT AGCTGAGATGAG GGCTCGCCCCCT CGTCCCGACACT TCCAGATCGCCA TAGCGCACAGCG CCTCGAGCGGTG GTAACGGCGCAG TGGCGGTTTTCA TGGCTTGTTATG ACTGTTTTTTGG GGTACAGTCTAT GCCTCGGGCATC CAAGCAGCAAGC GCGTTACGCCGT GGGTCGATGTTT GATGTTATGGAG CAGCAACGATGT TACGCAGCAGGG CAGTCGCCCTAA AACAAAGTAAA CATCATGAGGGA AGCGGTGATCGC CGAAGTATCGAC TCAACTATCAGA GGTAGTTGGCGT CATCGAGCGCCA TCTCGAACCGAC GTTGCTGGCCGT ACATTTGTACGG CTCCGCAGTGGA TGGCGGCCTGAA GCCACACAGTGA TATTGATTTGCT GGTTACGGTGAC CGTAAGGCTTGA TGAAACAACGCG GCGAGCTTTGAT CAACGACCTTTT GGAAACTTCGGC TTCCCCTGGAGA GAGCGAGATTCT CCGCGCTGTAGA AGTCACCATTGT TGTGCACGACGA CATCATTCCGTG GCGTTATCAGC TAAGCGCGAACT GCAATTTGGAGA ATGGCAGCGCAA TGACATTCTTGC AGGTATCTTCGA GCCAGCCACGAT CGACATTGATCT GGCTATCTTGCT | 57 |

Figure 15A:
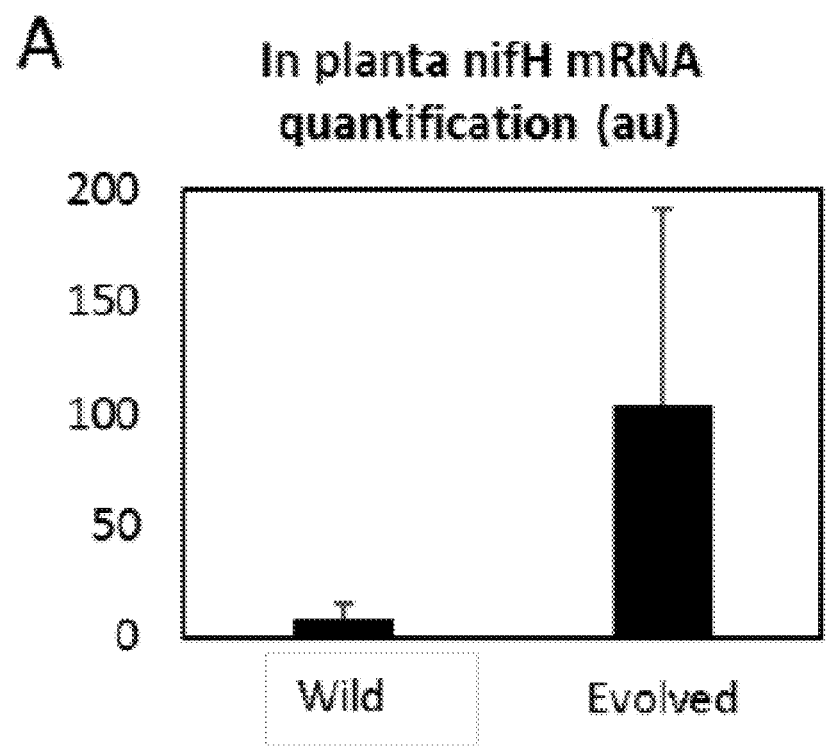
FIG. 15A depicts evolved strains that show significantly higher nifH production in the root tissue, as measured by in planta transcriptomic study.

| | | | | | | | |
|---|---|---|---|---|---|---|---|
| | | | | | | | GACAAAAGCAA |
| | | | | | | | GAGAACATAGCG |
| | | | | | | | TTGCCTTGGTAG |
| | | | | | | | GTCCAGCGGCGG |
| | | | | | | | AGGAACTCTTTG |
| | | | | | | | ATCCGGTTCCTG |
| | | | | | | | AACAGGATCTAT |
| | | | | | | | TTGAGGCGCTAA |
| | | | | | | | ATGAAACCTTAA |
| | | | | | | | CGCTATGGAACT |
| | | | | | | | CGCCGCCCGACT |
| | | | | | | | GGGCTGGCGATG |
| | | | | | | | AGCGAAATGTAG |
| | | | | | | | TGCTTACGTTGT |
| | | | | | | | CCCGCATTTGGT |
| | | | | | | | ACAGCGCAGTAA |
| | | | | | | | CCGGCAAAATCG |
| | | | | | | | CGCCGAAGGATG |
| | | | | | | | TCGCTGCCGACT |
| | | | | | | | GGGCAATGGAGC |
| | | | | | | | GCCTGCCGGCCC |
| | | | | | | | AGTATCAGCCCG |
| | | | | | | | TCATACTTGAAG |
| | | | | | | | CTAGACAGGCTT |
| | | | | | | | ATCTTGGACAAG |
| | | | | | | | AAGAAGATCGCT |
| | | | | | | | TGGCCTCGCGCG |
| | | | | | | | CAGATCAGTTGG |
| | | | | | | | AAGAATTTGTCC |
| | | | | | | | ACTACGTGAAAG |
| | | | | | | | GCGAGATCACCA |
| | | | | | | | AGGTAGTCGGCA |
| | | | | | | | AATAATGTCTAA |
| | | | | | | | CAATTCGTTCAA |
| | | | | | | | GCCGACGCCGCT |
| | | | | | | | TCGCGGCGCGGC |
| | | | | | | | TTAACTCAAGCG |
| | | | | | | | TTAGATGCACTA |
| | | | | | | | AGCACATAATTG |
| | | | | | | | CTCACAGCCAAA |
| | | | | | | | CTATCAGGTCAA |
| | | | | | | | GTCTGCTTTTATT |
| | | | | | | | ATTTTTAAGCGT |
| | | | | | | | GCATAATAAGCC |
| | | | | | | | CTACACAAATGG |
| | | | | | | | TACCCGACCGGT |
| | | | | | | | GGTGAATTTAAT |
| | | | | | | | CTCGCTGACGTG |
| | | | | | | | TAGACATTCCCT |
| | | | | | | | TATCCAGACGCT |
| | | | | | | | GATCGCCCATCA |
| | | | | | | | TCGCGGTTCTTT |
| | | | | | | | AGATCTCTCGGT |
| | | | | | | | CCGCCCTGATGG |
| | | | | | | | CGGCACCTTGCT |
| | | | | | | | GACGTTACGCCT |
| | | | | | | | GCCGGTACAGCA |
| | | | | | | | GGTTATCACCGG |
| | | | | | | | AGGCTTAAAATG |
| | | | | | | | A |
| 40 | FIG. 15A | Wild | CI006 | Isolated strain from *Enterobacter* genera | None | WT | |
| 41 | FIG. 15A | Evolved | CM013 | Mutant of CI006 | Disruption of nifL gene with a kanamycin resistance expression cassette (KanR) encoding the aminoglycoside O-phospho- | ΔnifL::KanR | CTGATCCTTCAA CTCAGCAAAAGT TCGATTTATTCA ACAAAGCCACGT TGTGTCTCAAAA TCTCTGATGTTA CATTGCACAAGA TAAAATATATC ATCATGAACAAT AAAACTGTCTGC TTACATAAACAG | 58 |

-continued

Figure 15B:
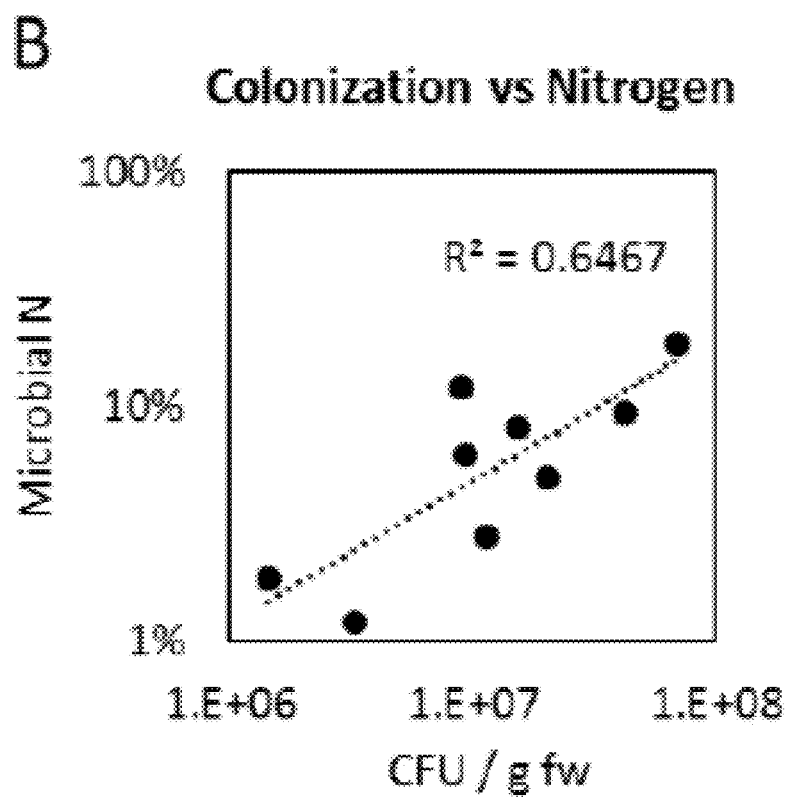
FIG. 15B depicts that rate of fixed nitrogen found in plant tissue is correlated with the rate in which that particular plant is colonized by HoME optimized strain.

| | | | | transferase gene aph1 inserted. | | TAATACAAGGGG TGTTATGAGCCA TATTCAACGGGA AACGTCTTGCTC CAGGCCGCGATT AAATTCCAACAT GGATGCTGATTT ATATGGGTATAA ATGGGCTCGCGA TAATGTCGGGCA ATCAGGTGCGAC AATCTATCGATT GTATGGGAAGCC CGATGCGCCAGA GTTGTTTCTGAA ACATGGCAAAGG TAGCGTTGCCAA TGATGTTACAGA TGAGATGGTCAG ACTAAACTGGCT GACGGAATTTAT GCCTCTTCCGAC CATCAAGCATTT TATCCGTACTCC TGATGATGCATG GTTACTCACCAC TGCGATCCCCGG GAAAACAGCATT CCAGGTATTAGA AGAATATCCTGA TTCAGGTGAAAA TATTGTTGATGC GCTGGCAGTGTT CCTGCGCCGGTT GCATTCGATTCC TGTTTGTAATTGT CCTTTTAACAGC GATCGCGTATTT CGTCTCGCTCAG GCGCAATCACGA ATGAATAACGGT TTGGTTGATGCG AGTGATTTTGAT GACGAGCGTAAT GGCTGGCCTGTT GAACAAGTCTGG AAAGAAATGCAT AAGCTTTTGCCA TTCTCACCGGAT TCAGTCGTCACT CATGGTGATTTC TCACTTGATAAC CTTATTTTTGACG AGGGGAAATTAA TAGGTTGTATTG ATGTTGGACGAG TCGGAATCGCAG ACCGATACCAGG ATCTTGCCATCC TATGGAACTGCC TCGGTGAGTTTT CTCCTTCATTAC AGAAACGGCTTT TTCAAAAATATG GTATTGATAATC CTGATATGAATA AATTGCAGTTTC ATTTGATGCTCG ATGAGTTTTTCT AATAAGCCTTGA CCCTACGATTCC CGCTATTTCATTC ACTGACCGGAGG TTCAAAATGA | |
| 42 | FIG. 15B | No name | CM011 | Mutant of CI019 | Disruption of nifL gene with a spectinomycin | ΔnifL::SpecR | ATGAGCATCACG GCGTTATCAGCA TCATTTCCTGAG GGGAATATCGCC | 59 |

| | |
|---|---|
| resistance expression cassette (SpecR) encoding the streptomycin 3"-O-adenylyl-transferase gene aadA inserted. | AGCCGCTTGTCG CTGCAACATCCT TCACTGTTTTATA CCGTGGTTGAAC AATCTTCGGTGG CGAGCGTGTTGA GTCATCCTGACT AGCTGAGATGAG GGCTCGCCCCCT CGTCCCGACACT TCCAGATCGCCA TAGCGCACAGCG CCTCGAGCGGTG GTAACGGCGCAG TGGCGGTTTTCA TGGCTTGTTATG ACTGTTTTTTGG GGTACAGTCTAT GCCTCGGGCATC CAAGCAGCAAGC GCGTTACGCCGT GGGTCGATGTTT GATGTTATGGAG CAGCAACGATGT TACGCAGCAGGG CAGTCGCCCTAA AACAAAGTTAAA CATCATGAGGGA AGCGGTGATCGC CGAAGTATCGAC TCAACTATCAGA GGTAGTTGGCGT CATCGAGCGCCA TCTCGAACCGAC GTTGCTGGCCGT ACATTTGTACGG CTCCGCAGTGGA TGGCGGCCTGAA GCCACACAGTGA TATTGATTTGCT GGTTACGGTGAC CGTAAGGCTTGA TGAAACAACGCG GCGAGCTTTGAT CAACGACCTTTT GGAAACTTCGGC TTCCCCTGGAGA GAGCGAGATTCT CCGCGCTGTAGA AGTCACCATTGT TGTGCACGACGA CATCATTCCGTG GCGTTATCCAGC TAAGCGCGAACT GCAATTTGGAGA ATGGCAGCGCAA TGACATTCTTGC AGGTATCTTCGA GCCAGCCACGAT CGACATTGATCT GGCTATCTTGCT GACAAAAGCAA GAGAACATAGCG TTGCCTTGGTAG GTCCAGCGGCGG AGGAACTCTTTG ATCCGGTTCCTG AACAGGATCTAT TTGAGGCGCTAA ATGAAACCTTAA CGCTATGGAACT CGCCGCCCGACT GGGCTGGCGATG AGCGAAATGTAG TGCTTACGTTGT CCCGCATTTGGT ACAGCGCAGTAA CCGGCAAAATCG CGCCGAAGGATG |

| | | | | | | | | |
|---|---|---|---|---|---|---|---|---|
| | | | | | | | TCGCTGCCGACT GGGCAATGGAGC GCCTGCCGGCCC AGTATCAGCCCG TCATACTTGAAG CTAGACAGGCTT ATCTTGGACAAG AAGAAGATCGCT TGGCCTCGCGCG CAGATCAGTTGG AAGAATTTGTCC ACTACGTGAAAG GCGAGATCACCA AGGTAGTCGGCA AATAATGTCTAA CAATTCGTTCAA GCCGACGCCGCT TCGCGGCGCGGC TTAACTCAAGCG TTAGATGCACTA AGCACATAATTG CTCACAGCCAAA CTATCAGGTCAA GTCTGCTTTTATT ATTTTTAAGCGT GCATAATAAGCC CTACACAAATGG TACCCGACCGGT GGTGAATTTAAT CTCGCTGACGTG TAGACATTCCCT TATCCAGACGCT GATCGCCCATCA TCGCGGTTCTTT AGATCTCTCGGT CCGCCCTGATGG CGGCACCTTGCT GACGTTACGCCT GCCGGTACAGCA GGTTATCACCGG AGGCTTAAAATG A | |
| 43 | FIG. 16B | Strain 5 | CI008 | Isolated strain from *Burkholderia genera* | None | WT | | |
| 44 | FIG. 16B | Strain 1 | CM011 | Mutant of CI019 | Disruption of nifL gene with a spectinomycin resistance expression cassette (SpecR) encoding the streptomycin 3"-O-adenylyl-transferase gene aadA inserted. | ΔnifL::SpecR | ATGAGCATCACG GCGTTATCAGCA TCATTTCCTGAG GGGAATATCGCC AGCCGCTTGTCG CTGCAACATCCT TCACTGTTTTATA CCGTGGTTGAAC AATCTTCGGTGG CGAGCGTGTTGA GTCATCCTGACT AGCTGAGATGAG GGCTCGCCCCCT CGTCCCGACACT TCCAGATCGCCA TAGCGCACAGCG CCTCGAGCGGTG GTAACGGCGCAG TGGCGGTTTTCA TGGCTTGTTATG ACTGTTTTTTGG GGTACAGTCTAT GCCTCGGGCATC CAAGCAGCAAGC GCGTTACGCCGT GGGTCGATGTTT GATGTTATGGAG CAGCAACGATGT TACGCAGCAGGG CAGTCGCCCTAA | 60 |

-continued

```
AACAAAGTTAAA
CATCATGAGGGA
AGCGGTGATCGC
CGAAGTATCGAC
TCAACTATCAGA
GGTAGTTGGCGT
CATCGAGCGCCA
TCTCGAACCGAC
GTTGCTGGCCGT
ACATTTGTACGG
CTCCGCAGTGGA
TGGCGGCCTGAA
GCCACACAGTGA
TATTGATTTGCT
GGTTACGGTGAC
CGTAAGGCTTGA
TGAAACAACGCG
GCGAGCTTTGAT
CAACGACCTTTT
GGAAACTTCGGC
TTCCCCTGGAGA
GAGCGAGATTCT
CCGCGCTGTAGA
AGTCACCATTGT
TGTGCACGACGA
CATCATTCCGTG
GCGTTATCCAGC
TAAGCGCGAACT
GCAATTTGGAGA
ATGGCAGCGCAA
TGACATTCTTGC
AGGTATCTTCGA
GCCAGCCACGAT
CGACATTGATCT
GGCTATCTTGCT
GACAAAAGCAA
GAGAACATAGCG
TTGCCTTGGTAG
GTCCAGCGGCGG
AGGAACTCTTTG
ATCCGGTTCCTG
AACAGGATCTAT
TTGAGGCGCTAA
ATGAAACCTTAA
CGCTATGGAACT
CGCCGCCCGACT
GGGCTGGCGATG
AGCGAAATGTAG
TGCTTACGTTGT
CCCGCATTTGGT
ACAGCGCAGTAA
CCGGCAAAATCG
CGCCGAAGGATG
TCGCTGCCGACT
GGGCAATGGAGC
GCCTGCCGGCCC
AGTATCAGCCCG
TCATACTTGAAG
CTAGACAGGCTT
ATCTTGGACAAG
AAGAAGATCGCT
TGGCCTCGCGCG
CAGATCAGTTGG
AAGAATTTGTCC
ACTACGTGAAAG
GCGAGATCACCA
AGGTAGTCGGCA
AATAATGTCTAA
CAATTCGTTCAA
GCCGACGCCGCT
TCGCGGCGCGGC
TTAACTCAAGCG
TTAGATGCACTA
AGCACATAATTG
CTCACAGCCAAA
CTATCAGGTCAA
GTCTGCTTTTATT
ATTTTTAAGCGT
GCATAATAAGCC
```

-continued

CTACACAAATGG
TACCCGACCGGT
GGTGAATTTAAT
CTCGCTGACGTG
TAGACATTCCCT
TATCCAGACGCT
GATCGCCCATCA
TCGCGGTTCTTT
AGATCTCTCGGT
CCGCCCTGATGG
CGGCACCTTGCT
GACGTTACGCCT
GCCGGTACAGCA
GGTTATCACCGG
AGGCTTAAAATG
A

Table of Strains

| Sort | First Reference | Current Name | Universal Name | Lineage | Mutagenic DNA Description | Genotype | Gene 2 mutation | SEQ ID NO: |
|---|---|---|---|---|---|---|---|---|
| 34 | FIG. 4D | Evolved | CM029 | Mutant of CI006 | Disruption of nifL gene with a fragment of the region upstream of the ompX gene inserted (Prm5) and deletion of the 1287 bp after the start codon of the glnE gene containing the adenylyl-removing domain of glutamate-ammonia-ligase adenylyl-transferase (ΔglnE-AR_KO1). | ΔnifL::Prm5 ΔglnE-AR_KO1 | ATGTTTAACGAT CTGATTGGCGAT GATGAAACGGA TTCGCCGGAAGA TGCGCTTTCTGA GAGCTGGCGCG AATTGTGGCAGG ATGCGTTGCAGG AGGAGGATTCC ACGCCCGTGCTG GCGCATCTCTCA GAGGACGATCG CCGCCGCGTGGT GGCGCTGATTGC CGATTTTCGCAA AGAGTTGGATA AACGCACCATTG GCCCGCGAGGG CGGCAGGTACTC GATCACTTAATG CCGCATCTGCTC AGCGATGTATGC TCGCGCGACGAT GCGCCAGTACCG CTGTCACGCCTG ACGCCGCTGCTC ACCGGAATTATT ACCCGCACCACT TACCTTGAGCTG CTAAGTGAATTT CCCGGCGCACTG AAACACCTCATT TCCCTGTGTGCC GCGTCGCCGATG GTTGCCAGTCAG CTGGCGCGCTAC CCGATCCTGCTT GATGAATTGCTC GACCCGAATAC GCTCTATCAACC GACGGCGATGA ATGCCTATCGCG ATGAGCTGCGCC AATACCTGCTGC GCGTGCCGGAA GATGATGAAGA GCAACAGCTTGA GGCGCTGCGGC AGTTTAAGCAGG CGCAGTTGCTGC GCGTGGCGGCG GCGGATATTGCC GGTACGTTGCCA GTAATGAAAGT GAGCGATCACTT AACCTGGCTGGC | 61 |

-continued

```
GGAAGCGATTAT
TGATGCGGTGGT
GCAGCAAGCCT
GGGGGCAGATG
GTGGCGCGTTAT
GGCCAGCCAAC
GCATCTGCACGA
TCGCGAAGGGC
GCGGTTTTGCGG
TGGTCGGTTATG
GCAAGCTGGGC
GGCTGGGAGCT
GGGTTACAGCTC
CGATCTGGATCT
GGTATTCCTGCA
CGACTGCCCGAT
GGATGTGATGAC
CGATGGCGAGC
GTGAAATCGATG
GTCGCCAGTTCT
ATTTGCGTCTCG
CGCAGCGCGTG
ATGCACCTGTTT
AGCACGCGCAC
GTCGTCCGGCAT
CCTTTATGAAGT
TGATGCGCGTCT
GCGTCCATCTGG
CGCTGCGGGAT
GCTGGTCACTAC
TACGGAATCGTT
CGCCGATTACCA
GCAAAACGAAG
CCTGGACGTGGG
AACATCAGGCG
CTGGCCCGTGCG
CGCGTGGTGTAC
GGCGATCCGCA
ACTGACCGCCGA
ATTTGACGCCAT
TCGCCGCGATAT
TCTGATGACGCC
TCGCGACGGCGC
AACGCTGCAAA
CCGACGTGCGA
GAAATGCGCGA
GAAAATGCGTG
CCCATCTTGGCA
ACAAGCATAAA
GACCGCTTCGAT
CTGAAAGCCGAT
GAAGGCGGTAT
CACCGACATCGA
GTTTATCGCCCA
ATATCTGGTGCT
GCGCTTTGCCCA
TGACAAGCCGA
AACTGACGCGCT
GGTCGGATAATG
TGCGCATTCTCG
AAGGGCTGGCG
CAAAACGGCAT
CATGGAGGAGC
AGGAAGCGCAG
GCATTGACGCTG
GCGTACACCACA
TTGCGTGATGAG
CTGCACCACCTG
GCGCTGCAAGA
GTTGCCGGGACA
TGTGGCGCTCTC
CTGTTTTGTCGC
CGAGCGTGCGCT
TATTAAAACCAG
CTGGGACAAGT
GGCTGGTGGAA
CCGTGCGCCCCG
GCGTAA
```

Notwithstanding the appended claims, the disclosure set forth herein is also defined by the following clauses:

1. A method of producing one or more bacteria, comprising:
   (a) isolating bacteria from tissue or soil of a first plant;
   (b) introducing genetic variation into one or more of the bacteria to produce one or more variant bacteria;
   (c) exposing a plurality of plants to the variant bacteria;
   (d) isolating bacteria from tissue or soil of one of the plurality of plants, wherein the plant from which the bacteria is isolated has an improved trait relative to other plants in the plurality of plants; and
   (e) repeating steps (b) to (d) with bacteria isolated in step (d).

2. The method of clause 1, wherein the improved trait is enhanced nitrogen fixation in the plant from which bacteria are isolated.

3. The method of clause 1, wherein the genetic variation is a variation in a gene selected from the group consisting of: nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ.

4. The method of clause 1, wherein the genetic variation is a variation in a gene encoding a protein with functionality selected from the group consisting of: glutamine synthetase, glutaminase, glutamine synthetase adenylyltransferase, transcriptional activator, anti-transcriptional activator, pyruvate flavodoxin oxidoreductase, flavodoxin, or NAD+-dinitrogen-reductase ADP-D-ribosyltransferase.

5. The method of clause 1, wherein the genetic variation is a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD.

6. The method of clause 1, wherein the genetic variation is a knock-out mutation.

7. The method of clause 1, wherein the genetic variation results in elimination or abolishment of activity of a protein domain.

8. The method of clause 1, wherein the genetic variation alters or abolishes a regulatory sequence of a target gene.

9. The method of clause 1, wherein the genetic variation comprises insertion of a heterologous regulatory sequence.

10. The method of clause 1, wherein the genetic variation comprises insertion of a regulatory sequence found within a genome of a bacterial species or genus corresponding to the bacteria into which the genetic variation is introduced.

11. The method of clause 0, wherein the regulatory sequence is selected based on expression level of a gene in a bacterial culture or within plant tissue.

12. The method of clause 1, wherein the genetic variation is produced by chemical mutagenesis.

13. The method of clause 1, wherein step (c) further comprises exposing the plants to biotic or abiotic stressors.

14. The method of clause 2, wherein bacteria isolated after repeating steps (b) to (d) one or more times produce 1% or more of nitrogen in a second plant of the same type as the first plant.

15. The method of clause 2, wherein bacteria isolated after repeating steps (b) to (d) one or more times exhibit at least a 2-fold increase in nitrogen fixation as compared to bacteria isolated form the first plant.

16. The method of clause 14, wherein the second plant is grown in the presence of fertilizer supplemented with glutamine, ammonia, or other chemical source of nitrogen.

17. The method of clause 1, wherein the first plant is an agricultural crop plant.

18. The method of clause 17, wherein the agricultural crop plant is selected from barley, rice, maize, wheat, sorghum, sweet corn, sugar cane, onions, tomatoes, strawberries, or asparagus.

19. The method of clause 1, wherein the first or plants in the plurality of plants are a model plant.

20. The method of clause 19, wherein the model plant is selected from *Setaria*, *Brachypodium*, or *Arabidopsis*.

21. The method of clause 1, wherein the genetic variation is a pre-determined genetic variation that is specifically introduced to a target site.

22. The method of clause 1, wherein the genetic variation is a random mutation within the target site.

23. The method of clause 1, wherein step (a) further comprises performing genetic analysis of isolated bacteria.

24. The method of clause 1, wherein step (b) further comprises applying a selection pressure to enrich for bacteria comprising the genetic variation.

25. The method of clause 24, wherein the selection pressure comprises cleaving genomes lacking the genetic variation introduced to a target site, wherein cleavage occurs within 100 nucleotides of the target site.

26. The method of clause 24, further comprising isolating bacteria that survive the selection pressure.

27. The method of clause 25, wherein cleavage is directed by a site-specific nuclease selected from the group consisting of a Zinc Finger nuclease, a CRISPR nuclease, a TALE nuclease, or a meganuclease.

28. The method of clause 27, wherein the site-specific nuclease is a CRISPR nuclease.

29. The method of clause 1, wherein the genetic variation is an insertion or deletion of one or more nucleotides.

30. The method of clause 1, wherein bacteria isolated after repeating steps (b) to (d) one or more times are endophytic, epiphytic, or rhizospheric.

31. The method of clause 1, wherein bacteria isolated after repeating steps (b) to (d) one or more times comprise a plurality of different bacterial taxa.

32. The method of clause 1, wherein the bacteria are isolated from plant tissue.

33. The method of clause 1, wherein isolating bacteria in step (a) comprises isolating bacteria from a seed of the first plant.

34. A method of increasing nitrogen fixation in a plant, comprising exposing the plant to bacteria comprising one or more genetic variations introduced into one or more genes regulating nitrogen fixation, wherein the bacteria produce 1% or more of nitrogen in the plant.

35. The method of clause 34, wherein the bacteria produce 5% or more of nitrogen in the plant.

36. The method of clause 34, wherein the bacteria produce 10% or more of nitrogen in the plant.

37. The method of clause 34, wherein the bacteria produce the nitrogen in the presence of fertilizer supplemented with glutamine, ammonia, or other chemical source of supplemental nitrogen.

38. The method of clause 34, wherein the genetic variation is a variation in a gene selected from the group consisting of: nifA, nifL, ntrB, ntrC, glutamine synthetase, glnA, glnB, glnK, draT, amtB, glutaminase, glnD, glnE, nifJ, nifH, nifD, nifK, nifY, nifE, nifN, nifU, nifS, nifV, nifW, nifZ, nifM, nifF, nifB, and nifQ.

39. The method of clause 34, wherein the genetic variation is a mutation that results in one or more of: increased expression or activity of nifA or glutaminase; decreased expression or activity of nifL, ntrB, glutamine synthetase, glnB, glnK, draT, amtB; decreased adenylyl-removing activity of GlnE; or decreased uridylyl-removing activity of GlnD.

40. The method of clause 34, wherein the genetic variation (a) is a knock-out mutation; (b) alters or abolishes a regulatory sequence of a target gene; or (c) comprises insertion of a heterologous regulatory sequence.

41. The method of clause 34, wherein the bacteria are of the genus *Enterobacter*.

42. The method of clause 34, wherein the bacteria are of the genus *Rahnella*.

43. The method of claim 34, wherein the bacteria are endophytic, epiphytic, or rhizospheric.

44. The method of clause 34, wherein the bacteria comprise a plurality of different bacterial taxa.

45. The method of clause 34, wherein the plant is an agricultural crop plant.

46. The method of any one of clauses 34-45, wherein the plant is a non-leguminous plant.

47. The method of clause 45, wherein the agricultural crop plant is selected from sorghum, canola, tomato, strawberry, barley, rice, maize, and wheat.

48. The method of clause 45, wherein the plant is a genetically modified organism (GMO).

49. The method of clause 45, wherein the plant is not a genetically modified organism (GMO).

50. The method of clause 45, wherein the plant has been genetically engineered or bred for efficient nitrogen use.

51. A bacterial population comprising bacteria comprising one or more genetic variations introduced into one or more genes regulating nitrogen fixation, wherein the bacteria produce 1% or more of nitrogen in a plant grown in the presence of the population of bacteria.

52. The bacterial population of clause 51, wherein the bacteria produce the nitrogen in the presence of fertilizer supplemented with glutamine, ammonia, or other chemical source of supplemental nitrogen.

53. The bacterial population of clause 51, wherein the genetic variation is a variation in a gene selected from the group consisting of: nifA, nifL, ntrB, ntrC, glutamine synthetase, glnA, glnB, glnK, draT, amtB, glutaminase, glnD, glnE, nifJ, nifH, nifD, nifK, nifY, nifE, nifN, nifU, nifS, nifV, nifW, nifZ, nifM, nifF, nifB, and nifQ.

54. The bacterial population of clause 51, wherein the genetic variation is a mutation that results in one or more of: increased expression of nifA or glutaminase; decreased expression of nifL, ntrB, glutamine synthetase, glnB, glnK, draT, amtB; decreased adenylyl-removing activity of GlnE; or decreased uridylyl-removing activity of GlnD.

55. The bacterial population of clause 51, wherein the genetic variation (a) is a knock-out mutation; (b) alters or abolishes a regulatory sequence of a target gene; or (c) comprises insertion of a heterologous regulatory sequence.

56. The bacterial population of clause 51, wherein the bacteria are *Enterobacter*.

57. The bacterial population of clause 51, wherein the bacteria are *Rahnella*.

58. The bacterial population of clause 51, wherein the bacteria are endophytic, epiphytic, or rhizospheric.

59. The bacterial population of clause 51, wherein bacteria comprise a plurality of different bacterial taxa.

60. A composition comprising the bacterial population of any one of clauses 51-59.

61. The composition of clause 60, wherein the composition comprises the bacterial population coated on a surface of a seed.

62. The composition of clause 60, wherein the composition is formulated as a liquid or powder.

63. A bacterium having an ATCC deposit number of PTA-122293 or PTA-122294.

What is claimed is:

1. A composition comprising:
an engineered diazotroph comprising at least one genetic variation introduced in a nitrogen fixation genetic regulatory network, whereby the engineered diazotroph comprises increased expression or activity of nifH, increased expression or activity of nifA, and decreased expression or activity of nifL, wherein the at least one genetic variation comprises genetic material that originates from the same genus as said engineered diazotroph, whereby the engineered diazotroph has increased nitrogen fixation activity as compared to an unmodified organism of the same species as the engineered diazotroph; and
a plant seed.

2. The composition of claim 1, wherein said plant seed is a non-leguminous plant seed.

3. The composition of claim 1, wherein said plant seed is a cereal plant seed.

4. The composition of claim 1, wherein said plant seed is a seed of a plant selected from the group consisting of corn, wheat, rice, and sorghum.

5. The composition of claim 1, wherein said engineered diazotroph is present as a coating on said plant seed.

6. The composition of claim 5, wherein said engineered diazotroph is within a seed coating that is coated on a portion of said plant seed.

7. The composition of claim 1, wherein said engineered diazotroph is an engineered bacterium.

8. The composition of claim 1, wherein said engineered diazotroph further comprises a genetic variation introduced within a nitrogen assimilation genetic regulatory network.

9. The composition of claim 8, wherein said genetic variation alters activity or expression of glnE.

10. The composition of claim 1, wherein said engineered diazotroph further comprises a genetic variation that alters activity or expression of a gene selected from the group consisting of amtB, ntrB, ntrC, polynucleotide encoding glutamine synthetase, glnA, glnB, glnK, drat, polynucleotide encoding glutaminase, and glnD.

11. The composition of claim 1, wherein said genetic material that originates from said same genus as said engineered diazotroph comprises a regulatory element.

12. The composition of claim 11, wherein said regulatory element is a promoter.

13. The composition of claim 12, wherein said promoter is active in the presence of exogenous nitrogen.

14. The composition of claim 1, wherein said engineered diazotroph has increased nitrogen fixation activity in the presence of at least 0.01 mM fixed nitrogen as compared to an unmodified diazotroph of said same species as said engineered diazotroph in the presence of the same concentration of fixed nitrogen.

15. The composition of claim 1, wherein said engineered diazotroph has at least two-fold increased nitrogen fixation activity in a field comprising exogenous nitrogen, as compared to an unmodified diazotroph of said same species as said engineered diazotroph in said field.

16. The composition of claim 15, wherein said field has a fixed nitrogen concentration of at least 0.01 mM.

17. The composition of claim 1, wherein said engineered diazotroph is an epiphyte.

18. The composition of claim 1, wherein said engineered diazotroph is an endophyte.

19. The composition of claim 1, wherein said engineered diazotroph is a rhizophyte.

20. The composition of claim 1, wherein said genetic material of said engineered diazotroph does not comprise genetic material that originates from a different genus than said engineered diazotroph.

21. The composition of claim 1, wherein said genetic material of said engineered diazotroph does not comprise genetic material that originates from a different species than said engineered diazotroph.

22. The composition of claim 1, wherein the engineered diazotroph is of a genus selected from the group consisting of *Enterobacter, Rahnella, Kosakonia, Burkholderia*, and *Klebsiella*.

* * * * *

SEQUENCE LISTING

```
<160> NUMBER OF SEQ ID NOS: 61

<210> SEQ ID NO 1
<211> LENGTH: 9
<212> TYPE: PRT
<213> ORGANISM: Unknown
<220> FEATURE:
<223> OTHER INFORMATION: Description of Unknown:
      "LAGLIDADG" family peptide motif sequence

<400> SEQUENCE: 1

Leu Ala Gly Leu Ile Asp Ala Asp Gly
1               5

<210> SEQ ID NO 2
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gttgatcaga ccgatgttcg gaccttccaa ggtttcgatc ggacatacgc gaccgtagtg    60
ggtcgggtgt acgtctcgaa cttcaaagcc                                     90

<210> SEQ ID NO 3
```

```
<211> LENGTH: 257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gcctctcggg gcgcttttt  ttattccggc actagccgct attaataaaa atgcaaatcg      60
gaatttacta tttaacgcga gattatctaa gatgaatccg atggaagcgc gctgttttca     120 ctcgccttt  taaagttacg tgatgatttc gatgcttctt tgagcgaacg atcaaaaata     180
agcgtattca ggtaaaaaaa tattctcatc acaaaaaagt ttgtgtaata cttgtaacgc     240
tacatggaga ttaactc                                                    257

<210> SEQ ID NO 4
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ggttcacata aacataatta tcgccacggc gatagccgta cgcttttgc  gtcacaacat      60 ccatggtgaa gccggctttt tcaagaacac gcgccacctc atcgggtctt aaatacatac     120
tcattcctca ttatctttta ccgcacgtta accttacctt attcattaaa ggcaacgctt     180
tcggaatatt ccataaaggg ctatttacag cataattcaa aatcttgtcc tacacttata     240
gactcaatgg aattaaggga                                                 260

<210> SEQ ID NO 5
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gcgcggaaaa tcgacgcata gcgcattctc agaagccggc ctggtctcgg tggaaaagcg      60
aatctttccc acgaccgccg ggcctttaac aaaagaatca atgacctgat taatgtcgct     120
atccattctc tctccgcgta atgcgatctt ttttcatcat acctaacaaa ctggcagagg     180
gaaaagccgc gcggttttc  tgcgaagtgt attgtaagat ttgtttgata tgttatatcg     240
taacatatta ttgcaaacat                                                 260

<210> SEQ ID NO 6
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
ctgacgaagc gagttacatc accggtgaaa ctctgcacgt caacggcgga atgtatatgg      60
tctgaccgag atttgcgcaa aacgctcagg aaccgcgcag tctgtgcggt tcactgtaat     120
gttttgtaca aaatgatttg cgttatgagg gcaaacagcc gcaaaatagc gtaaaatcgt     180
ggtaagacct gccgggattt agttgcaaat ttttcaacat tttatacact acgaaaacca     240
```
tcgcgaaagc gagttttga                                                  259

<210> SEQ ID NO 7
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
acgcctgggg cgccgaccag cgggaagagt gatttggcca acgaggcgcc gctctgaatg     60
gaaatcatgg cgattaaaat aaccagtatc ggcaaccatg ccggtacctt acgagacgag    120
ccgggcatcc tttctcctgt caattttgtc aaatgcggta aaggttccag tgtaattgaa    180
ttaccccgcg ccggttgagc taatgttgaa aaaaagggtc ttaaaagcag tacaataggg    240
cgggtctgaa gataatttca                                                260

<210> SEQ ID NO 8
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
tctgattcct gatgaaaata aacgcgacct tgaagaaatt ccggataacg ttatcgccga     60
tttagatatc catccggtga aacgaatcga ggaagttctg gcacttgcgc tacagaacga    120
accgtttgga atggaagtcg tcacggcaaa atagtgattt cgcgcaaata gcgctaagaa    180
aaatagggct ggtaagtaaa ttcgtacttg ccagccttt tttgtgtagc taacttagat     240
cgctggcagg ggggtcaatt                                                260

<210> SEQ ID NO 9
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gtaagaaagt cggcctgcgt aaagcacgtc gtcgtcctca gttctccaaa cgttaattgt     60
tttctgctca cgcagaacaa tttgcgaaaa aacccgcttc ggcgggtttt tttatggata    120
aatttgccat tttccctcta caaacgcccc attgttacca cttttcagc atttccagaa     180 tccctcacc acaacgtctt caaaatctgg taaactatca tccatttttc tgcccaaatg    240
caggtgattg ttcattttt                                                 259

<210> SEQ ID NO 10
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gtcaaagccg tattatcgac cccttaggga caacgcttgc cggggcggga gagcggccgc     60

```
agttgatttt tgccgaactt tcagctgatt atattcagca ggtacgcgag cgcctgccgg      120
tgttgcgcaa tcgccgcttt gcgccaccgc aattattatg acgttttttt aaacaaggct      180
tgattcacct tgttacagat tgctattgtg tccgcgcgtc aaatagccgt taattgtatg      240
cgtgtatgat ggcgtattcg                                                  260
```

<210> SEQ ID NO 11
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gaggcggtgg ttgaccgtat cggtcccgag catcatgagc tttcggggcg agcgaaagat      60
atgggatcgg cggcggtact gctggcgatt atcatcgcgc tgatcgcgtg gggaacgctg      120
ctgtgggcga actaccgcta agtcttgtcg tagctgctcg caaaacggaa agaaactcct      180
gatttttgtg tgaaatgtgg ttccaaaatc accgttagct gtatatactc acagcataac      240
tgtatataca cccaggggc                                                   260
```

<210> SEQ ID NO 12
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
taagaaaagc ggcctgtacg aagacggcgt acgtaaagac aggctggata acgacgatat      60
gatcgatcag ctggaagcgc gtattcgcgc taaagcatcg atgctggatg aggcgcgtcg      120
tatcgatatc cagcaggttg aagcgaaata acgtgttggg aagcgatacg cttcccgtgt      180
atgattgaac ctgcgggcgc gaggcgccgg ggttcatttt tgtatatata aagagaataa      240
acgtggcaaa gaacattcaa                                                  260
```

<210> SEQ ID NO 13
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
atgaatcgta ctaaactggt actgggcgcg gtaatcctgg gttctactct gctggctggt      60
tgctccagca atgctaaaat cgatcagctg tcttctgacg ttcagactct gaacgctaaa      120
gttgaccagc tgagcaacga cgtgaacgca atgcgttccg acgttcaggc tgctaaagat      180
gacgcagctc gcgctaacca gcgtctggac aacgcagcta ctaaataccg taagtaa        237
```

<210> SEQ ID NO 14
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atggccaacc gagcaaaccg caacaacgta gaagagagcg ctgaagatat ccataacgat      60
gtcagccaat tagcggatac gctggaagag gtgctgaaat cgtggggcag cgacgccaaa     120
gacgaagcgg aggccgcgcg caaaaaagcg caggcgctgc tgaaagagac ccgcgcccgg     180
cttaacggca acaaccgcgt ccagcaggcg gcgtgcgacg ccatgggctg cgctgacagc     240
tacgtgcgcg acaaaccgtg gcaaagcgtc ggcgccgcag cagccgttgg ggtatttatt     300
ggcgtattac tgaatttacg tcgataa                                          327

<210> SEQ ID NO 15
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atgaccaaaa agatttccgc cctagcgttt ggcattggca tggtaatggc gagcagccag      60
gcttttgccc acggtcacca tagtcatggc ccggcgctga ccgaagcgga acaaaaggcg     120
agtgaaggca ttttgctga ccaggacgta aaggacaggg cgctgagcga ctgggagggg      180
atctggcagt cggttaaccc ctatctgctg aacggggatt tagatccggt tctggagcag     240
aaggccaaaa aggccggtaa aagcgtggcg gaatatcggg aatattataa gaagggctac     300
gctaccgatg tcgaccagat tggtatcgag gataacgtca tggagtttca cgtcgggaaa     360
accgtcaacg cctgtaagta cagctattcc ggttacaaaa ttctgaccta cgcatccggt     420
aaaaaaggcg tgcgctacct gttcgaatgc cagcaggcgg attcaaaagc gccgaagttt     480
gttcagttta gcgatcacac catcgcgcca cgcaagtccc agcatttcca catctttatg     540
ggcaatgagt cccaggaagc gctgctgaaa gagatggata actggccaac ctactatcct     600
tatgcgctgc ataaagagca gattgtcgac gaaatgctgc accactaa                 648

<210> SEQ ID NO 16
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atgagcacta tcgaagaacg cgttaagaaa attatcggcg aacagctggg cgttaagcag      60
gaagaagtta ccaacaatgc ttccttcgtt gaagacctgg cgctgattc tcttgacacc     120 gttgagctgt aatggctct ggaagaagag tttgatactg agattccgga cgaagaagct     180
gagaaaatca ctactgttca ggctgccatt gattacatca acggccacca ggcgtaa       237

<210> SEQ ID NO 17
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atgaataaaa ttgcacgttt ttcagcactg gccgttgttc tggctgcatc cgtaggtacc      60
actgctttcg ctgcgacttc taccgttacc ggtggctacg cgcagagcga catgcagggt     120
```

```
gaagcgaaca aagctggcgg tttcaacctg aagtaccgct acgagcaaga caacaacccg      180
ctgggtgtta tcggttcttt cacctacacc gaaaaagatc gttctgaatc tggcgtttac      240
aaaaaaggcc agtactacgg catcaccgca ggtccggctt accgtctgaa cgactgggct      300
agcatctacg gcgtagtggg tgttggttac ggtaaattcc aggacaacag ctacccgaac      360
aaatctgata tgagcgacta cggtttctct tacggcgctg gtctgcagtt caacccgatc      420
gaaaacgttg ccctggactt ctcctacgag cagtctcgca ttcgtaacgt tgacgttggc      480
acctggattg ctggcgtagg ttaccgcttc taa                                  513
```

<210> SEQ ID NO 18
<211> LENGTH: 273
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
gtgaataaat ctcaactgat tgacaaaatt gctgccggtg cggacatttc taaagccgca       60
gctggacgtg cgttagatgc tttaatcgct tctgttactg aatctctgca ggctggagat      120
gacgttgcgc tggtagggtt tggtactttt gctgttaaag agcgcgctgc ccgtactggt      180
cgcaatccgc aaacaggcaa agaaatcacc attgctgctg ctaaagttcc gggtttccgc      240
gcaggtaaag cgctgaaaga cgcggtaaac tga                                  273
```

<210> SEQ ID NO 19
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
atggctgtcg ctgccaacaa acgttcggta atgacgctgt tttctggtcc tactgacatc       60
tatagccatc aggtccgcat cgtgctggcc gaaaaaggtg ttagttttga gatagagcac      120
gtggagaagg acaacccgcc tcaggatctg attgacctca acccgaatca aagcgtaccg      180
acgcttgtga tcgtgagct cactctgtgg gaatctcgca tcattatgga atatctggat      240 gagcgttttcc cgcatccgcc gctcatgccg gtttacccgg tggcgcgtgg ggaaagccgt      300
ctgtatatgc agcgtatcga aaaggactgg tattcgttga tgaataccat tcagaccggt      360
accgctgcgc aggctgatac tgcgcgtaag cagctgcgtg aagaactaca ggcgattgcg      420
ccagttttca cccagaagcc ctacttcctg agcgatgagt tcagcctggt ggactgctac      480
ctggcaccac tgctgtggcg tctgccggtt ctcggcgtag agctggtcgg cgctggcgcg      540
aaagagctta aggctatat gactcgcgta tttgagcgcg actctttcct cgcttcttta      600
actgaagccg aacgtgaaat gcgtctcggt cggggctaa                            639
```

<210> SEQ ID NO 20
<211> LENGTH: 204
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
atgggtgaga ttagtattac caaactgctg gtagtcgcag cgctgattat cctggtgttt    60
ggtaccaaaa agttacgcac gctgggtgga gacctgggct cggctatcaa aggctttaaa   120
aaagccatga gcgatgacga tgacagtgcg aagaagacca gtgctgaaga agcgccggca   180
cagaagctct ctcataaaga gtaa                                          204
```

<210> SEQ ID NO 21
<211> LENGTH: 609
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atgaaagcgt taacgaccag gcagcaagag gtgtttgatc tcattcggga tcatatcagc    60
cagacgggca tgccgccgac gcgtgcggag attgctcagc gcttggggtt tcgctcccca   120
aacgcggcgg aagagcatct gaaagcgctg gcgcgtaaag gcgcaatcga gatcgtttcc   180
ggcgcctccc gcggtattcg tctgctgacg gaagaagaaa ccggtctgcc gcttattggc   240
cgcgtcgcgg caggtgagcc gctgctagcg cagcagcaca ttgaaggcca ctaccaggtg   300
gacccggcca tgtttaagcc gaacgccgat tttctgctgc gtgttagcgg tatgtcgatg   360
aaggatatcg gtattctcga tggcgacctg ctggctgtcc ataaaacgca ggatgtgcgc   420
aatggtcagg tggttgtggc gcgtatcgac gaagaagtga ccgtgaagcg tctgaaaaaa   480
cagggtaacg tcgtggaatt gctgccggaa aacagcgaat tctcgccgat cgtggtcgac   540
cttcgcgaac aaagctttac tattgaaggc ctggccgtcg gcgttatccg caacggcaac   600
tggcaataa                                                           609
```

<210> SEQ ID NO 22
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
atgaacgatt atctgccggg cgaaaccgct ctctggcagc gcattgaagg ctcactgaag    60
caggtgcttg gtagctacgg ttacagcgaa atccgtttgc cgattgtaga gcagaccccg   120
ttattcaaac gcgctatcgg cgaagtgacc gacgtggttg aaaaagagat gtacaccttt   180
gaggaccgta acggcgatag cctgactcta cgtccggaag gcacggctgg ctgcgtacgc   240
gccggtatcg aacatggtct cctgtacaat caagaacagc gcctgtggta cattgggccg   300
atgttccgcc acgaacgtcc gcaaaaaggc cgctaccgtc agttccacca gattggcgcc   360
gaagcgtttg gcctgcaggg gccggatatc gatgccgagc tgattatgct gaccgcccgc   420
tggtggcgcg agctgggcat ctccggccac gttgcgctgg agctgaactc tatcggttcg   480
ctggaggctc gcgctaacta tcgcgacgcg ctggtggcct atcttgagca gtttaaagat   540
aagctggacg aagactgcaa acgccgcatg tacaccaacc cgctgcgcgt gctggattct   600
aaaaacccgg acgtccaggc gctgctgaac gacgccccga cgctgggcga ctatcttgat   660
gaagagtcca aaacgcattt tgccgggctg tgcgcgctgc tggatgatgc cggtattcgc   720
tataccgtga atcagcgtct ggtacgcggt ctcgactact acaaccgcac cgtgtttgag   780
```

| | |
|---|---|
| tgggtcacca ccagcctcgg ttcccagggc accgtctgcg ccggaggccg ttacgatggt | 840 |
| ctggttgagc agcttggcgg tcgcgctacc cctggcgtcg gctttgcgat ggggctggaa | 900 |
| cgtcttgttt tactggttca ggcagtgaat ccggaattta agccgatcc tgttgtcgat | 960 |
| atatacctgg tagcctccgg aactgacacc cagtccgcag caatgcgtct ggctgaacag | 1020 |
| gtacgcgatg cgttacccgg cgttaagctg atgaccaacc atggcggcgg caactttaag | 1080 |
| aagcagtttg cgcgcgctga taaatggggc gctcgcgttg cgctggtgct gggcgaatca | 1140 |
| gaaatcgccg acggaaacgt ggtagtgaaa gatttacgct caggtgagca aactaccgta | 1200 |
| acgcaggata gcgttgctgc gcatttgcgc acacttctgg gttaa | 1245 |

<210> SEQ ID NO 23
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

| | |
|---|---|
| atgaaaaaga ccaaaattgt ttgcaccatc ggtccgaaaa ccgaatccga agagatgttg | 60 |
| accaaaatgc tggacgcggg catgaacgtt atgcgtctga acttctctca cggtgactat | 120 |
| gcggaacacg tcagcgcat ccagaatctg cgcaatgtga tgagtaaaac cggtaagaaa | 180 |
| gcggcaatcc tgctggacac caaaggtccg gaaatccgta ccattaagct ggaaggcggc | 240 |
| aacgacgtct ccctgaaagc gggccagacc ttcaccttca ccaccgataa atccgttgtc | 300 |
| ggtaataacg aaatcgttgc ggtgacctat gaaggcttca ccagcgacct gagcgttggc | 360 |
| aacacggtac tggttgacga tggtctgatc ggtatggaag tgaccgctat cgaaggcaac | 420 |
| aaagttgttt gtaaagtgct gaacaacggc gacctcggcg agaacaaagg cgttaacctg | 480 |
| ccgggcgtat ctatcgcgct gccggcgctg gctgaaaaag acaaacagga tctgatcttc | 540 |
| ggttgcgaac agggcgttga ctttgttgcg gcatcctta tccgtaagcg ttctgacgtt | 600 |
| gttgaaatcc gtgagcacct gaaagccac ggcggcgaga agatccagat catctccaaa | 660 |
| atcgaaaacc aggaaggcct gaacaacttc gacgaaatcc tcgaagcctc tgacggcatc | 720 |
| atggtagccc gtggcgacct gggcgttgaa atcccggttg aagaagttat cttcgcgcag | 780 |
| aagatgatga tcgagaaatg tatccgcgcg cgtaaagtcg ttatcaccgc gacccagatg | 840 |
| ctggattcca tgatcaaaaa cccgcgtccg acccgtgcgg aagcaggcga cgtggccaac | 900 |
| gccatcctcg acggcaccga cgcagttatg ctgtccggcg aatccgcgaa aggtaaatac | 960 |
| ccgctggaag cggtcaccat catggcgacc atctgcgaac gtaccgaccg cgtcatgacc | 1020 |
| agccgtcttg agtacaacaa cgacaaccgt aagctgcgca tcaccgaagc ggtgtgccgc | 1080 |
| ggtgcggtag aaacggctga aaaactggaa gcgccgctga tcgttgtggc aacccagggc | 1140 |
| ggtaaatccg cgcgcgccgt acgtaaatac ttcccggatg ccactatcct ggcgctgacc | 1200 |
| accaacgaaa ccaccgcgcg tcagctggtg ctgagcaaag cgttgtggc acagctggtt | 1260 |
| gaagatatct cctctaccga tgcgttctac atccagggta agaactggc gctgcagagc | 1320 |
| ggtctggcgc gtaaaggcga cgtggttgtt atggtttccg cgcgcgttagt cccgagcgga | 1380 |
| accaccaata ccgcttccgt gcacgtgctg taa | 1413 |

<210> SEQ ID NO 24
<211> LENGTH: 351
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 24
atgtatttaa gacccgatga ggtggcgcgt gttcttgaaa aagccggctt caccatggat      60
gttgtgacgc aaaaagcgta cggctatcgc cgtggcgata attatgttta tgtgaaccgt     120
gaagctcgta tggggcgtac cgcgttaatt attcatccgg ctttaaaaga gcgcagcaca     180
acgcttgcgg agcccgcgtc ggatatcaaa acctgcgatc attatgagca gttcccgctc     240
tatttagcgg gggatgctca acagcattat ggtattccac acgggttcag ttcgcgaatg     300
gcgcttgagc gttttctgag tggcctgttt ggcgaaacgc agtatagctg a              351

<210> SEQ ID NO 25
<211> LENGTH: 864
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggatagcg acattaatca ggtcattgat tcttttgtta aaggcccggc ggtcgtggga      60
aagattcgct tttccaccga gaccaggccg gcttctgaga atgcgctatg cgtcgatttt     120
ccgcgcctcg aaatcatgct tgcgggtcag cttcacgatc cggcgattaa agccgatcgc     180
gcccagctca tgccgcacga tgtgctgtat attcccgctg gcggatggaa tgacccgcaa     240
tggctggcgc cctccactct gctcactatc ttatttggta acagcagct  ggaattcgtc     300 ctgcgccact gggacggcag cgcgcttaac gtgctggata acagcaggt  tccgcgccgc     360 ggtccccggg tcggctcttt tctgctgcag gcgctgaatg aaatgcagat gcagccgcgg     420
gagcagcaca cggcccgctt tattgtcacc agcctgctca gccactgtgc cgatctgctg     480
ggcagccagg tacaaacctc atcgcgcagc caggcgcttt ttgaagcgat tcgtaagcat     540
attgacgccc actttgccga cccgttaacc cgggagtcgg tggcgcaggc gtttaccctc     600 tcgccaaaact atctatccca cctgttccag aaatgcgggc aatgggctt  taacgagtat     660 ctgaatcaca tccgcctgga gcaggccaga atgctgttaa aaggcacga  tatgaaagtg     720 aaagatatcg cccacgcctg cggtttcgcc gacagcaact acttctgccg cctgtttcgc     780
aaaaacaccg aacgctcgcc gtcggagtat cgccgtcaat atcacagcca gctgacggaa     840
aaaacagccc cggcaaaaaa ctag                                             864

<210> SEQ ID NO 26
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atgagttttg aaggaaaaat cgcgctggtt accggtgcaa gtcgcgggat tggccgcgca      60
atcgctgaaa cgctcgttgc ccgtggcgcg aaagttatcg ggactgcgac cagcgaaagc     120
ggcgcgcagg cgatcagcga ttatttaggt gctaacggta aggtctgct  gctgaatgtg     180 accgatcctg catctattga atctgttctg ggaaatattc gcgcagaatt tggtgaagtt     240
```

```
gatatcctgg tgaacaatgc cgggatcact cgtgataacc tgttaatgcg catgaaagat      300
gatgagtgga acgatattat cgaaaccaac ctgtcatctg ttttccgtct gtcaaaagcg      360
gtaatgcgcg ctatgatgaa aaagcgtcat ggacgtatta tcactatcgg ttctgtggtt      420
ggtaccatgg gaaatgcggg tcaggccaac tacgctgcgg cgaaagcggg tctgattggc      480
ttcagtaaat cactggctcg cgaagttgcg tcccgcggta ttactgtaaa cgttgttgct      540
ccgggcttta ttgaaacgga catgacgcgt gcgctgaccg atgagcagcg tgcgggtacg      600
ctggcggcag ttcctgcggg gcgcctcggc tctccaaatg aaatcgccag tgcggtggca      660
tttttagcct ctgacgaagc gagttacatc accggtgaaa ctctgcacgt caacggcgga      720
atgtatatgg tctga                                                        735
```

<210> SEQ ID NO 27
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

```
atgcccggct cgtctcgtaa ggtaccggca tggttgccga tactggttat tttaatcgcc       60
atgatttcca t                                                            71
```

<210> SEQ ID NO 28
<211> LENGTH: 2355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
atgaatcctg agcgttctga acgcattgaa atccccgtat tgccgttgcg cgatgtggtg       60
gtttatccgc acatggtcat acccctgttt gtagggcggg aaaaatctat ccgttgtctc      120
gaagcagcca tggaccatga taaaaaaatc atgctggttg cgcagaaaga agcctcgacg      180
gatgagccgg gtgtaaacga tcttttcacc gtcgggaccg tggcgtctat tttgcaaatg      240
ctgaagctac cggacggtac tgttaaagtg ctggtcgaag gtttgcagcg cgcgcgcatc      300
tctgcgctgt ctgataatgg cgaacatttt tcggcgaagg cggaatacct tgaatcgccg      360
gcgattgacg aacgcgagca ggaagtgctg gttcgtaccg ctatcagcca gtttgaaggc      420
tacatcaagc tgaacaaaaa aatccctccg gaagtgctga cgtcgctgaa tagcatcgac      480
gatccggcgc gtctggcgga taccatcgct gcgcatatgc cgctgaagct ggcggacaaa      540
cagtccgtgc tggagatgtc cgacgttaac gagcgtctgg aatatctgat ggcgatgatg      600
gagtcggaaa tcgatctgct gcaggtggag aagcgtattc gcaaccgcgt gaaaaagcag      660
atggagaaat ctcagcgcga gtactatctg aatgagcaaa tgaaagccat tcaaaaagag      720
ctcggcgaga tggacgacgc cccggacgag aacgaagcgc tgaagcgtaa gatcgacgcg      780
gcgaaaatgc cgaaagaggc aaaagagaaa accgaagcgg aactgcaaaa actgaaaatg      840
atgtccccga tgtcggcgga agcgaccgtc gttcgcggct acatcgactg gatggtgcag      900
gtaccgtgga acgctcgcag caaggttaaa aaagacctgc gtcaggctca ggagatcctc      960
gataccgatc actacggcct tgagcgcgtg aaggatcgca ttcttgagta cctcgcggta     1020
cagagccgtg ttaacaagct caagggccgg atcctgtgcc tggttgggcc tccgggggta     1080
```

```
ggtaaaacct ctctcggcca atccatcgcc aaagcaactg gacgcaaata tgtgcgtatg   1140
gcgctgggcg gcgtgcgtga tgaagcggaa atccgcggtc accgccgtac ctatattggc   1200
tcaatgccgg gcaaactgat ccagaaaatg gctaaagtgg gcgttaaaaa cccgctgttc   1260
ttgctggatg agatcgacaa gatgtcttct gacatgcgcg gcgatccggc ctcggcgctg   1320
ctggaggtgt tggatccgga acagaacgtg gcctttaacg accactatct ggaagtggat   1380
tacgatctca gcgacgtgat gttcgttgcg acctctaact ccatgaacat cccggcgccg   1440
ctgctggatc gtatggaagt gatccgcctc tccggctata ccgaagatga gaagctaaac   1500
atcgccaaac gccatctgct gtcaaaacag attgagcgta acgcgctcaa gaaaggcgag   1560
ctgacggtgg atgacagcgc gattatcggc atcattcgct actacacccg tgaagcaggc   1620
gtgcgtggtc tggagcgtga aatctcgaaa ctgtgccgca aagcggtgaa acagctgctg   1680
ctggataagt cgctgaaaca catcgagatt aacggcgaca acctgcacga tttccttggc   1740
gtgcagcgct acgactatgg tcgtgcggat agcgaaaacc gcgtaggtca ggtgaccgga   1800
ctggcgtgga cggaagtggg cggcgatctg ctgaccattg aaaccgcctg cgttccgggt   1860
aaaggcaaac tgacctacac cggttcactg ggtgaagtca tgcaggaatc catccaggcg   1920
gcgctgacgg tggttcgttc acgtgcggat aagctgggta ttaactcaga cttttacgaa   1980
aaacgtgata ttcacgttca cgtgccggaa ggcgcgacgc cgaaggatgg tccaagcgcc   2040
ggtatcgcga tgtgcaccgc gctggtttcc tgtctgacgg gtaatccggt acgcgccgac   2100
gtggcgatga ccggtgagat taccctccgt ggccaggtat tgccgattgg tggtctgaag   2160
gaaaaactgt tggccgcgca tcgcggcggc attaagactg ttctgattcc tgatgaaaat   2220
aaacgcgacc ttgaagaaat tccggataac gttatcgccg atttagatat ccatccggtg   2280
aaacgaatcg aggaagttct ggcacttgcg ctacagaacg aaccgtttgg aatggaagtc   2340
gtcacggcaa aatag                                                   2355
```

<210> SEQ ID NO 29
<211> LENGTH: 393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
atggctgaaa atcaatacta cggcaccggt cgccgcaaaa gttccgcagc tcgcgttttc    60
atcaaaccgg gcaacggtaa aatcgttatc aaccagcgtt ctctggaaca gtacttcggt   120
cgtgaaactg cccgcatggt agttcgtcag ccgctggaac tggtcgacat ggttgagaaa   180
ttagatctgt acatcaccgt taaaggtggt ggtatctctg gtcaggctgg tgcgatccgt   240
cacggtatca cccgcgctct gatggagtac gacgagtccc tgcgtggcga actgcgtaaa   300
gctggtttcg ttactcgtga tgctcgtcag gttaacgta agaaagtcgg cctgcgtaaa   360
gcacgtcgtc gtcctcagtt ctccaaacgt taa                                393
```

<210> SEQ ID NO 30
<211> LENGTH: 789
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
atgtttgttg ctgccggaca atttgccgta acgccggact ggacgggaaa cgcgcagacc    60
tgcgtcagca tgatgcgcca ggccgcggag cgggggggcgt cgcttctggt tctgcctgag   120
gcgttgctgg cgcgagacga taacgatgcg gatttatcgg ttaaatccgc ccagcagctg   180
gatggcggct tcttacagct cttgctggcg gagagcgaaa acagcgcttt gacgacggtg   240
ctgaccctgc atatcccttc cggcgaaggt cgagcgacga atacgctggt ggccctgcgt   300
caggggaaga ttgtggcgca atatcagaaa ctgcatctct atgatgcgtt caatatccag   360
gaatccaggc tggtcgatgc cgggcggcaa attccgccgc tgatcgaagt cgacgggatg   420
cgcgtcgggc tgatgacctg ctacgattta cgtttccctg agctggcgct gtcgttagcg   480
ctcagcggcg cgcagctcat agtgttgcct gccgcgtggg taaaagggcc gctgaaggaa   540
catcactggg cgacgctgct ggcggcgcgg gcgctggata caacctgcta tattgtcgcc   600
gcaggagagt gcgggacgcg taatatcggt caaagccgta ttatcgaccc cttagggaca   660
acgcttgccg gggcgggaga gcggccgcag ttgattttttg ccgaactttc agctgattat   720
attcagcagg tacgcgagcg cctgccggtg ttgcgcaatc gccgctttgc gccaccgcaa   780
ttattatga                                                          789
```

<210> SEQ ID NO 31
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
atggccaata ataccactgg gttaaccccga attattaaag cggccgggta ttcctggaaa    60
ggattccgtg cggcgtgggt caatgaggcc gcatttcgtc aggaaggcat cgcggccgtt   120
attgccgtgg cgatcgcctg ctggttggac gtcgatgcca tcacgcgggt gctgctcatt   180
agctcggtcc tgttagtgat gatagttgaa attatcaata gcgcgattga ggcggtggtt   240
gaccgtatcg gtcccgagca tcatgagctt tcggggcgag cgaaagatat gggatcggcg   300
gcggtactgc tggcgattat catcgcgctg atcgcgtggg aacgctgct gtgggcgaac   360
taccgctaa                                                          369
```

<210> SEQ ID NO 32
<211> LENGTH: 1122
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
atgcataacc aggctccgat tcaacgtaga aaatcaaaac gaatttacgt tgggaatgtg    60
ccgattggcg atggcgcccc catcgccgta cagtcgatga caaacacgcg caccaccgat   120
gtggcggcga cggtaaatca aattaaagcc ctcgagcgcg ttggcgcgga tatcgtgcgc   180
gtttcggtgc cgacgatgga tgcggcgaa gcgttcaaac ttatcaaaca gcaggttaac   240
gtcccgctgg ttgccgatat ccacttcgat taccgcattg cgctgaaggt agcggaatac   300
ggcgttgatt gcctgcgtat taaccccggc aatatcggca cgaagagcg tatccgcatg   360
gtggtggact gcgctcgcga taaaaatatt cctatccgta tcggggtaaa cgccggttct   420
```

```
ctggaaaaag atctccagga aaaatacggc gaaccgactc cgcaggcgct gctggaatcg      480
gcaatgcgcc atgttgatca tctcgatcgt ctcaacttcg atcagtttaa agtcagcgta      540
aaagcctccg atgtgttcct cgcggttgaa tcctatcgcc tgttggcgaa acagatcgat      600
cagcctctgc acctcgggat caccgaagcg ggcggcgcgc gcagcggcgc ggtgaagtcc      660
gcgatcggcc tcggcctgct gctgtctgaa gggattggcg atacgctgcg cgtctctctg      720
gcggcggatc ccgttgaaga gatcaaagtg ggcttcgata ttctcaagtc gctgcgtatt      780
cgctctcgcg ggatcaactt tattgcctgc ccgacctgtt cacgtcagga gtttgacgtt      840
atcggtaccg ttaacgcgct ggagcagcgc ctggaagata tcattacgcc gatggatatt      900
tcgatcattg gctgcgtggt aaacggtccc ggcgaggcgc tggtttccac cctcggcgta      960
accggcggca ataagaaaag cggcctgtac gaagacggcg tacgtaaaga caggctggat     1020
aacgacgata tgatcgatca gctggaagcg cgtattcgcg ctaaagcatc gatgctggat     1080
gaggcgcgtc gtatcgatat ccagcaggtt gaagcgaaat aa                        1122
```

<210> SEQ ID NO 33
<211> LENGTH: 876
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
atgagccata ttcaacggga aacgtcttgc tccaggccgc gattaaattc caacatggat       60
gctgatttat atgggtataa atgggctcgc gataatgtcg ggcaatcagg tgcgacaatc      120
tatcgattgt atgggaagcc cgatgcgcca gagttgtttc tgaaacatgg caaaggtagc      180
gttgccaatg atgttacaga tgagatggtc agactaaact ggctgacgga atttatgcct      240
cttccgacca tcaagcattt tatccgtact cctgatgatg catggttact caccactgcg      300
atccccggga aaacagcatt ccaggtatta gaagaatatc ctgattcagg tgaaaatatt      360
gttgatgcgc tggcagtgtt cctgcgccgg ttgcattcga ttcctgtttg taattgtcct      420
tttaacagcg atcgcgtatt tcgtctcgct caggcgcaat cacgaatgaa taacggtttg      480
gttgatgcga gtgattttga tgacgagcgt aatggctggc ctgttgaaca agtctggaaa      540
gaaatgcata agcttttgcc attctcaccg gattcagtcg tcactcatgg tgatttctca      600
cttgataacc ttattttga cgaggggaaa ttaataggtt gtattgatgt tggacgagtc      660
ggaatcgcag accgatacca ggatcttgcc atcctatgga actgcctcgg tgagttttct      720
ccttcattac agaaacggct ttttcaaaaa tatggtattg ataatcctga tatgaataaa      780
ttgcagtttc atttgatgct cgatgagttt ttctaataag cctgcctggt tctgcgtttc      840
ccgctcttta ataccctgac cggaggtgag caatga                                876
```

<210> SEQ ID NO 34
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
atgagcatca cggcgttatc agcatcattt cctgagggga atatcgccag ccgcttgtcg       60
```

```
ctgcaacatc cttcactgtt ttataccgtg gttgaacaat cttcggtggc gagcgtgttg      120
agtcatcctg actagctgag atgagggctc gccccctcgt cccgacactt ccagatcgcc      180
atagcgcaca gcgcctcgag cggtggtaac ggcgcagtgg cggttttcat ggcttgttat      240
gactgttttt ttggggtaca gtctatgcct cgggcatcca agcagcaagc gcgttacgcc      300
gtgggtcgat gtttgatgtt atggagcagc aacgatgtta cgcagcaggg cagtcgccct      360
aaaacaaagt taaacatcat gagggaagcg gtgatcgccg aagtatcgac tcaactatca      420
gaggtagttg gcgtcatcga gcgccatctc gaaccgacgt tgctggccgt acatttgtac      480
ggctccgcag tggatggcgg cctgaagcca cacagtgata ttgatttgct ggttacggtg      540
accgtaaggc ttgatgaaac aacgcggcga gctttgatca cgaccttttt ggaaacttcg      600
gcttcccctg gagagagcga gattctccgc gctgtagaag tcaccattgt tgtgcacgac      660
gacatcattc cgtggcgtta ccagctaag cgcgaactgc aatttggaga atggcagcgc      720
aatgacattc ttgcaggtat cttcgagcca gccacgatcg acattgatct ggctatcttg      780
ctgacaaaag caagagaaca tagcgttgcc ttggtaggtc cagcggcgga ggaactcttt      840
gatccggttc ctgaacagga tctatttgag gcgctaaatg aaaccttaac gctatggaac      900
tcgccgcccg actgggctgg cgatgagcga aatgtagtgc ttacgttgtc ccgcatttgg      960
tacagcgcag taaccggcaa aatcgcgccg aaggatgtcg ctgccgactg gcaatggag      1020 cgcctgccgg cccagtatca gcccgtcata cttgaagcta gacaggctta tcttggacaa      1080
gaagaagatc gcttggcctc gcgcgcagat cagttggaag aatttgtcca ctacgtgaaa      1140
ggcgagatca ccaaggtagt cggcaaataa tgtctaacaa ttcgttcaag ccgacgccgc      1200
ttcgcggcgc ggcttaactc aagcgttaga tgcactaagc acataattgc tcacagccaa      1260
actatcaggt caagtctgct tttattattt ttaagcgtgc ataataagcc ctacacaaat      1320
ggtacccgac cggtggtgaa tttaatctcg ctgacgtgta gacattccct tatccagacg      1380
ctgatcgccc atcatcgcgg ttctttagat ctctcggtcc gccctgatgg cggcaccttg      1440
ctgacgttac gcctgccggt acagcaggtt atcaccggag gcttaaaatg a              1491
```

<210> SEQ ID NO 35
<211> LENGTH: 1021
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
ctgatccttc aactcagcaa aagttcgatt tattcaacaa agccacgttg tgtctcaaaa      60
tctctgatgt tacattgcac aagataaaaa tatatcatca tgaacaataa aactgtctgc      120
ttacataaac agtaatacaa ggggtgttat gagccatatt caacgggaaa cgtcttgctc      180
caggccgcga ttaaattcca acatggatgc tgatttatat gggtataaat gggctcgcga      240
taatgtcggg caatcaggtg cgacaatcta tcgattgtat gggaagcccg atgcgccaga      300
gttgtttctg aaacatggca aaggtagcgt tgccaatgat gttacagatg agatggtcag      360
actaaactgg ctgacggaat ttatgcctct tccgaccatc aagcatttta tccgtactcc      420
tgatgatgca tggttactca ccactgcgat ccccgggaaa acagcattcc aggtattaga      480
agaatatcct gattcaggtg aaaatattgt tgatgcgctg gcagtgttcc tgcgccggtt      540
gcattcgatt cctgtttgta attgtccttt taacagcgat cgcgtatttc gtctcgctca      600
```

| | |
|---|---|
| ggcgcaatca cgaatgaata acggtttggt tgatgcgagt gattttgatg acgagcgtaa | 660 |
| tggctggcct gttgaacaag tctggaaaga aatgcataag cttttgccat tctcaccgga | 720 |
| ttcagtcgtc actcatggtg atttctcact tgataacctt atttttgacg aggggaaatt | 780 |
| aataggttgt attgatgttg gacgagtcgg aatcgcagac cgataccagg atcttgccat | 840 |
| cctatggaac tgcctcggtg agttttctcc ttcattacag aaacggcttt tcaaaaata | 900 |
| tggtattgat aatcctgata tgaataaatt gcagtttcat ttgatgctcg atgagttttt | 960 |
| ctaataagcc ttgaccctac gattcccgct atttcattca ctgaccggag gttcaaaatg | 1020 |
| a | 1021 |

<210> SEQ ID NO 36
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

| | |
|---|---|
| atgaagatag caacaatgaa aacaggtctg ggagcgttgg ctcttcttcc ctgatccttc | 60 |
| aactcagcaa aagttcgatt tattcaacaa agccacgttg tgtctcaaaa tctctgatgt | 120 |
| tacattgcac aagataaaaa tatatcatca tgaacaataa aactgtctgc ttacataaac | 180 |
| agtaatacaa ggggtgttat gagccatatt caacgggaaa cgtcttgctc ccgtccgcgc | 240 |
| ttaaactcca acatggacgc tgatttatat gggtataaat gggctcgcga taatgtcggg | 300 |
| caatcaggtg cgacaatcta tcgcttgtat gggaagcccg atgcgccaga gttgtttctg | 360 |
| aaacatggca aaggtagcgt tgccaatgat gttacagatg agatggtccg tctcaactgg | 420 |
| ctgacggagt ttatgcctct cccgaccatc aagcatttta tccgtactcc tgatgatgcg | 480 |
| tggttactca ccaccgcgat tcctgggaaa acagccttcc aggtattaga agaatatcct | 540 |
| gattcaggtg aaaatattgt tgatgcgctg gccgtgttcc tgcgccggtt acattcgatt | 600 |
| cctgttttgta attgtccttt taacagcgat cgtgtatttc gtcttgctca ggcgcaatca | 660 |
| cgcatgaata acggtttggt tgatgcgagt gattttgatg acgagcgtaa tggctggcct | 720 |
| gttgaacaag tctggaaaga aatgcacaag ctcttgccat tctcaccgga ttcagtcgtc | 780 |
| actcatggtg atttctcact tgataacctt atttttgacg aggggaaatt aataggttgt | 840 |
| attgatgttg gacgggtcgg aatcgcagac cgttaccagg accttgccat tctttggaac | 900 |
| tgcctcggtg agttttctcc ttcattacag aaacggcttt tcaaaaata tggtattgat | 960 |
| aatcctgata tgaataaatt gcagtttcat ttgatgctcg atgagttttt ctaataagcc | 1020 |
| tgtgaagggc tggacgtaaa cagccacggc gaaaacgcct acaacgcctg a | 1071 |

<210> SEQ ID NO 37
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

| | |
|---|---|
| atgaccctga atatgatgct cgataacgcc gtacccgagg cgattgccgg ctgatccttc | 60 |
| aactcagcaa aagttcgatt tattcaacaa agccacgttg tgtctcaaaa tctctgatgt | 120 |
| tacattgcac aagataaaaa tatatcatca tgaacaataa aactgtctgc ttacataaac | 180 |

```
agtaatacaa ggggtgttat gagccatatt caacgggaaa cgtcttgctc ccgtccgcgc      240
ttaaactcca acatggacgc tgatttatat gggtataaat gggctcgcga taatgtcggg      300
caatcaggtg cgacaatcta tcgcttgtat gggaagcccg atgcgccaga gttgtttctg      360
aaacatggca aggtagcgt tgccaatgat gttacagatg atggtccg tctcaactgg        420 ctgacggagt ttatgcctct cccgaccatc aagcatttta tccgtactcc tgatgatgcg      480
tggttactca ccaccgcgat tcctgggaaa acagccttcc aggtattaga agaatatcct     540
gattcaggtg aaaatattgt tgatgcgctg gccgtgttcc tgcgccggtt acattcgatt      600
cctgtttgta attgtccttt taacagcgat cgtgtatttc gtcttgctca ggcgcaatca      660
cgcatgaata acggtttggt tgatgcgagt gattttgatg acgagcgtaa tggctggcct      720
gttgaacaag tctggaaaga atgcacaag ctcttgccat tctcaccgga ttcagtcgtc      780
actcatggtg atttctcact tgataacctt attttttgacg aggggaaatt aataggttgt    840
attgatgttg gacgggtcgg aatcgcagac cgttaccagg accttgccat tctttggaac    900
tgcctcggtg agttttctcc ttcattacag aaacggcttt ttcaaaaata tggtattgat    960
aatcctgata tgaataaatt gcagtttcat ttgatgctcg atgagttttt ctaataagcc    1020
ttggttctgc gtttcccgct ctttaatacc ctgaccggag gtgagcaatg a             1071
```

<210> SEQ ID NO 38
<211> LENGTH: 426
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 38

```
atgaccctga atatgatgat ggatgccggc ggacatcatc gcgacaaaca atattaatac     60
cggcaaccac accggcaatt tacgagactg cgcaggcatc cttttctcccg tcaattctg    120 tcaaataaag taaaagaggc agtctacttg aattaccccc ggctggttga gcgtttgttg   180
aaaaaaagta actgaaaaat ccgtagaata gcgccactct gatggttaat taacctattc    240
aattaagaat tatctggatg aatgtgccat taaatgcgca gcataatggt gcgttgtgcg   300
ggaaaactgc ttttttttga aagggttggt cagtagcgga aacaactcac ttcacacccc   360 gaaggggggaa gttgcctgac cctacgattc ccgctatttc attcactgac cggaggttca   420
aaatga                                                               426
```

<210> SEQ ID NO 39
<211> LENGTH: 446
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 39

```
atgaccctga atatgatgat ggatgccggc tcaccacggc gataaccata ggttttcggc     60
gtggccacat ccatggtgaa tcccactttt tccagcacgc gcgccacttc atcgggtctt    120
aaatacatag attttcctcg tcatctttcc aaagcctcgc caccttacat gactgagcat   180
ggaccgtgac tcagaaaatt ccacaaacga acctgaaagg cgtgattgcc gtctggcctt    240
aaaaattatg gtctaaacta aaatttacat cgaaaacgag ggaggatcct atgtttaaca    300
```

```
aaccgaatcg ccgtgacgta gatgaaggtg ttgaggatat aaccacgat gttaaccagc    360 tcgaactcac ttcacacccc gaaggggggaa gttgcctgac cctacgattc cgctatttc    420 attcactgac cggaggttca aaatga                                          446
```

<210> SEQ ID NO 40
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
atgaccctga atatgatgat ggatgccggc tgacgaggca ggttacatca ctggtgaaac     60
cctgcacgtc aatggcggaa tgtatatggt ttaaccacga tgaaaattat ttgcgttatt    120
agggcgaaag gcctcaaaat agcgtaaaat cgtggtaaga actgccggga tttagttgca    180 aattttttcaa cattttatac actacgaaaa ccatcgcgaa agcgagtttt ataggaaat    240 ttaagagtat gagcactatc gaagaacgcg ttaagaaaat tatcggcgaa cagctgggcg    300
ttaagcagga agaagttacc aacaatgctt ccttcgttga agacctgggc gctgattctc    360
ttgacaccga actcacttca caccccgaag ggggaagttg cctgacccta cgattcccgc    420
tatttcattc actgaccgga ggttcaaaat ga                                    452
```

<210> SEQ ID NO 41
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
atgaccctga atatgatgat ggatgccggc cgtcctgtaa taataaccgg acaattcgga     60
ctgattaaaa aagcgcccctt gtggcgcttt ttttatattc ccgcctccat ttaaaataaa    120
aaatccaatc ggatttcact atttaaactg gccattatct aagatgaatc cgatggaagc    180 tcgctgttttt aacacgcgtt ttttaacctt ttattgaaag tcggtgcttc tttgagcgaa    240
cgatcaaatt taagtggatt cccatcaaaa aaatattctc aacctaaaaa agtttgtgta    300
atacttgtaa cgctacatgg agattaactc aatctagagg gtattaataa tgaatcgtac    360
taaactggta ctgggcgcaa ctcacttcac accccgaagg gggaagttgc ctgaccctac    420
gattcccgct atttcattca ctgaccggag gttcaaaatg a                          461
```

<210> SEQ ID NO 42
<211> LENGTH: 463
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
atgaccctga atatgatgat ggatgccggc atattgacac catgacgcgc gtaatgctga     60
ttggttctgt gacgctggta atgattgtcg aaattctgaa cagtgccatc gaagccgtag    120
tagaccgtat tggtgcagaa ttccatgaac tttccgggcg ggcgaaggat atggggtcgg    180
cggcggtgct gatgtccatc ctgctggcga tgtttacctg gatcgcatta ctctggtcac    240
```

```
attttcgata acgcttccag aattcgataa cgccctggtt ttttgcttaa atttggttcc    300
aaaatcgcct ttagctgtat atactcacag cataactgta tatacaccca gggggcggga    360
tgaaagcatt aacggccagg aactcacttc acaccccgaa gggggaagtt gcctgaccct    420
acgattcccg ctatttcatt cactgaccgg aggttcaaaa tga                      463
```

<210> SEQ ID NO 43
<211> LENGTH: 428
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
atgaccctga atatgatgat ggatgccggc atcatattgc gctccctggt tatcatttgt    60
tactaaatga atgttataa tataacaatt ataaatacca catcgctttc aattcaccag    120
ccaaatgaga ggagcgccgt ctgacatagc cagcgctata aaacatagca ttatctatat    180
gtttatgatt aataactgat ttttgcgttt tggatttggc tgtggcatcc ttgccgctct    240
tttcgcagcg tctgcgtttt tgccctccgg tcagggcatt taagggtcag caatgagttt    300
ttacgcaatt acgattcttg ccttcggcat gtcgatggat gctttaactc acttcacacc    360 ccgaagggg aagttgcctg accctacgat tcccgctatt tcattcactg accggaggtt    420
caaaatga                                                              428
```

<210> SEQ ID NO 44
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
atgaccctga atatgatgat ggatgccggc cgcgtcaggt tgaacgtaaa aaagtcggtc    60
tgcgcaaagc acgtcgtcgt ccgcagttct ccaaacgtta attggtttct gcttcggcag    120
aacgattggc gaaaaaaccc ggtgcgaacc gggttttttt atggataaag atcgtgttat    180
ccacagcaat ccattgatta tctcttcttt ttcagcattt ccagaatccc ctcaccacaa    240
agcccgcaaa atctggtaaa ctatcatcca attttctgcc caaatggctg ggattgttca    300 tttttttgttt gccttacaac gagagtgaca gtacgcgcgg gtagttaact caacatctga    360
ccggtcgata actcacttca caccccgaag ggggaagttg cctgacccta cgattcccgc    420
tatttcattc actgaccgga ggttcaaaat ga                                   452
```

<210> SEQ ID NO 45
<211> LENGTH: 410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
atgaccctga atatgatgat ggatgccggc cctgtatgaa gatggcgtgc gcaaagatcg    60
cctggataac agcgatatga ttagccagct tgaagcccgc attcgcgcga aagcgtcaat    120
gctggacgaa gcgcgtcgta tcgatgtgca acaggtagaa aaataaggtt gctgggaagc    180
```

```
ggcaggcttc cgtgtatga tgaacccgcc cggcgcgacc cgttgttcgt cgcggccccg      240
agggttcatt ttttgtatta ataaagagaa taaacgtggc aaaaaatatt caagccattc      300
gcggcatgaa cgattatctg cctggcgaac tcacttcaca ccccgaaggg ggaagttgcc      360
tgaccctacg attcccgcta tttcattcac tgaccggagg ttcaaaatga                  410
```

<210> SEQ ID NO 46
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
atgaaaaaga ttgatgcgat tattaaacct ttcaaactgg atgacgtgcg ctgatccttc      60
aactcagcaa aagttcgatt tattcaacaa agccacgttg tgtctcaaaa tctctgatgt     120
tacattgcac aagataaaaa tatatcatca tgaacaataa aactgtctgc ttacataaac     180
agtaatacaa ggggtgttat gagccatatt caacgggaaa cgtcttgctc ccgtccgcgc     240
ttaaactcca acatggacgc tgatttatat gggtataaat gggctcgcga taatgtcggg     300
caatcaggtg cgacaatcta tcgcttgtat gggaagcccg atgcgccaga gttgtttctg     360
aaacatggca aaggtagcgt tgccaatgat gttacagatg agatggtccg tctcaactgg     420
ctgacggagt ttatgcctct cccgaccatc aagcatttta tccgtactcc tgatgatgcg     480
tggttactca ccaccgcgat tcctgggaaa acagccttcc aggtattaga agaatatcct     540
gattcaggtg aaaatattgt tgatgcgctg gccgtgttcc tgcgccggtt acattcgatt     600
cctgtttgta attgtccttt taacagcgat cgtgtatttc gtcttgctca ggcgcaatca     660
cgcatgaata acggtttggt tgatgcgagt gattttgatg acgagcgtaa tggctggcct     720
gttgaacaag tctggaaaga atgcacaag ctcttgccat tctcaccgga ttcagtcgtc      780
actcatggtg atttctcact tgataacctt attttgacg aggggaaatt aataggttgt      840
attgatgttg acgggtcgg aatcgcagac cgttaccagg accttgccat tctttggaac      900
tgcctcggtg agttttctcc ttcattacag aaacggcttt ttcaaaaata tggtattgat      960
aatcctgata tgaataaatt gcagtttcat ttgatgctcg atgagttttt ctaataagcc     1020
tcgcgcgtga ttcgtatccg caccggcgaa gaagacgacg cggcgattta a              1071
```

<210> SEQ ID NO 47
<211> LENGTH: 1295
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
atgaccatga acctgatgac ggatgtcgtc tcagccaccg ggatcgccgg gttgctttca      60
cgacaacacc cgacgctgtt ttttacacta attgaacagg cccccgtggc gatcacgctg     120
acggataccg ctgcccgcat tgtctatgcc aacccgggcg tgttgagtca tcctgactag     180
ctgagatgag ggctcgcctg atccttcaac tcagcaaaag ttcgatttat tcaacaaagc     240
cacgttgtgt ctcaaaatct ctgatgttac attgcacaag ataaaaatat atcatcatga     300
acaataaaac tgtctgctta cataaacagt aatacaaggg gtgttatgag ccatattcaa     360
cgggaaacgt cttgctccag gccgcgatta aattccaaca tggatgctga tttatatggg     420
```

```
tataaatggg ctcgcgataa tgtcgggcaa tcaggtgcga caatctatcg attgtatggg     480
aagcccgatg cgccagagtt gtttctgaaa catggcaaag gtagcgttgc caatgatgtt     540
acagatgaga tggtcagact aaactggctg acggaattta tgcctcttcc gaccatcaag     600
cattttatcc gtactcctga tgatgcatgg ttactcacca ctgcgatccc cgggaaaaca     660
gcattccagg tattagaaga atatcctgat tcaggtgaaa atattgttga tgcgctggca     720
gtgttcctgc gccggttgca ttcgattcct gtttgtaatt gtccttttaa cagcgatcgc     780
gtatttcgtc tcgctcaggc gcaatcacga atgaataacg gtttggttga tgcgagtgat     840
tttgatgacg agcgtaatgg ctggcctgtt gaacaagtct ggaaagaaat gcataagctt     900
ttgccattct caccggattc agtcgtcact catggtgatt tctcacttga taaccttatt     960
tttgacgagg ggaaattaat aggttgtatt gatgttggac gagtcggaat cgcagaccga    1020
taccaggatc ttgccatcct atggaactgc ctcggtgagt tttctccttc attacagaaa    1080 cggcttttc aaaaatatgg tattgataat cctgatatga ataaattgca gtttcatttg    1140
atgctcgatg agttttctcta ataagcctga ccggtggtga atttaatctc gctgacgtgt    1200
agacattcat cgatctgcat ccacggtccg gcggcggtac ctgcctgacg ctacgtttac    1260
cgctctttta tgaactgacc ggaggcccaa gatga                                1295

<210> SEQ ID NO 48
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
atgagcatca cggcgttatc agcatcattt cctgagggga atatcgccag ccgcttgtcg      60
ctgcaacatc cttcactgtt ttataccgtg gttgaacaat cttcggtggc gagcgtgttg     120
agtcatcctg actagctgag atgagggctc gcccctcgt cccgacactt ccagatcgcc     180
atagcgcaca cgcctcgag cggtggtaac ggcgcagtgg cggttttcat ggcttgttat     240
gactgttttt ttggggtaca gtctatgcct cgggcatcca agcagcaagc gcgttacgcc     300
gtgggtcgat gtttgatgtt atggagcagc aacgatgtta cgcagcaggg cagtcgccct     360
aaaacaaagt taaacatcat gagggaagcg gtgatcgccg aagtatcgac tcaactatca     420
gaggtagttg gcgtcatcga gcgccatctc gaaccgacgt tgctggccgt acatttgtac     480
ggctccgcag tggatggcgg cctgaagcca cacagtgata ttgatttgct ggttacggtg     540
accgtaaggc ttgatgaaac aacgcggcga gctttgatca cgacctttt ggaaacttcg     600 gcttcccctg gagagagcga gattctccgc gctgtagaag tcaccattgt tgtgcacgac     660
gacatcattc cgtggcgtta tccagctaag cgcgaactgc aatttggaga atggcagcgc     720
aatgacattc ttgcaggtat cttcgagcca gccacgatcg acattgatct ggctatcttg    780
ctgacaaaag caagagaaca tagcgttgcc ttggtaggtc cagcggcgga ggaactcttt    840
gatccggttc ctgaacagga tctatttgag gcgctaaatg aaaccttaac gctatggaac    900
tcgccgcccg actgggctgg cgatgagcga aatgtagtgc ttacgttgtc ccgcatttgg    960
tacagcgcag taaccggcaa aatcgcgccg aaggatgtcg ctgccgactg gcaatggag    1020 cgcctgccgc cccagtatca gcccgtcata cttgaagcta gacaggctta tcttggacaa    1080
gaagaagatc gcttggcctc gcgcgcagat cagttggaag aatttgtcca ctacgtgaaa    1140
```

```
ggcgagatca ccaaggtagt cggcaaataa tgtctaacaa ttcgttcaag ccgacgccgc    1200
ttcgcggcgc ggcttaactc aagcgttaga tgcactaagc acataattgc tcacagccaa    1260
actatcaggt caagtctgct tttattattt ttaagcgtgc ataataagcc ctacacaaat    1320
ggtacccgac cggtggtgaa tttaatctcg ctgacgtgta gacattccct tatccagacg    1380
ctgatcgccc atcatcgcgg ttctttagat ctctcggtcc gccctgatgg cggcaccttg    1440
ctgacgttac gcctgccggt acagcaggtt atcaccggag gcttaaaatg a             1491
```

<210> SEQ ID NO 49
<211> LENGTH: 1021
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
ctgatccttc aactcagcaa aagttcgatt tattcaacaa agccacgttg tgtctcaaaa      60
tctctgatgt tacattgcac aagataaaaa tatatcatca tgaacaataa aactgtctgc     120
ttacataaac agtaatacaa ggggtgttat gagccatatt caacgggaaa cgtcttgctc     180
caggccgcga ttaaattcca acatggatgc tgatttatat gggtataaat gggctcgcga     240
taatgtcggg caatcaggtg cgacaatcta tcgattgtat gggaagcccg atgcgccaga     300
gttgtttctg aaacatggca aaggtagcgt tgccaatgat gttacagatg agatggtcag     360
actaaactgg ctgacggaat ttatgcctct tccgaccatc aagcatttta tccgtactcc     420
tgatgatgca tggttactca ccactgcgat ccccgggaaa acagcattcc aggtattaga     480
agaatatcct gattcaggtg aaaatattgt tgatgcgctg gcagtgttcc tgcgccggtt     540
gcattcgatt cctgtttgta attgtccttt taacagcgat cgcgtatttc gtctcgctca     600
ggcgcaatca cgaatgaata acggtttggt tgatgcgagt gattttgatg acgagcgtaa     660
tggctggcct gttgaacaag tctggaaaga atgcataag cttttgccat tctcaccgga      720
ttcagtcgtc actcatggtg atttctcact tgataacctt attttttgacg aggggaaatt     780 aataggttgt attgatgttg gacgagtcgg aatcgcagac cgataccagg atcttgccat     840
cctatggaac tgcctcggtg agttttctcc ttcattacag aaacggcttt ttcaaaaata     900
tggtattgat aatcctgata tgaataaatt gcagtttcat ttgatgctcg atgagttttt     960
ctaataagcc ttgaccctac gattcccgct atttcattca ctgaccggag gttcaaaatg    1020
a                                                                    1021
```

<210> SEQ ID NO 50
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
atgaccctga atatgatgct cgataacgcc gtacccgagg cgattgccgg ctgatccttc     60
aactcagcaa aagttcgatt tattcaacaa agccacgttg tgtctcaaaa tctctgatgt    120
tacattgcac aagataaaaa tatatcatca tgaacaataa aactgtctgc ttacataaac    180
agtaatacaa ggggtgttat gagccatatt caacgggaaa cgtcttgctc ccgtccgcgc    240
```

```
ttaaactcca acatggacgc tgatttatat gggtataaat gggctcgcga taatgtcggg      300
caatcaggtg cgacaatcta tcgcttgtat gggaagcccg atgcgccaga gttgtttctg      360
aaacatggca aggtagcgtt tgccaatgat gttacagatg agatggtccg tctcaactgg      420
ctgacggagt ttatgcctct cccgaccatc aagcatttta tccgtactcc tgatgatgcg      480
tggttactca ccaccgcgat tcctgggaaa acagccttcc aggtattaga agaatatcct      540
gattcaggtg aaaatattgt tgatgcgctg ccgtgttcc tgcgccggtt acattcgatt       600
cctgtttgta attgtccttt taacagcgat cgtgtatttc gtcttgctca ggcgcaatca      660
cgcatgaata acggtttggt tgatgcgagt gattttgatg acgagcgtaa tggctggcct      720
gttgaacaag tctggaaaga aatgcacaag ctcttgccat tctcaccgga ttcagtcgtc      780
actcatggtg atttctcact tgataacctt atttttgacg aggggaaatt aataggttgt      840
attgatgttg gacgggtcgg aatcgcagac cgttaccagg accttgccat tctttggaac      900
tgcctcggtg agttttctcc ttcattacag aaacggcttt ttcaaaaata tggtattgat      960
aatcctgata tgaataaatt gcagtttcat ttgatgctcg atgagttttt ctaataagcc     1020
ttggttctgc gtttcccgct ctttaatacc ctgaccggag gtgagcaatg a              1071

<210> SEQ ID NO 51
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
atgaccctga atatgatgat ggatgccggc cgtcctgtaa taataaccgg acaattcgga       60
ctgattaaaa aagcgcccctt gtggcgcttt ttttatattc ccgcctccat ttaaaataaa     120
aaatccaatc ggatttcact atttaaactg gccattatct aagatgaatc cgatggaagc     180
tcgctgtttt aacacgcgtt ttttaacctt ttattgaaag tcggtgcttc tttgagcgaa     240
cgatcaaatt taagtggatt cccatcaaaa aaatatctc aacctaaaaa agtttgtgta     300
atacttgtaa cgctacatgg agattaactc aatctagagg gtattaataa tgaatcgtac     360
taaactggta ctgggcgcaa ctcacttcac accccgaagg gggaagttgc ctgaccctac     420
gattcccgct atttcattca ctgaccggag gttcaaaatg a                         461

<210> SEQ ID NO 52
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
atgaccctga atatgatgat ggatgccggc ggacatcatc gcgacaaaca atattaatac       60
cggcaaccac accggcaatt tacgagactg cgcaggcatc ctttctcccg tcaatttctg     120
tcaaataaag taaagagggc agtctacttg aattacccccc ggctggttga gcgtttgttg    180
aaaaaaagta actgaaaaat ccgtagaata gcgccactct gatggttaat taacctattc     240
aattaagaat tatctggatg aatgtgccat taaatgcgca gcataatggt gcgttgtgcg     300
ggaaaactgc ttttttttga aagggttggt cagtagcgga acaactcac ttcacacccc      360 gaaggggaa gttgcctgac cctacgattc ccgctatttc attcactgac cggaggttca    420
``` aaatga                                                                426

<210> SEQ ID NO 53
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
atgaccctga atatgatgat ggatgccggc tgacgaggca ggttacatca ctggtgaaac    60
cctgcacgtc aatggcggaa tgtatatggt ttaaccacga tgaaaattat ttgcgttatt   120
agggcgaaag gcctcaaaat agcgtaaaat cgtggtaaga actgccggga tttagttgca   180
aatttttcaa cattttatac actacgaaaa ccatcgcgaa agcgagtttt gataggaaat   240
ttaagagtat gagcactatc gaagaacgcg ttaagaaaat tatcggcgaa cagctgggcg   300
ttaagcagga agaagttacc aacaatgctt ccttcgttga agacctgggc gctgattctc   360
ttgacaccga actcacttca caccccgaag ggggaagttg cctgacccta cgattcccgc   420
tatttcattc actgaccgga ggttcaaaat ga                                 452

<210> SEQ ID NO 54
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atgaccctga atatgatgat ggatgccggc ggacatcatc gcgacaaaca atattaatac    60
cggcaaccac accggcaatt tacgagactg cgcaggcatc ctttctcccg tcaatttctg   120
tcaaataaag taaagaggc agtctacttg aattacccc ggctggttga gcgtttgttg    180
aaaaaaagta actgaaaaat ccgtagaata gcgccactct gatggttaat taacctattc   240
aattaagaat tatctggatg aatgtgccat taaatgcgca gcataatggt gcgttgtgcg   300
ggaaaactgc tttttttga aagggttggt cagtagcgga acaactcac ttcacacccc    360 gaaggggga gttgcctgac cctacgattc ccgctatttc attcactgac cggaggttca   420
aaatga                                                              426

<210> SEQ ID NO 55
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atgaccctga atatgatgat ggatgccggc cgtcctgtaa aataaccgg acaattcgga     60 ctgattaaaa aagcgccctt gtggcgcttt ttttatattc ccgcctccat ttaaaataaa   120
aaatccaatc ggatttcact atttaaactg gccattatct aagatgaatc cgatggaagc   180
tcgctgtttt aacacgcgtt ttttaacctt ttattgaaag tcggtgcttc tttgagcgaa   240
cgatcaaatt taagtggatt cccatcaaaa aaatattctc aacctaaaaa agtttgtgta   300
atacttgtaa cgctacatgg agattaactc aatctagagg gtattaataa tgaatcgtac   360

```
taaactggta ctgggcgcaa ctcacttcac accccgaagg gggaagttgc ctgaccctac    420
gattcccgct atttcattca ctgaccggag gttcaaaatg a                        461
```

<210> SEQ ID NO 56
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
atgagcatca cggcgttatc agcatcattt cctgagggga atatcgccag ccgcttgtcg     60
ctgcaacatc cttcactgtt ttataccgtg gttgaacaat cttcggtggc gagcgtgttg    120
agtcatcctg actagctgag atgagggctc gccccctcgt cccgacactt ccagatcgcc    180
atagcgcaca gcgcctcgag cggtggtaac ggcgcagtgg cggttttcat ggcttgttat    240
gactgttttt ttggggtaca gtctatgcct cgggcatcca agcagcaagc gcgttacgcc    300
gtgggtcgat gtttgatgtt atggagcagc aacgatgtta cgcagcaggg cagtcgccct    360
aaaacaaagt taaacatcat gagggaagcg gtgatcgccg aagtatcgac tcaactatca    420
gaggtagttg gcgtcatcga gcgccatctc gaaccgacgt tgctggccgt acatttgtac    480
ggctccgcag tggatggcgg cctgaagcca cacagtgata ttgatttgct ggttacggtg    540
accgtaaggc ttgatgaaac aacgcggcga gctttgatca cgacctttt ggaaacttcg    600 gcttcccctg gagagagcga gattctccgc gctgtagaag tcaccattgt tgtgcacgac    660
gacatcattc cgtggcgtta tccagctaag cgcgaactgc aatttggaga atggcagcgc    720
aatgacattc ttgcaggtat cttcgagcca gccacgatcg acattgatct ggctatcttg    780
ctgacaaaag caagagaaca tagcgttgcc ttggtaggtc cagcggcgga ggaactcttt    840
gatccggttc ctgaacagga tctatttgag gcgctaaatg aaaccttaac gctatggaac    900
tcgccgcccg actgggctgg cgatgagcga aatgtagtgc ttacgttgtc ccgcatttgg    960
tacagcgcag taaccggcaa aatcgcgccg aaggatgtcg ctgccgactg ggcaatggag   1020
cgcctgccgg cccagtatca gcccgtcata cttgaagcta gacaggctta tcttggacaa   1080
gaagaagatc gcttggcctc gcgcgcagat cagttggaag aatttgtcca ctacgtgaaa   1140
ggcgagatca ccaaggtagt cggcaaataa tgtctaacaa ttcgttcaag ccgacgccgc   1200
ttcgcggcgc ggcttaactc aagcgttaga tgcactaagc acataattgc tcacagccaa   1260
actatcaggt caagtctgct tttattattt ttaagcgtgc ataataagcc ctacacaaat   1320
ggtacccgac cggtggtgaa tttaatctcg ctgacgtgta gacattccct tatccagacg   1380
ctgatcgccc atcatcgcgg ttctttagat ctctcggtcc gccctgatgg cggcaccttg   1440
ctgacgttac gcctgccggt acagcaggtt atcaccggag gcttaaaatg a             1491
```

<210> SEQ ID NO 57
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
atgagcatca cggcgttatc agcatcattt cctgagggga atatcgccag ccgcttgtcg     60
```

```
ctgcaacatc cttcactgtt ttataccgtg gttgaacaat cttcggtggc gagcgtgttg    120
agtcatcctg actagctgag atgagggctc gccccctcgt cccgacactt ccagatcgcc    180
atagcgcaca gcgcctcgag cggtggtaac ggcgcagtgg cggttttcat ggcttgttat    240
gactgttttt ttgggtaca gtctatgcct cgggcatcca agcagcaagc gcgttacgcc     300
gtgggtcgat gtttgatgtt atggagcagc aacgatgtta cgcagcaggg cagtcgccct    360
aaaacaaagt taaacatcat gagggaagcg gtgatcgccg aagtatcgac tcaactatca    420
gaggtagttg gcgtcatcga gcgccatctc gaaccgacgt tgctggccgt acatttgtac    480
ggctccgcag tggatggcgg cctgaagcca cacagtgata ttgatttgct ggttacggtg    540
accgtaaggc ttgatgaaac aacgcggcga gctttgatca acgaccttt ggaaacttcg     600 gcttcccctg gagagagcga gattctccgc gctgtagaag tcaccattgt tgtgcacgac    660
gacatcattc cgtggcgtta ccagctaag cgcgaactgc aatttggaga atggcagcgc     720
aatgacattc ttgcaggtat cttcgagcca gccacgatcg acattgatct ggctatcttg    780
ctgacaaaag caagagaaca tagcgttgcc ttggtaggtc cagcggcgga ggaactcttt    840
gatccggttc ctgaacagga tctatttgag gcgctaaatg aaaccttaac gctatggaac    900
tcgccgcccg actgggctgg cgatgagcga aatgtagtgc ttacgttgtc ccgcatttgg    960
tacagcgcag taaccggcaa aatcgcgccg aaggatgtcg ctgccgactg gcaatggag    1020 cgcctgccgg cccagtatca gcccgtcata cttgaagcta gacaggctta tcttggacaa    1080
gaagaagatc gcttggcctc gcgcgcagat cagttggaag aatttgtcca ctacgtgaaa    1140
ggcgagatca ccaaggtagt cggcaaataa tgtctaacaa ttcgttcaag ccgacgccgc    1200
ttcgcggcgc ggcttaactc aagcgttaga tgcactaagc acataattgc tcacagccaa    1260
actatcaggt caagtctgct tttattattt ttaagcgtgc ataataagcc ctacacaaat    1320
ggtacccgac cggtggtgaa tttaatctcg ctgacgtgta gacattccct tatccagacg    1380
ctgatcgccc atcatcgcgg ttctttagat ctctcggtcc gccctgatgg cggcaccttg    1440
ctgacgttac gcctgccggt acagcaggtt atcaccggag gcttaaaatg a             1491
```

<210> SEQ ID NO 58
<211> LENGTH: 1021
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
ctgatccttc aactcagcaa aagttcgatt tattcaacaa agccacgttg tgtctcaaaa     60
tctctgatgt tacattgcac aagataaaaa tatatcatca tgaacaataa aactgtctgc    120
ttacataaac agtaatacaa ggggtgttat gagccatatt caacgggaaa cgtcttgctc    180
caggccgcga ttaaattcca acatggatgc tgatttatat gggtataaat gggctcgcga    240
taatgtcggg caatcaggtg cgacaatcta tcgattgtat gggaagcccg atgcgccaga    300
gttgtttctg aaacatggca aaggtagcgt tgccaatgat gttacagatg agatggtcag    360
actaaactgg ctgacggaat ttatgcctct tccgaccatc aagcatttta tccgtactcc    420
tgatgatgca tggttactca ccactgcgat ccccgggaaa acagcattcc aggtattaga    480
agaatatcct gattcaggtg aaaatattgt tgatgcgctg gcagtgttcc tgcgccggtt    540
gcattcgatt cctgtttgta attgtccttt taacagcgat cgcgtatttc gtctcgctca    600
```

```
ggcgcaatca cgaatgaata acggtttggt tgatgcgagt gattttgatg acgagcgtaa    660
tggctggcct gttgaacaag tctggaaaga aatgcataag cttttgccat tctcaccgga    720
ttcagtcgtc actcatggtg atttctcact tgataacctt attttgacg aggggaaatt    780 aataggttgt attgatgttg gacgagtcgg aatcgcagac cgataccagg atcttgccat    840
cctatggaac tgcctcggtg agttttctcc ttcattacag aaacggcttt ttcaaaaata    900
tggtattgat aatcctgata tgaataaatt gcagtttcat ttgatgctcg atgagttttt    960
ctaataagcc ttgaccctac gattcccgct atttcattca ctgaccggag gttcaaaatg   1020
a                                                                    1021
```

<210> SEQ ID NO 59
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
atgagcatca cggcgttatc agcatcattt cctgagggga atatcgccag ccgcttgtcg     60
ctgcaacatc cttcactgtt ttataccgtg gttgaacaat cttcggtggc gagcgtgttg    120
agtcatcctg actagctgag atgagggctc gcccctcgt cccgacactt ccagatcgcc    180
atagcgcaca gcgcctcgag cggtggtaac ggcgcagtgg cggttttcat ggcttgttat    240
gactgttttt ttggggtaca gtctatgcct cgggcatcca agcagcaagc gcgttacgcc    300
gtgggtcgat gtttgatgtt atggagcagc aacgatgtta cgcagcaggg cagtcgccct    360
aaaacaaagt taaacatcat gagggaagcg gtgatcgccg aagtatcgac tcaactatca    420
gaggtagttg gcgtcatcga gcgccatctc gaaccgacgt tgctggccgt acatttgtac    480
ggctccgcag tggatggcgg cctgaagcca cacagtgata ttgatttgct ggttacggtg    540
accgtaaggc ttgatgaaac aacgcggcga gctttgatca cgacctttt ggaaacttcg    600 gcttcccctg gagagagcga gattctccgc gctgtagaag tcaccattgt tgtgcacgac    660
gacatcattc cgtggcgtta ccagctaag cgcgaactgc aatttggaga atggcagcgc    720
aatgacattc ttgcaggtat cttcgagcca gccacgatcg acattgatct ggctatcttg    780
ctgacaaaag caagagaaca tagcgttgcc ttggtaggtc cagcggcgga ggaactcttt    840
gatccggttc ctgaacagga tctatttgag gcgctaaatg aaaccttaac gctatggaac    900
tcgccgcccg actgggctgg cgatgagcga aatgtagtgc ttacgttgtc ccgcatttgg    960
tacagcgcag taaccggcaa aatcgcgccg aaggatgtcg ctgccgactg ggcaatggag   1020
cgcctgccgg cccagtatca gcccgtcata cttgaagcta cagcagctta tcttggacaa   1080
gaagaagatc gcttggcctc gcgcgcagat cagttggaag aatttgtcca ctacgtgaaa   1140
ggcgagatca ccaaggtagt cggcaaataa tgtctaacaa ttcgttcaag ccgacgccgc   1200
ttcgcggcgc ggcttaactc aagcgttaga tgcactaagc acataattgc tcacagccaa   1260
actatcaggt caagtctgct tttattattt ttaagcgtgc ataataagcc ctacacaaat   1320
ggtacccgac cggtggtgaa tttaatctcg ctgacgtgta acattccct tatccagacg   1380 ctgatcgccc atcatcgcgg ttctttagat ctctcggtcc gccctgatgg cggcaccttg   1440
ctgacgttac gcctgccggt acagcaggtt atcaccggag cttaaaatg a            1491
```

<210> SEQ ID NO 60

```
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
atgagcatca cggcgttatc agcatcattt cctgagggga atatcgccag ccgcttgtcg      60
ctgcaacatc cttcactgtt ttataccgtg gttaacaat cttcggtggc gagcgtgttg     120
agtcatcctg actagctgag atgagggctc gccccctcgt cccgacactt ccagatcgcc    180
atagcgcaca gcgcctcgag cggtggtaac ggcgcagtgg cggttttcat ggcttgttat    240
gactgttttt ttggggtaca gtctatgcct cgggcatcca agcagcaagc gcgttacgcc    300
gtgggtcgat gtttgatgtt atggagcagc aacgatgtta cgcagcaggg cagtcgccct    360
aaaacaaagt taaacatcat gagggaagcg gtgatcgccg aagtatcgac tcaactatca    420
gaggtagttg gcgtcatcga gcgccatctc gaaccgacgt tgctggccgt acatttgtac    480
ggctccgcag tggatggcgg cctgaagcca cacagtgata ttgatttgct ggttacggtg    540
accgtaaggc ttgatgaaac aacgcggcga gctttgatca cgacctttt ggaaacttcg     600 gcttcccctg gagagagcga gattctccgc gctgtagaag tcaccattgt tgtgcacgac    660
gacatcattc cgtggcgtta tccagctaag cgcgaactgc aatttggaga atggcagcgc    720
aatgacattc ttgcaggtat cttcgagcca gccacgatcg acattgatct ggctatcttg    780
ctgacaaaag caagagaaca tagcgttgcc ttggtaggtc cagcggcgga ggaactcttt    840
gatccggttc ctgaacagga tctatttgag gcgctaaatg aaaccttaac gctatggaac    900
tcgccgcccg actgggctgg cgatgagcga aatgtagtgc ttacgttgtc ccgcatttgg    960
tacagcgcag taaccggcaa aatcgcgccg aaggatgtcg ctgccgactg gcaatggag   1020 cgcctgccgg cccagtatca gcccgtcata cttgaagcta gacaggctta tcttggacaa   1080
gaagaagatc gcttggcctc gcgcgcagat cagttggaag aatttgtcca ctacgtgaaa   1140
ggcgagatca ccaaggtagt cggcaaataa tgtctaacaa ttcgttcaag ccgacgccgc   1200
ttcgcggcgc ggcttaactc aagcgttaga tgcactaagc acataattgc tcacagccaa   1260
actatcaggt caagtctgct tttattattt ttaagcgtgc ataataagcc ctacacaaat   1320
ggtacccgac cggtggtgaa tttaatctcg ctgacgtgta gcattccct tatccagacg    1380 ctgatcgccc atcatcgcgg ttctttagat ctctcggtcc gccctgatgg cggcaccttg   1440
ctgacgttac gcctgccggt acagcaggtt atcaccggag gcttaaaatg a            1491

<210> SEQ ID NO 61
<211> LENGTH: 1563
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atgtttaacg atctgattgg cgatgatgaa acggattcgc cggaagatgc gctttctgag      60
agctggcgcg aattgtggca ggatgcgttg caggaggagg attccacgcc cgtgctggcg    120
catctctcag aggacgatcg ccgccgcgtg gtgcgctga ttgccgattt tcgcaaagag     180
ttggataaac gcaccattgg cccgcgaggg cggcaggtac tcgatcactt aatgccgcat    240
ctgctcagcg atgtatgctc gcgcgacgat gcgccagtac cgctgtcacg cctgacgccg    300
```

-continued

```
ctgctcaccg gaattattac ccgcaccact taccttgagc tgctaagtga atttcccggc    360
gcactgaaac acctcatttc cctgtgtgcc gcgtcgccga tggttgccag tcagctggcg    420
cgctacccga tcctgcttga tgaattgctc gacccgaata cgctctatca accgacggcg    480
atgaatgcct atcgcgatga gctgcgccaa tacctgctgc gcgtgccgga agatgatgaa    540
gagcaacagc ttgaggcgct gcggcagttt aagcaggcgc agttgctgcg cgtggcggcg    600
gcggatattg ccggtacgtt gccagtaatg aaagtgagcg atcacttaac ctggctggcg    660
gaagcgatta ttgatgcggt ggtgcagcaa gcctggggc agatggtggc gcgttatggc     720
cagccaacgc atctgcacga tcgcgaaggg cgcggttttg cggtggtcgg ttatggcaag    780
ctgggcggct gggagctggg ttacagctcc gatctggatc tggtattcct gcacgactgc    840
ccgatggatg tgatgaccga tggcgagcgt gaaatcgatg gtcgccagtt ctatttgcgt    900
ctcgcgcagc gcgtgatgca cctgtttagc acgcgcacgt cgtccggcat cctttatgaa    960
gttgatgcgc gtctgcgtcc atctggcgct gcggggatgc tggtcactac tacggaatcg   1020
ttcgccgatt accagcaaaa cgaagcctgg acgtgggaac atcaggcgct ggcccgtgcg   1080
cgcgtggtgt acggcgatcc gcaactgacc gccgaatttg acgccattcg ccgcgatatt   1140
ctgatgacgc ctcgcgacgg cgcaacgctg caaaccgacg tgcgagaaat gcgcgagaaa   1200
atgcgtgccc atcttggcaa caagcataaa gaccgcttcg atctgaaagc cgatgaaggc   1260
ggtatcaccg acatcgagtt tatcgcccaa tatctggtgc tgcgctttgc ccatgacaag   1320
ccgaaactga cgcgctggtc ggataatgtg cgcattctcg aagggctggc gcaaaacggc   1380
atcatggagg agcaggaagc gcaggcattg acgctggcgt acaccacatt gcgtgatgag   1440
ctgcaccacc tggcgctgca agagttgccg ggacatgtgg cgctctcctg ttttgtcgcc   1500
gagcgtgcgc ttattaaaac cagctgggac aagtggctgg tggaaccgtg cgccccggcg   1560
taa                                                                 1563
```